United States Patent
Wai et al.

(10) Patent No.: US 7,435,735 B2
(45) Date of Patent: Oct. 14, 2008

(54) HYDROXY PYRIDOPYRROLOPYRAZINE DIONE COMPOUNDS USEFUL AS HIV INTEGRASE INHIBITORS

(75) Inventors: John S. Wai, Harleysville, PA (US); Thorsten E. Fisher, Hatfield, PA (US); Linghang Zhuang, Chalfont, PA (US); Donnette D. Staas, Harleysville, PA (US); Terry A. Lyle, Lederach, PA (US); Boyoung Kim, Lansdale, PA (US); Mark W. Embrey, North Wales, PA (US); Catherine M. Wiscount, Allentown, PA (US); Lekhanh O. Tran, Norristown, PA (US); Melissa Egbertson, Ambler, PA (US); Kelly L. Savage, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 346 days.

(21) Appl. No.: 10/576,328

(22) PCT Filed: Oct. 18, 2004

(86) PCT No.: PCT/US2004/034420

§ 371 (c)(1),
(2), (4) Date: Apr. 19, 2006

(87) PCT Pub. No.: WO2005/041664

PCT Pub. Date: May 12, 2005

(65) Prior Publication Data

US 2007/0093496 A1    Apr. 26, 2007

Related U.S. Application Data

(60) Provisional application No. 60/512,678, filed on Oct. 20, 2003.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *C07D 471/00* | (2006.01) |
| *C07D 487/00* | (2006.01) |
| *C07D 241/36* | (2006.01) |

(52) U.S. Cl. .................... 514/250; 544/345
(58) Field of Classification Search ............. 544/345; 514/250
See application file for complete search history.

(56) References Cited

U.S. PATENT DOCUMENTS

| 3,891,643 A * | 6/1975 | Sellstedt et al. .............. 260/250 |
| 5,294,620 A | 3/1994 | Ratcliffe et al. |
| 6,262,055 B1 | 7/2001 | Young et al. |
| 6,306,891 B1 | 10/2001 | Selnick et al. |
| 6,380,249 B1 | 4/2002 | Young et al. |
| 2003/0055071 A1 | 3/2003 | Anthony et al. |
| 2005/0025774 A1 | 2/2005 | Crescenzi et al. |
| 2005/0075356 A1 | 4/2005 | Di Francesco et al. |
| 2006/0046985 A1 | 3/2006 | Crescenzi et al. |

FOREIGN PATENT DOCUMENTS

| WO | WO 01/00578 A1 | 1/2001 |
| WO | WO 02/30426 A1 | 4/2002 |
| WO | WO 02/30930 A2 | 4/2002 |
| WO | WO 02/36734 A2 | 5/2002 |
| WO | WO 02/055079 A2 | 7/2002 |
| WO | WO 2004/058756 A1 | 7/2002 |
| WO | WO 03/035076 A1 | 5/2003 |
| WO | WO 03/035077 A1 | 5/2003 |
| WO | WO 03/062204 A1 | 7/2003 |
| WO | WO 03/077857 A2 | 8/2003 |

OTHER PUBLICATIONS

Ratner, L., et al., "Complete nucleotide sequence of the AIDS virus, HTLV-III", Nature, vol. 313, pp. 277-284 (1985).
Toh, H., et al., "Close structural resemblance between putative polymerase of a Drosophila transposable genetic element 17.6 and pol gene product of Moloney murine leukaemia virus", The EMBO Journal, vol. 4, No. 5, pp. 1267-12-72 (1985).
Power, M. D., et al., "Nucleotide Sequence of SRV-1, a Type D Simian Acquired Immune Deficiency Syndrome Retrovirus", Science, vol. 231, pp. 1567-1572 (1986).
Pearl, L., et al., "A structural model for the retriviral proteases", Nature, vol. 329, pp. 351-354 (1987).

* cited by examiner

*Primary Examiner*—Zachary C Tucker
(74) *Attorney, Agent, or Firm*—Kenneth R. Walton; Sheldon O. Heber

(57) ABSTRACT

Hydroxy-substituted pyridopyrrolopyrazine dione compounds are inhibitors of HIV integrase and inhibitors of HIV replication. In one embodiment, the dione compounds are of Formula (I): (I) wherein a, b, A, B, $R^1$, $R^2$, $R^3$, $R^4$, $R^5$, $R^6$, $R^7$ and $R^8$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

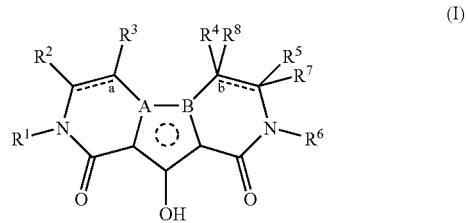

12 Claims, No Drawings

HYDROXY PYRIDOPYRROLOPYRAZINE DIONE COMPOUNDS USEFUL AS HIV INTEGRASE INHIBITORS

This application is the National Stage of International Application No. PCT/US2004/034420, filed on Oct. 18, 2004, which claims the benefit of U.S. Provisional Application No. 60/512,678, filed Oct. 20, 2003, the disclosure of which is hereby incorporated by reference in its entirety.

FIELD OF THE INVENTION

The present invention is directed to hydroxy-substituted pyridopyrrolopyrazine dione compounds and pharmaceutically acceptable salts thereof, their synthesis, and their use as inhibitors of the HIV integrase enzyme. The compounds of the present invention and their pharmaceutically acceptable salts are useful for preventing or treating infection by HIV and for treating, delaying the onset of, or preventing AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, integrase and an HIV protease [Toh et al., *EMBO J.* 1985, 4: 1267; Power et al., *Science* 1986, 231: 1567; Pearl et al., *Nature* 1987, 329: 351]. All three enzymes have been shown to be essential for the replication of HIV.

It is known that some antiviral compounds which act as inhibitors of IV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of ITV integrase and inhibitors of HIV replication. The inhibition of integrase in vitro and of HIV replication in cells is a direct result of inhibiting the strand transfer reaction catalyzed by the recombinant integrase in vitro in HIV infected cells. A particular advantage of the present invention is highly specific inhibition of HIV integrase and HIV replication.

The following references are of interest as background:

U.S. Pat. No. 5,294,620 discloses certain 1,6-naphthyridin-2-one derivatives having angiotensin II antagonist activity.

U.S. Pat. No. 6,380,249, U.S. Pat. No. 6,306,891, and U.S. Pat. No. 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 and WO 02/30930 disclose certain 8-hydroxy-1,6-naphthyridine-7-carboxamides as HIV integrase inhibitors, wherein the carboxamido nitrogen is directly or indirectly attached to phenyl or phenyl fused to a carbocycle. WO 02/30426 discloses another group of 8-hydroxy-1,6-naphthyridine-7-carboxamides as HIV integrase inhibitors, wherein the carboxamido nitrogen is directly or indirectly attached to a heterocycle. WO 02/055079 discloses still another group of 8-hydroxy-1,6-naphthyridine-7-carboxamides as HIV integrase inhibitors, wherein the carboxamido nitrogen is part of a heterocyclic ring system.

WO 02/036734 discloses certain aza- and polyaza-naphthalenyl ketones to be HIV integrase inhibitors. The ketones include certain 1-aryl-1-(poly)azanaphthylenyl methanones and 1-heterocyclyl-1-(poly)azanaphthylenyl methanones. Quinolinyl, naphthyridinyl, and quinoxalinyl are disclosed as suitable (poly)azanaphthalenyl groups in the ketones.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/077857 discloses N-(substituted benzyl)-8-hydroxy-1,6-naphthyridine-7-carboxamides that are useful as HIV integrase inhibitors.

WO 03/062204 discloses certain hydroxynaphthyridinone carboxamides that are useful as HIV integrase inhibitors.

SUMMARY OF THE INVENTION

The present invention is directed to hydroxy-substituted pyridopyrrolopyrazine dione compounds. These compounds and their pharmaceutically acceptable salts are useful in the inhibition of HIV integrase, the prevention of infection by HIV, the treatment of infection by HIV and in the prevention, treatment, and delay in the onset of AIDS, either as compounds or their pharmaceutically acceptable salts, or as pharmaceutical composition ingredients, whether or not in combination with other HIV/AIDS antivirals, anti-infectives, immunomodulators, antibiotics or vaccines. More particularly, the present invention includes compounds of Formula I and pharmaceutically acceptable salts thereof:

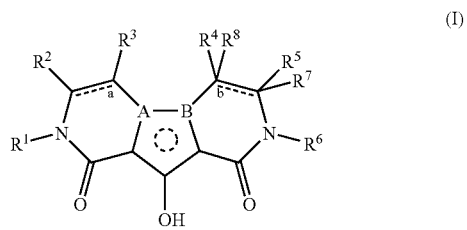

(I)

wherein:

bond "a" in the ring is a single bond or a double bond;

bond "b" in the ring is a single bond or a double bond, with the proviso that when bond "b" is a double bond, $R^7$ and $R^8$ are both absent;

one of A and B is N, and the other of A and B is C;

⋯⟳⋯ denotes that the central 5-membered ring is pyrrolyl;

$R^1$ is $-C_{1-6}$ alkyl-$R^J$, wherein $R^J$ is:

(A) aryl which is optionally substituted with from 1 to 5 substituents each of which is independently
  (1) $-C_{1-6}$ alkyl, optionally substituted with from 1 to 3 substituents each of which is independently $-OH$, $-O-C_{1-6}$ alkyl, $-O-C_{1-6}$ haloalkyl, $-CN$, $-NO_2$, $-N(R^a)R^b$, $-C(=O)N(R^a)R^b$, $-C(=O)R^a$, $-CO_2R^c$, $-S(O)_nR^c$, $-SO_2N(R^a)R^b$, $-N(R^a)C(=O)R^b$, $-N(R^a)CO_2R^c$, $-N(R^a)SO_2R^c$, $-N(R^a)SO_2N(R^a)R^b$, $-OC(=O)N(R^a)R^b$, or $-N(R^a)C(=O)N(R^a)R^b$,
  (2) $-O-C_{1-6}$ alkyl, optionally substituted with from 1 to 3 substituents each of which is independently $-OH$, $-O-C_{1-6}$ alkyl, $-O-C_{1-6}$ haloalkyl, $-S(O)_nR^c$, $-C(=O)N(R^a)R^b$, $-SO_2N(R^a)R^b$, $-N(R^a)C(=O)R^b$, $-N(R^a)CO_2R^c$, $-N(R^a)SO_2R^c$, $-N(R^a)SO_2N(R^a)R^b$, $-OC(=O)N(R^a)R^b$, or $-N(R^a)C(=O)N(R^a)R^b$,
  (3) $-C_{1-6}$ haloalkyl,
  (4) $-O-C_{1-6}$ haloalkyl,
  (5) $-OH$,
  (6) halo,
  (7) $-CN$,
  (8) $-NO_2$,
  (9) $-N(R^a)R^b$,
  (10) $-C(=O)N(R^a)R^b$,
  (11) $-C(=O)R^a$,
  (12) $-CO_2R^c$,
  (13) $-SR^c$,
  (14) $-S(=O)R^c$,
  (15) $-SO_2R^c$,
  (16) $-N(R^a)SO_2R^c$,
  (17) $-SO_2N(R^a)R^b$,
  (18) $-N(R^a)C(=O)R^b$,
  (19) $-N(R^a)CO_2R^c$,
  (20) phenyl, or
  (21) benzyl; or (B) a 5- or 6-membered heteroaromatic ring containing from 1 to 4 heteroatoms independently selected from N, O and S; wherein the heteroaromatic ring is
  (i) optionally substituted with from 1 to 4 substituents each of which is independently halogen, $-OH$, $-C_{1-6}$ alkyl, $-C_{1-6}$ haloalkyl, $-O-C_{1-6}$ alkyl, or $-O-C_{1-6}$ haloalkyl; and
  (ii) optionally substituted with 1 or 2 substituents each of which is independently aryl or $-C_{1-6}$ alkyl-aryl;

$R^2$ is:
  (1) $-H$,
  (2) $-C_{1-6}$ alkyl,
  (3) $-C_{1-6}$ haloalkyl, or
  (4) $-C_{1-6}$ alkyl substituted with one of $-OH$, $-O-C_{1-6}$ alkyl, $-O-C_{1-6}$ haloalkyl, $-CN$, $-NO_2$, $-N(R^a)R^b$, $-C(=O)N(R^a)R^b$, $-C(=O)R^a$, $-CO_2R^c$, $-S(O)_nR^c$, $-SO_2N(R^a)R^b$, $-N(R^a)C(=O)R^b$, $-N(R^a)CO_2R^c$, $-N(R^a)SO_2R^c$, $-N(R^a)SO_2N(R^a)R^b$, $-OC(=O)N(R^a)R^b$, $-N(R^a)C(=O)N(R^a)R^b$, or $-N(R^a)-OR^b$;

$R^3$ is:
  (1) $-H$,
  (2) $-C_{1-6}$ alkyl optionally substituted with one of $-OH$, $-O-C_{1-6}$ alkyl, $-O-C_{1-6}$ haloalkyl, $-CN$, $-NO_2$, $-N(R^a)R^b$, $-C(=O)N(R^a)R^b$, $-C(=O)R^a$, $-CO_2R^c$, $-S(O)_nR^c$, $-SO_2N(R^a)R^b$, $-N(R^a)C(R^b)=O$, $-N(R^a)SO_2R^c$, $-N(R^a)SO_2N(R^a)R^b$, $-OC(=O)N(R^a)R^b$, $-N(R^a)C(=O)N(R^a)R^b$, $-O-C_{1-6}$ alkyl-C(=O)N(R^a)R^b$, $-S-C_{1-6}$ alkyl-C(=O)N(R^a)R^b$, $-N(R^a)-C^{1-6}$ alkyl-C(=O)N(R^a)R^b$, $-N(SO_2R^c)-C_{1-6}$ alkyl-C(=O)N(R^a)R^b$, or $-N(R^a)-OR^b$;
  (3) $-C_{1-6}$ haloalkyl,
  (4) $-C(=O)R^a$,
  (5) $-CO_2R^c$,
  (6) $-C(=O)N(R^a)R^b$,
  (7) $-SO_2N(R^a)R^b$,
  (8) $-C_{2-6}$ alkenyl,
  (9) $-C_{2-6}$ alkenyl-C(=O)$-N(R^a)R^b$,
  (10) $-C_{2-5}$ alkynyl,
  (11) $-C_{2-5}$ alkynyl-CH_2N(R^a)R^b$,
  (12) $-C_{2-5}$ alkynyl-CH_2OR^a$,
  (13) $-C_{2-5}$ alkynyl-CH_2S(O)_nR^c$,
  (14) $-R^K$,
  (15) $-C_{1-6}$ alkyl substituted with $R^K$,
  (16) $-C_{1-6}$ haloalkyl substituted with $R^K$,
  (17) $-C_{1-6}$ alkyl-O$-R^K$,
  (18) $-C_{1-6}$ alkyl-O$-C_{1-6}$ alkyl-$R^K$,
  (19) $-C_{1-6}$ alkyl-S(O)$_n$$-R^K$,
  (20) $-C_{1-6}$ alkyl-S(O)$_n$$-C_{1-6}$ alkyl-$R^K$,
  (21) $-C_{1-6}$ alkyl-N(R^a)$-R^K$,
  (22) $-C_{1-6}$ alkyl-N(R^a)$-C_{1-6}$ alkyl-$R^K$,
  (23) $-C_{1-6}$ alkyl-N(R^a)$-C_{1-6}$ alkyl-OR$^K$, with the proviso that the $-N(R^a)-$ moiety and the $-OR^K$ moiety are not both attached to the same carbon of the $-C_{1-6}$ alkyl- moiety,
  (24) $-C_{1-6}$ alkyl-C(=O)$-R^K$,
  (25) $-C_{1-6}$ alkyl-C(=O)N(R^a)$-R^K$,
  (26) $-C_{1-6}$ alkyl-N(R^a)C(=O)$-R^K$,
  (27) $-C_{1-6}$ alkyl-C(=O)N(R^a)$-C_{1-6}$ alkyl-$R^K$,
  (28) $-C_{1-6}$ alkyl-N(R^a)$-S(O)_nR^K$,
  (29) $-C_{1-6}$ alkyl-N(R^a)$-C_{1-6}$ alkyl-S(O)$_n$$R^K$,
  (30) halogen,
  (31) $-C(=O)N(R^d)R^e$,
  (32) $-C(=O)N(R^a)OR^b$,
  (33) $-CN$,
  (34) $-N(R^a)C(=O)R^b$,
  (35) $-N(R^a)CO_2R^c$,
  (36) $-N(R^a)SO_2R^c$,
  (37) $-N(R^a)C(=O)C(=O)N(R^a)R^b$,
  (38) $-N(R^a)C(=O)C(=O)N(R^d)R^e$,
  (39) $-N(R^a)C(=O)N(R^a)R^b$,
  (40) $-N=C(R^a)N(R^a)R^b$,
  (41) $-N=C[N(R^a)R^b]-N-(R^a)R^b$,
  (42) $-SR^c$,
  (43) $-S(O)R^c$,
  (44) $-SO_2R^c$, or
  (45) $-SO_2N(R^a)R^b$;

wherein $R^K$ is
  (i) aryl, which is optionally substituted with from 1 to 5 substituents each of which is independently $-C_{1-6}$ alkyl, $-C_{1-6}$ alkyl-OH, $-C_{1-6}$ alkyl-O$-C_{1-6}$ alkyl, $-C_{1-6}$ alkyl-O$-C_{1-6}$ haloalkyl, $-C_{1-6}$ alkyl-N(R^a)R^b$, $-C_{1-6}$ alkyl-C(=O)N(R^a)R^b$, $-C_{1-6}$ alkyl-C(=O)R^a$, $-C_{1-6}$ alkyl-CO_2R^c$, $-C_{1-6}$ alkyl-S(O)$_n$R^c$, $-O-C_{1-6}$ alkyl, $-C_{1-6}$ haloalkyl, $-O-C_{1-6}$ haloalkyl, $-OH$, halo, $-CN$, $-NO_2$, $-N(R^a)R^b$, $-C(=O)N(R^a)R^b$, $-C(=O)R^a$, $-CO_2R^c$, $-S(O)$_n$R^c$, or $-SO_2N(R^a)R^b$;

(ii) a 4- to 7-membered saturated or mono-unsaturated heterocyclic ring containing at least one carbon atom and from 1 to 4 heteroatoms independently selected from N, O and S, wherein the heterocyclic ring is:
  (a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
  (b) optionally mono-substituted with aryl or HetA;
    wherein HetA is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl; or
(iii) a 5- or 6-membered heteroaromatic ring containing from 1 to 4 heteroatoms independently selected from N, O and S, wherein the heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl;

$R^4$ is:
 (1) —H,
 (2) —$C_{1-6}$ alkyl,
 (3) —$C_{1-6}$ alkyl substituted with OH, $SR^c$, $S(O)R^c$, $SO_2R^c$, or —$N(R^a)SO_2R^c$,
 (4) —$C_{1-6}$ alkyl substituted with —$C_{3-8}$ cycloalkyl,
 (5) —$C_{1-6}$ alkyl substituted with aryl, wherein the aryl is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl,
 (6) —$CO_2R^c$,
 (7) —$C(=O)N(R^a)R^b$,
 (8) —$C(=O)N(R^d)R^e$, or
 (9) aryl which is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl;

$R^5$ is:
 (1) —H,
 (2) —$C_{1-6}$ alkyl, or
 (3) —$C_{1-6}$ alkyl substituted with —$C(=O)N(R^a)R^b$ or —$C(=O)N(R^d)R^e$;

$R^6$ is —H, —$C_{1-6}$ alkyl, $R^L$, or —$C_{1-6}$ alkyl-$R^L$, wherein $R^L$ is:
(A) aryl which is optionally substituted with from 1 to 5 substituents each of which is independently
 (1) —$C_{1-6}$ alkyl, optionally substituted with from 1 to 3 substituents each of which is independently —OH, —O—$C_{1-6}$ alkyl, —O—$C_{1-6}$ haloalkyl, —CN, —$NO_2$, —$N(R^a)R^b$, —$C(=O)N(R^a)R^b$, —$C(=O)R^a$, —$CO_2R^c$, —$S(O)_nR^c$, —$SO_2N(R^a)R^b$, —$N(R^a)C(=O)R^b$, —$N(R^a)CO_2R^c$, —$N(R^a)SO_2R^c$, —$N(R^a)SO_2N(R^a)R^b$, —$OC(=O)N(R^a)R^b$, or —$N(R^a)C(=O)N(R^a)R^b$,
 (2) —O—$C_{1-6}$ alkyl, optionally substituted with from 1 to 3 substituents each of which is independently —OH, —O—$C_{1-6}$ alkyl, —O—$C_{1-6}$ haloalkyl, —$S(O)_nR^c$, —$C(=O)N(R^a)R^b$, —$SO_2N(R^a)R^b$, —$N(R^a)C(=O)R^b$, —$N(R^a)CO_2R^c$, —$N(R^a)SO_2R^c$, —$N(R^a)SO_2N(R^a)R^b$, —$OC(=O)N(R^a)R^b$, or —$N(R^a)C(=O)N(R^a)R^b$,
 (3) —$C_{1-6}$ haloalkyl,
 (4) —O—$C_{1-6}$ haloalkyl,
 (5) —OH,
 (6) halo,
 (7) —CN,
 (8) —$NO_2$,
 (9) —$N(R^a)R^b$,
 (10) —$C(=O)N(R^a)R^b$,
 (11) —$C(=O)R^a$,
 (12) —$CO_2R^c$,
 (13) —$SR^c$,
 (14) —$S(=O)R^c$,
 (15) —$SO_2R^c$,
 (16) —$N(R^a)SO_2R^c$,
 (17) —$SO_2N(R^a)R^b$,
 (18) —$N(R^a)C(=O)R^b$,
 (19) —$N(R^a)CO_2R^c$,
 (20) phenyl, or
 (21) benzyl,
(B) a 5- or 6-membered heteroaromatic ring containing from 1 to 4 heteroatoms independently selected from N, O and S; wherein the heteroaromatic ring is
 (i) optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl; and
 (ii) optionally substituted with 1 or 2 substituents each of which is independently aryl or —$C_{1-6}$ alkyl-aryl, or
(C) a —$C_{3-8}$ cycloalkyl which is optionally substituted with 1 to 3 substituents each of which is independently a —$C_{1-6}$ alkyl group;

$R^7$ is —H or —$C_{1-6}$ alkyl; or alternatively $R^5$ and $R^7$ together form oxo (=O) or thioxo (=S), or $R^5$ and $R^7$ together with the ring carbon atom to which they are both attached form —$C_{3-8}$ cycloalkyl;

$R^8$ is —H or —$C_{1-6}$ alkyl; or alternatively $R^4$ and $R^8$ together with the ring carbon atom to which they are both attached form —$C_{3-8}$ cycloalkyl;

or alternatively $R^7$ and $R^8$ are absent, and $R^4$ and $R^5$ together with the ring carbon atoms to which each is attached and with bond "b" form:
 (i) a benzene ring or a 6-membered heteroaromatic ring containing 1 or 2 nitrogen atoms, wherein the fused ring is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl, or
 (ii) a $C_{3-6}$ cycloalkane ring;

each $R^a$ and $R^b$ is independently —H or —$C_{1-6}$ alkyl;

each $R^c$ is independently a —$C_{1-6}$ alkyl;

each $R^d$ and $R^e$ together with the N atom to which they are both attached form a 4- to 7-membered saturated heterocyclic ring optionally containing a heteroatom in addition to the nitrogen attached to $R^d$ and $R^e$ selected from N, O, and S, where the S is optionally oxidized to S(O) or $S(O)_2$, and wherein the saturated heterocyclic ring is optionally substituted with 1 or 2 $C_{1-6}$ alkyl groups; and each n is independently an integer equal to 0, 1 or 2.

A first embodiment of the present invention includes compounds of Formula II and pharmaceutically acceptable salts thereof:

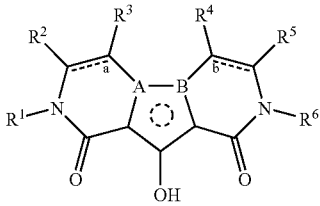

(II)

wherein
A, B, ⋯○⋯$R^1$, $R^2$, $R^a$, $R^b$, $R^c$ and n are as originally defined above in Formula I;
bond "a" in the ring is a single bond or a double bond;
bond "b" in the ring is a single bond or a double bond;
$R^3$ is:
(1) —H,
(2) —$C_{1-6}$ alkyl optionally substituted with one of —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^c$, —S(O)$_n R^c$, —$SO_2$N($R^a$)$R^b$, —N($R^a$)—C($R^b$)=O, —N($R^a$)$SO_2R^c$, —N($R^a$)$SO_2$N($R^a$)$R^b$, —OC(=O)N($R^a$)$R^b$, —N($R^a$)C(=O)N($R^a$)$R^b$, —O—$C_{1-6}$ alkyl-C(=O)N($R^a$)$R^b$, —S—$C_{1-6}$ alkyl-C(=O)N($R^a$)$R^b$, —N($R^a$)—$C_{1-6}$ alkyl-C(=O)N($R^a$)$R^b$, —N($SO_2R^c$)—$C_{1-6}$ alkyl-C(=O)N($R^a$)$R^b$, or —N($R^a$)—$OR^b$;
(3) —$C_{1-6}$ haloalkyl,
(4) —C(=O)$R^a$,
(5) —$CO_2R^c$,
(6) —C(=O)N($R^a$)$R^b$,
(7) —$SO_2$N($R^a$)$R^b$,
(8) —$C_{2-6}$ alkenyl,
(9) —$C_{2-6}$ alkenyl-C(=O)—N($R^a$)$R^b$,
(10) —$C_{2-5}$ alkynyl,
(11) —$C_{2-5}$ alkynyl-$CH_2$N($R^a$)$R^b$,
(12) —$C_{2-5}$ alkynyl-$CH_2OR^a$,
(13) —$C_{2-5}$ alkynyl-$CH_2$S(O)$_n R^c$,
(14) —$R^K$,
(15) —$C_{1-6}$ alkyl substituted with $R^K$,
(16) —$C_{1-6}$ haloalkyl substituted with $R^K$,
(17) —$C_{1-6}$ alkyl-O—$R^K$,
(18) —$C_{1-6}$ alkyl-O—$C_{1-6}$ alkyl-$R^K$,
(19) —$C_{1-6}$ alkyl-S(O)$_n$—$R^K$,
(20) —$C_{1-6}$ alkyl-S(O)$_n$—$C_{1-6}$ alkyl-$R^K$,
(21) —$C_{1-6}$ alkyl-N($R^a$)—$R^K$,
(22) —$C_{1-6}$ alkyl-N($R^a$)—$C_{1-6}$ alkyl-$R^K$,
(23) —$C_{1-6}$ alkyl-N($R^a$)—$C_{1-6}$ alkyl-$OR^K$, with the proviso that the —N($R^a$)— moiety and the —$OR^K$ moiety are not both attached to the same carbon of the —$C_{1-6}$ alkyl- moiety,
(24) —$C_{1-6}$ alkyl-C(=O)—$R^K$,
(25) —$C_{1-6}$ alkyl-C(=O)N($R^a$)—$R^K$,
(26) —$C_{1-6}$ alkyl-N($R^a$)C(=O)—$R^K$,
(27) —$C_{1-6}$ alkyl-C(=O)N($R^a$)—$C_{1-6}$ alkyl-$R^K$,
(28) —$C_{1-6}$ alkyl-N($R^a$)—S(O)$_n R^K$, or
(29) —$C_{1-6}$ alkyl-N($R^a$)—$C_{1-6}$ alkyl-S(O)$_n R^K$;
wherein $R^K$ is
(i) aryl, which is optionally substituted with from 1 to 5 substituents each of which is independently —$C_{1-6}$ alkyl, —$C_{1-6}$ alkyl-OH, —$C_{1-6}$ alkyl-O—$C_{1-6}$ alkyl, —$C_{1-6}$ alkyl-O—$C_{1-6}$ haloalkyl, —$C_{1-6}$ alkyl-N($R^a$)$R^b$, —$C_{1-6}$ alkyl-C(=O)N($R^a$)$R^b$, —$C_{1-6}$ alkyl-C(=O)$R^a$, —$C_{1-6}$ alkyl-$CO_2R^c$, —$C_{1-6}$ alkyl-S(O)$_n R^c$, —O—$C_{1-6}$ alkyl, —$C_{1-6}$ haloalkyl, —O—$C_{1-6}$ haloalkyl, —OH, halo, —CN, —$NO_2$, —N($R^a$)$R^b$, —C(=O)N($R^a$)$R^b$, —C(=O)$R^a$, —$CO_2R^c$, —S(O)$_n R^c$, or —$SO_2$N($R^a$)$R^b$;

(ii) a 4- to 7-membered saturated or mono-unsaturated heterocyclic ring containing at least one carbon atom and from 1 to 4 heteroatoms independently selected from N, O and S, wherein the heterocyclic ring is:
(a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
(b) optionally mono-substituted with aryl or HetA;
wherein HetA is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl; or (iii) a 5- or 6-membered heteroaromatic ring containing from 1 to 4 heteroatoms independently selected from N, O and S, wherein the heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl;

$R^4$ is —H or —$C_{1-6}$ alkyl;
$R^5$ is —H or —$C_{1-6}$ alkyl;
$R^6$ is —H, —$C_{1-6}$ alkyl, or —$C_{1-6}$ alkyl-$R^L$, wherein $R^L$ is:
(A) aryl which is optionally substituted with from 1 to 5 substituents each of which is independently
(1) —$C_{1-6}$ alkyl, optionally substituted with from 1 to 3 substituents each of which is independently —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^c$, —S(O)$_n R^c$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, or —N($R^a$)C(=O)N($R^a$)$R^b$,
(2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_n R^c$, —C(=O)N($R^a$)$R^b$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, or —N($R^a$)C(=O)N($R^a$)$R^b$,
(3) —$C_{1-6}$ haloalkyl,
(4) —O—$C_{1-6}$ haloalkyl,
(5) —OH,
(6) halo,
(7) —CN,
(8) —$NO_2$,
(9) —N($R^a$)$R^b$,
(10) —C(=O)N($R^a$)$R^b$,
(11) —C(=O)$R^a$,
(12) —$CO_2R^c$,
(13) —$SR^c$,
(14) —S(=O)$R^c$,
(15) —$SO_2R^c$,
(16) —N($R^a$)$SO_2R^c$,
(17) —$SO_2$N($R^a$)$R^b$,
(18) —N($R^a$)C(=O)$R^b$,

(19) —N(R$^a$)CO$_2$R$^c$,
(20) phenyl, or
(21) benzyl, or (B) a 5- or 6-membered heteroaromatic ring containing from 1 to 4 heteroatoms independently selected from N, O and S; wherein the heteroaromatic ring is
   (i) optionally substituted with from 1 to 4 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl; and
   (ii) optionally substituted with 1 or 2 substituents each of which is independently aryl or —C$_{1-6}$ alkyl-aryl.

The present invention also includes pharmaceutical compositions containing a compound of Formula I or Formula II and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the hydroxy-substituted pyridopyrrolopyrazine diones of Formula I above, which includes as a subset the compounds embraced by Formula II above. These compounds and pharmaceutically acceptable salts thereof are HIV integrase inhibitors. A second embodiment of the present invention is a compound of Formula I, or a pharmaceutically acceptable salt thereof, wherein R$^1$ is —C$_{1-4}$ alkyl-R$^J$, wherein R$^J$ is phenyl which is optionally substituted with from 1 to 3 substituents each of which is independently:

(1) —C$_{1-4}$ alkyl, optionally mono-substituted with —OH, —O—C$_{1-4}$ alkyl, —O—C$_{1-4}$ haloalkyl, —CN, —N(R$^a$)R$^b$, —C(=O)N(R$^a$)R$^b$, —C(=O)R$^a$, —CO$_2$R$^c$, —S(O)$_n$R$^c$, or —SO$_2$N(R$^a$)R$^b$,
(2) —O—C$_{1-4}$ alkyl,
(3) —C$_{1-4}$ haloalkyl,
(4) —O—C$_{1-4}$ haloalkyl,
(5) —OH,
(6) halo,
(7) —CN,
(8) —NO$_2$,
(9) —N(R$^a$)R$^b$,
(10) —SR$^c$,
(11) —S(=O)R$^c$,
(12) —SO$_2$R$^c$,
(13) —N(R$^a$)SO$_2$R$^c$,
(14) —SO$_2$N(R$^a$)R$^b$,
(15) —N(R$^a$)C(=O)R$^b$,
(16) —N(R$^a$)CO$_2$R$^c$, or
(17) phenyl;

and all other variables are as originally defined above (i.e., as defined in Formula I).

A third embodiment of the present invention is a compound of Formula II, or a pharmaceutically acceptable salt thereof, wherein R$^1$ is as defined in the second embodiment, and all other variables are as defined in the first embodiment.

A fourth embodiment of the present invention is a compound of Formula I, or a pharmaceutically acceptable salt thereof, wherein R$^1$ is —(CH$_2$)$_{1-3}$-phenyl, wherein the phenyl is optionally substituted with from 1 to 3 substituents each of which is independently (1) —C$_{1-4}$ alkyl, optionally mono-substituted with —OH, —O—C$_{1-4}$ alkyl, —O—C$_{1-4}$ haloalkyl, —CN, —N(R$^a$)R$^b$, —C(=O)N(R$^a$)R$^b$, —C(=O)R$^a$, —CO$_2$R$^c$, —S(O)$_n$R$^c$, or —SO$_2$N(R$^a$)R$^b$,
(2) —O—C$_{1-4}$ alkyl,
(3) —C$_{1-4}$ haloalkyl,
(4) —O—C$_{1-4}$ haloalkyl,
(5) —OH,
(6) halo,
(7) —CN,
(8) —NO$_2$,
(9) —N(R$^a$)R$^b$,
(10) —SR$^c$,
(11) —S(=O)R$^c$,
(12) —SO$_2$R$^c$,
(13) —N(R$^a$)SO$_2$R$^c$,
(14) —SO$_2$N(R$^a$)R$^b$,
(15) —N(R$^a$)C(=O)R$^b$,
(16) —N(R$^a$)CO$_2$R$^c$, or
(17) phenyl;

and all other variables are as originally defined above.

A fifth embodiment of the present invention is a compound of Formula II, or a pharmaceutically acceptable salt thereof, wherein R$^1$ is as defined in the fourth embodiment, and all other variables are as defined in the first embodiment.

A sixth embodiment of the present invention is a compound of Formula I, or a pharmaceutically acceptable salt thereof, wherein R$^1$ is —(CH$_2$)$_{1-3}$-phenyl, wherein the phenyl is optionally substituted with from 1 to 3 substituents each of which is independently methyl, ethyl, methoxy, ethoxy, trifluoromethyl, trifluoromethoxy, fluoro, bromo, chloro, CN, SCH$_3$, S(O)CH$_3$, SO$_2$CH$_3$, N(H)SO$_2$CH$_3$, N(CH$_3$)SO$_2$CH$_3$, SO$_2$N(CH$_3$)$_2$, SO$_2$NH$_2$, SO$_2$NH(CH$_3$), N(CH$_3$)C(=O)CH$_3$, N(H)C(=O)CH$_3$, N(CH$_3$)CO$_2$CH$_3$, or N(H)CO$_2$CH$_3$; and all other variables are as originally defined above.

A seventh embodiment of the present invention is a compound of Formula II, or a pharmaceutically acceptable salt thereof, wherein R$^1$ is as defined in the sixth embodiment, and all other variables are as defined in the first embodiment.

An eighth embodiment of the present invention is a compound of Formula I, or a pharmaceutically acceptable salt thereof, wherein R$^1$ is —CH$_2$-phenyl, wherein the phenyl is substituted with 1 or 2 substituents each of which is independently methyl, methoxy, fluoro, bromo, or chloro; and all other variables are as originally defined above.

A ninth embodiment of the present invention is a compound of Formula II, or a pharmaceutically acceptable salt thereof, wherein R$^1$ is as defined in the eighth embodiment, and all other variables are as defined in the first embodiment.

A tenth embodiment of the present invention is a compound of Formula I, or a pharmaceutically acceptable salt thereof, wherein R$^1$ is:

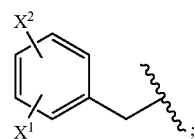

wherein X$^1$ and X$^2$ are each independently
(1) —H,
(2) methyl,
(3) ethyl,
(4) methoxy, (5) ethoxy,
(6) —CF$_3$,
(7) fluoro,
(8) bromo,
(9) chloro,
(10) —CN,
(11) —S—CH$_3$, or
(12) phenyl;

and all other variables are as originally defined.

An eleventh embodiment of the present invention is a compound of Formula II, or a pharmaceutically acceptable salt thereof, wherein R$^1$ is as defined in the tenth embodiment, and all other variables are as defined in the first embodiment.

A twelfth embodiment of the present invention is a compound of Formula I, or a pharmaceutically acceptable salt thereof, wherein R$^1$ is 4-fluorobenzyl or 3-chloro-4-fluorobenzyl; and all other variables are as originally defined.

A thirteenth embodiment of the present invention is a compound of Formula II, or a pharmaceutically acceptable salt thereof, wherein R$^1$ is as defined in the twelfth embodiment, and all other variables are as defined in the first embodiment.

A fourteenth embodiment of the present invention is a compound of Formula I, or a pharmaceutically acceptable salt thereof, wherein R$^1$ is 4-fluorobenzyl; and all other variables are as originally defined.

A fifteenth embodiment of the present invention is a compound of Formula II, or a pharmaceutically acceptable salt thereof, wherein R$^1$ is as defined in the fourteenth embodiment; and all other variables are as defined in the first embodiment.

A sixteenth embodiment of the present invention is a compound of Formula I, or a pharmaceutically acceptable salt thereof, wherein R$^2$ is:
(1) —H
(2) —C$_{1-4}$ alkyl, or
(3) —C$_{1-4}$ alkyl substituted with one of —CN, —N(R$^a$)R$^b$, —C(=O)N(R$^a$)R$^b$, —C(=O)R$^a$, —CO$_2$R$^c$, —S(O)$_n$R$^c$, —SO$_2$N(R$^a$)R$^b$, —N(R$^a$)C(=O)R$^b$, —N(R$^a$)CO$_2$R$^c$, —N(R$^a$)SO$_2$R$^c$, —N(R$^a$)SO$_2$N(R$^a$)R$^b$, or —N(R$^a$)C(=O)N(R$^a$)R$^b$;

and all other variables are as originally defined or as defined in any one of the preceding embodiments of a compound of Formula I.

A seventeenth embodiment of the present invention is a compound of Formula II, or a pharmaceutically acceptable salt thereof, wherein R$^2$ is as defined in the sixteenth embodiment; and all other variables are as defined in the first embodiment or in any one of the other preceding embodiments of a compound of Formula II.

An eighteenth embodiment of the present invention is a compound of Formula I, or a pharmaceutically acceptable salt thereof, wherein R$^2$ is —H or —C$_{1-4}$ alkyl; and all other variables are as originally defined or as defined in any one of the preceding embodiments of a compound of Formula I. In an aspect of this embodiment, R$^2$ is —H or —C$_{1-3}$ alkyl. In another aspect of this embodiment, R$^2$ is —H.

A nineteenth embodiment of the present invention is a compound of Formula II, or a pharmaceutically acceptable salt thereof, wherein R$^2$ is —H or —C$_{1-4}$ alkyl; and all other variables are as defined in the first embodiment or as defined in any one of the other preceding embodiments of a compound of Formula II. In an aspect of this embodiment, R$^2$ is —H or —C$_{1-3}$ alkyl. In another aspect of this embodiment, R$^2$ is —H.

A twentieth embodiment of the present invention is a compound of Formula I, or a pharmaceutically acceptable salt thereof, wherein R$^3$ is:
(1) —H,
(2) —C$_{1-4}$ alkyl optionally substituted with one of —OH, —O—C$_{1-4}$ alkyl, —O—C$_{1-4}$ haloalkyl, —CN, —N(R$^a$)R$^b$, —C(=O)N(R$^a$)R$^b$, —C(=O)R$^a$, —CO$_2$R$^c$, —S(O)$_n$R$^c$, —SO$_2$N(R$^a$)R$^b$, —N(R$^a$)—C(R$^b$)=O, —N(R$^a$)SO$_2$R$^c$, —N(R$^a$)SO$_2$N(R$^a$)R$^b$, or —N(R$^a$)—OR$^b$,
(3) —CO$_2$R$^c$,
(4) —C(=O)N(R$^a$)R$^b$,
(5) —R$^K$,
(6) —C$_{1-4}$ alkyl substituted with R$^K$,
(7) —C$_{1-4}$ alkyl-O—R$^K$,
(8) —C$_{1-4}$ alkyl-O—C$_{1-4}$ alkyl-R$^K$,
(9) halogen,
(10) —C(=O)N(R$^d$)R$^e$,
(11) —C(=O)N(R$^a$)OR$^b$,
(12) —CN,
(13) —N(R$^a$)C(=O)R$^b$,
(14) —N(R$^a$)CO$_2$R$^c$,
(15) —N(R$^a$)SO$_2$R$^c$,
(16) —N(R$^a$)C(=O)C(=O)N(R$^a$)R$^b$,
(17) —N(R$^a$)C(=O)C(=O)N(R$^d$)R$^e$,
(18) —N(R$^a$)C(=O)N(R$^a$)R$^b$,
(19) —SR$^c$,
(20) —S(O)R$^c$, or
(21) —SO$_2$R$^c$;

and all other variables are as originally defined or as defined in any one of the preceding embodiments of a compound of Formula I.

A twenty-first embodiment of the present invention is a compound of Formula I, or a pharmaceutically acceptable salt thereof, wherein R$^3$ is:
(1) —H,
(2) —C$_{1-4}$ alkyl optionally substituted with one of —OH, —O—C$_{1-4}$ alkyl, —O—C$_{1-4}$ haloalkyl, —CN, —N(R$^a$)R$^b$, —C(=O)N(R$^a$)R$^b$, —C(=O)R$^a$, —CO$_2$R$^c$, —S(O)$_n$R$^c$, —SO$_2$N(R$^a$)R$^b$, —N(R$^a$)—C(R$^b$)=O, —N(R$^a$)SO$_2$R$^c$, —N(R$^a$)SO$_2$N(R$^a$)R$^b$, or —N(R$^a$)—OR$^b$,
(3) —C(=O)N(R$^a$)R$^b$,
(4) —R$^K$,
(5) —C$_{1-4}$ alkyl substituted with R$^K$,
(6) —C$_{1-4}$ alkyl-O—R$^K$, or
(7) —C$_{1-4}$ alkyl-O—C$_{1-4}$ alkyl-R$^K$;

and all other variables are as originally defined or as defined in any one of the preceding embodiments of a compound of Formula I.

A twenty-second embodiment of the present invention is a compound of Formula II, or a pharmaceutically acceptable salt thereof, wherein R$^3$ is as defined in the twenty-first embodiment; and all other variables are as defined in the first embodiment or as defined in any one of the other preceding embodiments of a compound of Formula II.

A twenty-third embodiment of the present invention is a compound of Formula I, or a pharmaceutically acceptable salt thereof, wherein R$^K$ in the definition of R$^3$ is:
(i) phenyl, which is optionally substituted with from 1 to 3 substituents each of which is independently —C$_{1-4}$ alkyl, —C$_{1-4}$ alkyl-OH, —C$_{1-4}$ alkyl-O—C$_{1-4}$ alkyl, —C$_{1-4}$ alkyl-O—C$_{1-4}$ haloalkyl, —C$_{1-4}$ alkyl-N(R$^a$)R$^b$, —C$_{1-4}$ alkyl-C(=O)N(R$^a$)R$^b$, —C$_{1-4}$ alkyl-C(=O)R$^a$, —C$_{1-4}$ alkyl-CO$_2$R$^c$, —C$_{1-4}$ alkyl-S(O)$_n$R$^c$, —O—C$_{1-4}$ alkyl, —C$_{1-4}$ haloalkyl, —O—C$_{1-4}$ haloalkyl, —OH, halo, —N(R$^a$)R$^b$, —C(=O)N(R$^a$)R$^b$, —C(=O)R$^a$, —CO$_2$R$^c$, —S(O)$_n$R$^c$, or —SO$_2$N(R$^a$)R$^b$;

(ii) a 4- to 7-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is:

(a) optionally substituted with from 1 to 4 substituents each of which is independently halogen, —C$_{1-4}$ alkyl, —C$_{1-4}$ haloalkyl, —O—C$_{1-4}$ alkyl, —O—C$_{1-4}$ haloalkyl, or oxo; and (b) optionally mono-substituted with phenyl or HetA; wherein HetA is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —OH, —C$_{1-4}$ alkyl, —C$_{1-4}$ haloalkyl, —O—C$_{1-4}$ alkyl, or —O—C$_{1-4}$ haloalkyl; or (iii) a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —OH, —C$_{1-6}$ alkyl, —C$_{1-6}$ haloalkyl, or —O—C$_{1-6}$ alkyl, —O—C$_{1-6}$ haloalkyl (or, alternatively, —OH, —C$_{1-4}$ alkyl, —C$_{1-4}$ haloalkyl, or —O—C$_{1-4}$ alkyl, —O—C$_{1-4}$ haloalkyl);

and all other variables are as originally defined or as defined in any one of the preceding embodiments of a compound of Formula I.

A twenty-fourth embodiment of the present invention is a compound of Formula II, or a pharmaceutically acceptable salt thereof, wherein R$^K$ in the definition of R$^3$ is as defined in the twenty-third embodiment; and all other variables are as defined in the first embodiment or as defined in any one of the other preceding embodiments of a compound of Formula II.

In an aspect of each of the twenty-third and twenty-fourth embodiments, the saturated heterocyclic ring in (ii) is selected from the group consisting of piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, and dioxanyl;

the HetA substituent is selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl; and the heteroaromatic ring in (iii) is selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl.

A twenty-fifth embodiment of the present invention is a compound of Formula I, or a pharmaceutically acceptable salt thereof, wherein R$^3$ is (1) —H, (2) —C$_{1-3}$ alkyl, (3) —CH$_2$CH$_2$OH, (4) —C(CH$_3$)$_2$OH, (5) —CO$_2$CH$_3$, (6) —C(=O)NH$_2$, (7) —C(=O)NH(CH$_3$), (8) —C(=O)N(CH$_3$)$_2$, (9) phenyl which is optionally substituted with from 1 to 3 substituents each of which is independently methyl, ethyl, methoxy, ethoxy, trifluoromethyl, trifluoromethoxy, fluoro, bromo, chloro, SCH$_3$, S(O)CH$_3$, SO$_2$CH$_3$, SO$_2$N(CH$_3$)$_2$, SO$_2$NH$_2$, or SO$_2$NH(CH$_3$), (10) a 5- or 6-membered heteroaromatic ring selected from the group consisting of oxazolyl, oxadiazolyl, thiazolyl, thiadiazolyl, imidazolyl, pyrrolyl, triazolyl, pyridinyl, pyrimidinyl, pyrazinyl, and pyridazinyl, wherein the heteroaromatic ring is optionally substituted with 1 or 2 substituents each of which is independently methyl or ethyl,

(11) 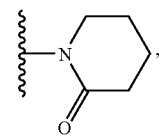

(12) 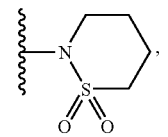

(13) 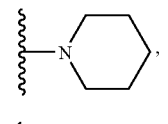

(14) 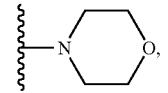

(15) 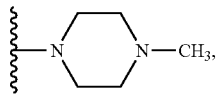

(16) 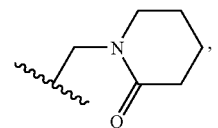

(17) 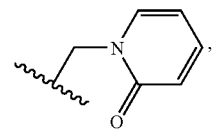

(18) 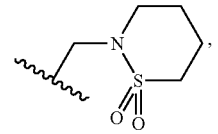

(19) 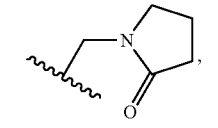

(20) 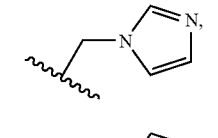

(21) 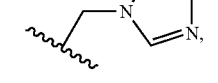

(22) chloro, (23) bromo, (24) fluoro,

(25) 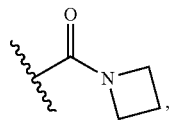

(26) 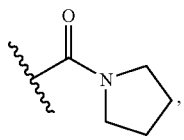

(27) 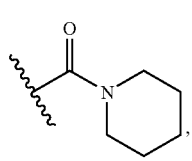

(28) 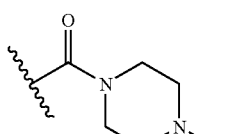

(29) 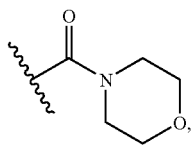

(30) 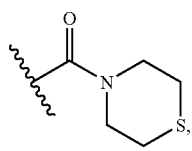

(31) —C(=O)N(CH$_3$)OCH$_3$, (32) CN, (33) —N(H)C(=O)CH$_3$, (34) —N(CH$_3$)C(=O)CH$_3$, (35) —N(H)CO$_2$CH$_3$, (36) —N(CH$_3$)CO$_2$CH$_3$, (37) —N(CH$_3$)CO$_2$CH$_2$CH$_3$, (38) —N(H)SO$_2$CH$_3$, (39) —N(CH$_3$)SO$_2$CH$_3$, (40) —N(H)C(=O)C(=O)N(CH$_3$)$_2$, (41) —N(CH$_3$)C(=O)C(=O)N(CH$_3$)$_2$,

(42) 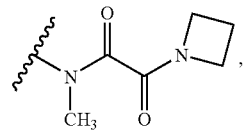

(43) 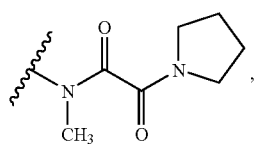

(44) 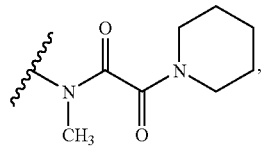

(45) 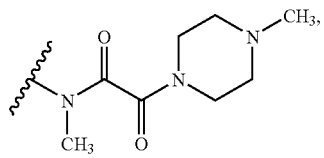

(46) 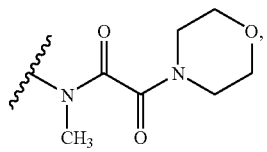

(47) 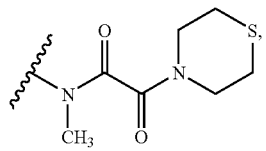

(48) —SCH$_3$, (49) —S(O)CH$_3$, or (50) —SO$_2$CH$_3$; and all other variables are as originally defined or as defined in any one of the preceding embodiments of a compound of Formula I.

A twenty-sixth embodiment of the present invention is a compound of Formula I, or a pharmaceutically acceptable salt thereof, wherein R$^3$ is —H, methyl, ethyl, isopropyl, n-propyl, —CO$_2$CH$_3$, —C(=O)NH$_2$, —C(=O)NH(CH$_3$), —C(=O)N(CH$_3$)$_2$, phenyl, oxadiazolyl (optionally substituted with methyl), chloro, bromo,

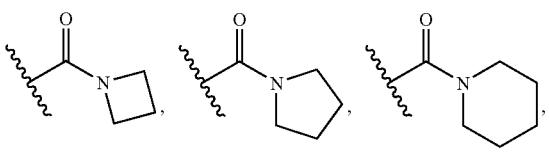

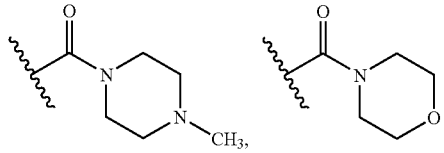

—C(=O)N(CH$_3$)OCH$_3$, CN, —N(CH$_3$)C(=O)CH$_3$, —N(CH$_3$)CO$_2$CH$_3$, —N(CH$_3$)CO$_2$CH$_2$CH$_3$, —N(CH$_3$)SO$_2$CH$_3$, —N(CH$_3$)C(=O)C(=O)N(CH$_3$)$_2$, —SCH$_3$, —S(O)CH$_3$, or —SO$_2$CH$_3$; and all other variables are as originally defined or as defined in any one of the preceding embodiments of a compound of Formula I.

A twenty-seventh embodiment of the present invention is a compound of Formula I, or a pharmaceutically acceptable salt thereof, wherein $R^3$ is —H or —$C_{1-4}$ alkyl; and all other variables are as originally defined or as defined in any one of the preceding embodiments of a compound of Formula I. In an aspect of this embodiment, $R^3$ is —H or —$C_{1-3}$ alkyl. In an aspect of this embodiment, $R^3$ is —H.

A twenty-eighth embodiment of the present invention is a compound of Formula II, or a pharmaceutically acceptable salt thereof, wherein $R^3$ is —H or —$C_{1-4}$ alkyl; and all other variables are as defined in the first embodiment or as defined in any one of the preceding embodiments of a compound of Formula II. In an aspect of this embodiment, $R^3$ is —H or —$C_{1-3}$ alkyl. In an aspect of this embodiment, $R^3$ is —H.

A twenty-ninth embodiment of the present invention is a compound of Formula I, or a pharmaceutically acceptable salt thereof, wherein $R^2$ is —H and $R^3$ is —H or —$C_{1-3}$ alkyl; and all other variables are as originally defined or as defined in any one of the preceding embodiments of a compound of Formula I. In an aspect of this embodiment, bond "a" in the ring is a single bond.

A thirtieth embodiment of the present invention is a compound of Formula I, or a pharmaceutically acceptable salt thereof, wherein $R^2$ and $R^3$ are both —H; and all other variables are as originally defined or as defined in any one of the preceding embodiments of a compound of Formula I. In an aspect of this embodiment, bond "a" in the ring is a single bond.

A thirty-first embodiment of the present invention is a compound of Formula II, or a pharmaceutically acceptable salt thereof, wherein $R^2$ and $R^3$ are both —H; and all other variables are as defined in the first embodiment or as defined in any one of the other preceding embodiments of a compound of Formula II. In an aspect of this embodiment, bond "a" in the ring is a single bond.

A thirty-second embodiment of the present invention is a compound of Formula I, or a pharmaceutically acceptable salt thereof, wherein $R^6$ is —H, —$C_{1-4}$ alkyl, $R^L$, or —$C_{1-4}$ alkyl-$R^L$, wherein $R^L$ is:

(A) phenyl which is optionally substituted with from 1 to 3 substituents each of which is independently:
  (1) —$C_{1-4}$ alkyl, optionally mono-substituted with —OH, O—$C_{1-4}$ alkyl, —O—$C_{1-4}$ haloalkyl, —CN, —N($R^a$)$R^b$, —C(=O)N($R^a$)$R^b$, —C(=O)$R^a$, —CO$_2R^c$, —S(O)$_nR^c$, or —SO$_2$N($R^a$)$R^b$,
  (2) —O—$C_{1-4}$ alkyl,
  (3) —$C_{1-4}$ haloalkyl,
  (4) —O—$C_{1-4}$ haloalkyl,
  (5) —OH,
  (6) halo,
  (7) —CN,
  (8) —NO$_2$,
  (9) —N($R^a$)$R^b$,
  (10) —S$R^c$,
  (11) —S(=O)$R^c$,
  (12) —SO$_2R^c$,
  (13) —N($R^a$)SO$_2R^c$,
  (14) —SO$_2$N($R^a$)$R^b$,
  (15) —N($R^a$)C(=O)$R^b$,
  (16) —N($R^a$)CO$_2R^c$, or
  (17) phenyl,
(B) a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —OH, —$C_{1-4}$ alkyl, —$C_{1-4}$ haloalkyl, or —O—$C_{1-4}$ alkyl, —O—$C_{1-4}$ haloalkyl, or (C) a —$C_{3-7}$ cycloalkyl which is optionally substituted with 1 to 3 substituents each of which is independently a —$C_{1-4}$ alkyl group;

and all other variables are as originally defined or as defined in any one of the preceding embodiments of a compound of Formula I.

A thirty-third embodiment of the present invention is a compound of Formula I, or a pharmaceutically acceptable salt thereof, wherein $R^6$ is:
(1) —H,
(2) —$C_{1-3}$ alkyl,
(3) phenyl which is optionally substituted with from 1 to 3 substituents each of which is independently methyl, ethyl, methoxy, ethoxy, trifluoromethyl, trifluoromethoxy, fluoro, bromo, chloro, CN, SCH$_3$, S(O)CH$_3$, SO$_2$CH$_3$, N(H)SO$_2$CH$_3$, N(CH$_3$)SO$_2$CH$_3$, SO$_2$N(CH$_3$)$_2$, SO$_2$NH$_2$, SO$_2$NH(CH$_3$), N(CH$_3$)C(=O)CH$_3$, N(H)C(=O)CH$_3$, N(CH$_3$)CO$_2$CH$_3$, or N(H)CO$_2$CH$_3$,
(4) a 5- or 6-membered heteroaromatic ring selected from the group consisting of oxazolyl, oxadiazolyl, thiazolyl, thiadiazolyl, imidazolyl, pyrrolyl, triazolyl, pyridinyl, pyrimidinyl, pyrazinyl, and pyridazinyl, wherein the heteroaromatic ring is optionally substituted with 1 or 2 substituents each of which is independently methyl or ethyl,
(5) —$C_{3-5}$ cycloalkyl,
(6) —(CH$_2$)$_{1-3}$-phenyl, wherein the phenyl is optionally substituted with from 1 to 3 substituents each of which is independently methyl, ethyl, methoxy, ethoxy, trifluoromethyl, trifluoromethoxy, fluoro, bromo, chloro, CN, SCH$_3$, S(O)CH$_3$, SO$_2$CH$_3$, N(H)SO$_2$CH$_3$, N(CH$_3$)SO$_2$CH$_3$, SO$_2$N(CH$_3$)$_2$, SO$_2$NH$_2$, SO$_2$NH(CH$_3$), N(CH$_3$)C(=O)CH$_3$, N(H)C(=O)CH$_3$, N(CH$_3$)CO$_2$CH$_3$, or N(H)CO$_2$CH$_3$,
(7) —(CH$_2$)$_{1-3}$-HetC, wherein HetC is a 5- or 6-membered heteroaromatic ring selected from the group consisting of oxazolyl, oxadiazolyl, thiazolyl, thiadiazolyl, imidazolyl, pyrrolyl, triazolyl, pyridinyl, pyrimidinyl, pyrazinyl, and pyridazinyl, wherein the heteroaromatic ring is optionally substituted with 1 or 2 substituents each of which is independently methyl or ethyl, or
(8) —(CH$_2$)$_{1-3}$—$C_{3-5}$ cycloalkyl;

and all other variables are as originally defined or as defined in any one of the preceding embodiments of a compound of Formula I.

A thirty-fourth embodiment of the present invention is a compound of Formula I, or a pharmaceutically acceptable salt thereof, wherein $R^6$ is (1) —H, (2) methyl, (3) ethyl, (4) phenyl, (5) pyridinyl, (6) cyclopropyl, (7) —CH$_2$-phenyl or —CH$_2$CH$_2$-phenyl, wherein the phenyl is optionally substituted with 1 or 2 substituents each of which is independently methyl, ethyl, methoxy, ethoxy, trifluoromethyl, trifluoromethoxy, fluoro, bromo, or chloro, (8) —CH$_2$-pyridinyl, or (9) —CH$_2$-cyclopropyl; and all other variables are as originally defined or as defined in any one of the preceding embodiments of a compound of Formula I.

A thirty-fifth embodiment of the present invention is a compound of Formula I, or a pharmaceutically acceptable salt thereof, wherein $R^6$ is —H, —$C_{1-4}$ alkyl, or —(CH$_2$)$_{1-3}$-phenyl, wherein the phenyl is optionally substituted with from 1 to 3 substituents each of which is independently
(1) —$C_{1-4}$ alkyl, optionally mono-substituted with —OH, —O—$C_{1-4}$ alkyl, —O—$C_{1-4}$ haloalkyl, —CN, —N($R^a$)$R^b$, —C(=O)N($R^a$)$R^b$, —C(=O)$R^a$, —CO$_2R^c$, —S(O)$_nR^c$, or —SO$_2$N($R^a$)$R^b$, (2) —O—$C_{1-4}$ alkyl,
(3) —$C_{1-4}$ haloalkyl,
(4) —O—$C_{1-4}$ haloalkyl,
(5) —OH,
(6) halo,
(7) —CN,
(8) —$NO_2$,
(9) —$N(R^a)R^b$,
(10) —$SR^c$,
(11) —S(=O)$R^c$,
(12) —$SO_2R^c$,
(13) —$N(R^a)SO_2R^c$,
(14) —$SO_2N(R^a)R^b$,
(15) —$N(R^a)C(=O)R^b$,
(16) —$N(R^a)CO_2R^c$, or
(17) phenyl;

and all other variables are as originally defined or as defined in any one of the preceding embodiments of a compound of Formula I.

A thirty-sixth embodiment of the present invention is a compound of Formula II, or a pharmaceutically acceptable salt thereof, wherein $R^6$ is as defined in the thirty-fifth embodiment; and all other variables are as defined in the first embodiment or as defined in any one of the other preceding embodiments of a compound of Formula II. In an aspect of this embodiment, the compound is as defined in the thirty-sixth embodiment, with the proviso that when $R^6$ is —($CH_2$)$_{1-3}$-phenyl wherein the phenyl is optionally substituted in the manner described, then A is N and B is C.

A thirty-seventh embodiment of the present invention is a compound of Formula I, or a pharmaceutically acceptable salt thereof, wherein $R^6$ is —H, —$C_{1-4}$ alkyl, or

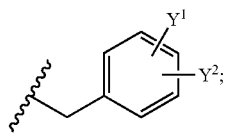

wherein $Y^1$ and $Y^2$ are each independently
(1) —H,
(2) methyl,
(3) ethyl,
(4) methoxy,
(5) ethoxy,
(6) —$CF_3$,
(7) fluoro,
(8) bromo,
(9) chloro,
(10) —CN,
(11) —S—$CH_3$, or
(12) phenyl;

and all other variables are as originally defined or as defined in any one of the preceding embodiments of a compound of Formula I.

A thirty-eighth embodiment of the present invention is a compound of Formula II, or a pharmaceutically acceptable salt thereof, wherein $R^6$ is as defined in the thirty-seventh embodiment; and all other variables are as defined in the first embodiment or as defined in any one of the other preceding embodiments of a compound of Formula II. In an aspect of this embodiment, the compound is as defined in the thirty-eighth embodiment, with the proviso that when $R^6$ is the defined benzyl group, then A is N and B is C.

A thirty-ninth embodiment of the present invention is a compound of Formula II, or a pharmaceutically acceptable salt thereof, wherein $R_6$ is —H, —$C_{1-4}$ alkyl, or 4-fluorobenzyl; and all other variables are as defined in the first embodiment, or as defined in any one of the other preceding embodiments of a compound of Formula II. In an aspect of this embodiment, the compound is as defined in the thirty-ninth embodiment, with the proviso that when $R^6$ is 4-fluorobenzyl, then A is N and B is C.

A fortieth embodiment of the present invention is a compound of Formula I, or a pharmaceutically acceptable salt thereof, wherein $R^6$ is —H or —$C_{1-6}$ alkyl; and all other variables are as originally defined or as defined in any one of the preceding embodiments of a compound of Formula I. In an aspect of this embodiment, $R^6$ is —H or —$C_{1-4}$ alkyl.

A forty-first embodiment of the present invention is a compound of Formula II, or a pharmaceutically acceptable salt thereof, wherein $R^6$ is —H or —$C_{1-6}$ alkyl; and all other variables are as defined in the first embodiment or as defined in any one of the preceding embodiments of a compound of Formula II. In an aspect of this embodiment, $R^6$ is —H or —$C_{1-4}$ alkyl.

A forty-second embodiment of the present invention is a compound of Formula I, or a pharmaceutically acceptable salt thereof, wherein:
$R^4$ is:
(1) —H,
(2) —$C_{1-4}$ alkyl,
(3) —$C_{1-4}$ alkyl substituted with OH, $SR^c$, S(O)$R^c$, $SO_2R^c$, or —$N(R^a)SO_2R^c$,
(4) —$C_{1-4}$ alkyl substituted with —$C_{3-7}$ cycloalkyl,
(5) —$C_{1-4}$ alkyl substituted with phenyl, wherein the phenyl is optionally substituted with from 1 to 3 substituents each of which is independently halogen, —OH, —$C_{1-4}$ alkyl, —$C_{1-4}$ haloalkyl, —O—$C_{1-4}$ alkyl, or —O—$C_{1-4}$ haloalkyl,
(6) —$CO_2R^c$,
(7) —C(=O)$N(R^a)R^b$,
(8) —C(=O)$N(R^d)R^e$, or
(9) phenyl which is optionally substituted with from 1 to 3 substituents each of which is independently halogen, —OH, —$C_{1-4}$ alkyl, —$C_{1-4}$ haloalkyl, —O—$C_{1-4}$ alkyl, or —O—$C_{1-4}$ haloalkyl;
$R^5$ is:
(1) —H,
(2) —$C_{1-4}$ alkyl, or
(3) —$C_{1-4}$ alkyl substituted with —C(=O)$N(R^a)R^b$ or —C(=O)$N(R^d)R^e$;
$R^7$ is —H or —$C_{1-4}$ alkyl; or alternatively $R^5$ and $R^7$ together form oxo (=O), or $R^5$ and $R^7$ together with the ring carbon atom to which they are both attached form —$C_{3-7}$ cycloalkyl;
$R^8$ is —H or —$C_{1-4}$ alkyl; or alternatively $R^4$ and $R^8$ together with the ring carbon atom to which they are both attached form —$C_{3-7}$ cycloalkyl;
or alternatively $R^7$ and $R^8$ are absent, and $R^4$ and $R^5$ together with the ring carbon atoms to which each is attached and with bond "b" form:
  (i) a benzene or pyridine ring which is optionally substituted with from 1 to 3 substituents each of which is independently halogen, —OH, —$C_{1-4}$ alkyl, —$C_{1-4}$ haloalkyl, —O—$C_{1-4}$ alkyl, or —O—$C_{1-4}$ haloalkyl, or
  (ii) a $C_{3-6}$ cycloalkane ring;

and all other variables are as originally defined or as defined in any one of the preceding embodiments of a compound of Formula I.

The ring formed by $R^4$ and $R^5$ together the ring carbons to which each is attached and with bond "b" is fused to the tricyclic core of the compound of Formula I, and the one or more optional substituents on the ring are attached to one or more non-fused ring atoms.

A forty-third embodiment of the present invention is a compound of Formula I, or a pharmaceutically acceptable salt thereof, wherein:

$R^4$ is: (1) —H, (2) —$C_{1-3}$ alkyl, (3) —$(CH_2)_{2-3}OH$, (4) —$CH_2$—$SCH_3$, (5) —$CH_2$—$SO_2CH_3$, (6) —$CH_2$—$N(H)SO_2CH_3$, (7) —$CH_2$—$N(CH_3)SO_2CH_3$, (8) —$(CH_2)_{1-3}$—$C_{3-5}$ cycloalkyl, (9) —$(CH_2)_{1-3}$-phenyl, wherein the phenyl is optionally substituted with from 1 to 3 substituents each of which is independently chloro, bromo, fluoro, methyl, ethyl, trifluoromethyl, methoxy, ethoxy, or trifluoromethoxy, (10) —$CO_2CH_3$, (11) —$C(=O)NH_2$, (12) —$C(=O)NH(CH_3)$, (13) —$C(=O)N(CH_3)_2$,

(14) 

(15) 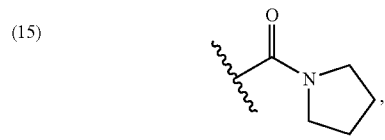

(16) 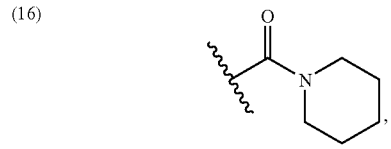

(17) 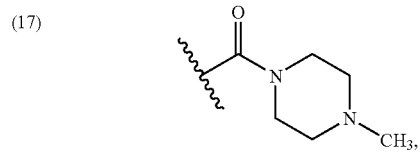

(18) 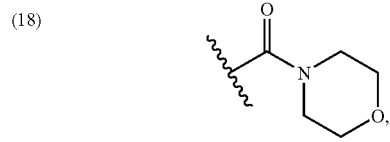

(19) 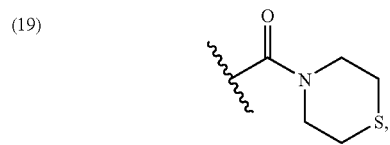

or (20) phenyl which is optionally substituted with from 1 to 3 substituents each of which is independently chloro, bromo, fluoro, methyl, ethyl, trifluoromethyl, methoxy, ethoxy, or trifluoromethoxy;

$R^5$ is: (1) —H, (2) —$C_{1-3}$ alkyl, (3) —$(CH_2)_{1-2}$—$C(=O)NH_2$, (4) —$(CH_2)_{1-2}$—$C(=O)NH(CH_3)$, (5) —$(CH_2)_{1-2}$—$C(=O)N(CH_3)_2$,

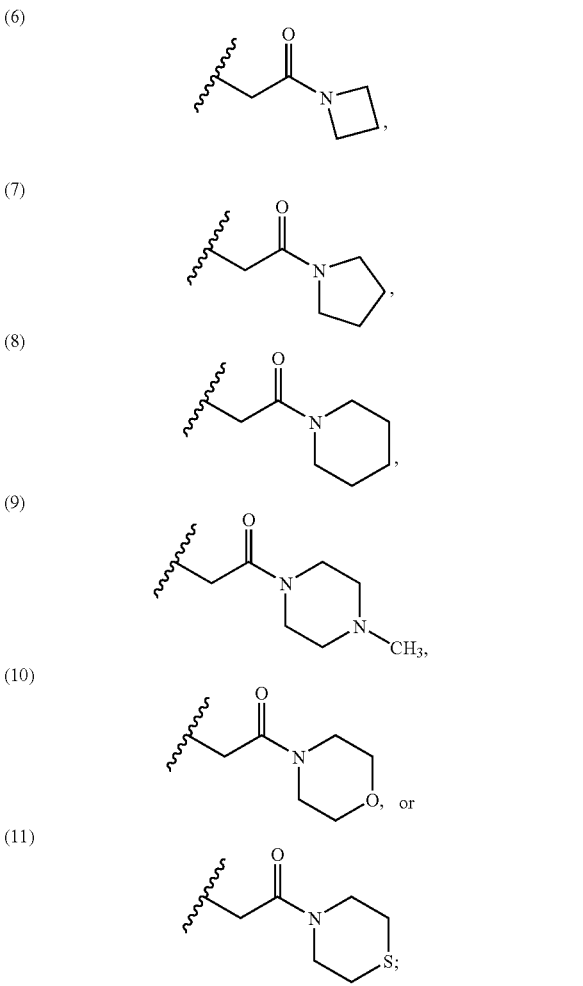

$R^7$ is —H or methyl; or alternatively $R^5$ and $R^7$ together form oxo (=O), or $R^5$ and $R^7$ together with the ring carbon atom to which they are both attached form —$C_{3-5}$ cycloalkyl;

$R^8$ is —H or methyl; or alternatively $R^4$ and $R^8$ together with the ring carbon atom to which they are both attached form —$C_{3-5}$ cycloalkyl; and or alternatively $R^7$ and $R^8$ are absent, and $R^4$ and $R^5$ together with the ring carbon atoms to which each is attached and with bond "b" form:

(i) a benzene or pyridine ring which is optionally substituted with from 1 to 3 substituents each of which is independently chloro, bromo, fluoro, methyl, ethyl, trifluoromethyl, methoxy, ethoxy, or trifluoromethoxy, or (ii) a cycloalkane ring which is cyclopropane, cyclopentane, or cyclohexane;

and all other variables are as originally defined or as defined in any one of the preceding embodiments of a compound of Formula I.

A forty-fourth embodiment of the present invention is a compound of Formula I, or a pharmaceutically acceptable salt thereof, wherein $R^4$ is —H or —$C_{1-3}$ alkyl; $R^5$ is —H or —$C_{1-3}$ alkyl; $R^7$ and $R^8$ are both —H when bond "b" is a single bond and both absent when bond "b" is a double bond; and all other variables are as originally defined or as defined in any one of the preceding embodiments of a compound of Formula I. In an aspect of this embodiment, bond "b" in the ring is a single bond.

A forty-fifth embodiment of the present invention is a compound of Formula I, or a pharmaceutically acceptable salt thereof, wherein one of $R^4$ and $R^5$ is —H; the other of $R^4$ and $R^5$ is —H or —$C_{1-3}$ alkyl; $R^7$ and $R^8$ are both —H when bond "b" is a single bond and both absent when bond "b" is a double bond; and all other variables are as originally defined or as defined in any one of the preceding embodiments of a compound of Formula I. In an aspect of this embodiment, bond "b" in the ring is a single bond. In another aspect of this embodiment, $R^4$ and $R^5$ are both —H.

A forty-sixth embodiment of the present invention is a compound of Formula II, or a pharmaceutically acceptable salt thereof, wherein $R^4$ and $R^5$ are both —H; and all other variables are as defined in the first embodiment or as defined in any one of the other preceding embodiments of a compound of Formula II. In an aspect of this embodiment, bond "b" in the ring is a single bond.

A forty-seventh embodiment of the present invention is a compound of Formula II, or a pharmaceutically acceptable salt thereof, wherein $R^2$, $R^3$, $R^4$ and $R^5$ are all —H; and all other variables are as defined in the first embodiment or as defined in any one of the other preceding embodiments of a compound of Formula II. In an aspect of this embodiment, bond "a" and bond "b" are both single bonds.

A forty-eighth embodiment of the present invention is a compound of Formula II, or a pharmaceutically acceptable salt thereof, wherein all of the variables are as defined in the first embodiment, with the proviso that when $R^2$, $R^3$, $R^4$ and $R^5$ are all the same (i.e., they are either all —H or all the same —$C_{1-6}$ alkyl group, such as all being methyl) and $R^6$ is —$C_{1-6}$ alkyl-$R^L$, then A is N and B is C.

A forty-ninth embodiment of the present invention is a compound of Formula IA, or a pharmaceutically acceptable salt thereof:

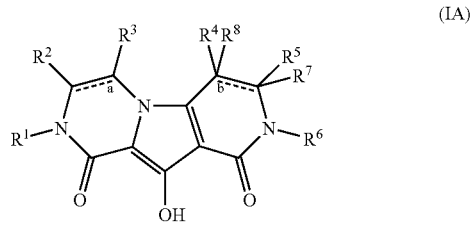

(IA)

wherein each of the variables set forth in Formula IA is as originally defined or as defined in any one of the preceding embodiments of a compound of Formula I.

A fiftieth embodiment of the present invention is a compound of Formula IB, or a pharmaceutically acceptable salt thereof:

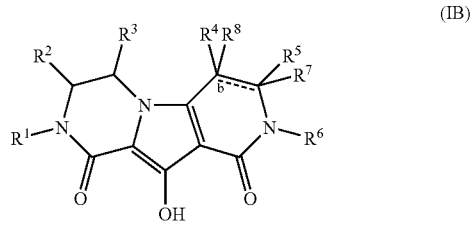

(IB)

wherein bond "b" in the ring is a single bond or a double bond, with the proviso that (i) when "b" is a single bond, $R^7$ and $R^8$ are both —H, and (ii) when "b" is a double bond, $R^7$ and $R^8$ are both absent;

$R^4$ is:
(1) —H,
(2) —$C_{1-6}$ alkyl,
(3) —$C_{1-6}$ alkyl substituted with OH, $SR^c$, $S(O)R^c$, $SO_2R^c$, or —$N(R^a)SO_2R^c$,
(4) —$C_{1-6}$ alkyl substituted with —$C_{3-8}$ cycloalkyl,
(5) —$C_{1-6}$ alkyl substituted with aryl, wherein the aryl is optionally substituted with from 1 to 3 substituents each of which is independently halogen, —OH, —$C_{1-6}$ alkyl, —$C_{1-6}$ haloalkyl, —O—$C_{1-6}$ alkyl or —O—$C_{1-6}$ haloalkyl,
(6) —$CO_2R^c$,
(7) —$C(=O)N(R^a)R^b$,
(8) —$C(=O)N(R^d)R^e$, or
(9) aryl which is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl; and $R^5$ is:
(1) —H,
(2) —$C_{1-6}$ alkyl, or
(3) —$C_{1-6}$ alkyl substituted with —$C(=O)N(R^a)R^b$ or —$C(=O)N(R^d)R^e$;

and all other variables are as originally defined. Aspects of this embodiment include those in which the compound of Formula IB is as just defined, wherein the definition of one or more of the variables $R^1$, $R^2$, $R^3$, $R^4$, $R^5$, and $R^6$ is replaced with the definition from any one of the preceding embodiments of a compound of Formula I.

A fifty-first embodiment of the present invention is a compound of Formula IC, or a pharmaceutically acceptable salt thereof:

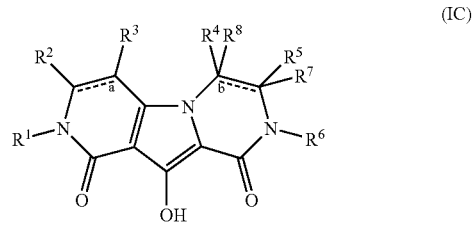

(IC)

wherein each of the variables set forth in Formula IC is as originally defined or as defined in any one of the preceding embodiments of a compound of Formula I.

A fifty-second embodiment of the present invention is a compound of Formula ID, or a pharmaceutically acceptable salt thereof:

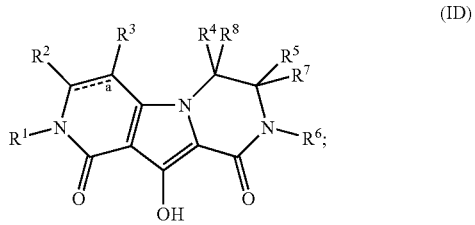

(ID)

wherein each of the variables set forth in Formula ID is as originally defined above or as defined in any of the preceding embodiments of a compound of Formula I.

A fifty-third embodiment of the present invention is a compound of Formula IIA, or a pharmaceutically acceptable salt thereof:

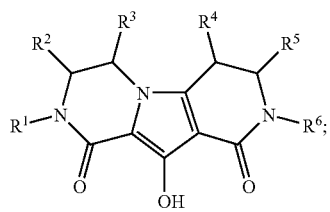

(IIA)

wherein each of the variables $R^1$, $R^2$, $R^3$, $R^4$, $R^5$, and $R^6$ is as originally defined above or as defined in any one of the preceding embodiments of a compound of Formula II.

A fifty-fourth embodiment of the present invention is a compound of Formula IIB, or a pharmaceutically acceptable salt thereof:

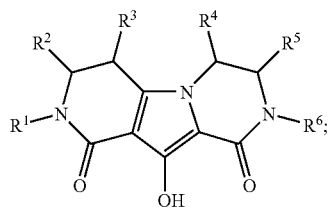

(IIB)

wherein each of the variables $R^1$, $R^2$, $R^3$, $R^4$, $R^5$, and $R^6$ is as originally defined above or as defined in any one of the preceding embodiments of a compound of Formula II.

A fifty-fifth embodiment of the present invention is a compound of Formula I, wherein each $R^a$ and $R^b$ is independently —H or —$C_{1-4}$ alkyl; each $R^c$ is independently a —$C_{1-4}$ alkyl; and all other variables are as originally defined or as defined in any one of the foregoing embodiments of a compound of Formula I.

A fifty-sixth embodiment of the present invention is a compound of Formula II, wherein each $R^a$ and $R^b$ is independently —H or —$C_{1-4}$ alkyl; each $R^c$ is independently a —$C_{1-4}$ alkyl; and all other variables are as defined in the first embodiment or as defined in any one of the other preceding embodiments of a compound of Formula II.

A fifty-seventh embodiment of the present invention is a compound of Formula I, wherein each $R^a$ and $R^b$ is independently —H, methyl or ethyl; each $R^c$ is independently methyl or ethyl; and all other variables are as originally defined or as defined in any one of the foregoing embodiments of a compound of Formula I.

A fifty-eighth embodiment of the present invention is a compound of Formula II, wherein each $R^a$ and $R^b$ is independently —H, methyl or ethyl; each $R^c$ is independently methyl or ethyl; and all other variables are as defined in the first embodiment or as defined in any one of the other preceding embodiments of a compound of Formula II.

In an aspect of each of the fifty-seventh and fifty-eighth embodiments, each $R^a$ and $R^b$ is independently —H or methyl, and each $R^c$ is methyl.

A fifty-ninth embodiment of the present invention is a compound of Formula I, wherein each $R^d$ and $R^e$ together with the N atom to which they are both attached form a 4- to 6-membered saturated heterocyclic ring optionally containing a heteroatom in addition to the nitrogen attached to $R^d$ and $R^e$ selected from N, O, and S, where the S is optionally oxidized to S(O) or S(O)$_2$, and wherein the saturated heterocyclic ring is optionally substituted with a $C_{1-4}$ alkyl group; and all other variables are as originally defined or as defined in any one of the foregoing embodiments of a compound of Formula I.

A sixtieth embodiment of the present invention is a compound of Formula I, wherein each $R^d$ and $R^e$ together with the N atom to which they are both attached form a saturated heterocyclyl selected from the group consisting of 1-azetidinyl, 1-pyrrolidinyl, 1-piperidinyl, 4-methyl-1-piperazinyl, 4-morpholinyl, and 4-thiomorpholinyl; and all other variables are as originally defined or as defined in any one of the foregoing embodiments of a compound of Formula I.

A first class of the present invention includes compounds of Formula I, and pharmaceutically acceptable salts thereof, wherein $R^1$ is as defined in the second embodiment; $R^2$ is as defined in the sixteenth embodiment; $R^3$ is as defined in the twentieth embodiment; $R^K$ is as defined in the twenty-third embodiment; $R^4$, $R^5$, $R^7$ and $R^8$ are each as defined in the forty-second embodiment; $R^6$ is as defined in the thirty-second embodiment; each $R^a$ and $R^b$ are as defined in the fifty-sixth embodiment; each $R^d$ and $R^e$ are as defined in the fifty-ninth embodiment; and all other variables are as originally defined.

A second class of the present invention includes compounds of Formula I, and pharmaceutically acceptable salts thereof, wherein $R^1$ is as defined in the fourth embodiment; $R^2$ is —H or —$C_{1-3}$ alkyl; $R^3$ is as defined in the twenty-fifth embodiment; $R^4$, $R^5$, $R^7$ and $R^8$ are each as defined in the forty-third embodiment; and $R^6$ is as defined in the thirty-third embodiment; and all other variables are as originally defined.

A third class of the present invention includes compounds of Formula I, and pharmaceutically acceptable salts thereof, wherein $R^1$ is —CH$_2$-phenyl, wherein the phenyl is substituted with 1 or 2 substituents each of which is independently methyl, methoxy, fluoro, bromo, or chloro;

$R^2$ is —H;

$R^3$ is —H, methyl, ethyl, isopropyl, n-propyl, —CO$_2$CH$_3$, —C(=O)NH$_2$, —C(=O)NH(CH$_3$), —C(=O)N(CH$_3$)$_2$, phenyl, oxadiazolyl (optionally substituted with methyl), chloro, bromo,

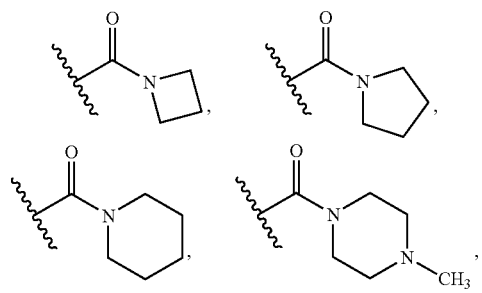

-continued

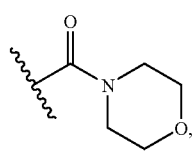

—C(=O)N(CH$_3$)OCH$_3$, CN, —N(CH$_3$)C(=O)CH$_3$, —N(CH$_3$)CO$_2$CH$_3$, —N(CH$_3$)CO$_2$CH$_2$CH$_3$, —N(CH$_3$)SO$_2$CH$_3$, —N(CH$_3$)C(=O)C(=O)N(CH$_3$)$_2$, —SCH$_3$, —S(O)CH$_3$, or —SO$_2$CH$_3$;

R$^4$ is —H, methyl, ethyl, isopropyl, n-propyl, —(CH$_2$)$_2$OH, —CH$_2$-cyclopropyl, CH$_2$-phenyl, —CO$_2$CH$_3$, —C(=O)NH$_2$, —C(=O)NH(CH$_3$), —C(=O)N(CH$_3$)$_2$,

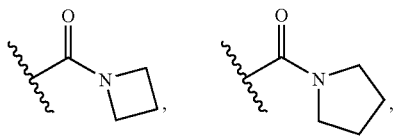

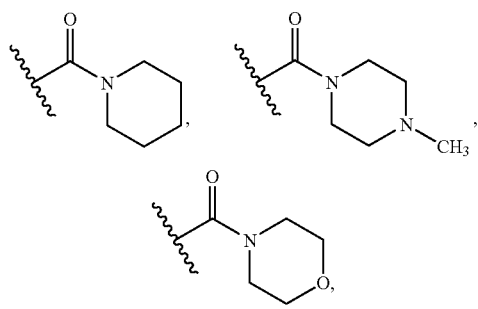

or phenyl;

R$^5$ is —H, methyl, —CH$_2$—C(=O)NH(CH$_3$), or —CH$_2$—C(=O)N(CH$_3$)$_2$;

R$^6$ is (1) —H, (2) methyl, (3) ethyl, (4) phenyl, (5) pyridinyl, (6) cyclopropyl, (7) —CH$_2$-phenyl or —CH$_2$CH$_2$-phenyl, wherein the phenyl is optionally substituted with 1 or 2 substituents each of which is independently methyl, ethyl, methoxy, ethoxy, trifluoromethyl, trifluoromethoxy, fluoro, bromo, or chloro, (8) —CH$_2$-pyridinyl, or (9) —CH$_2$-cyclopropyl;

R$^7$ is —H or methyl; or alternatively R$^5$ and R$^7$ together form oxo (=O), or R$^5$ and R$^7$ together with the ring carbon atom to which they are both attached form cyclopropyl;

R$^8$ is —H or methyl; or alternatively R$^4$ and R$^8$ together with the ring carbon atom to which they are both attached form cyclopropyl or cyclopentyl; and or alternatively R$^7$ and R$^8$ are absent, and R$^4$ and R$^5$ together with the ring carbon atoms to which each is attached and with bond "b" form a benzene ring which is optionally substituted with 1 or 2 substituents each of which is independently chloro, bromo, fluoro, methyl, ethyl, trifluoromethyl, methoxy, ethoxy, or trifluoromethoxy; and all other variables are as originally defined.

A fourth class of the present invention includes compounds of Formula III, and pharmaceutically acceptable salts thereof:

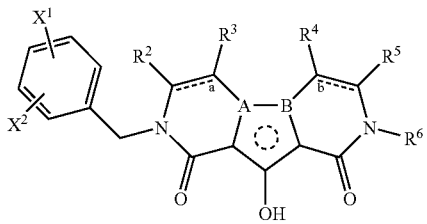

(III)

wherein bond "a" in the ring is a single bond or a double bond;

bond "b" in the ring is a single bond or a double bond;

one of A and B is N, and the other of A and B is C;

⋯⃝⋯ denotes that the central 5-membered ring is pyrrolyl;

X$^1$ and X$^2$ are each independently
(1) —H,
(2) methyl,
(3) ethyl,
(4) methoxy,
(5) ethoxy,
(6) —CF$_3$,
(7) fluoro,
(8) bromo,
(9) chloro,
(10) —CN,
(11) —S—CH$_3$, or
(12) phenyl; and R$^2$ is —H, methyl, or (CH$_2$)$_{1-2}$C(=O)N(CH$_3$)$_2$;

R$^3$ is —H, methyl, or (CH$_2$)$_{1-2}$N(CH$_3$)—OCH$_3$;

R$^4$ and R$^5$ are each independently —H or methyl;

R$^6$ is —H, —C$_{1-4}$ alkyl, or

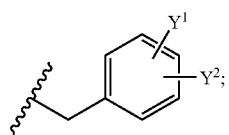

wherein Y$^1$ and Y$^2$ are each independently
(1) —H,
(2) methyl,
(3) ethyl,
(4) methoxy,
(5) ethoxy,
(6) —CF$_3$,
(7) fluoro,
(8) bromo,
(9) chloro,
(10) —CN,
(11) —S—CH$_3$, or
(12) phenyl.

A feature of this class are the compounds of Formula III and pharmaceutically acceptable salts thereof, with the proviso that when $R^2$, $R^3$, $R^4$, and $R^5$ are all the same and $R^6$ is a benzyl group as defined in the fourth class, then A is N and B is C.

A sub-class of the fourth class includes compounds of Formula IIIA, and pharmaceutically acceptable salts thereof:

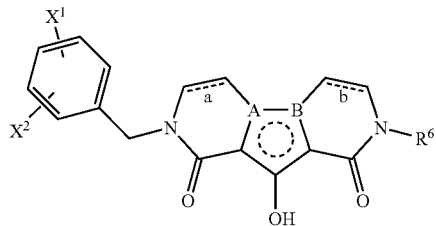

(IIIA)

wherein bond "a", bond "b", A, B, "··○··", $X^1$, $X^2$, and $R^6$ are each as defined above in Formula III. In a feature of this sub-class, when $R^6$ is the benzyl group as defined in Formula III, then A is N and B is C.

Another sub-class of the fourth class includes compounds of Formula IIIB, and pharmaceutically acceptable salts thereof:

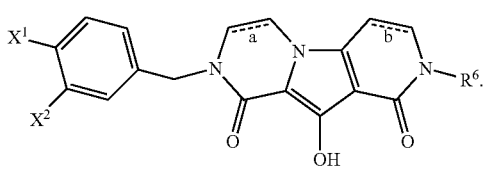

(IIIB)

Another sub-class of the fourth class includes compounds of Formula IIIC, and pharmaceutically acceptable salts thereof:

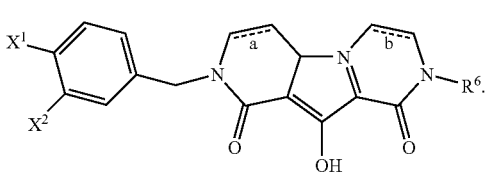

(IIIC)

A sixty-first embodiment of the present invention is a compound, or a pharmaceutically acceptable salt thereof, selected from the group consisting of:

8-(3-chloro-4-fluorobenzyl)-10-hydroxy-2-methyl-3,4,7,8-tetrahydropyrido-[3',4':4,5]pyrrolo[1,2-a]pyrazine-1,9 (2H,6H)-dione;

2-(4-fluorobenzyl)-10-hydroxy-3,4,7,8-tetrahydropyrido-[3',4':4,5]pyrrolo[1,2-a]pyrazine-1,9(2H,6H)-dione;

8-(4-fluorobenzyl)-10-hydroxy-2,4-dimethyl-7,8-dihydro-pyrido-[3',4':4,5]pyrrolo[1,2-a]pyrazine-1,9(2H,6H)-dione;

8-(4-fluorobenzyl)-10-hydroxy-6-{2-[methoxy(methyl) amino]ethyl}-2-methyl-3,4,7,8-tetrahydropyrido-[3',4':4, 5]pyrrolo[1,2-a]pyrazine-1,9(2H,6H)-dione;

8-(3,4-dichlorobenzyl)-10-hydroxy-2-methyl-3,4,7,8-tetrahydropyrido-[3',4':4,5]pyrrolo-[1,2-a]pyrazine-1,9(2H, 6H)-dione;

8-(3-chlorobenzyl)-10-hydroxy-2-methyl-3,4,7,8-tetrahydropyrido-[3',4':4,5]pyrrolo[1,2-a]pyrazine-1,9(2H,6H)-dione;

8-(4-fluorobenzyl)-10-hydroxy-2-methyl-3,4,7,8-tetrahydropyrido-[3',4':4,5]pyrrolo[1,2-a]pyrazine-1,9(2H,6H)-dione;

8-(3,4-difluorobenzyl)-10-hydroxy-2-methyl-3,4,7,8-tetrahydropyrido-[3',4':4,5]pyrrolo-[1,2-a]pyrazine-1,9(2H, 6H)-dione;

2,8-bis(4-fluorobenzyl)-10-hydroxy-3,4,7,8-tetrahydropyrido-[3',4':4,5]pyrrolo[1,2-a]pyrazine-1,9(2H,6H)-dione;

2-(3,4-dimethoxybenzyl)-8-(4-fluorobenzyl)-10-hydroxy-3, 4,7,8-tetrahydropyrido-[3',4':4,5]pyrrolo[2-a]pyrazine-1, 9(2H,6H)-dione;

8-(4-fluorobenzyl)-10-hydroxy-3,4,7,8-tetrahydropyrido-[3',4':4,5]pyrrolo[1,2-a]pyrazine-1,9(2H,6H)-dione;

8-(4-fluorobenzyl)-10-hydroxy-2-ethyl-3,4,7,8-tetrahydropyrido-[3',4':4,5]pyrrolo[1,2-a]pyrazine-1,9(2H,6H)-dione;

2-(4-fluorobenzyl)-10-hydroxy-8-methyl-3,4,7,8-tetrahydropyrido-[3',4':4,5]pyrrolo[1,2-a]pyrazine-1,9(2H,6H)-dione;

8-(4-fluorobenzyl)-2-hydroxy-2-methyl-7,8-tetrahydropyrido-[3',4':4,5]pyrrolo[1,2-a]pyrazine-1,9(2H,6H)-dione; and 8-(4-fluorobenzyl)-10-hydroxy-7-(2-dimethylamino-2-oxo-ethyl)-2-methyl-3,4,7,8-tetrahydropyrido-[3',4':4,5]pyrrolo[1,2-a]pyrazine-1,9(2H,6H)-dione.

A sixty-second embodiment of the present invention is a compound, or a pharmaceutically acceptable salt thereof, selected from the group consisting of the compounds set forth in Examples 16 to 106 below; 2-(3-chloro-4-fluorobenzyl)-10-hydroxy-4-bromo-8-methyl-7,8-dihydropyrido-[3',4':4, 5]pyrrolo[1,2-a]pyrazine-1,9(2H,6H)-dione; 2-(3-chloro-4-fluorobenzyl)-10-hydroxy-4-methylthio-8-methyl-7,8-dihydropyrido-[3',4':4,5]pyrrolo[1,2-a]pyrazine-1,9(2H, 6H)-dione; and 2-(3-chloro-4-fluorobenzyl)-10-hydroxy-4-methylsulfonyl-8-methyl-7,8-dihydropyrido-[3',4':4,5] pyrrolo[1,2-a]pyrazine-1,9(2H,6H)-dione. In an aspect of this embodiment, the compound, or a pharmaceutically acceptable salt thereof, is selected from the group consisting of the compounds set forth in Examples 16 to 106.

It is to be understood that additional embodiments of the present invention include, but are not limited to, compounds of any of Formulas I, IA, IB, IC and ID, wherein each of two or three or more of the variables contained therein (e.g., $R^1$, $R^2$, $R^3$, $R^4$, $R^5$, $R^6$, $R^7$ and $R^8$) is independently defined in accordance with its definition in any one of the embodiments of a compound of Formula I or aspects thereof as set forth above. Any and all possible combinations of these variables in each of Formulas I, IA, IB, IC and ID are additional embodiments within the scope of the present invention, except of course for combinations that would not result in a stable compound.

It is similarly understood that additional embodiments of the present invention include, but are not limited to, compounds of any of Formulas II, IIA, and IIB, wherein each of two or three or more of the variables contained therein (e.g., $R^1$, $R^2$, $R^3$, $R^4$, $R^5$ and $R^6$) is independently defined in accordance with its definition in any one of the embodiments of a compound of Formula II or aspects thereof as set forth above, or in accordance with its definition in any one of the foregoing classes of compounds of Formula I set forth above or a subclass thereof. Any and all possible combinations of these variables in each of Formulas II, IIA and IIB are additional embodiments within the scope of the present invention.

Other embodiments of the present invention include the following:

(a) A pharmaceutical composition comprising a therapeutically effective amount of a compound of the invention (e.g., a compound of Formula I, IA, IB, IC, ID, II, IIA, IIB, III, IIIA, or IIIB, or any of the specific compounds set forth above) and a pharmaceutically acceptable carrier.

(b) A pharmaceutical composition which comprises the product prepared by combining (e.g., mixing) a therapeutically effective amount of a compound of the invention and a pharmaceutically acceptable carrier.

(c) The pharmaceutical composition of (a) or (b), further comprising a therapeutically effective amount of an HIV infection/AIDS treatment agent selected from the group consisting of UV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of the invention and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of the invention.

(h) A method of preventing or treating infection by HIV in a subject in need thereof which comprises administering to the subject a therapeutically effective amount of a compound of the invention.

(i) The method of (h), wherein the compound of the invention is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of the invention.

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, or an aspect or feature or sub-feature thereof, described above.

In all of the foregoing embodiments describing compositions, combinations and methods, the compound may optionally be used in the form of a pharmaceutically acceptable salt.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "-alkyl-" refers to any linear or branched chain alkylene (or alternatively "alkanediyl") having a number of carbon atoms in the specified range. Thus, for example, "—$C_{1-6}$ alkyl-" refers to a $C_1$ to $C_6$ linear or branched alkylene. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "alkenyl" means any linear or branched chain alkenyl group having a number of carbon atoms in the specified range. Thus, for example, "$C_{2-6}$ alkenyl" (or "$C_2$-$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl).

The term "-alkenyl-" refers to any linear or branched chain alkenylene (or alternatively "alkenediyl") having a number of carbon atoms in the specified range. Thus, for example, "—$C_{2-6}$ alkenyl-" refers to a $C_2$ to $C_6$ linear or branched alkenylene.

The term "alkynyl" means any linear or branched chain alkynyl group having a number of carbon atoms in the specified range. Thus, for example, "$C_{2-6}$ alkynyl" (or "$C_2$-$C_6$ alkynyl") refers to all of the hexynyl and pentynyl isomers as well as 1-butynyl, 2-butynyl, 3-butynyl, 1-propynyl, 2-propynyl, and ethynyl (or acetylenyl).

The term "-alkynyl-" refers to any linear or branched chain alkynylene (or alternatively "alkynediyl") having a number of carbon atoms in the specified range. Thus, for example, "—$C_{2-5}$ alkynyl-" refers to a $C_2$ to $C_5$ linear or branched alkynylene.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4} CF_3$ (i.e., trifluoromethyl, 2,2,2-trifluoroethyl, 3,3,3-trifluoro-n-propyl, etc.).

The term "aryl" refers to aromatic mono- and poly-carbocyclic ring systems, wherein the individual carbocyclic rings in the polyring systems may be fused or attached to each other via a single bond. Suitable aryl groups include, but are not limited to, phenyl, naphthyl, and biphenylenyl. A subset of aryl groups particularly suitable for use in the present invention is phenyl and naphthyl. Still another particularly suitable subset of aryl groups is phenyl per se.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

When any variable (e.g., $R^a$, $R^b$, or $R^c$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "each aryl is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The symbol " ∿∿∿ " in front of an open bond in the structural formula of a group marks the point of attachment of the group to the rest of the molecule.

In instances where a hydroxy (—OH) substituent(s) is (are) permitted on a heteroaromatic ring and keto-enol tautomerism is possible, it is understood that the substituent might in fact be present, in whole or in part, in the keto form, as exemplified here for a hydroxypyridinyl substituent:

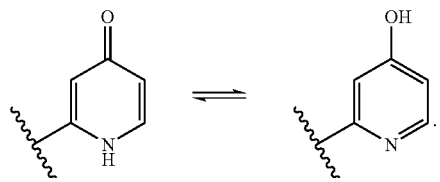

Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, compounds of the present invention can exist as tautomers, such as the following:

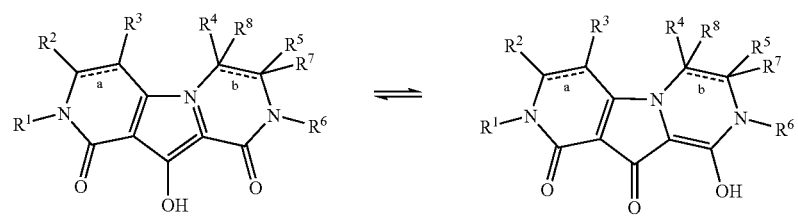

or such as the following (wherein A is N and B is C):

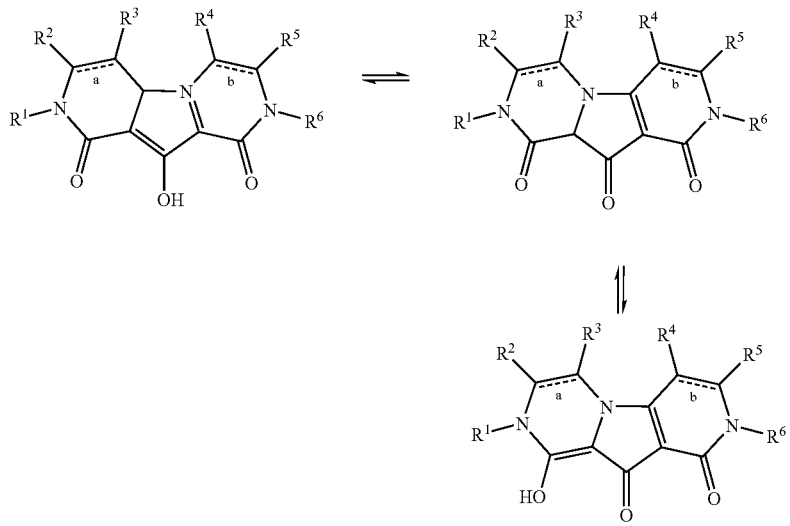

The present invention includes all tautomeric forms, individually and in mixtures.

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention can also act as inhibitors of HIV ribonuclease H (RNase H). The human immunodeficiency virus type 1 (HIV-1) reverse transcriptase (RT) catalyzes the conversion of genomic RNA into double-stranded proviral DNA after cell entry, utilizing the RNA- and DNA-dependent polymerase and RNase H activities of the enzyme. HIV-1 RT is an asymmetric dimer consisting of p66 and p51 polypeptides. The catalytic activities of RT are conducted at discrete sites in the p66 subunit; i.e., the N terminus of p66 catalyzes the RNA- and DNA-dependent DNA polymerase activity, and the p15 domain at the C terminus catalyzes RNase H activity. RNase H is required to cleave the RNA strand of the RNA:DNA heteroduplex intermediates in reverse transcription. The compounds of the present invention can selectively bind to and inhibit the RNase H domain of HIV-1 RT. The RNase H inhibition activity of the compounds can be measured using suitable assays known in the art, such as the assay described in Shaw-Reid et al., *J. Biol. Chem* 2003, 278 (5): 2777-2780. Accordingly, the present invention includes a method of inhibiting HIV RNase H in a subject in need of such inhibition which comprises administering to the subject an effective amount of a compound of the invention. The present invention further includes a compound of the present invention (i) for use in, (ii) for use as a medicament for, or (iii) for use in the preparation of a medicament for inhibiting HIV RNase H.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention can be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional nontoxic pharmaceutically-acceptable carriers, adjuvants and vehicles.

The term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HIV infection or AIDS), "administration" and its variants are each understood to include concurrent and sequential provision of the compound and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (which may be alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation or prophylaxis of the symptoms of the disease or condition being treated or prevented. The term also includes herein the amount of active compound sufficient to inhibit HIV integrase and/or RNase H and thereby elicit the response being sought. When the active compound (i.e., active ingredient) is administered as the salt, references to the amount of active ingredient are to the free acid or free base form of the compound.

The pharmaceutical compositions can be in the form of orally-administrable suspensions or tablets or capsules, nasal sprays, sterile injectable preparations (for example, as sterile injectable aqueous or oleagenous suspensions), or suppositories. These compositions can be prepared by methods and contain excipients which are well known in the art. Suitable methods and ingredients are described in *Remington's Pharmaceutical Sciences,* 18$^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the compounds of the present invention with one or more agents useful in the treatment or prevention of HIV infection or AIDS. For example, the compounds of this invention may be effectively administered, whether at periods of pre-exposure and/or post-exposure, in combination with effective amounts of one or more of the IV/AIDS antivirals, imunomodulators, antiinfectives, or vaccines useful for treating HIV infection or AIDS. Suitable antiviral agents include those listed in the following Table:

ANTIVIRALS

| Drug Name | Manufacturer (Tradename and/or, Location) | Indication (Activity) |
|---|---|---|
| abacavir GW 1592 1592U89 | Glaxo Welcome (ZIAGEN ®) | HIV infection, AIDS, ARC (nucleoside reverse transcriptase inhibitor) |
| abacavir + lamivudine + zidovudine | GlaxoSmithKline (TRIZIVIR ®) | HIV infection, AIDS, ARC (nucleoside reverse transcriptase inhibitors) |
| acemannan | Carrington Labs (Irving, TX) | ARC |
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | GlaxoSmithKline | Kaposi's sarcoma, HIV, in combination w/Retrovir |

-continued

ANTIVIRALS

| Drug Name | Manufacturer (Tradename and/or, Location) | Indication (Activity) |
|---|---|---|
| AMD3100 | AnorMed | HIV infection, AIDS, ARC (CXCR4 antagonist) |
| amprenavir 141 W94 GW 141 VX478 (Vertex) | GlaxoSmithKline (AGENERASE ®) | HIV infection, AIDS, ARC (protease inhibitor) |
| ansamycin LM 427 | Adria Laboratories (Dublin, OH) Erbamont (Stamford, CT) | ARC |
| antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers Squibb (REYATAZ ™) | HIV infection, AIDS, ARC (protease inhibitor) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| capravirine (AG-1549, S-1153) | Pfizer | HIV infection, AIDS, ARC (non-nucleoside reverse transcriptase inhibitor) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (non-nucleoside reverse transcriptase inhibitor) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nuclesodie reverse transcriptase inhibitor) |
| ddI (didanosine, dideoxyinosine) | Bristol-Myers Squibb (VIDEX ®) | HIV infection, AIDS, ARC; combination with AZT/d4T (nucleoside reverse transcriptase inhibitor) |
| DPC 681 & DPC 684 | DuPont | HIV infection, AIDS, ARC (protease inhibitors) |
| DPC 961 & DPC 083 | Bristol-Myers Squibb (from DuPont Pharma) | HIV infection AIDS, ARC (non-nucleoside reverse transcriptase inhibitors) |
| EL10 | Elan Corp, PLC (Gainesville, GA) | HIV infection |
| efavirenz (DMP 266) | Bristol-Myers Squibb (SUSTIVA ®) Merck (STOCRIN ®) | HIV infection, AIDS, ARC (non-nucleoside RT inhibitor) |
| famciclovir | Novartis (FAMVIR ®) | herpes zoster, herpes simplex |
| emtricitabine FTC | Gilead (from Triangle Pharmaceuticals) (COVIRACIL ®) Emory University | HIV infection, AIDS, ARC (nucleoside reverse transcriptase inhibitor) |
| emvirine | Gilead (from Triangle Pharmaceuticals) (COACTINON ®) | HIV infection, AIDS, ARC (non-nucleoside reverse transcriptase inhibitor) |
| enfuvirtide T-20 | Trimeris & Roche (FUZEON ®) | HIV infection, AIDS, ARC (fusion inhibitor) |
| HBY097 | Hoechst Marion Roussel | HIV infection, AIDS, ARC (non-nucleoside reverse transcriptase inhibitor) |
| fosamprenavir | Glaxo Smith Kline | HIV infection, AIDS, ARC (prodrug of amprenavir) |

-continued

ANTIVIRALS

| Drug Name | Manufacturer (Tradename and/or, Location) | Indication (Activity) |
|---|---|---|
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, (protease inhibitor) |
| ISIS 2922 | ISIS Pharmaceuticals | CMV retinitis |
| JE2147/AG1776 | Agouron | HIV infection, AIDS, ARC (protease inhibitor) |
| KNI-272 | Nat'l Cancer Institute | HIV-assoc. diseases |
| lamivudine, 3TC | GlaxoSmithKline (EPIVIR ®) | HIV infection, AIDS, ARC (nucleoside reverse transcriptase inhibitor) |
| lamivudine + zidovudine | GlaxoSmithKline (COMBIVIR ®) | HIV infection, AIDS, ARC (nucleoside reverse transcriptase inhibitor) |
| lobucavir | Bristol-Myers Squibb | CMV infection |
| lopinavir (ABT-378) | Abbott | HIV infection, AIDS, ARC (protease inhibitor) |
| lopinavir + ritonavir (ABT-378/r) | Abbott (KALETRA ®) | HIV infection, AIDS, ARC (protease inhibitor) |
| mozenavir (DMP-450) | AVID (Camden, NJ) | HIV infection, AIDS, ARC (protease inhibitor) |
| nelfinavir | Agouron (VIRACEPT ®) | HIV infection, AIDS, ARC (protease inhibitor) |
| nevirapine | Boeheringer Ingleheim (VIRAMUNE ®) | HIV infection, AIDS, ARC (non-nucleoside reverse transcriptase inhibitor) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (NORVIR ®) | HIV infection, AIDS, ARC (protease inhibitor) |
| saquinavir | Hoffmann-LaRoche (FORTOVASE ®) | HIV infection, AIDS, ARC (protease inhibitor) |
| stavudine; d4T didehydrodeoxy-thymidine | Bristol-Myers Squibb (ZERIT ®) | HIV infection, AIDS, ARC (nucleoside reverse transcriptase inhibitor) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boehringer Ingelheim | HIV infection, AIDS, ARC (protease inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| valaciclovir | GlaxoSmithKline | genital HSV & CMV infections |
| virazole | Viratek/ICN | asymptomatic HIV positive, |

-continued

ANTIVIRALS

| Drug Name | Manufacturer (Tradename and/or, Location) | Indication (Activity) |
|---|---|---|
| ribavirin | (Costa Mesa, CA) | LAS, ARC |
| zidovudine; AZT | GlaxoSmithKline (RETROVIR ®) | HIV infection, AIDS, ARC, Kaposi's sarcoma in combination with other therapies (nucleoside reverse transcriptase inhibitor) |

The HIV/AIDS antiviral agents, immunomodulators, and anti-infectives listed in the Table in US-2003-0055071 A1, the disclosure of which is hereby incorporated by reference in its entirety, are also suitable for use in combination with compounds of the present invention. It will be understood that the scope of combinations of the compounds of this invention with the HIV/AIDS antivirals, immunomodulators, anti-infectives or vaccines is not limited to the list in the above Table and in the Table in US-2003-0055071 A1, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference*, 54$^{th}$ edition, Medical Economics Company, 2000, and the 58$^{th}$ edition, 2004. The dosage ranges for a compound of the invention in these combinations are the same as those set forth above herein.

In such combinations the compound of the present invention and other active agents may be administered together in a single composition or separately. Where separate administration is employed, the administration of one element may be prior to, concurrent with, or subsequent to the administration of other agent(s).

Abbreviations used in the instant specification, particularly the Schemes and Examples, include the following:
AIDS=acquired immunodeficiency syndrome
ARC=AIDS related complex
BOC or Boc=t-butyloxycarbonyl
CBZ=carbobenzoxy (alternatively, benzyloxycarbonyl)
DMF=dimethylformamide
EDC or EDAC=1-ethyl-3-(3-dimethylaminopropyl)carbodiimide
ES-MS=electron spray mass spectroscopy
Et=ethyl
EtOAc=ethyl acetate
FT/APCI=fourier transform/atmospheric pressure chemical ionization (mass spectroscopy)
HIV=human immunodeficiency virus
HOBT or HOBt=1-hydroxy benzotriazole hydrate
HPLC=high performance liquid chromatography
HRMS=high resolution mass spectroscopy
Me=methyl
NMR=nuclear magnetic resonance
TFA=trifluoroacetic acid
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

A general method for the preparation of compounds of the present invention embraced by Formula I in which bonds "a" and "b" are both single, A=N, and B=C is shown in Scheme 1, wherein a solution of piperazinone 1-2 and dihydropyridinone 1-1 in a solvent—such as 1,2-dichlorobenzene (typically preferred), ethylene glycol, acetonitrile, or the like—is heated at between 150 to 250° C. in a microwave oven to afford 1-3. Progress of the reaction can be monitored with LC-MS. The required piperazinones 1-2 can be prepared via various routes known in the art, such as alkylation of piperazinone and cyclization of appropriately substituted piperazinone precursors. Suitable methods for preparing piperazinones are described in "Syntheses and Transformations of piperazinone Rings. A Review" Dinsmore, C. & Beshore D., *Org. Prep. Proced. Int.* 2002, 34: 367-404. Methods for preparing the various piperazinones (i.e., piperazinones 1-2, 2-2, and 5-1) required for the synthesis of the tricyclic target inhibitors depicted in Schemes 1 to 9 are depicted in Scheme 10, Part A to F. The dihydropyridinones 1-4 can be prepared by treatment of appropriated substituted β-aminoesters with alkyl 3-chloro-3-oxopropionates, followed by a based catalyzed cyclization (see, e.g., Deslongchamps, G. et al. *Tetrahedron* 1998, 54: 9043-54). The hydroxypyridinones can be readily O-methylated with diazomethane.

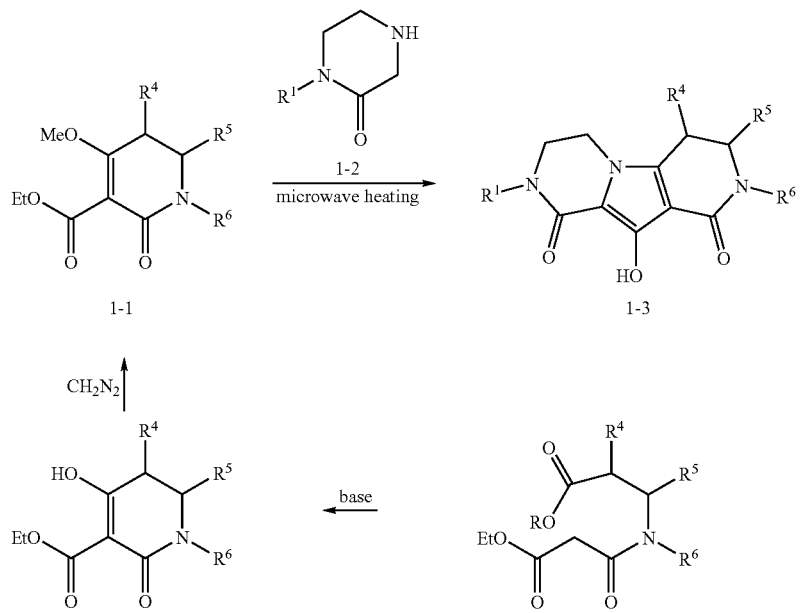

A general method for the preparation of compounds of the present invention embraced by Formula I in which bonds "a" and "b" are both single, A=C, and B=N is shown in Scheme 2, wherein a mixture of piperazinone 2-2 and dihydropyridinone triflate 2-1 is heated at between 150 to 250 C in a microwave oven either neat or as a solution in a suitable solvent (e.g., ethylene glycol, 1,2-dichlorobenzene, or acetonitrile) to afford 2-3. Progress of the reaction can be monitored with LC-MS. The required piperazinones and dihydropyridinones can be prepared as set forth in the discussion of Scheme 1 above (see also Scheme 10 below). Treatment of the hydroxydihydropyridinone 2-4 with triflate anhydride can provide the triflate 2-1.

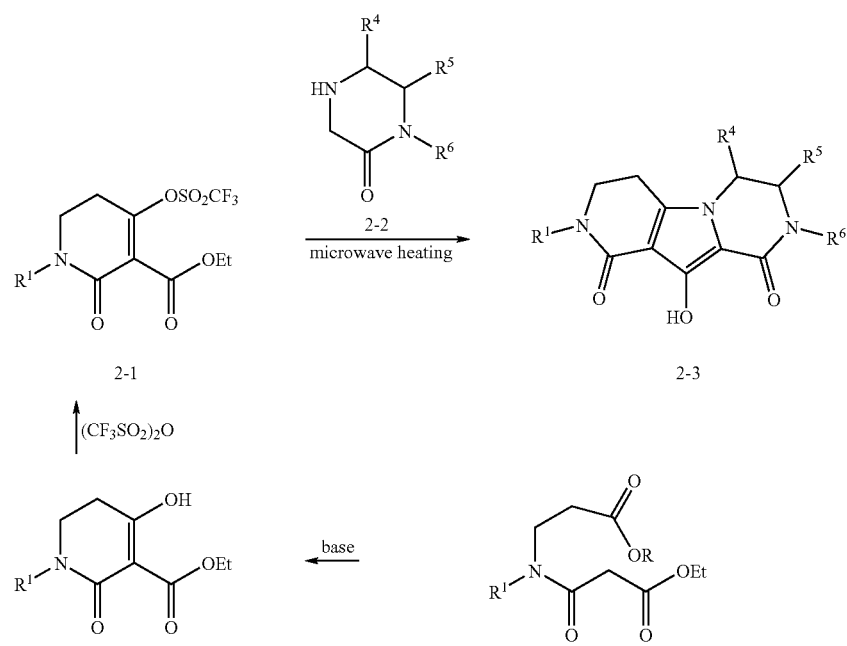

A general method for the preparation of compounds of the present invention embraced by Formula I in which one of the bonds "a" and "b" is double, A=C, and B=N is shown in Scheme 3, wherein piperazinone 1-2 is reacted with diethyl ethoxymethylenemalonate to provide the adduct 3-2, which can be cyclize in the presence of base to provide 3-3. Ester-amide exchange leads to 3-4 which can be brominated and the hydroxy group appropriately protected. The amide side chain on 3-5 can then be alkylated, and the resultant product 3-6 can be cyclized to 3-7 in the presence of a Pd catalyst (Littke et al J. Am. Chem. Soc., 2001, 6989). Removal of protecting group on 3-7 provides the target compound 3-8.

Alternatively, preparation of compounds of the present invention embraced by Formula I in which one or both of the bonds "a" and "b" is double can be prepared via direct oxidation of the saturated analogs with a suitable oxidant.

A general method for the preparation of compounds of the present invention embraced by Formula I in which one of the bonds "a" and "b" is double, A=C, and B=N is shown in Scheme 4, wherein tetrahydropyridopyrrolopyrazinedione 4-1 (prepared by reaction of dihydropyridinone 1-1 with piperazinone in 1,2-dichlorobenzene as described in scheme 1) is treated with toluenesulfonyl chloride to provide the tosylate-

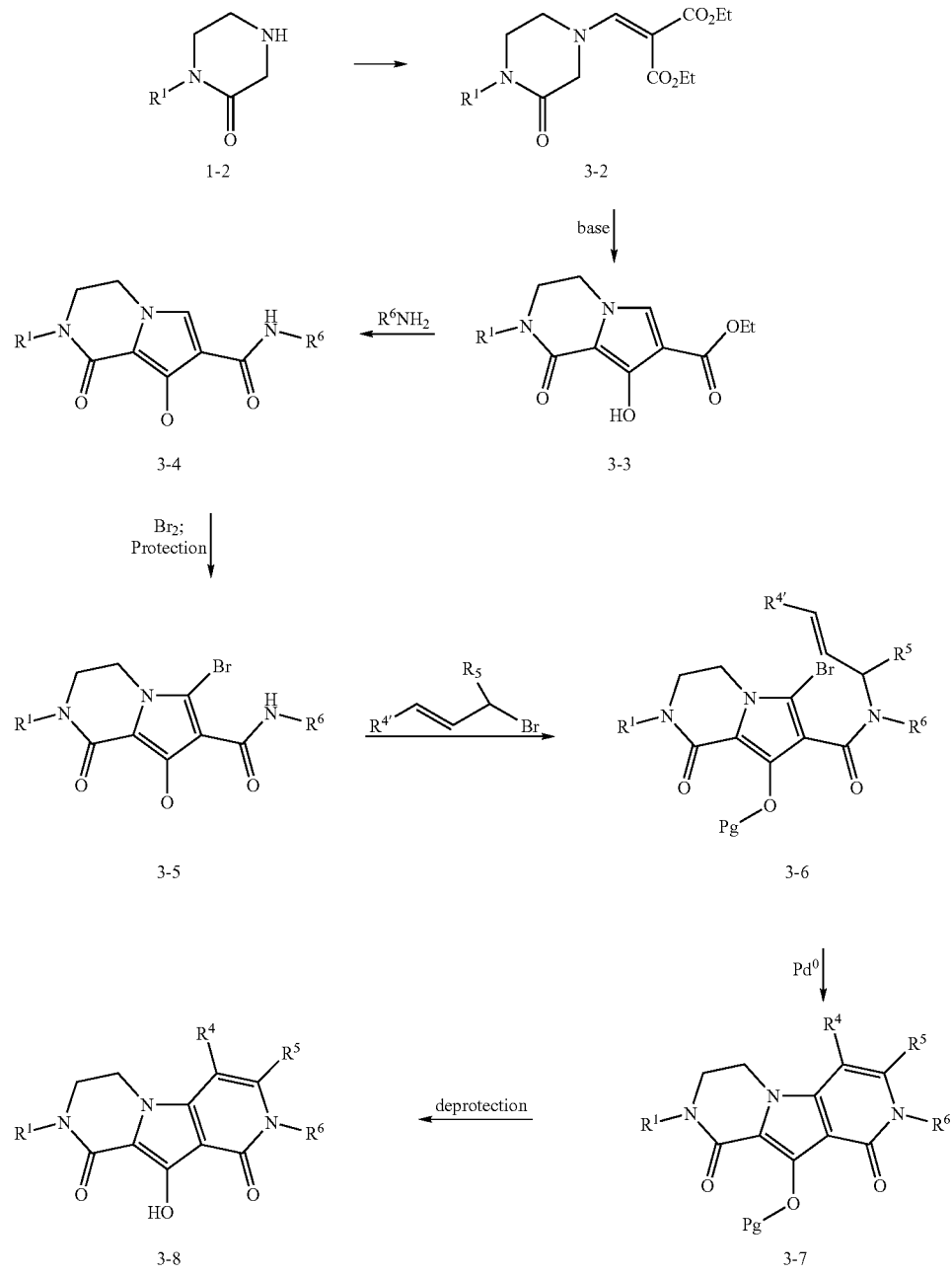

SCHEME 3

Pg = Protecting group 4-2. Intermediate 4-2 can be selectively N-alkylated by treatment with an appropriate base and alkylating reagent. Alternatively, intermediate 4-1 could be arylated with corresponding aryl bromide or heteroaryl bromide in the presence of a palladium catalyst (Steinhuebel, D et al *Tet. Lett.* 2004, 3305). Removal of protecting group on 4-3 with a solution of sodium alkoxide in alcohol provides the target compound 4-4.

SCHEME 4

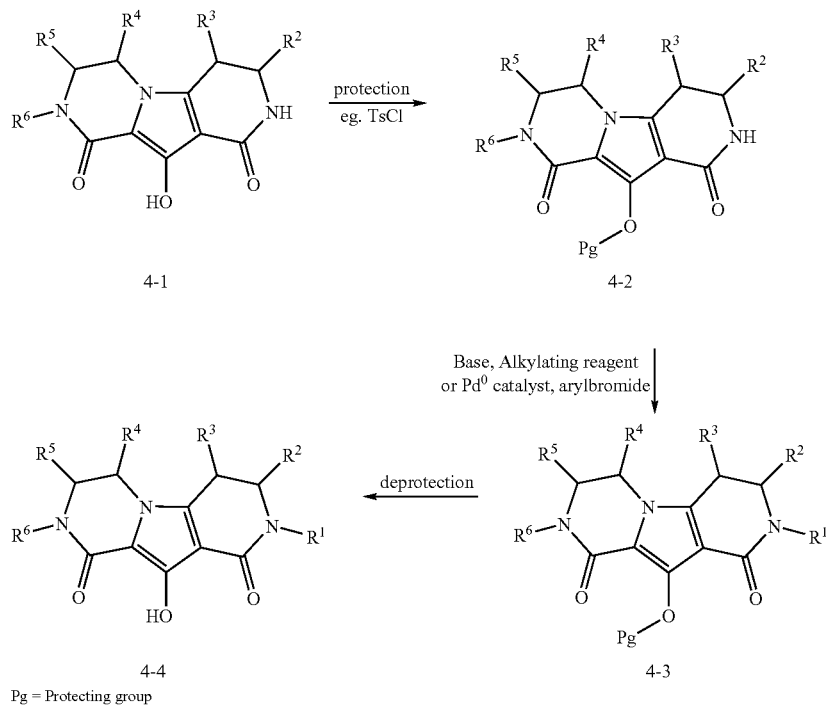

Pg = Protecting group

A general method for the preparation of compounds of the present invention embraced by Formula I in which one of the bonds "a" and "b" is double, A=C, and B=N is shown in Scheme 5, wherein appropriated substituted piperazinone 5-1 is reacted with diethyl ethoxymethylenemalonate to provide the adduct 5-2, which can be cyclize in the presence of base to provide 5-3. Ester 5-3 is hydrolyzed, and the resultant acid is coupled with an appropriate primary amine to provide amide 5-4. The hydroxy group on intermediate 5-4 is protected, for example as the corresponding methyl or benzyl ether. Bromination of which provided the necessary bromide 5-5. The amide side chain on 5-5 can then be alkylated, and the resultant product 5-6 can be cyclized to in the presence of a Pd° catalyst (Littke et al *J. Am. Chem. Soc.,* 2001, 6989). Depending on the nature of the substituents on the alkyl substituent, different ratio of a mixture of cyclization products 5-7 and 5-8 can be obtained. Hydrogenation/removal of the hydroxyl protecting group provides the target compounds 5-9 or/and 5-10, which can be purified by preparative high pressure liquid chromatograph. When a benzyl protecting group is used, concurrent hydrogenation/protecting group removal proceeds in the same operation.

SCHEME 5

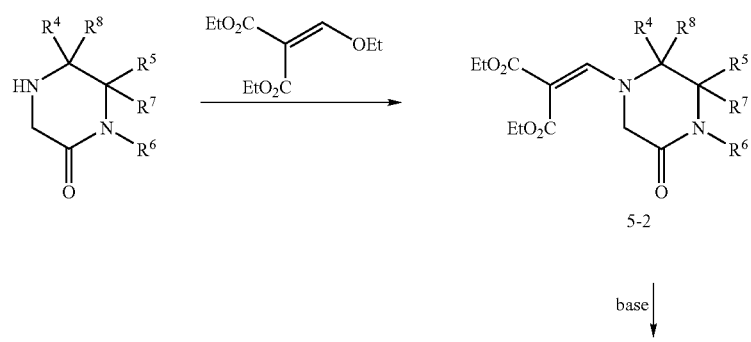

base

-continued
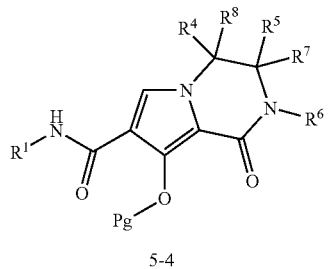
5-4
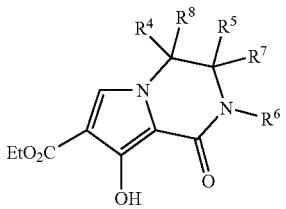
5-3
1. NaOH
2. R¹NH₂, coupling reagent
1. Protection
2. Br₂
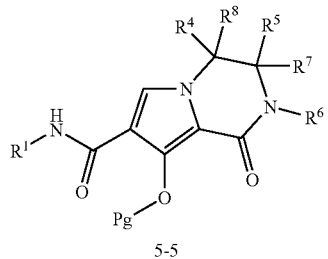
5-5
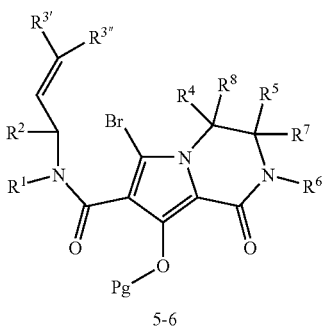
5-6
base
Pd⁰
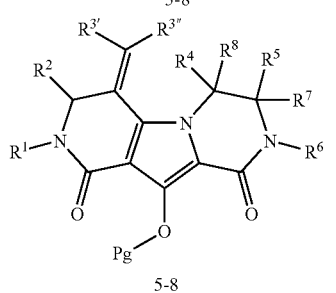
5-8
+
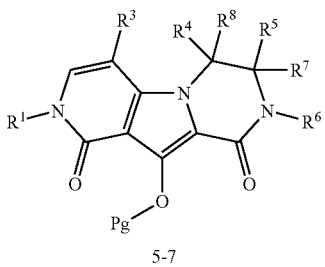
5-7
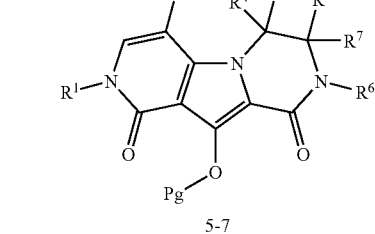
5-8  +  5-7
hydrogenation/deprotection
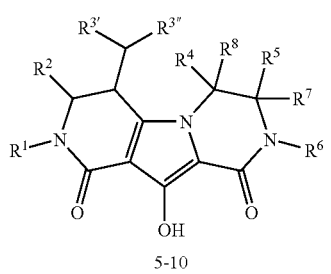
5-10
+
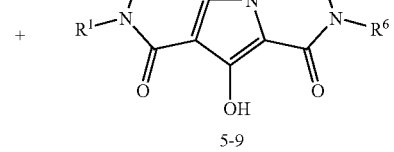
5-9
Pg = Protecting group A general method for the preparation of compounds of the present invention embraced by Formula I in which one of the bonds "a" and "b" is double, A=C, and B=N is shown in Scheme 6, wherein appropriated substituted 8-hydroxy-1-oxo-1,2,3,4-tetrahydropyrrolopyrazine carboxylate 6-1 is protected as methyl ether or benzyl ether. Bromination of which provided the necessary bromide 6-2. Treatment of the bromide 6-2 with n-butyl lithium, followed by addition of dialkyl oxalate provides the corresponding ketoester 6-3. Reaction of 6-3 with appropriate olefination reagent such Wittig reagent (Ohsugi et al, *Tetrahedron,* 2003, 1859) or Tebbe reagent (Pine et al *J Org Chem.,* 1985, 1212) provides the alkylidene ester 6-4. Alternatively, the bromide 6-2 could be converted directly to the alkylidene ester 6-4 by a palladium catalyzed coupling (Levin et al *Tet. Lett.* 1993, 6211) with an appropriate trialkylstannyl alkenoate (Zhang et al *J Org Chem,* 1990, 1857). Reaction of the resulting alkenoate 6-4 with an appropriate primary amine provided the tricyclic intermediate 6-5. Removal of the protecting group on the hydroxyl group provides target compound 6-6. Further transformation of the ester group on the tricyclic intermediate 6-5 to appropriate amide, and removal of the protecting group provides the product 6-8.

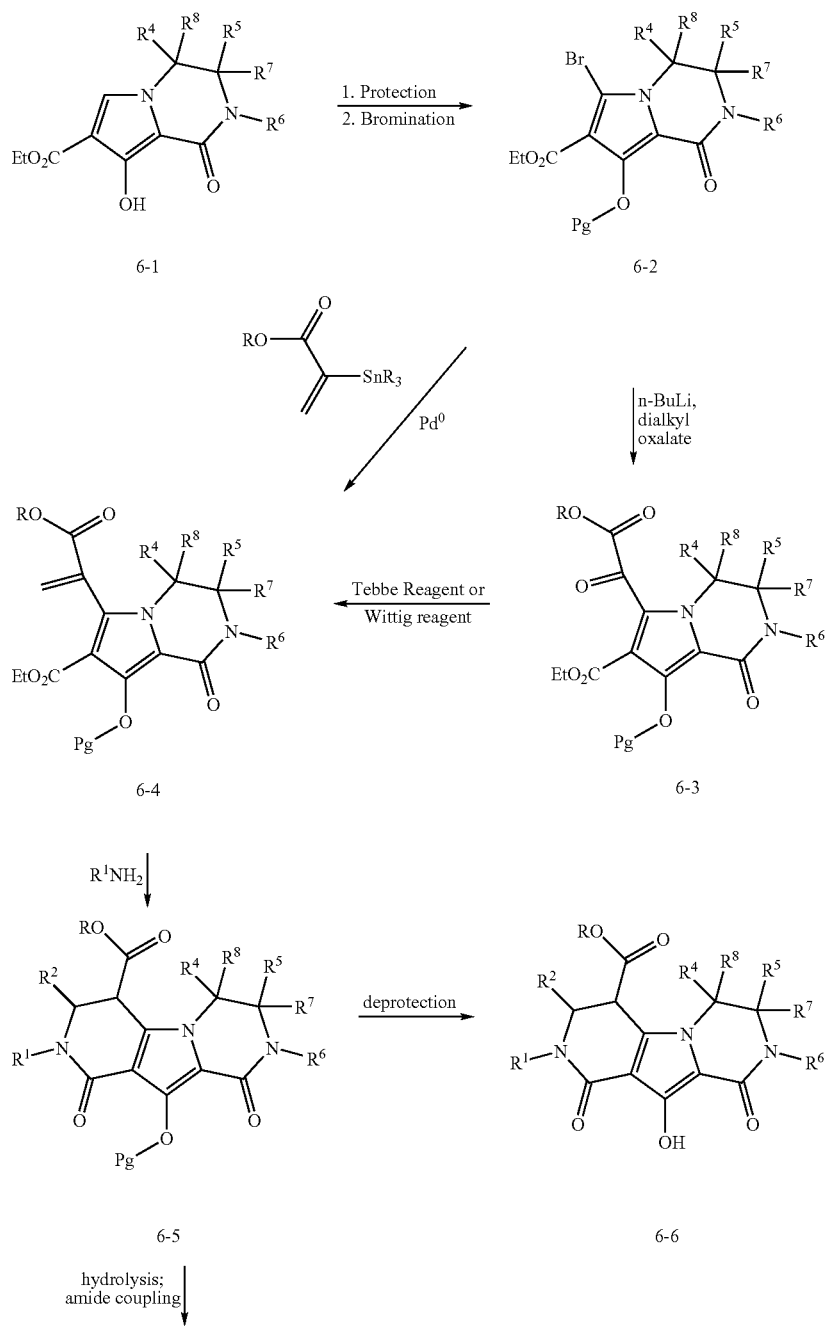

SCHEME 6

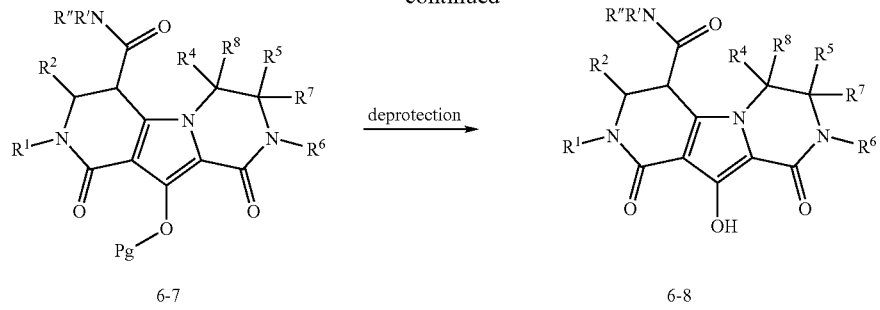

6-7
Pg = Protecting group 6-8

A general method for the preparation of compounds of the present invention embraced by Formula I in which one of the bonds "a" and "b" is double, A=C, and B=N is shown in Scheme 7, wherein appropriated substituted tricyclic ester 6-5 is treated with an oxidant such as manganese dioxide (Brimble et al Aust. J. Chem., 1988, 1583) or DDQ, the corresponding unsaturated tricyclic intermediate 7-1 is obtained. Alternatively, treatment of alkylidene ester 6-4 with ammonia, and oxidation of the resultant addition/cyclization product with manganese dioxide provides intermediate 7-2. Treatment, of 7-2 with base followed by an appropriate alkylating reagent provides the unsaturated intermediate 7-1. Removal of the protecting group on the hydroxyl group provides target compound 7-3. Further transformation of the ester group on the tricyclic intermediate 7-1 to appropriate amide, and removal of the protecting group provides the product 7-5.

SCHEME 7

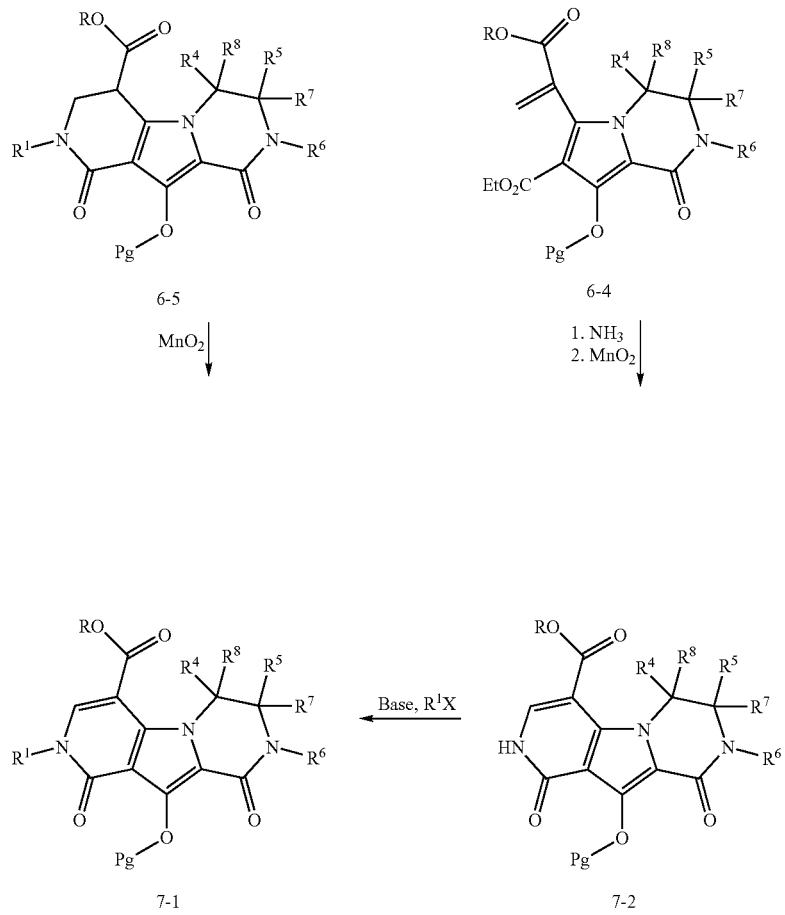

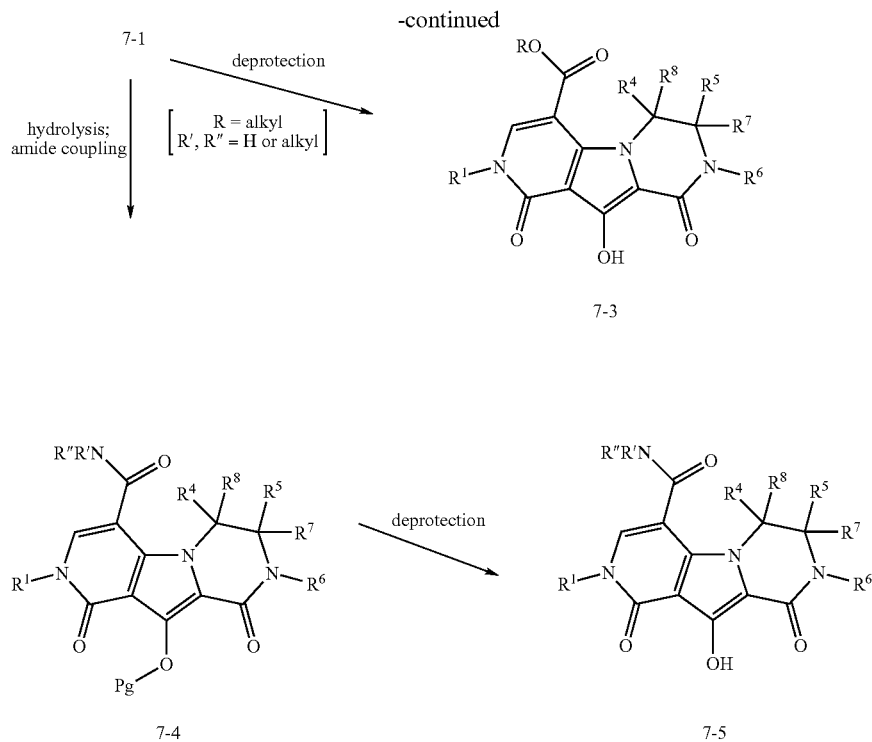

A general method for the preparation of compounds of the present invention embraced by Formula I in which one of the bonds "a" and "b" is double, A=C, and B=N is shown in Scheme 8, wherein appropriated substituted tricyclic ester 7-1 is hydrolyzed to the corresponding acid 8-1. Coupling of the acid with ammonia provide the corresponding primary amide 8-2. Dehydration of the amide provides the nitrile 8-3 (Carling et al, *J. Med. Chem.,* 1997, 754). Removal of the protecting group on the hydroxyl group provides target compound 8-4. Alternatively, treatment of acid 8-1 with an acyl-hydrazine provides the intermediate 8-5. Further transformation with a dehydrating reagent provides the corresponding oxadiazole 8-6 (Brain et al *Tet. Lett.,* 1999, 3275), and removal of the protecting group affords the product 8-7. The nitrile group on intermediate 8-3 and carboxylic group on intermediate 8-1 can be converted to various heterocylces, such as tetrazole (Duncia et al, *J. Org. Chem.,* 1991, 2395), triazole (Omodei-Sale et al, *J. Med. Chem.,* 1983, 1187), pyrazole and imidazole (Young, et al *J. Med. Chem.,* 2004, 2995).

SCHEME 8

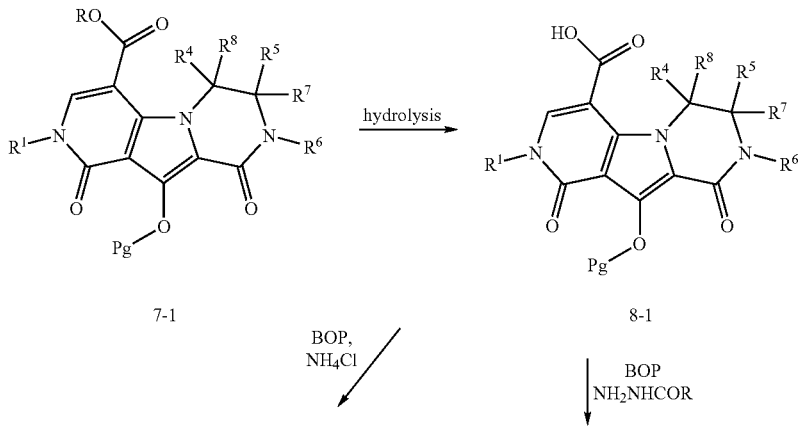

-continued
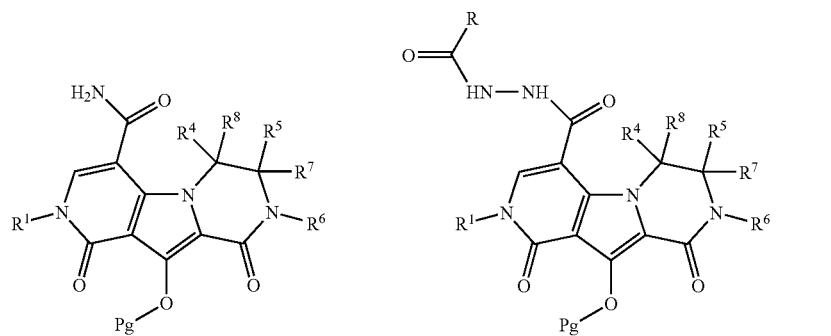
8-2 | 8-5
dehydration ↓ | dehydration ↓
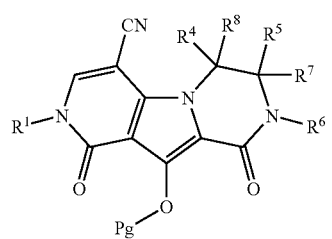 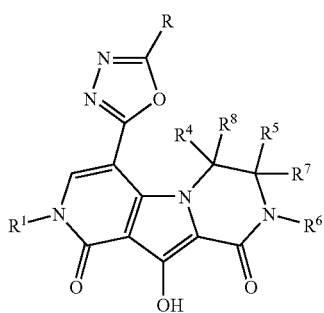
8-3 | 8-6
deprotection ↓ | deprotection ↓
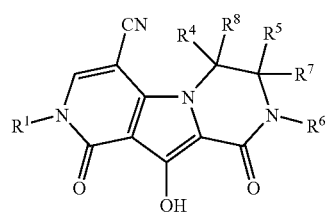
8-4 | 8-7
R = alkyl
Pg = protecting group A general method for the preparation of compounds of the present invention embraced by Formula I in which one of the bonds "a" and "b" is double, A=C, and B=N is shown in Scheme 9, wherein appropriated substituted tricyclic acid 8-1 is converted to the corresponding amino derivative 9-1 when treated with a mixture of diphenylphosphorylazide and tert-butanol (Koskinen et al *J Org Chem.*, 1993, 879). The resultant N-Boc amino tricyclic intermediate 9-1 could be sulfonated with an appropriate alkyl or aryl sulfonyl halide to provide intermediate 9-2. The Boc protecting group is removed by treatment with trifluoroacetic acid or HCl. Reaction of the resultant sulfonamide with appropriate alkylating reagent in the presence of an appropriate base provides the penultimate intermediate 9-3. Removal of the protecting group on the hydroxyl group provides target compound 9-4. Furthermore, reaction of 9-1 with a base, followed by addition of an appropriate alkylating reagent provides intermediate 9-5. The Boc protecting group is removed by treatment with trifluoroacetic acid or HCl. Reaction of the resultant amine with various acylating reagents such as acid anhydrides, alkyl isocyanate, alkyl chloroformate, etc provides the intermediate 9-6. Removal of the protecting group affords the product 9-7.

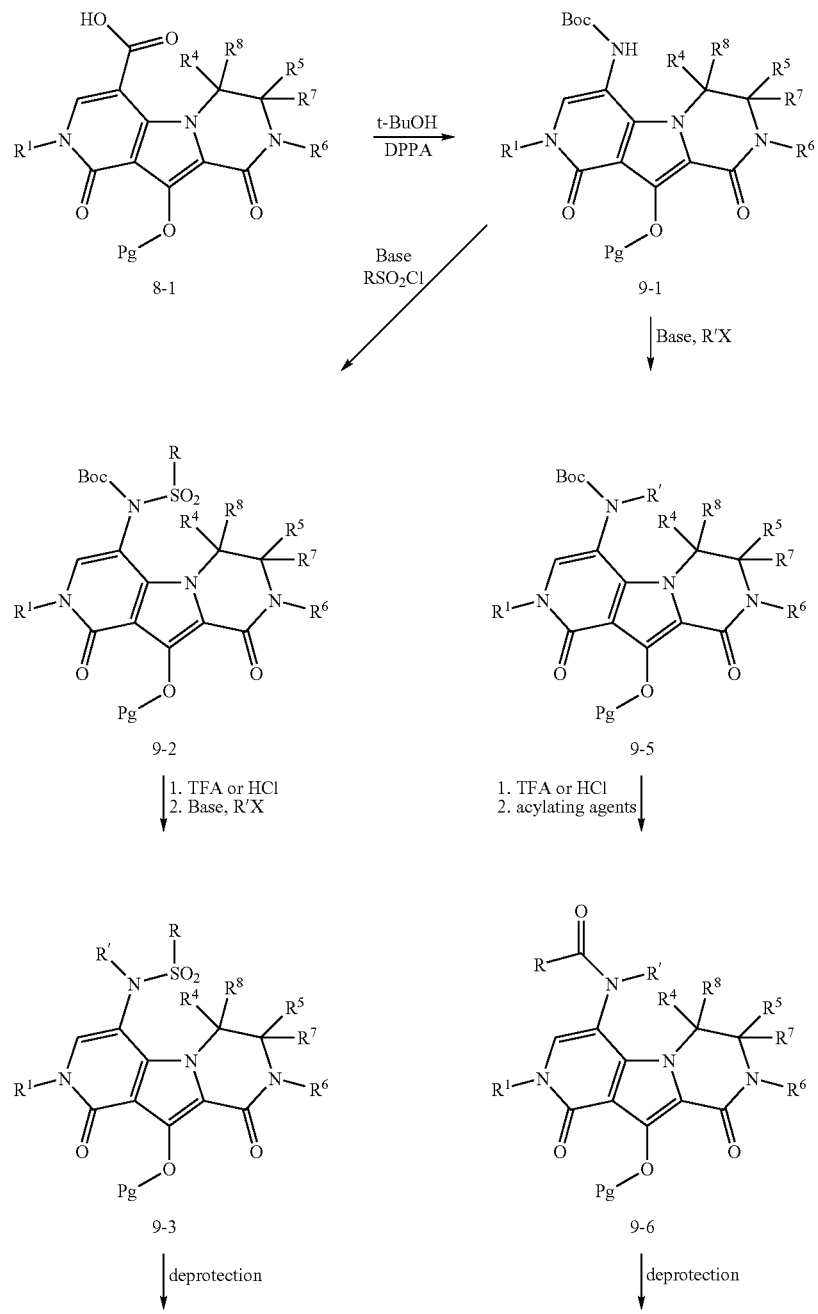

SCHEME 9

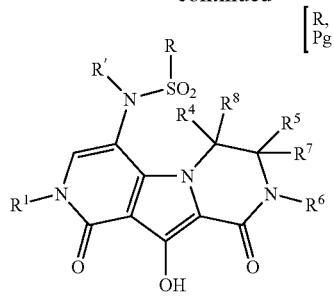

9-4

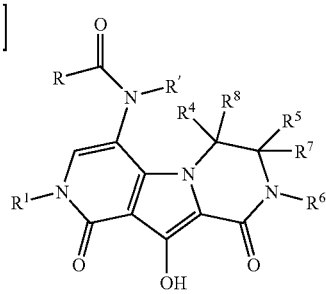

9-7

The piperazin-2-one 10-1 can be obtained by alkylation of amine-protected piperazin-2-one 10-2 followed by deprotection, as depicted in Part A of Scheme 10 and described in Choi et al., *J. Med. Chem.* 1999, 3647; Najman-Bronzewska et al., *Pharmazie* 1997, 198; Fryer et al., *J. Org. Chem.* 1991, 3715, or routine variations thereof. Alternatively, piperazin-2-one 10-1 could derived from cyclization of the dialkylacetal precursor 10-4, followed by catalytic hydrogenation of the cyclization product 10-5 as depicted in Part B of Scheme 2 and described in DiMaio et al, *JCS Perkin* 1, 1989, 1687 and Kitamura et al., *J. Med. Chem.,* 2001, 2438. Sequential hydrogenation of the olefin (eg. platinum on charcoal, etc) followed by cleavage of the CBz protecting group (eg. palladium on charcoal, palladium hydroxide on charcoal, etc) in a suitable protic solvent (eg alcohol, etc) under an atmosphere of hydrogen gas provided the required piperazin-2-one 10-1. Similarly, reaction of glycinamide 10-6 with pyruvic aldehyde provided the key pyrazinone 10-7, which was hydrogenated to provide piperazin-2-one 10-1 as depicted in Part C of scheme 10 as described in Wilfred et al., *JCS Chem Comm.,* 1980, 334. Alternatively, stepwise reductive alkylation of aldehyde 10-8 with a suitably substituted primary amine and treatment of the resultant product with haloacetyl halide (such as chloroacetyl chloride, bromo acetylbromide) provided the intermediate 10-9. Based induced cyclization, followed by deprotection of the amino group provided piperazin-2-one 10-1 as depicted in Part D of scheme 10 and described in Williams, et al., *J. Med. Chem.,* 1999, 3779, and Lewis, et al., *J. Med. Chem.,* 1995, 923. Similarly, treatment of the appropriately protected diamine derivative 10-11 with haloacetyl halide (such as chloroacetyl chloride, bromo acetylbromide) provided the intermediate 10-12. Based induced cyclization, followed by deprotection of the amino group provided piperazin-2-one 10-1 as depicted in Part E of scheme 10. In addition, conversion of the N-Boc diacid 10-13 to the corresponding monoamide 10-14, and treatment of which with an appropriate Grignard reagent provides the corresponding ketone 10-15. Stepwise reductive alkylation with an appropriate amine provides the corresponding aminoacid 10-16. Intramolecular amide coupling, followed by removal of the CBz protecting group provides the required piperazinone 10-1 as depicted in Part F of scheme 10 and described in Boger et al *Helv. Chem. Acta* 2000, 1825.

Piperazin-2-one 10-1 can alternatively be also prepared using methods described in Bernotas et al., *Tetrahedron Lett.* 1996, 7339; Saari et al., *J. Med. Chem.* 1990, 2590; Sugihara et al., *J. Med. Chem.* 1998, 489, Dinsmore et al, *Organic Prep. & Procedures International.* 2002, 369, or routine variations thereof.

Scheme 10

Part A:

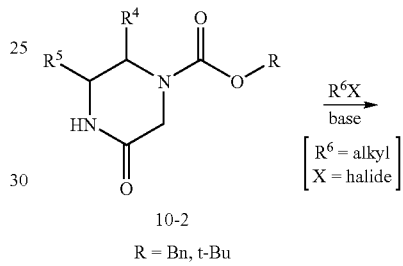

10-2

R = Bn, t-Bu

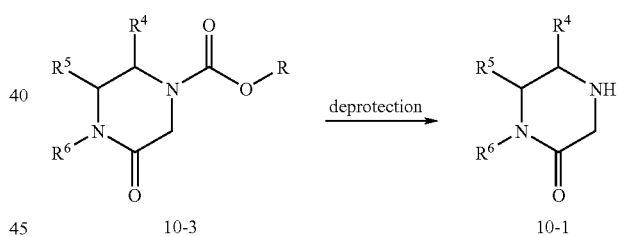

10-3     10-1

Part B:

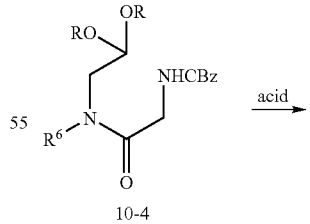

10-4

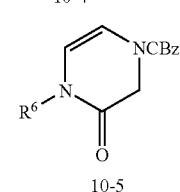

10-5

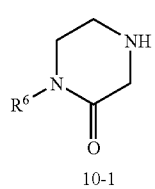

10-1

Part C:

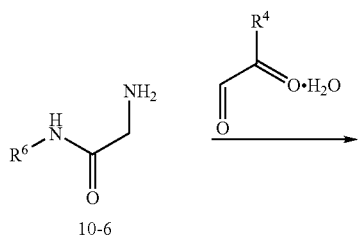

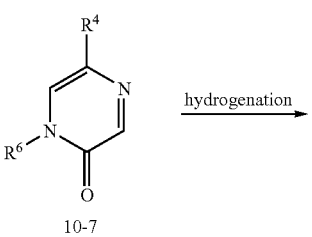

Part D:

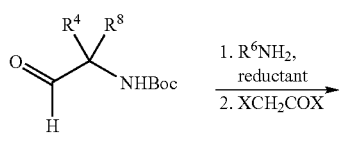

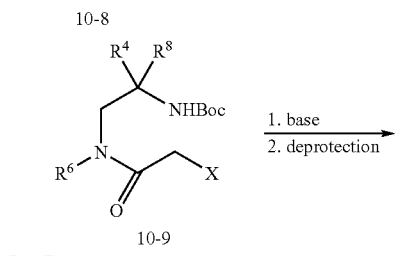

Part E:

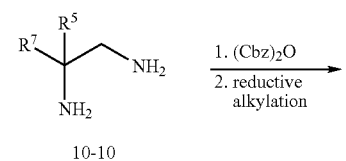

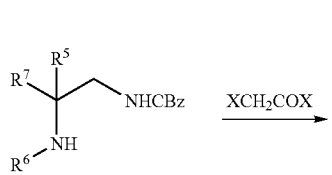

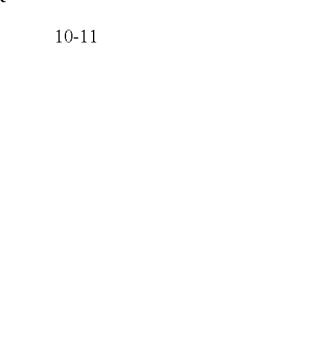

Part F:

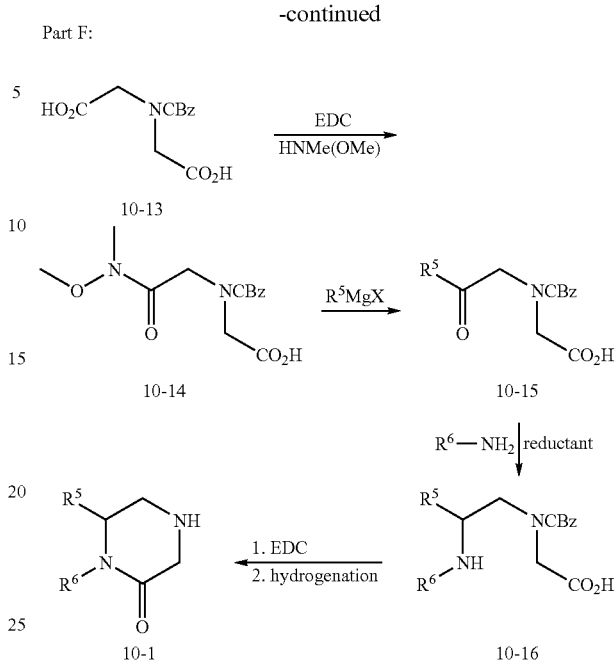

The following examples serve only to illustrate the invention and its practice. The examples are not to be construed as limitations on the scope or spirit of the invention.

EXAMPLE 1

8-(3-Chloro-4-fluorobenzyl)-10-hydroxy-2-methyl-3,4,7,8-tetrahydropyrido-[3',4':4,5]pyrrolo[1,2-a]pyrazine-1,9(2H,6H)-dione

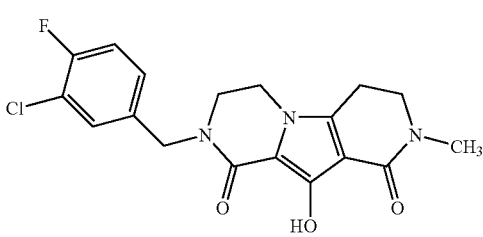

Step 1: tert-Butyl 4-(3-chloro-4-fluorobenzyl)-3-oxopiperazine-1-carboxylate

To a cold (0° C.) suspension of tert-butyl 3-oxopiperazine-1-carboxylate (2.0 g, 9.99 mmol) in DMF (20 mL) under an atmosphere of nitrogen, a solution of lithium bis(trimethylsilyl)amide in THF (10.69 mL, 10.69 mmol) was added and stirred at the temperature for 30 min. The resultant clear red brown solution was treated with 3-chloro-4-fluorobenzyl bromide (2.34 mL, 10.49 mmol), and stirred at 0° C. for 2 hours. The product mixture was concentrated under vacuum, and the residue partitioned between water and ethyl acetate. The organic extract was washed successively with 5% aq $KHSO_4$, sat. $NaHCO_3$, and brine. The organic fraction was dried over anhydrous magnesium sulfate, filtered, and concentrated under vacuum. The residue was subjected to column chromatography on silica gel eluting with a 0-100% gradient of ethyl acetate in hexane. Collection and concentration of appropriate fractions provided the benzylated product.

$^1$H NMR (400 MHz, CDCl$_3$) δ 7.32 (dd, J=6.7, 1.8 Hz, 1H), 7.17-7.09 (m, 2H), 4.55 (s, 2H), 4.16 (s, 2H), 3.61 (t, J=5.3 Hz, 2H), 3.27 (t, J=5.3 Hz, 2H), 1.47 (s, 9H).

Step 2: 1-(3-Chloro-4-fluorobenzyl)piperazin-2-one

To a cold (0° C.) solution of tert-butyl 4-(3-chloro-4-fluorobenzyl)-3-oxopiperazine-1-carboxylate (3.3 g, 9.63 mmol) in ethyl acetate (150 mL), anhydrous hydrogen chloride gas was bubbled for ten minutes. The resultant solution was stirred at 0° C. for 1 hour, and concentrated under vacuum. The residue was treated with chloroform saturated with ammonia gas. The resultant white suspension was stirred at room temperature for 15 minutes and filtered through a pad of Celite. The filtrate was concentrated under vacuum. The residue was redissolved in benzene, filtered, and concentrated under vacuum to provide the title piperazinone as pale yellow viscous oil.

$^1$H NMR (400 MHz, CDCl$_3$) δ 7.36 (s, 1H), 7.32 (dd, J=6.9, 2.2 Hz, 1H), 7.18-7.08 (m, 2H), 4.54 (s, 2H), 3.61 (s, 2H), 3.23 (t, J=5.3 Hz, 2H), 3.06 (t, J=5.3 Hz, 2H).

ES MS M+1=243

Step 3: Ethyl 3-[N-(3-ethoxy-3-oxopropyl)-N-methylamino]-3-oxopropanoate

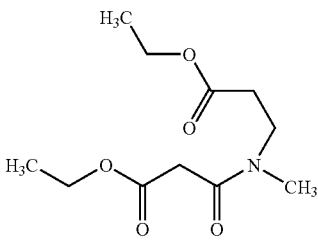

To a cold (0° C.) solution of methylamine in ethanol (400 mL; 33% wt), ethyl acrylate (39.7 g, 0.397 mol) was added over a period of 20 minutes. The reaction mixture was stirred at 0° C. for 2 hours, and concentrated under vacuum. The crude product was used without further purification. The above crude product (21.8 g, 0.166 mol), diisopropylethylamine (28.9 mL, 0.166 mol), and 4-(N,N-dimethylamino) pyridine (2 g, 16 mmol) was dissolved in dichloromethane (300 mL) and cooled to 0° C. The mixture was treated with ethyl 3-chloro-3-oxopropionate (21.3 mL, 0.166 mol) and stirred at 0° C. for one hour. The mixture was allowed to warm up to room temperature and stirred overnight. The reaction mixture was partitioned with aq HCl (400 mL, 1M). The organic extract was washed with brine, dried over anhydrous magnesium sulfate, filtered, and concentrated under vacuum to provide the title compound as yellow oil

ES MS M+1=246

Step 4: Ethyl 4-methoxy-1-methyl-2-oxo-1,2,5,6-tetrahydropyridine-3-carboxylate

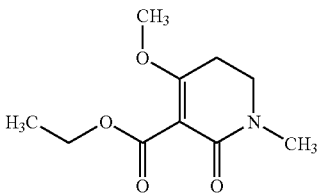

To a solution of sodium ethoxide in ethanol at 0° C. under an atmosphere of nitrogen [prepared by dissolving sodium metal (8.34 g, 0.36 mol) in absolute ethanol (150 mL)], a solution of ethyl 3-[N-(3-ethoxy-3-oxopropyl)-N-methylamino]-3-oxo-propanoate (89.0 g, 0.36 mol) in ethanol (500 mL) was added over a period of 45 minutes. The resultant solution was stirred at 0° C. for one hour. The mixture was allowed to warm up to room temperature and stirred overnight. The reaction mixture was concentrated under vacuum, and the residue partitioned between dichloromethane and 2M aq HCl. The organic extract was washed with brine, dried over anhydrous magnesium sulfate, filtered, and concentrated under vacuum. The residue was subjected to column chromatography on silica gel eluting with ethyl acetate. Collection and concentration of appropriate fractions provided the cyclization product as pale yellow solid.

To a cold (0° C.) solution of the above ethyl 4-methoxy-1-methyl-2-oxo-1,2,5,6-tetrahydropyridine-3-carboxylate (5.0 g, 25 mmol) in THF (100 mL), an ice cold solution of diazomethane in diethyl ether [prepared by addition of 1-methyl-3-nitro-1-nitrosoguanidine (13.8 g, 94 mmol) into a cold (0° C.) mixture of diethyl ether (150 mL) and 40% aq KOH (100 mL)] was added. The resultant solution was stirred at 0° C. for two hours. The mixture was allowed to warm up to room temperature and purged with nitrogen for a half hour, and then stood at room temperature overnight. The product mixture was concentrated under vacuum, and the residue was subjected to column chromatography on silica gel eluting with ethyl acetate. Collection and concentration of appropriate fractions provided the title compound as pale yellow solid.

$^1$H NMR (400 MHz, CDCl$_3$) δ 4.31 (q, J=7.1 Hz, 2H), 3.82 (s, 3H), 3.41 (t, J=7.0 Hz, 2H), 2.95 (s, 3H), 2.60 (t, J=7.0 Hz, 2H), 4.31 (t, J=7.1 Hz, 3H).

ES MS M+1=214

Step 5: 8-(3-Chloro-4-fluorobenzyl)-10-hydroxy-2-methyl-3,4,7,8-tetrahydro-pyrido-[3',4':4,5]pyrrolo[1,2-a]pyrazine-1,9(2H,6H)-dione A mixture of ethyl 4-methoxy-1-methyl-2-oxo-1,2,5,6-tetrahydropyridine-3-carboxylate (0.27 g, 1.27 mmol) and 1-(3-chloro-4-fluorobenzyl)piperazin-2-one (0.92 g, 3.80 mmol) in ethylene glycol (2.5 mL) was heated in a sealed tube at 250° C. in a microwave reactor for 20 minutes with stirring. The resultant solution was diluted with methanol (2.5 mL) and cooled to 0° C. The white solid precipitate was filtered, washed successively with cold methanol and diethyl ether, and then dried under vacuum to provide the title compound.

$^1$H NMR (400 MHz, DMSO-d$_6$) δ 8.38 (s, 1H), 7.52 (dd, J=7.3, 1.9 Hz, 1H), 7.42-7.31 (m, 2H), 4.57 (s, 2H), 3.98 (t, J=6.0 Hz, 2H), 3.55 (t, J=6.0 Hz, 2H), 3.50 (t, J=6.7 Hz, 2H), 2.89 (s, 3H), 2.83 (t, J=6.7 Hz, 2H).

ES MS M+1=378

EXAMPLE 2

2-(4-Fluorobenzyl)-10-hydroxy-3,4,7,8-tetrahydro-pyrido-[3',4':4,5]pyrrolo[1,2-a]pyrazine-1,9(2H,6H)-dione

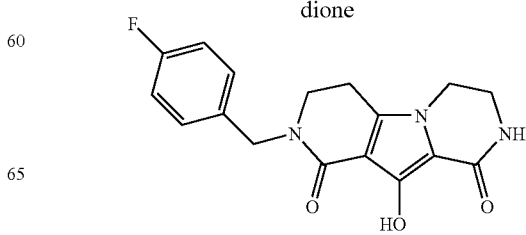

Step 1: Ethyl 3-[N-(3-ethoxy-3-oxopropyl)-N-(4-fluorobenzyl)]amino-3-oxopropanoate

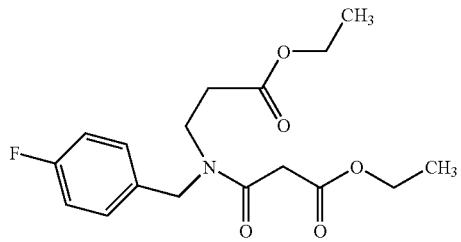

To a solution of 4-fluorobenzylamine (25.4 g, 0.20 mol) in ethanol (200 mL) at room temperature, ethyl acrylate (24.2 mL, 0.22 mol) was added. The reaction mixture was stirred at room temperature overnight and concentrated under vacuum. Residue ethanol and acrylate was removed by co-evaporation with toluene. The crude product was used without further purification. The above product (45.7 g, 0.20 mol), diisopropylethylamine (42.4 mL, 0.24 mol), and 4-(N,N-dimethylamino)pyridine (2.5 g, 20 mmol) was dissolved in dichloromethane (300 mL) and cooled to 0° C. The mixture was treated with a solution of ethyl 3-chloro-3-oxopropionate (28.7 mL, 0.22 mol) in chloroform (100 mL) and stirred at 0° C. for one hour. The mixture was allowed to warm up to room temperature and stirred overnight. The reaction mixture was partitioned with water. The organic extract was washed with brine, dried over anhydrous sodium sulfate, filtered, and concentrated under vacuum. The residue was subjected to column chromatography on silica gel eluting with 35% ethyl acetate in hexane. Collection and concentration of appropriate fractions provided title compound as yellow viscous oil

ES MS M+1=340

Step 2: Ethyl 1-(4-fluorobenzyl)-2-oxo-4-{[(trifluoromethyl)sulfonyl]oxy}-1,2,5,6-tetrahydropyridine-3-carboxylate

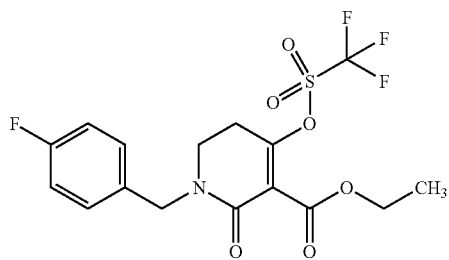

To a solution of sodium ethoxide (3.75 g, 55 mmol) in ethanol (120 mL) at 0° C. under an atmosphere of nitrogen, a solution of ethyl 3-[N-(3-ethoxy-3-oxopropyl)-N-(4-fluorobenzyl)]amino-3-oxopropanoate (17.8 g, 52 mol) in ethanol (50 mL) was added over a period of 15 minutes. The resultant solution was stirred at room temperature for two hours. The reaction mixture was concentrated under vacuum to about 100 mL, and was treated with diethyl ether (25 mL). The white precipitate was collected by filtration, washed with a cold mixture of EtOH and ether, 1:2 v/v, and air dried. The solid was partitioned between dichloromethane and 1M aq HCl. The organic extract was washed with brine, dried over anhydrous magnesium sulfate, filtered, and concentrated under vacuum. The residue was dissolved in toluene and concentrated to remove residual water. The resultant product was used without further purification.

To a cold (−78° C.) solution of the above ethyl 4-hydroxy-1-(4-fluorobenzyl)-2-oxo-1,2,5,6-tetrahydropyridine-3-carboxylate (1 g, 3.4 mmol) and diisopropylethylamine (0.71 mL, 4.1 mmol) in dichloromethane (40 mL), trifluoromethanesulfonic anhydride (0.63 mL, 3.7 mmol) was added over a period of 15 minutes. The resultant solution was allowed to warm up slowly to room temperature and stirred overnight. The mixture was diluted with dichloromethane (150 mL) and washed with cold (0° C.) deionized water. The organic extract was dried with anhydrous sodium sulfate, filtered, and concentrated under vacuum to provide the title compound as dark brown oil, which was used immediately in the following step.

Step 3: 2-(4-Fluorobenzyl)-10-hydroxy-3,4,7,8-tetrahydropyrido-[3',4':4,5]-pyrrolo[1,2-a]pyrazine-1,9(2H,6H)-dione A mixture of ethyl 1-(4-fluorobenzyl)-2-oxo-4-{[(trifluoromethyl)-sulfonyl]oxy}-1,2,5,6-tetrahydropyridine-3-carboxylate (0.67 g, 1.58 mmol) and piperazin-2-one (0.63 g, 6.3 mmol) was heated in a sealed tube at 180° C. in a microwave reactor for 10 minutes with stirring. The resultant solution was diluted with methanol and was subjected to HPLC purification on C-18 stationary phase eluted with water/acetonitrile/TFA mobile phase. Collection and lyophilization of appropriate fractions provided a semi-purified sample of title compound. Further purification of the product was achieved through formation of the corresponding tosylate. To a solution of the semipurified product (0.1 g, 0.30 mmol) and triethylamine (63 µL, 0.46 mmol) in dichloromethane (2 mL) at room temperature, toluenesulfonyl chloride (58 mg, 0.30 mmol) was added. The resultant solution was stirred at room temperature for two hours. The product was isolated and purified. A solution of the resultant tosylate (30 mg, 0.06 mmol) and sodium methoxide (10 mg, 0.18 mmol) in anhydrous methanol (0.5 mL) was heated at 60° C. for 1 hour. The resultant solution was concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, CDCl$_3$) δ7.47 (br s, 1H), 7.28 (dd, J=8.4, 5.3 Hz, 2H), 7.16 (t, J=8.6 Hz, 2H), 4.63 (s, 2H), 3.93 (br s, 2H), 3.68 (br s, 2H), 3.51 (t, J=7.0 Hz, 2H), 2.81 (t, J=7.0 Hz, 2H).

ES MS M+1=330

EXAMPLE 3

8-(4-Fluorobenzyl)-10-hydroxy-2,4-dimethyl-7,8-dihydropyrido-[3',4':4,5]pyrrolo[1,2-a]pyrazine-1,9(2H,6H)-dione

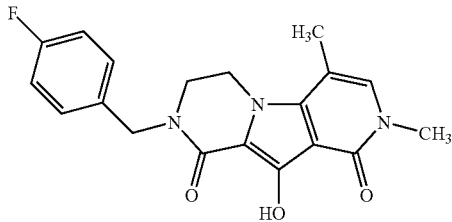

Step 1: N-(2,2-Dimethoxyethyl)-N-(4-fluorobenzyl)amine

A mixture of 4-fluorobenzaldehyde (227.6 g, 1.83 mol) and dimethoxy-ethylamine (192.6 g, 1.83 mol) in methanol (2.5 L) was heated at 65° C. for 1.5 h. The solution was allowed to cool to room temperature overnight and treated with sodium borohydride (47.6 g 1.26 mol) in portions over a period of 2 h. The resultant mixture was stirred at room temperature for 3 h and quenched with water (1 L). The product mixture was concentrated to about 1 L and extracted with diethyl ether (3×). The ethereal extracts were combined, washed with brine, dried over anhydrous sodium sulfate, filtered, and concentrated under vacuum to provide the title compound as yellow oil.

$^1$H NMR (400 MHz, CDCl$_3$) δ 7.28 (dd, J=5.5, 8.6 Hz, 2H), 7.00 (t, J=6.8 Hz, 2H), 4.48 (t, J=5.5 Hz, 1H), 3.77 (s, 2H), 3.37 (s, 6H), 2.73 (d, J=5.5 Hz, 2H).

ES MS M+1=214

Step 2: N$^2$-Benzyloxycarbonyl-N$^1$-(2,2-dimethoxyethyl)-N$^1$-(4-fluorobenzyl)-glycinamide

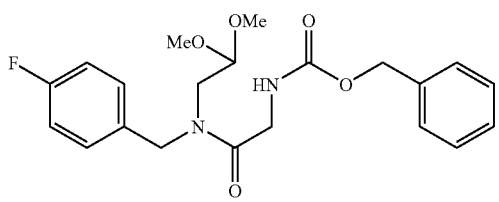

To a solution of N-(2,2-dimethoxyethyl)-N-(4-fluorobenzyl)amine (50.6 g, 237.3 mmol), N-CBZ-glycine (54.6 g, 260.8 mmol), EDC (50.0 g, 260.8 mmol), and HOBt (4.2 g, 27 mmol) in anhydrous DMF (500 mL), N,N-diisopropylethylamine (~10 mL) was added until the solution is about pH 7. The reaction mixture was stirred at room temperature overnight and concentrated under vacuum. The residue was partitioned between dichloromethane (1 L) and water (250 mL). The organic extract was washed with brine, dried over anhydrous sodium sulfate, filtered, and concentrated under vacuum to provide the title compound.

ES MS M-OCH$_3$=374

Step 3: 4-Benzyloxycarbonyl-1-(4-fluorobenzyl)-3,4-dihydropyrazin-2(1H)-one

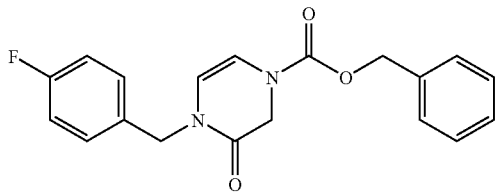

To a solution of N$^2$-benzyloxycarbonyl-N$^1$-(2,2-dimethoxyethyl)-N$^1$-(4-fluorobenzyl)glycinamide (61.5 g, 152 mmol) and p-toluenesulfonic acid monohydrate (3 g) in toluene (450 mL) was stirred at 75° C. for 5 days. Each day an additional 3 g of toluenesulfonic acid was added. The resultant reaction mixture was cooled to room temperature and filtered through a pad of Celite. The filtrate was concentrated under vacuum, and the residue dissolved in dichloromethane. The organic solution was washed successively with saturated aqueous sodium bicarbonate, brine, dried over anhydrous sodium sulfate, filtered, and concentrated under vacuum. The residual solid was subjected to column chromatography on silica gel eluting with dichloromethane and then 5% ethyl acetate in dichloromethane. Appropriate fractions were collected and concentrated under vacuum. Residual ethyl acetate and dichloromethane was removed by co-evaporation with toluene for 3 time for subsequent hydrogenation. The residue was triturated with hexane, and filtered to provide the cyclization product as an off-white solid.

$^1$H NMR (400 MHz, CDCl$_3$) δ 7.37 (br s, 5H), 7.23 (m, 2H), 7.02 (t, J=8.6 Hz, 2H), 6.44 (d, J=6.0 Hz, 1/2H), 6.32 (d, J=6.0 Hz, 1/2H), 5.53 (d, J=6.0 Hz, 1/2H), 5.42 (d, J=6.0 Hz, 1/2H), 5.21 (s, 2H), 4.65 (s, 2H), 4.38 (s, 2H).

ES MS M+1=341

Step 4: 1-(4-Fluorobenzyl)piperazin-2-one

A mixture of 4-benzyloxycarbonyl-1-(4-fluorobenzyl)-3,4-dihydro-pyrazin-2(1H)-one (0.5 g, 1.45 mmol) and Pearlman's catalyst (26 mg; 20% palladium hydroxide on carbon) in methanol (25 mL) was stirred under an atmosphere of hydrogen (1 atm) at room temperature overnight. The product mixture was filtered through a pad of Celite, and concentrated under vacuum to provide 1-(4-fluorobenzyl)piperazin-2-one.

$^1$H NMR (400 MHz, d$_6$ DMSO) δ 7.29 (dd, J=8.4, 5.7 Hz, 2H), 7.16 (t, J=9.0 Hz, 2H), 4.48 (s, 2H), 3.28 (s, 2H), 3.14 (t, J=5.3 Hz, 2H), 2.84 (t, J=5.3 Hz, 2H).

ES MS M+1=209

Step 5: Ethyl 2-(4-fluorobenzyl)-8-hydroxy-1-oxo-1,2,3,4-tetrahydropyrrolo[1,2-a]-pyrazine-7-carboxylate

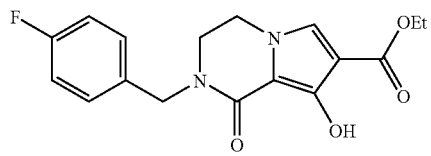

A mixture of 1-(4-fluorobenzyl)piperazin-2-one (10.0 g, 48.0 mmol) and diethyl ethoxymethylenemalonate (10.9 g, 50.4 mmol) in toluene (250 mL) was heated in a sealed tube at 80° C. for 4 hours. The resultant mixture was concentrated under vacuum. The residue was dissolved in anhydrous DMF (350 mL), cooled to 0° C. under an atmosphere of nitrogen, and treated with a solution of lithium bis(trimethylsilyl)amide in THF (1 M, 57.4 mL, 57.4 mmol). The reaction mixture was stirred at room temperature overnight and concentrated under vacuum. The residue was partitioned between ethyl acetate and dilute aqueous HCl. The organic extract was washed with brine, dried over anhydrous magnesium sulfate, filtered, and concentrated under vacuum. The residue was triturated with diethyl ether, and the solid precipitated was filtered to provide the title compound.

¹H NR (400 MHz, DMSO-d₆) δ 8.54 (s, 1H), 7.40 (dd, J=8.3, 5.8 Hz, 2H), 7.36 (s, 1H), 7.17 (t, J=8.3 Hz, 2H), 4.59 (s, 2H), 4.18 (q, J=7.1 Hz, 2H), 4.01 (t, J=5.3 Hz, 2H), 3.53 (t, J=5.3 Hz, 2H), 1.24 (t, J=7.1 Hz, 3H).

ES MS M+1=333

Step 6: 2-(4-Fluorobenzyl)-8-hydroxy-N-methyl-1-oxo-1,2,3,4-tetrahydro-pyrrolo[1,2-a]pyrazine-7-carboxamide

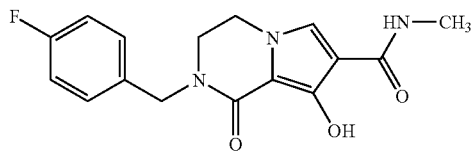

Anhydrous methylamine gas was bubbled through a mixture of ethyl 2-(4-fluorobenzyl)-8-hydroxy-1-oxo-1,2,3,4-tetrahydropyrrolo[1,2-a]pyrazine-7-carboxylate (3.0 g, 9.0 mmol) and anhydrous aluminum chloride (3.0 g, 22.5 mmol) in anhydrous chloroform (45 mL) at 0° C. for 5 minutes. The resultant mixture was heated in a seal tube at 70° C. overnight and concentrated under vacuum. The residue partitioned between aqueous HCl and chloroform. The organic extract was dried over anhydrous magnesium sulfate, filtered, and concentrated under vacuum to provide the title compound.

¹H NMR (400 MHz, DMSO-d₆) δ 7.71 (br q, J=4.6, 1H), 7.35 (dd, J=8.6, 5.7 Hz, 2H), 7.24 (s, 1H), 7.17 (t, J=8.6 Hz, 2H), 4.59 (s, 2H), 4.07 (t, J=5.3 Hz, 2H), 3.50 (t, J=5.3 Hz, 2H), 2.74 (s, 3H).

ES MS M+1=318

Step 7: 6-Bromo-2-(4-fluorobenzyl)-8-benzyloxy-N-methyl-1-oxo-1,2,3,4-tetrahydro-pyrrolo[1,2-a]pyrazine-7-carboxamide

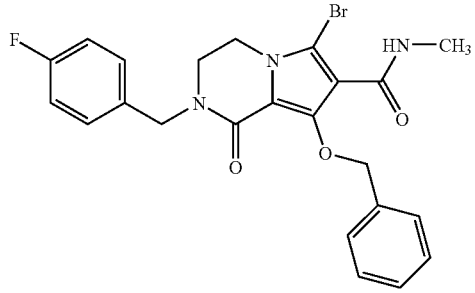

To a mixture of 2-(4-fluorobenzyl)-8-hydroxy-N-methyl-1-oxo-1,2,3,4-tetrahydro-pyrrolo[1,2-a]pyrazine-7-carboxamide (0.30 g, 0.95 mmol) and sodium carbonate (0.24 g, 2.84 mmol) in dichloromethane (10 mL) at room temperature, a solution of bromine in dichloromethane was added (0.95 mmol). The reaction mixture was stirred at room temperature for 30 minutes, filtered, and concentrated under vacuum to provide the bromination product.

¹H NMR (400 MHz, DMSO-d₆) δ 9.01 (br s, 1H), 7.30 (dd, J=8.6, 5.7 Hz, 2H), 7.03 (t, J=8.6 Hz, 2H), 4.69 (br s, 2H), 4.05 (br s, 2H), 3.59 (br s, 2H), 2.99 (s, 3H).

ES MS M+1=396, 398 (1:1)

A mixture of the above bromination product (1.1 g, 2.8 mmol), cesium carbonate (0.57 g, 3.3 mmol), and benzyl bromide (0.57 g, 3.3 mmol) in DMF (5 mL) was stirred at room temperature overnight. The reaction mixture was concentrated under vacuum and the residue was partitioned between dichloromethane and dilute aqueous HCl. The organic extract was washed with brine, dried over anhydrous magnesium sulfate, filtered, and concentrated under vacuum. The residue was subjected to column chromatography on silica gel eluting with ethyl acetate in hexane. Appropriate fractions were collected and concentrated under vacuum to provide the title compound.

ES MS M+1=486,488

Step 8: N-Alkyl-8-benzyloxy-6-bromo-2-(4-fluorobenzyl)-N-methyl-1-oxo-1,2,3,4-tetrahydro-pyrrolo[1,2-a]pyrazine-7-carboxamide

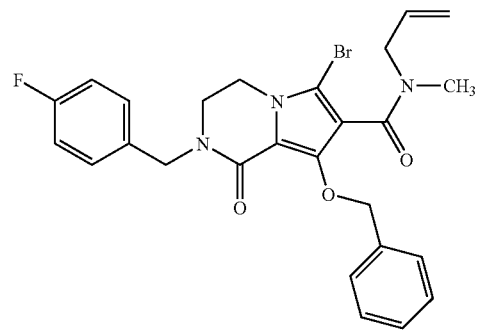

To a cold (0° C.) suspension of 6-bromo-2-(4-fluorobenzyl)-8-benzyloxy-N-methyl-1-oxo-1,2,3,4-tetrahydro-pyrrolo[1,2-a]pyrazine-7-carboxamide (0.10 g, 0.21 mmol) in DMF (4 mL) under an atmosphere of nitrogen, a solution of lithium bis(trimethylsilyl)amide in THF (1 M, 0.24 mL, 0.24 mmol) was added and stirred at the temperature for 30 min. The resultant clear red brown solution was treated with allyl bromide (0.021 mL, 0.247 mmol), and stirred at 0° C. for 3 hours. The product mixture was concentrated under vacuum, and the residue partitioned between water and dichloromethane. The organic extract was washed successively with 5% aq KHSO₄, sat. NaHCO₃, and brine. The organic fraction was dried over anhydrous sodium sulfate, filtered, and concentrated under vacuum. The residue was subjected to column chromatography on silica gel eluting with a 0-100% gradient of ethyl acetate in hexane. Collection and concentration of appropriate fractions provided the alkylation product.

ES MS M+1=526,528

Step 9: 8-(4-Fluorobenzyl)-10-benzyloxy-2,4-dimethyl-7,8-dihydropyrido-[3',4':4,5]pyrrolo[1,2-a]pyrazine-1,9(2H, 6H)-dione

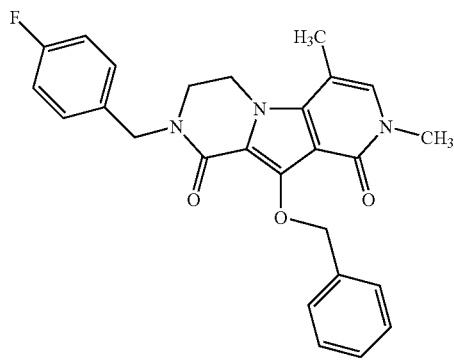

To mixture of N-alkyl-8-benzyloxy-6-bromo-2-(4-fluorobenzyl)-N-methyl-1-oxo-1,2,3,4-tetrahydro-pyrrolo[1,2-a]pyrazine-7-carboxamide (80 mg, 0.15 mmol) and N-dicyclohexyl-N-methylamine (45 mg, 0.23 mmol) in dioxane (4 mL) purged with nitrogen, Pd$_2$(dba)$_3$ (14 mg, 0.015 mmol), and tri-tert-butylphosphine (6 mg, 0.03 mmol) were added. The reaction mixture was stirred at room temperature for 36 hours. The reaction mixture was filtered through a pad of Celite, and the filtrate concentrated under vacuum. The residue was partitioned between water and dichloromethane. The organic extract was washed successively with aq HCl and brine. The organic fraction was dried over anhydrous sodium sulfate, filtered, and concentrated under vacuum. The residue was subjected to column chromatography on silica gel eluting with a 0-100% gradient of ethyl acetate in hexane. Collection and concentration of appropriate fractions provided the cyclization product.

$^1$H NMR (400 MHz, CDCl$_3$) δ7.72 (d, J=7.5, 2H), 7.36-7.26 (m, 5H), 7.01 (t, J=8.6 Hz, 2H), 6.74 (s, 1H), 5.47 (s, 2H), 4.71 (s, 2H), 4.32 (t, J=5.5 Hz, 2H), 3.50 (s, 3H), 3.49 (t, J=5.4 Hz, 2H), 2.28 (s, 3H).

ES MS M+1=446

Step 10: 8-(4-Fluorobenzyl)-10-hydroxy-2,4-dimethyl-7,8-dihydropyrido-[3',4':4,5]pyrrolo[1,2-a]pyrazine-1,9(2H,6H)-dione A mixture of 8-(4-fluorobenzyl)-10-benzyloxy-2,4-dimethyl-7,8-dihydropyrido-[3',4':4,5]pyrrolo[1,2-a]pyrazine-1,9(2H,6H)-dione (27 mg, 0.06 mmol) and Pearlman's catalyst (2.5 mg, 20% Pd(OH)$_2$ on carbon) in ethanol (5 mL) was stirred under an atmosphere of hydrogen gas (1 atm) at room temperature for 1 hr. The reaction product precipitated out of solution. The suspension was treated with chloroform, and the mixture was filtered through a pad of Celite. The filtrate was concentrated under vacuum, and the residue recrystallized from ethanol to provide the title product.

$^1$H NMR (400 MHz, CDCl$_3$) δ8.58 (s, 1H), 7.32 (dd, J=8.5, 5.3 Hz, 1H), 7.03 (t, J=8.6 Hz, 2H), 6.73 (s, 1H), 4.69 (s, 2H), 4.31 (t, J=5.4 Hz, 2H), 3.55 (t, J=5.4 Hz, 2H), 3.48 (s, 3H), 2.27 (s, 3H).

ES MS M+1=356

EXAMPLE 4

8-(4-Fluorobenzyl)-10-hydroxy-6-{2-[methoxy(methyl)amino]ethyl}-2-methyl-3,4,7,8-tetrahydropyrido-[3',4':4,5]pyrrolo[1,2-a]pyrazine-1,9(2H,6H)-dione

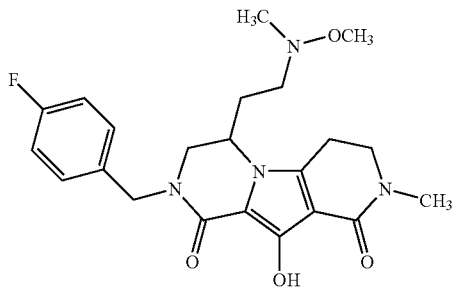

Step 1: Methyl N-(4-fluorobenzyl)glycinate

To a solution of methyl bromoacetate (24.0 mL, 253.5 mmol) in anhydrous THF (264 mL) was added triethylamine (35.34 mL, 253.5 mmol). The cloudy mixture was treated rapidly with 4-fluorobenzylamine (30.3 mL, 263.7 mmol), and the resulting viscous mixture was stirred at ambient temperature under inert atmosphere for 18 h. TH was removed in vacuo, and the residue was suspended in diethyl ether. The mixture was filtered and the solids washed with excess diethyl ether. Concentration of the filtrate in vacuo afforded the product as a light yellow oil.

$^1$H NMR (400 MHz, CDCl$_3$) δ 7.31-7.27 (m, 2H), 7.04-6.99 (m, 2H), 3.77 (s, 2H), 3.74 (s, 3H), 3.41 (s, 2H), 1.82 (br s, 1H).

Step 2: Methyl N-(tert-butoxycarbonyl)-N-(4-fluorobenzyl)glycinate

To a solution of methyl N-(4-fluorobenzyl)glycinate (46.0 g, 233.3 mmol) in CH$_2$Cl$_2$ (350 mL) were added 4-dimethylaminopyridine (2.85 g, 23.33 mmol) and triethylamine (42.3 mL, 303.2 mmol). The solution was then treated with 1 M di-tert-butyl dicarbonate in THF (279.9 mL, 279.9 mmol), and the reaction was stirred at ambient temperature in a closed atmosphere for 18 h. The solvent was removed in vacuo, and the resulting residue was purified by silica gel chromatography using gradient elution (10% EtOAc/hexanes to 50% EtOc/hexanes) to afford the product as a light yellow oil.

$^1$H NMR (400 MHz, CDCl$_3$) δ 7.25-7.18 (m, 2H), 7.03-6.99 (m, 2H), 4.48 (d, J=14.4 Hz, 2H), 3.92 (s, 1H), 3.78 (s, 1H), 3.70 (s, 3H), 1.47 (d, J=2.4 Hz, 9H).

LCMS (M+1-100, for loss of BOC group)=198.0

Step 3: N-(tert-Butoxycarbonyl)-N-(4-fluorobenzyl)glycine

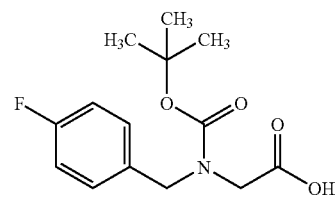

To a solution of methyl N-(tert-butoxycarbonyl)-N-(4-fluorobenzyl)glycinate (12.37 g, 41.63 mmol) in MeOH (180 mL) was added 5 N aqueous NaOH solution (18.32 mL, 91.58 mmol). The reaction was stirred under inert atmosphere at ambient temperature for 2 h. The solvent was removed in vacuo, and the remaining residue was taken up in water and washed twice with CHCl$_3$. The aqueous layer was cooled to 0° C., acidified to pH 2 with 1 N aqueous HCl solution, and saturated with NaCl. The mixture was extracted with EtOAc three times, and the organic layers were dried (MgSO$_4$) and concentrated in vacuo to afford the acid as a light yellow oil.

¹H NMR (400 MHz, CDCl₃) δ 7.26-7.23 (m, 2H), 7.03 (br s, 2H), 4.50 (d, J=13.6 Hz, 2H), 3.96 (br s, 1H), 3.83 (br s, 1H), 1.49 (s, 9H).

LCMS (M+1)=284.2

Step 4: tert-Butyl 2-(4-fluorobenzyl)-4-[methoxy(methyl) amino]-4-oxobutanoate

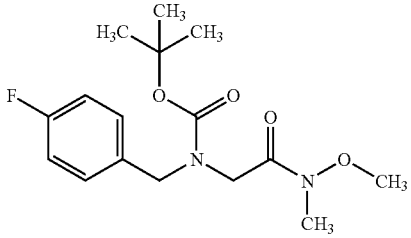

To a stirred solution of N-(tert-butoxycarbonyl)-N-(4-fluorobenzyl)glycine (10.52 g, 37.15 mmol) in CH₂Cl₂ (37 mL) was added N,O-dimethylhydroxylamine hydrochloride (3.62 g, 37.15 mmol). The resulting suspension was treated with N-methylmorpholine (4.08 mL, 37.15 mmol) and cooled to 0° C. Following treatment with 1 M N,N'-dicyclohexylcarbodiimide in CH₂Cl₂ (37.15 mL, 37.15 mmol), the reaction was allowed to warm to ambient temperature under inert atmosphere. After stirring for 66 h, the mixture was filtered and the solids washed with excess CH₂Cl₂. The filtrate was concentrated in vacuo and resuspended in EtOAc. After stirring for 1 h, the mixture was filtered and the solids washed with excess EtOAc, and the filtrate was again concentrated in vacuo to give an orange oil. Purification by silica gel chromatography using gradient elution (20% to 60% EtOAc/hexanes) afforded the Weinreb amide as a colorless oil.

¹H NMR (400 MHz, CDCl₃) δ 7.27-7.20 (m, 2H), 7.03-7.01 (m, 2H), 4.52 (d, J=13.6 Hz, 2H), 4.09 (s, 1H), 3.95 (s, 1H), 3.63 (d, J=20.4 Hz, 3H), 3.18 (s, 3H), 1.47 (s, 9H).

LCMS (M+1)=327.2

Step 5: tert-Butyl 4-fluorobenzyl {4-[methoxy(methyl) amino]-2-oxobutyl}-carbamate

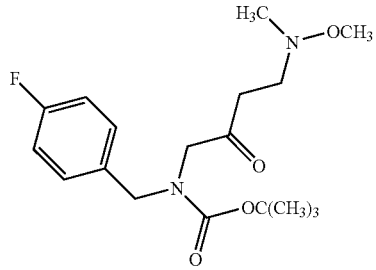

tert-Butyl 2-(4-fluorobenzyl)-4-[methoxy(methyl) amino]-4-oxobutanoate (4.91 g, 15.04 mmol) was azeotroped with anhydrous toluene (2×10 mL) and dissolved in anhydrous THF (25 mL). The solution was cooled to 0° C. and treated rapidly with 1 M vinyl magnesium bromide in THF (18.04 mL, 18.04 mmol). After stirring at 0° C. for 10 min, the reaction was allowed to warm to ambient temperature over 1 h and treated with water (18 mL). The mixture was stirred for 20 min and then partitioned between EtOAc and water. The organic layer was washed twice with water, dried (Na₂SO₄), and concentrated in vacuo to give a red oil. Purification by silica gel chromatography using gradient elution (20% to 80% EtOAc/hexanes) afforded the product as an orange oil.

¹H NMR (400 MHz, CDCl₃) δ 7.24-7.16 (m, 2H), 7.03-6.99 (m, 2H), 4.45 (d, J=17.2 Hz, 2H), 4.00 (s, 1H), 3.86 (s, 1H), 3.42 (s, 3H), 2.91-2.85 (m, 2H), 2.63-2.57 (m, 2H), 2.55 (s, 3H), 1.46 (d, J=6.4 Hz, 9H).

Step 6: Methyl N-{1-{[(tert-butoxycarbonyl)(4-fluorobenzyl)amino]methyl}-3-[methoxy(methyl)amino] propyl}glycinate

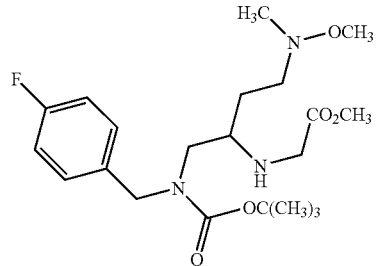

A mixture of glycine methyl ester (2.78 g, 22.14 mmol) in anhydrous THF (13.5 mL) was treated sequentially with triethylamine (3.03 mL, 21.55 mmol), a solution of tert-butyl 4-fluorobenzyl{4-[methoxy(methyl)amino]-2-oxobutyl}carbamate (1.50 g, 4.23 mmol) in anhydrous THF (8.5 mL), sodium triacetoxyborohydride (5.11 g, 24.11 mmol), and acetic acid (485 µL, 8.46 mmol). The mixture was stirred at ambient temperature under inert atmosphere for 42 h. Saturated aqueous NaHCO₃ solution was added to the reaction which was stirred until gas evolution ceased. The mixture was extracted into EtOAc, and the aqueous layer was saturated with NaCl and extracted into EtOAc again. The combined organic layers were washed with brine, dried over Na₂SO₄, and concentrated in vacuo to a pale yellow oil. Purification by silica gel chromatography using gradient elution (hexanes to 40% EtOAc/hexanes to EtOAc) afforded the amine as a colorless oil.

¹H NMR (400 MHz, CDCl₃) δ 7.19 (br s, 2H), 7.02-6.98 (m, 2H), 4.56-4.37 (m, 2H), 3.72 (s, 3H), 3.49 (s, 3H), 3.39 (br s, 2H), 3.05 (br s, 1H), 2.97 (br s, 1H), 2.66 (br s, 2H), 2.55 (s, 3H), 1.68-1.58 (m, 4H), 1.47 (br s, 9H).

LCMS (M+1)=428.4

Step 7: 1-(4-Fluorobenzyl)-5-{2-[methoxy(methyl)amino] ethyl}piperazine-2-one

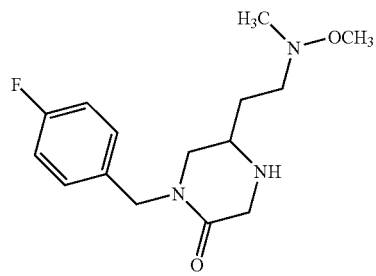

A solution of methyl N-{1-{[(tert-butoxycarbonyl)(4-fluorobenzyl)amino]methyl}-3-[methoxy(methyl)amino] propyl}glycinate (1.63 g, 3.82 mmol) in CH₂Cl₂ (41 mL) was treated with TFA (12.6 mL) at 0° C. The mixture was stirred at ambient temperature under inert atmosphere for 2 h and then concentrated in vacuo. The resulting oil was suspended in water (46 mL) and treated, portionwise, with solid $K_2CO_3$ (3.1 g). The reaction was heated to 100° C. for 30 min. After cooling to ambient temperature, the mixture was saturated with NaCl and extracted into $CH_2Cl_2$ three times. The combined organic layers were dried over $Na_2SO_4$ and concentrated in vacuo to an orange oil.

$^1$H NMR (400 MHz, CDCl$_3$) δ 7.29-7.23 (m, 2H), 7.05-6.99 (m, 2H), 4.63 (d, J=14.8 Hz, 1H), 4.47 (d, J=14.8 Hz, 1H), 3.62 (dt, J=17.2, 38.8 Hz, 2H), 3.47 (s, 3H), 3.12-3.10 (m, 1H), 3.08-2.94 (m, 2H), 2.71-2.62 (m, 2H), 2.55 (s, 3H), 1.82 (br s, 1H), 1.63 (dd, J=6.4, 12.4 Hz, 2H).

LCMS (M+1)=296.4

Step 8: 8-(4-Fluorobenzyl)-10-hydroxy-6-{2-[methoxy(methyl)amino]ethyl}-2-methyl-3,4,7,8-tetrahydropyrido-[3',4':4,5]pyrrolo[1,2-a]pyrazine-1,9(2H,6H)-dione 1-(4-Fluorobenzyl)-5-{2-[methoxy(methyl)amino]ethyl}piperazine-2-one (752 mg, 2.55 mmol) was azeotroped with anhydrous $CH_3CN$ (3×5 mL) and anhydrous toluene (3×5 mL) and dissolved in anhydrous ethylene glycol (1.7 mL) in a pressure vessel. To the solution was added ethyl 4-methoxy-1-methyl-2-oxo-1,2,5,6-tetrahydropyridine-3-carboxylate (181 mg, 0.85 mmol). The vessel was sealed under inert atmosphere, and the reaction was heated to 250° C. for 20 min under microwave reactor conditions. The reaction was cooled to ambient temperature and treated with MeOH (1.7 mL). Purification by reverse phase chromatography chromatography [95:5 water (+0.1% TFA)/CH$_3$CN (+0.1% TFA) to 5:95 water (+0.1% TFA)/CH$_3$CN (+0.1% TFA)] afforded the title compound as a light brown oil in the trifluoroacetate salt form.

$^1$H NMR (400 MHz, CDCl$_3$) δ 7.41-7.38 (m, 2H), 7.11-7.07 (m, 2H), 4.94 (d, J=14.8 Hz, 1H), 4.37-4.33 (m, 2H), 3.74 (dd, J=4.0, 13.2 Hz, 1H), 3.61 (t, J=6.8 Hz, 2H), 3.42 (s, 3H), 3.00 (s, 3H), 2.90 (t, J=6.8 Hz, 2H), 2.44 (s, 3H), 2.30-2.26 (m, 2H), 1.79-1.67 (m, 3H).

HRMS (FT/APCI) M+H: calcd for $(C_{22}H_{27}FN_4O_4)^+$ 431.2089, found 431.2068

EXAMPLES 5-15

The compounds in the following table were prepared in accordance with the procedure set forth in one of Examples 1 to 4 using the appropriate analogous starting materials.

| Example | Compound | Data |
|---|---|---|
| 5 | 8-(3,4-dichlorobenzyl)-10-hydroxy-2-methyl-3,4,7,8-tetrahydropyrido-[3',4':4,5]pyrrolo-[1,2-a]pyrazine-1,9(2H,6H)-dione<br>Prepared in the manner of Example 1. | $^1$H NMR(400MHz, DMSO-d$_6$) δ 8.39(s, 1H), 7.61(d, J=8.3Hz, 1H), 7.57(s, 1H), 7.30(d, J=8.3Hz, 1H), 4.59(s, 2H), 3.99(t, J=5.1Hz, 2H), 3.55(t, J=5.1Hz, 2H), 3.50(t, J=6.8Hz, 2H), 2.87(s, 3H), 2.83(t, J=6.8Hz, 2H). ES MS M + 1 = 394 |
| 6 | 8-(3-chlorobenzyl)-10-hydroxy-2-methyl-3,4,7,8-tetrahydropyrido-[3',4':4,5]pyrrolo[1,2-a]pyrazine-1,9(2H,6H)-dione<br>Prepared in the manner of Example 1. | $^1$H NMR(400MHz, DMSO-d$_6$) δ 8.38(br s, 1H), 7.41-7.33(m, 2H), 7.27(d, J=7.1Hz, 1H), 4.61(s, 2H), 3.98(t, J=5.3Hz, 2H), 3.54(t, J=5.3Hz, 2H), 3.50(t, J=6.8Hz, 2H), 2.87(s, 3H), 2.83(t, J=6.8Hz, 2H). ES MS M + 1 = 360 |

-continued

| Example | Compound | Data |
|---|---|---|
| 7 | 8-(4-fluorobenzyl)-10-hydroxy-2-methyl-3,4,7,8-tetra-hydropyrido-[3',4':4,5]pyrrolo[1,2-a]pyrazine-1,9(2H,6H)-dione<br><br>Prepared in the manner of Example 1, but using 1,2-dichlorobenzene in place of ethylene glycol. | $^1$H NMR(400MHz, DMSO-d$_6$) δ 8.38(s, 1H), 7.37-7.32(m, 2H), 7.20-7.15(m, 2H), 4.59(s, 2H), 3.97(t, J=5.5Hz, 2H), 3.51(t, J=5.5Hz, 2H), 3.49(t, J=6.7Hz, 2H), 2.87(s, 3H), 2.82(t, J=6.7Hz, 2H).<br>ES MS M + 1 = 344 |
| 8 | 8-(3,4-difluorobenzyl)-10-hydroxy-2-methyl-3,4,7,8-tetra-hydropyrido-[3',4':4,5]pyrrolo-[1,2-a]pyrazine-1,9(2H,6H)-dione<br><br>Prepared in the manner of Example 1. | $^1$H NMR(400MHz, DMSO-d$_6$) δ 8.38(s, 1H), 7.44-7.34(m, 2H), 7.17(br s, 1H), 4.59(s, 2H), 3.99(t, J=6.0Hz, 2H), 3.54(t, J=6.0Hz, 2H), 3.50(t, J=6.9Hz, 2H), 2.87(s, 3H), 2.83(t, J=6.9Hz, 2H).<br>ES MS M + 1 = 362 |
| 9 | 2,8-bis(4-fluorobenzyl)-10-hydroxy-3,4,7,8-tetra-hydropyrido-[3',4':4,5]pyrrolo[1,2-a]pyrazine-1,9(2H,6H)-dione<br><br>Prepared in the manner of Example 1. | $^1$H NMR(400MHz, DMSO-d$_6$) δ 7.55-7.30(m, 4H), 7.19-7.13(m, 4H), 4.59(s, 2H), 4.56(s, 2H), 3.96(t, J=5.3Hz, 2H), 3.50(t, J=5.5Hz, 2H), 3.43(t, J=7.0Hz, 2H), 2.79(t, J=7.0Hz, 2H).<br>ES MS M + 1 = 438 |
| 10 | 2-(3,4-dimethoxybenzyl)-8-(4-fluorobenzyl)-10-hydroxy-3,4,7,8-tetra-hydropyrido-[3',4':4,5]pyrrolo[1,2-a]pyrazine-1,9(2H,6H)-dione<br><br>Prepared in the manner of Example 1, but using 1,2-dichlorobenzene in place of ethylene glycol. | $^1$H NMR(400MHz, DMSO-d$_6$) δ 8.45(s, 1H), 7.35(dd, J=8.1, 5.9Hz, 1H), 7.17(t, J=8.4Hz, 2H), 6.90(t, J=8.2Hz, 1H), 6.86(s, 1H), 6.80(t, J=8.2Hz, 1H), 4.60(s, 2H), 4.50(s, 2H), 3.96(t, J=5.2Hz, 2H), 3.72(s, 6H), 3.50(t, J=5.2Hz, 2H), 3.41(t, J=6.5Hz, 2H), 2.77(t, J=6.5Hz, 2H).<br>ES MS M + 1 = 480 |

-continued

| Example | Compound | Data |
|---|---|---|
| 11 | 8-(4-fluorobenzyl)-10-hydroxy-3,4,7,8-tetrahydropyrido-[3',4':4,5]pyrrolo[1,2-a]pyrazine-1,9(2H,6H)-dione<br>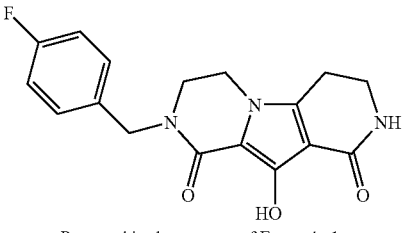<br>Prepared in the manner of Example 1. | $^1$H NMR(400MHz, DMSO-d$_6$) δ 7.35(dd, J=8.6, 6.0Hz, 2H), 7.17(t, J=9.0Hz, 2H), 7.09(br s, 1H), 4.59(s, 2H), 3.98(t, J=5.3Hz, 2H), 3.51(t, J=5.3Hz, 2H), 3.34(t, J=6.8Hz, 2H), 2.72(t, J=6.8Hz, 2H).<br>ES MS M + 1 = 330 |
| 12 | 8-(4-fluorobenzyl)-10-hydroxy-2-ethyl-3,4,7,8-tetra-hydropyrido-[3',4':4,5]pyrrolo[1,2-a]pyrazine-1,9(2H,6H)-dione<br>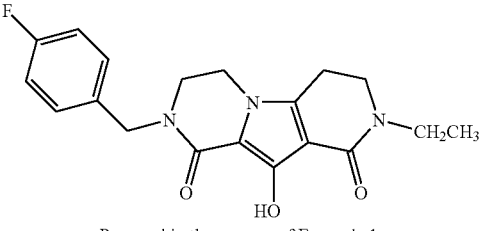<br>Prepared in the manner of Example 1. | $^1$H NMR(400MHz, DMSO-d$_6$) δ 7.35(dd, J=8.8, 5.6Hz, 2H), 7.17(t, J=9.0Hz, 2H), 4.59(s, 2H), 3.97(t, J=5.4Hz, 2H), 3.52-3.35(m, 6H), 2.80(t, J=7.0Hz, 2H), 1.05(t, J=7Hz, 3H).<br>ES MS M + 1 = 358 |
| 13 | 2-(4-fluorobenzyl)-10-hydroxy-8-methyl-3,4,7,8-tetra-hydropyrido-[3',4':4,5]pyrrolo[1,2-a]pyrazine-1,9(2H,6H)-dione<br>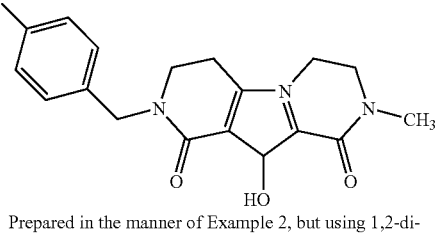<br>Prepared in the manner of Example 2, but using 1,2-dichlorobenzene in place of ethylene glycol. | $^1$H NMR(400MHz, DMSO-d$_6$) δ 8.37(br s, 1H), 7.32(dd, J=8.6, 5.8Hz, 2H), 7.15(t, J=9.0Hz, 2H), 4.55(s, 2H), 3.98(t, J=5.3Hz, 2H), 3.57(t, J=5.3Hz, 2H), 3.42(t, J=6.7Hz, 2H), 2.91(s, 3H), 2.81(t, J=6.7Hz, 2H).<br>ES MS M + 1 = 344 |
| 14 | 8-(4-fluorobenzyl)-10-hydroxy-2-methyl-7,8-tetra-hydropyrido-[3',4':4,5]pyrrolo[1,2-a]pyrazine-1,9(2H,6H)-dione<br>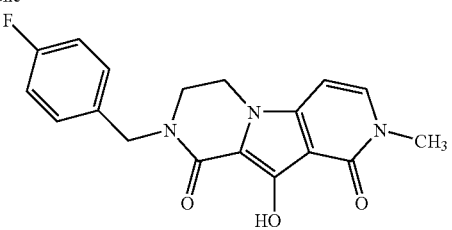<br>Isolated as a co-product of the compound prepared in Example 13. | $^1$H NMR(400MHz, DMSO-d$_6$) δ 7.42(d, J=7.5Hz, 1H), 7.38(dd, J=8.6, 5.6Hz, 2H), 7.18(t, J=9.0Hz, 2H), 6.42(d, J=7.5Hz, 1H), 4.64(s, 2H), 4.13(t, J=5.3Hz, 2H) 3.61(t, J=5.3Hz, 2H), 3.39(s, 3H).<br>ES MS M + 1 = 342 |

-continued

| Example | Compound | Data |
|---|---|---|
| 15 | 8-(4-fluorobenzyl)-10-hydroxy-7-(2-dimethylamino-2-oxo-ethyl)-2-methyl-3,4,7,8-tetrahydropyrido-[3',4':4,5]pyrrolo[1,2-a]pyrazine-1,9(2H,6H)-dione<br><br>[Structure with F-phenyl-CH2-N ring system, N(CH3)2 amide, HO, and N-CH3]<br><br>Prepared in the manner of Example 4, but using 1,2-dichlorobenzene in place of ethylene glycol. | $^1$H NMR(400MHz, DMSO-d$_6$) δ 7.35(dd, J=8.4, 5.7Hz, 2H), 7.17(t, J=8.8Hz, 2H), 5.08(d, J=15.2Hz, 1H), 4.13(d, J=15.2Hz, 1H), 4.04-3.85(m, 3H), 3.49(t, J=7.0Hz, 2H), 2.87(s, 3H), 2.82(s, 3H), 2.79(s, 3H), 2.53(m, 2H). ES MS M + 1 = 429 |

EXAMPLES 16-22

The compounds in the following table were prepared in accordance with the procedure set forth in one of Examples 1 to 4 using the appropriate analogous starting materials.

| Example | Compound | Data |
|---|---|---|
| 16 | 2-(4-Fluorobenzyl)-10-hydroxy-7-(2-dimethylamino-2-oxo-ethyl)-8-methyl-3,4,7,8-tetrahydropyrido-[3',4':4,5]pyrrolo[1,2-a]pyrazine-1,9(2H,6H)-dione<br><br>[Structure with F-phenyl-CH2-N ring system, (H3C)2N amide, HO, and N-CH3]<br><br>Prepared in the manner of Example 4, but using 1,2-dichlorobenzene in place of ethylene glycol. | $^1$H NMR(400MHz, DMSO-d$_6$) δ 7.34(dd, J=8.4, 5.7Hz, 2H), 7.16(t, J=8.8Hz, 2H), 4.55(m, 2H), 4.14-3.95(m, 3H), 3.61(t, J=7.0Hz, 2H), 3.18(d, 2H), 2.92(s, 3H), 2.88(s, 3H), 2.82(s, 3H). ES MS M + 1 = 429 |
| 17 | 9-(4-Fluorobenzyl)-7-hydroxy-10,11-dihydropyrido-[3',4':4,5]pyrrolo[1,2-a]quinoxaline-6,8(5H,9H)-dione<br><br>[Structure with F-phenyl-CH2-N, fused pyrrolo-quinoxaline, HO, NH]<br><br>Prepared in the manner of Example 4, but reacting 3,4-dihydroquinoxalin-2(1H)-one in 1,2-dichlorobenzene. | $^1$H NMR(400MHz, DMSO-d$_6$) δ 10.91(s, 1H), 8.84(s, 1H), 7.73(d, J=8.3Hz, 1H), 7.39(dd, J=8.6, 5.6Hz, 2H), 7.18(m, 5H), 4.67(s, 2H), 3.57(t, J=6.7Hz, 2H) 3.47(t, J=6.7Hz, 2H). ES MS M + 1 = 378 |

| Example | Compound | Data |
|---|---|---|
| 18 | 2-Chloro-9-(4-fluorobenzyl)-7-hydroxy-10,11-di-hydropyrido-[3',4':4,5]pyrrolo[1,2-a]quinoxaline-6,8(5H,9H)-dione | $^1$H NMR(400MHz, DMSO-d$_6$) δ 11.01(br s, 1H), 8.91(br s, 1H), 7.66(d, J=2.0Hz, 1H), 7.38(dd, J=8.6, 5.6Hz, 2H), 7.32(dd, J=8.6, 2.0Hz, 1H), 7.19(m, 3H), 4.67(s, 2H), 3.57(t, J=6.5Hz, 2H) 3.48(t, J=6.4Hz, 2H). ES MS M + 1 = 412 |
| 19 | 9-(4-Fluorobenzyl)-7-hydroxy-5-methyl-10,11-di-hydropyrido-[3',4':4,5]pyrrolo[1,2-a]quinoxaline-6,8(5H,9H)-dione | $^1$H NMR(400MHz, DMSO-d$_6$) δ 8.9(br s, 1H), 7.77(d, J=7.7Hz, 1H), 7.41(m, 4H), 7.20(m, 3H), 4.63(s, 2H), 3.57(t, J=6.7Hz, 2H) 3.46(m, 5H). ES MS M + 1 = 392 |
| 20 | 8-Ethyl-2-(4-fluorobenzyl)-10-hydroxy-6-methyl-3,4,7,8-tetra-hydropyrido-[3',4':4,5]pyrrolo[1,2-a]pyrazine-1,9(2H,6H)-dione | $^1$H NMR(400MHz, DMSO-d$_6$) δ 7.33(dd, J=5.5, 8.2Hz, 2H), 7.15(t, J=8.6Hz, 2H), 4.58(d, J=15.0Hz, 1H), 4.50(d, J=15.0Hz, 1H), 4.45(m, 1H), 3.75(m, 1H), 3.58-3.22(m, 5H), 2.84(m, 2H), 1.23(d, J=6.6Hz, 3H), 1.08(t, J=7.2Hz, 3H). ES MS M + 1 = 372 |
| | Prepared in the manner of Example 4, but using 1-ethyl-5-methylpiperazin-2-one (Yahiro et al, Bull. Chem. Soc. Jpn, 321—322, 1986) and 1,2-dichlorobenzene in place of ethylene glycol.<br>The racemic title product was separated into enantiomers. The enantiomer with 6(S)-Me stereochemistry was found to be more active. The absolute chemistry was confirmed by using the optically active piperazinone prepared according to the chemistry described in Example 45 starting with L-N-Boc-alanine. | |
| 21 | 8-Ethyl-2-(3-chloro-4-fluorobenzyl)-10-hydroxy-6-methyl-3,4,7,8-tetra-hydropyrido-[3',4':4,5]pyrrolo[1,2-a]pyrazine-1,9(2H,6H)-dione | $^1$H NMR(400MHz, DMSO-d$_6$) δ 7.49(dd, J=7.1, 1.8Hz, 1H), 7.38(t, J=8.9Hz, 1H), 7.32(m, 1H), 4.54(q, J=15.6Hz, 2H), 4.45(t, J=4.4Hz, 1H), 3.75(dd, J=12.9, 3.9Hz, 1H), 3.49(m, 3H), 3.31(m, 2H), 2.86(m, 2H), 1.24(d, J=6.5Hz, 3H), 1.08(t, J=7.1Hz, 3H). ES MS M + 1 = 406 |
| | The racemic title product was separated into enantiomers. The enantiomer with up-Me stereochemistry was found to be more active. | |

-continued

| Example | Compound | Data |
|---|---|---|
| 22 | 2-(4-Fluorobenzyl)-10-hydroxy-8-(2-phenylethyl)-3,4-dihydropyrido-[3',4':4,5]pyrrolo[1,2-a]pyrazine-1,7,9(2H,6H,8H)-trione | $^1$H NMR(400MHz, DMSO-$d_6$) δ 9.16(s, 1H), 7.35-7.15(m, 9H), 4.92(s, 2H), 4.57(s, 2H), 3.97(t, J=7.9Hz, 2H), 3.48(t, J=6.9Hz, 2H), 2.84(t, J=6.8Hz, 2H), 2.79(t, J=7.9Hz, 2H). ES MS M + 1 = 448 |

EXAMPLE 23

8-(4-Fluorobenzyl)-10-hydroxy-2-(pyridin-4-ylmethyl)-3,4,7,8-tetrahydropyrido-[3',4':4,5]pyrrolo[1,2-a]pyrazine-1,9(2H,6H)-dione

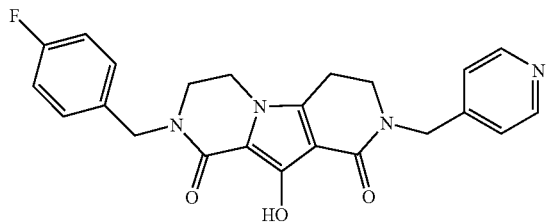

Step 1: 8-(4-Fluorobenzyl)-10-toluenesulfonyloxy-3,4,7,8-tetrahydropyrido-[3',4':4,5]pyrrolo[1,2-a]pyrazine-1,9(2H,6H)-dione To a solution of 8-(4-fluorobenzyl)-10-hydroxy-3,4,7,8-tetrahydropyrido-[3',4':4,5]pyrrolo[1,2-a]pyrazine-1,9(2H,6H)-dione (1.0 g, 3.0 mmol) and triethylamine (0.64 mL, 4.6 mmol) in dichloromethane (30 mL), p-toluenesulfonyl chloride (0.64 g, 3.34 mmol) was added. The reaction mixture was stirred at rt overnight and concentrated under vacuum. The residue was subjected to reverse phase preparative HPLC purification. Collection and lyophilization of appropriate fractions provided the titled compounds.

ES MS M+1=484

Step 2: 8-(4-Fluorobenzyl)-2-(4-pyridinylmethyl)-10-toluenesulfonyloxy-3,4,7,8-tetrahydropyrido-[3',4':4,5]pyrrolo[1,2-a]pyrazine-1,9(2H,6H)-dione To a cold (0° C.) solution of 8-(4-fluorobenzyl)-10-toluenesulfonyloxy-3,4,7,8-tetrahydropyrido-[3',4':4,5]pyrrolo[1,2-a]pyrazine-1,9(2H,6H)-dione (60 mg, 0.12 mmol) in anhydrous DMF (1 mL), a solution of lithium bis(trimethylsilyl)amide in THF (1 M, 1.5 eq) was added. The mixture was stirred at the same temperature for 30 minutes. A solution of 4-bromomethylpyridine in diethyl ether (generated from the corresponding hydrobromide salt through partition between aq sodium carbonate and ether, and drying the solution by passing it through a plug of activated basic alumina). The reaction mixture was stirred at rt for one hour and concentrated under vacuum. The residue was subjected to reverse phase preparative HPLC purification. Collection and lyophilization of appropriate fractions provided the titled compounds.

ES MS M+1=575

Step 3: 8-(4-Fluorobenzyl)-10-hydroxy-2-(pyridin-4-ylmethyl)-3,4,7,8-tetrahydropyrido-[3',4':4,5]pyrrolo[1,2-a]pyrazine-1,9(2H,6H)-dione A solution of 8-(4-fluorobenzyl)-2-(4-pyridinylmethyl)-10-toluenesulfonyloxy-3,4,7,8-tetrahydropyrido-[3',4':4,5]pyrrolo[1,2-a]pyrazine-1,9(2H,6H)-dione (10 mg, 0.017 mmol) and sodium methoxide (3 mg, 0.052 mmol) in anhydrous methanol (0.5 mL) was heated in an oil bath at 60° C. for one hour. The solution was subjected to reverse phase preparative HPLC purification. Collection and lyophilization of appropriate fractions provided the titled compounds.

$^1$H NMR (500 MHz, DMSO-$d_6$) δ 8.70 (br s, 2H), 7.63 (d, J=5.1 Hz, 2H), 7.35 (dd, J=8.7, 5.4 Hz, 2H), 7.18 (t, J=7.8 Hz, 2H), 4.74 (s, 2H), 4.61 (s, 2H), 4.0 (t, J=5.7 Hz, 2H), 3.57 (t, J=6.7 Hz, 2H), 3.53 (t, J=5.7 Hz, 2H), 2.89 (t, J=6.7 Hz, 2H).

ES MS M+1=421

EXAMPLES 24-28

The compounds in the following table were prepared in accordance with the procedure set forth in Example 23 using the appropriate analogous starting materials.

| Example | Compound | Data |
|---|---|---|
| 24 | 8-(4-Fluorobenzyl)-10-hydroxy-2-(pyridin-3-ylmethyl)-3,4,7,8-tetrahydropyrido-[3',4':4,5]pyrrolo[1,2-a]pyrazine-1,9(2H,6H)-dione | $^1$H NMR(400MHz, DMSO-d$_6$) δ 8.69(s, 1H), 8.66(d, J=4.9Hz, 1H), 8.09(d, J=8.0Hz, 1H), 7.70(d, J=6.5Hz, 1H), 7.35(dd, J=8.1, 5.8Hz, 2H), 7.17(t, J=8.7Hz, 2H), 4.67(s, 2H), 4.60(s, 2H), 3.97(t, J=5.7Hz, 2H), 3.53(m, 4H), 2.84(t, J=6.8Hz, 2H). ES MS M + 1 = 421 |
| 25 | 8-(4-Fluorobenzyl)-10-hydroxy-2-(pyridin-2-ylmethyl)-3,4,7,8-tetrahydropyrido-[3',4':4,5]pyrrolo[1,2-a]pyrazine-1,9(2H,6H)-dione | $^1$H NMR(400MHz, DMSO-d$_6$) δ 8.60(d, J=3.9Hz, 1H), 7.98(t, J=7.5Hz, 1H), 7.47(m, 2H), 7.35(dd, J=8.6, 5.7Hz, 2H), 7.18(t, J=8.8Hz, 2H), 4.73(s, 2H), 4.60(s, 2H), 3.99(t, J=5.7Hz, 2H), 3.61(t, J=6.8Hz, 2H), 3.52(t, J=5.7Hz, 2H), 2.87(t, J=6.8Hz, 2H). ES MS M + 1 = 421 |
| 26 | 2-(4-Fluorobenzyl)-10-hydroxy-8-(pyridin-3-ylmethyl)-3,4,7,8-tetrahydropyrido-[3',4':4,5]pyrrolo[1,2-a]pyrazine-1,9(2H,6H)-dione | $^1$H NMR(400MHz, DMSO-d$_6$) δ 8.55(s, 1H), 8.49(d, J=4.5Hz, 1H), 8.45(s, 1H), 7.71(d, J=7.8Hz, 1H), 7.37(dd, J=7.8, 4.8Hz, 1H), 7.32(dd, J=8.4, 5.7Hz, 2H), 7.16(t, J=8.9Hz, 2H), 4.64(s, 2H), 4.56(s, 2H), 3.98(t, J=5.7Hz, 2H), 3.56(t, J=5.7Hz, 2H), 3.40(t, J=6.8Hz, 2H), 2.80(t, J=6.8Hz, 2H). ES MS M + 1 = 421 |
| 27 | 2-(3-Chloro-4-fluorobenzyl)-10-hydroxy-8-(pyridin-3-ylmethyl)-3,4,7,8-tetrahydropyrido-[3',4':4,5]pyrrolo(1,2-a)pyrazine-1,9(2H,6H)-dione | $^1$H NMR(400MHz, DMSO-d$_6$) δ 8.82(s, 1H), 8.78(d, J=4.8Hz, 1H), 8.36(d, J=8.1Hz, 1H), 7.92(dd, J=8.0, 5.7Hz, 1H), 7.48(dd, J=7.1, 2.0Hz 1H), 7.39(t, J=8.9Hz, 1H), 7.30(m, 1H), 4.76(s, 2H), 4.56(s, 2H), 4.03(t, J=5.7Hz, 2H), 3.66(t, J=5.7Hz, 2H), 3.48(t, J=6.8Hz, 2H), 2.83(t, J=6.8Hz, 2H). ES MS M + 1 = 455 |

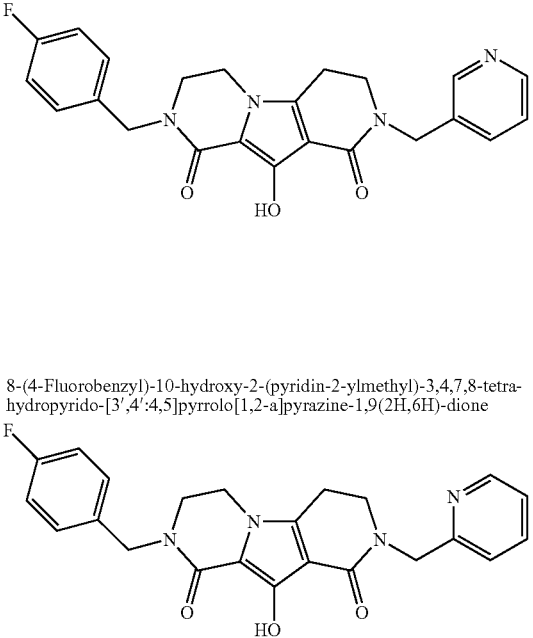

-continued

| Example | Compound | Data |
|---|---|---|
| 28 | 2-(Cyclopropylmethyl)-8-(4-fluorobenzyl)-10-hydroxy-3,4,7,8-tetra-hydropyrido-[3',4':4,5]pyrrolo[1,2-a]pyrazine-1,9(2H,6H)-dione | ¹H NMR(400MHz, CDCl3) δ 7.29(dd, J=8.4, 5.5Hz, 2H), 7.02(t, J=8.6Hz, 2H), 4.67(s, 2H), 3.89(t, J=5.7Hz, 2H), 3.67(t, J=6.8Hz, 2H), 3.49(t, J=5.7Hz, 2H), 3.36(d, J=7.0Hz, 2H), 2.80(t, J=6.8Hz, 2H), 1.00(m, 1H), 0.51(m, 2H), 0.27(m, 2H). ES MS M + 1 = 384 |

EXAMPLE 29

2-(4-Fluorobenzyl)-10-hydroxy-8-pyridin-2-yl-3,4,7,8-tetrahydropyrido-[3',4':4,5]pyrrolo[1,2-a]pyrazine-1,9(2H,6H)-dione

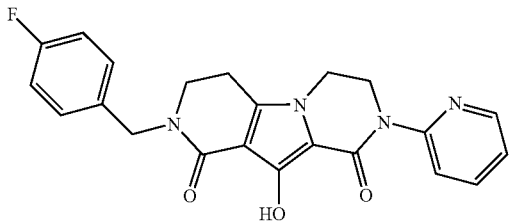

Step 1: 1-Pyridin-2-ylpiperazin-2-one

A mixture of 4-benzyloxycarbonyl-1-methyl-pyrazin-2(1H)-one (3.0 g, 12.8 mmol), 2-bromopyridine (2.02 g, 12.8 mmol), palladium acetate (0.29 g, 1.28 mmol), xantphos (1.11 g, 1.92 mmol), cesium carbonate (6.26 g, 19.2 mmol) in anhydrous dioxane (13 mL) in a sealed vessel was heated in an oil bath at 110° C. for 6 hrs. The resultant reaction mixture was cooled to room temperature, diluted with dichloromethane, filtered, and concentrated under vacuum. The residual solid was subjected to column chromatography on silica gel eluting with a ethyl acetate-hexane gradient. Concentration of appropriate fractions provide the pyridine intermediate. A mixture of 4-benzyloxycarbonyl-1-pyridin-2-ylpiperazin-2-one (1.50 g, 4.94 mmol) and Pearlmans catalyst (0.7 g) in ethanol (50 mL) was stirred under an atmosphere of hydrogen (1 atm) at room temperature for one hour. The product mixture was filtered through a pad of Celite, and concentrated under vacuum to provide the titled compound.

¹H NMR (400 MHz, CDCl₃) δ 8.43 (dd, J=1.8, 4.9 Hz, 1H), 7.93 (d, J=8.3 Hz, 1H), 7.69 (m, 1H), 7.10 (dd, J=4.9, 7.3 Hz, 1H), 4.00 (t, J=5.5 Hz, 2M, 3.72 (s, 2H), 3.23 (t, J=5.5 Hz, 2H).

Step 2: 2-(4-Fluorobenzyl)-10-hydroxy-8-pyridin-2-yl-3,4,7,8-tetrahydropyrido-[3',4':4,5]pyrrolo[1,2-a]pyrazine-1,9(2H,6H)-dione The title product was prepared as described in Example 1 substituting ethylene glycol with 1,2-dichlorbenzene as solvent.

¹H NMR (400 MHz, CDCl₃) δ 8.38 (m, 2H), 8.07 (d, J=8.4 Hz, 1H), 7.70 (m, 1H), 7.31 (dd, J=8.6, 5.5 Hz, 2H), 7.07 (m, 1H), 7.01 (t, J=8.7 Hz, 2H), 4.66 (s, 2H), 4.47 (t, J=5.6 Hz, 2H), 4.05 (t, J=5.6 Hz, 2H), 3.51 (t, J=6.9 Hz, 2H), 2.82 (t, J=6.8 Hz, 2H).

ES MS M+1=407

EXAMPLES 30-31

The compounds in the following table were prepared in accordance with the procedure set forth in Example 29 using the appropriate analogous starting materials.

| Example | Compound | Data |
|---|---|---|
| 30 | 2-(4-Fluorobenzyl)-10-hydroxy-8-pyridin-3-yl-3,4,7,8-tetra-hydropyrido-[3',4':4,5]pyrrolo[1,2-a]pyrazine-1,9(2H,6H)-dione | ¹H NMR(400MHz, DMSO-d₆) δ 8.76(d, J=2.0Hz, 1H), 8.48(d, J=4.4Hz, 1H), 8.02(d, J=8.2Hz, 1H), 7.63(dd, J=8.2, 4.9Hz 1H), 7.34(dd, J=8.6, 5.7Hz, 2H), 7.17(t, J=8.9Hz, 2H), 4.58(s, 2H), 4.13(m, 4H), 3.48(t, J=6.9Hz, 2H), 2.89(t, J=6.8Hz, 2H), ES MS M + 1 = 407 |

| Example | Compound | Data |
|---|---|---|
| 31 | 2-(4-Fluorobenzyl)-10-hydroxy-8-phenyl-3,4,7,8-tetra-hydropyrido-[3',4':4,5]pyrrolo[1,2-a]pyrazine-1,9(2H,6H)-dione | $^1$H NMR(400MHz, CDCl3) δ 8.27(br s, 1H), 7.42-7.22(m, 7H), 7.00(t, J=8.7Hz, 2H), 4.64(s, 2H), 4.08(s, 4H), 3.48(t, J=6.9Hz, 2H), 2.79(t, J=6.8Hz, 2H). ES MS M + 1 = 406 |

EXAMPLE 32

2-(3-Chloro-4-fluorobenzyl)-10-hydroxy-4,8-dimethyl-7,8-dihydropyrido-[3',4':4,5]pyrrolo[1,2-a]pyrazine-1,9(2H,6H)-dione

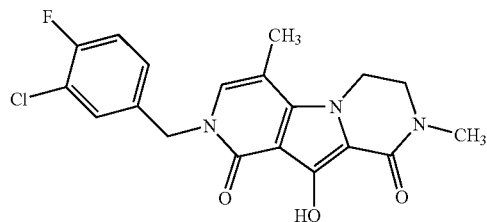

Step 1: N$^2$-Benzyloxycarbonyl-N$^1$-(2,2-dimethoxyethyl)-N$^1$-methylglycinamide A solution of N-(2,2-dimethoxyethyl)-N-methylamine (760 g, 6.38 mmol), N-CBZ-glycine (1337.6 g, 6.39 mol), EDC (1225.8 g, 6.39 mol), and HOBt (107.7 g, 0.70 mol), and N,N-diisopropylethylamine (172 mL) in anhydrous DMF (12 L) was stirred at room temperature overnight. The reaction mixture was diluted with water (24 L) and extracted with dichloromethane (3×10 L). The organic extracts were combined, dried over anhydrous magnesium sulfate, filtered, and concentrated under vacuum to provide the title compound.

ES MS M+1=311

Step 2: 4-Benzyloxycarbonyl-1-methyl-3,4-dihydropyrazin-2(1H)-one

A solution of N$^2$-benzyloxycarbonyl-N$^1$-(2,2-dimethoxyethyl)-N$^1$-methylglycinamide (1.9 Kg, 6.1 mol) and p-toluenesulfonic acid monohydrate (270 g) in toluene (29.4 L) was stirred at 80° C. for 4 hrs. The resultant reaction mixture was cooled to room temperature, washed with water (4×2 L), dried over anhydrous magnesium sulfate, filtered, and concentrated under vacuum. The residual solid was subjected to column chromatography on silica gel eluting with heptane-ethyl acetate. Concentration of appropriate fractions provide the cyclization product as off-white solid.

$^1$H NMR (400 MHz, CDCl$_3$) δ 7.37 (br s, 5H), 6.44 (d, J=6.0 Hz, 1/2H), 6.32 (d, J=6.0 Hz, 1/2H), 5.53 (d, J=6.0 Hz, 1/2H), 5.42 (d, J=6.0 Hz, 1/2H), 5.21 (s, 2H), 4.31 (s, 2H), 3.08 (s, 3H).

ES MS M+1=247

Step 3: 1-methylpiperazin-2-one

A mixture of 4-benzyloxycarbonyl-1-methyl-3,4-dihydropyrazin-2(1H)-one (510 g, 2.1 mol) and 10% Pt/C (40 g) in ethanol (12 L) was stirred under an atmosphere of hydrogen (1 atm) at room temperature overnight. Pearlmans catalyst (50 g; 20% Pd(OH)$_2$ on C) was added and stirred under an atmosphere of hydrogen gas for additional 24 hours. The product mixture was filtered through a pad of Celite, and concentrated under vacuum to provide 1-methylpiperazin-2-one.

$^1$H NMR (400 MHz, CDCl$_3$) δ 3.52 (s, 2H), 3.32 (t, J=5.7 Hz, 2H), 3.09 (t, J=5.7 Hz, 2H), 2.97 (s, 3H).

Step 4: Ethyl 8-hydroxy-2-methyl-1-oxo-1,2,3,4-tetrahydropyrrolo[1,2-a]-pyrazine-7-carboxylate A mixture of 1-methylpiperazin-2-one (183 g, 1.6 mol) and diethyl ethoxymethylenemalonate (346 g, 1.6 mol) in toluene (12 L) was heated at 100° C. overnight. The resultant mixture was concentrated under vacuum. The residue was dissolved in anhydrous THF (8 L), brought to reflux under an atmosphere of nitrogen, and treated with a solution of lithium bis(trimethylsilyl)amide in THF (1 M, 1.05 eq). The reaction mixture was allowed to cool to rt and concentrated under vacuum. The residue was partitioned between methylene chloride and dilute aqueous HCl. The organic extract was washed with brine, dried over anhydrous magnesium sulfate, filtered, and concentrated under vacuum. The residue was triturated with ethyl acetate, cooled to −20° C., and the solid precipitated was filtered to provide the title compound.

$^1$H NMR (400 MHz, DMSO-d$_6$) δ 8.50 (s, 1H), 7.33 (s, 1H), 4.18 (q, J=7.1 Hz, 2H), 4.11 (t, J=5.5 Hz, 2H), 3.59 (t, J=5.5 Hz, 2H), 2.92 (s, 3H), 1.24 (t, J=7.1 Hz, 3H).

ES MS M+1=239

Step 5: Ethyl 8-(benzyloxy)-2-methyl-1-oxo-1,2,3,4-tetrahydro-pyrrolo[1,2-a]-pyrazine-7-carboxylate To a solution of ethyl 8-hydroxy-2-methyl-1-oxo-1,2,3,4-tetrahydro-pyrrolo[1,2-a]-pyrazine-7-carboxylate (25.0 g, 104.9 mmol) in DMF (500 mL), potassium carbonate (58 g, 420 mmol) and benzyl bromide (14.9 mL, 126 mmol) was added. The reaction mixture was stirred at rt over night. The mixture was filtered and the filtrate concentrated under vacuum. The residue was partitioned between dichloromethane and brine. The organic extract was washed with brine, dried over sodium sulfate, filtered, and concentrated under vacuum. The residue was subjected to column chromatography on silica gel eluted with ethyl acetate to give titled material.

$^1$H NMR (400 MHz, CDCl$_3$) δ 7.62 (br d, J=7.5 Hz, 2H), 7.34-7.27 (m, 3H), 7.15 (s, 1H), 5.29 (s, 2H), 4.29 (q, J=7.0 Hz, 2H), 4.11 (t, J=5.8 Hz, 2H), 3.62 (t, J=5.7 Hz, 2H), 3.12 (s, 3H), 1.31 (t, J=7.2 Hz, 3H).

ES MS M+1=329

Step 6: 8-(Benzyloxy)-2-methyl-1-oxo-1,2,3,4-tetrahydro-pyrrolo[1,2-a]-pyrazine-7-carboxylic acid To a solution of ethyl 8-hydroxy-2-methyl-1-oxo-1,2,3,4-tetrahydro-pyrrolo[1,2-a]-pyrazine-7-carboxylate (0.28 g, 0.84 mmol) in ethanol (10 mL), aqueous sodium hydroxide (7 mL, 1M) was added. The reaction mixture was heated at 45° C. for 4 hours. The mixture was concentrated under vacuum. The residue was partitioned between dichloromethane and aq HCl. The organic extract was washed with brine, dried over sodium sulfate, filtered, and concentrated under vacuum. The residue was concentrated from toluene (3 times) to provide the titled acid as white solid.

$^1$H NMR (400 MHz, CDCl$_3$) δ 7.47 (br d, J=7.5 Hz, 2H), 7.39-7.34 (m, 3H), 7.22 (s, 1H), 5.53 (s, 2H), 4.16 (q, J=5.7 Hz, 2H), 3.68 (t, J=5.7 Hz, 2H), 3.16 (s, 3H).

Step 7: 8-(Benzyloxy)-N-(3-chloro-4-fluorobenzyl)-2-methyl-1-oxo-1,2,3,4-tetrahydropyrrolo-[1,2-a]pyrazine-7-carboxamide To a mixture of 8-(benzyloxy)-2-methyl-1-oxo-1,2,3,4-tetrahydro-pyrrolo[1,2-a]-pyrazine-7-carboxylic acid (200 mg, 0.67 mmol), 3-chloro-4-fluorobenzylamine (0.16 g, 1.00 mol), and benzotriazol-1-yloxy-tris(dimethylamino)phosphonium hexafluorophophate (BOP, 0.35 g, 0.79 mmol) in anhydrous dichloromethane (10 mL), diisopropylethylamine (0.17 g, 1.33 mmol) was added. The resultant solution was stirred at room temperature overnight. The reaction mixture was concentrated under vacuum, and the residue partitioned between dichloromethane and aq HCl. The organic extract was washed with aq sodium bicarbonate, dried over anhydrous sodium sulfate, filtered, and concentrated under vacuum to provide the titled amide.

$^1$H NMR (400 MHz, CDCl$_3$) δ 7.47 (br d, J=7.5 Hz, 2H), 7.32-7.18 (m), 7.01 (br d, 2H), 5.35 (s, 2H), 4.33 (d, J=6.1 Hz, 2H), 4.14 (q, J=5.7 Hz, 2H), 3.67 (t, J=5.7 Hz, 2H), 3.14 (s, 3H).

Step 8: 8-(Benzyloxy)-6-bromo-N-(3-chloro-4-fluorobenzyl)-2-methyl-1-oxo-1,2,3,4-tetrahydropyrrolo-[1,2-a]pyrazine-7-carboxamide To a mixture of 8-(benzyloxy)-N-(3-chloro-4-fluorobenzyl)-2-methyl-1-oxo-1,2,3,4-tetrahydropyrrolo-[1,2-a]pyrazine-7-carboxamide (0.23 g, 0.51 mmol) and sodium bicarbonate (0.52 g, 6.13 mmol) in dichloromethane (50 mL) at 0° C., a solution of bromine in dichloromethane (0.5 M, 1.1 mL, 0.55 mmol) was added. The reaction mixture was stirred at room temperature for 2 h, filtered, and concentrated under vacuum. The residue was subjected to column chromatography on silica gel eluted with ethyl acetate. Collection and concentration of appropriate fractions provided the titled product.

$^1$H NMR (400 MHz, CDCl$_3$) δ 7.62 (br d, J=7.5 Hz, 2H), 7.31-7.26 (m), 7.19 (br d, 2H), 7.11 (m, 2H), 5.29 (s, 2H), 4.32 (d, J=6.0 Hz, 2H), 4.18 (q, J=5.7 Hz, 2H), 3.67 (t, J=5.7 Hz, 2H), 3.14 (s, 3H).

Step 9: N-Alkyl-8-(benzyloxy)-6-bromo-N-(3-chloro-4-fluorobenzyl)-2-methyl-1-oxo-1,2,3,4-tetrahydropyrrolo-[1,2-a]pyrazine-7-carboxamide To a cold (0° C.) solution of 8-(benzyloxy)-6-bromo-N-(3-chloro-4-fluorobenzyl)-2-methyl-1-oxo-1,2,3,4-tetrahydro-pyrrolo-[1,2-a]pyrazine-7-carboxamide (0.26 g, 0.50 mmol) in anhydrous DMF (10 mL) under an atmosphere of nitrogen, a solution of lithium bis(trimethylsilyl)amide in THF (1 M, 0.55 mmol) was added. The reaction mixture was stirred at 0° C. for 15 minutes and treated with allyl bromide (0.13 mL, 1.5 mmol; passed through activated basic alumina). The reaction mixture was stirred at rt for 40 minutes and concentrated under vacuum. The residue was partitioned between methylene chloride and dilute aqueous HCl. The organic extract was washed with brine, dried over anhydrous magnesium sulfate, filtered, and concentrated under vacuum. The residue was subjected to column chromatography on silica gel eluted with ethyl acetate. Collection and concentration of appropriate fractions provided the titled product. ES MS M+1=560, 562 (1:1)

Step 10: 10-(Benzyloxy)-2-(3-chloro-4-fluorobenzyl)-4,8-diimethyl-7,8-dihydropyrido-[3',4':4,5]pyrrolo[1,2-a]pyrazine-1,9(2H,6H)-dione A mixture of N-alkyl-8-(benzyloxy)-6-bromo-N-(3-chloro-4-fluorobenzyl)-2-methyl-1-oxo-1,2,3,4-tetrahydro-pyrrolo-[1,2-a]pyrazine-7-carboxamide (0.18 g, 0.31 mmol), dicyclohexylmethyamine (0.11 mL, 0.50 mmol), tri-tert-butylphosphine (27 mg, 0.13 mmol), and Pd$_2$(dba)$_3$ (63 mg, 0.07 mmol) in anhydrous dioxane (10 mL) was purged with nitrogen and stirred at rt overnight. The reaction mixture was concentrated under vacuum. The residue was subjected to column chromatography on silica gel eluted with a methanol in ethyl acetate gradient. Appropriate fractions were collected and concentrated under vacuum. The residue was recrystallized from a mixture of ethyl acetate and hexane to provide the titled product as white solid.

$^1$H NMR (400 MHz, CDCl$_3$) δ 7.70 (d, J=7.5 Hz, 2H), 7.36-7.16 (m), 7.08 (t, J=8.6 Hz, 1H), 5.45 (s, 2H), 5.08 (s, 2H), 4.43 (d, J=5.9 Hz, 2H), 3.63 (d, J=5.9 Hz, 2H), 3.13 (s, 3H), 2.31 (s, 3H).

Step 11: 2-(3-Chloro-4-fluorobenzyl)-10-hydroxy-4,8-dimethyl-7,8-dihydropyrido-[3',4':4,5]pyrrolo[1,2-a]pyrazine-1,9(2H,6H)-dione A mixture of 10-(benzyloxy)-2-(3-chloro-4-fluorobenzyl)-4,8-dimethyl-7,8-dihydropyrido-[3',4':4,5]pyrrolo[1,2-a]pyrazine-1,9(2H,6H)-dione (0.20 g, 0.40 mmol) and 5% Pd/C (40 mg) in a mixture ethanol (100 mL) and acetic acid (11 mL) was stirred under an atmosphere of hydrogen gas (1 atm) at room temperature for 1 hr. The reaction mixture was filtered through a pad of Celite. The filtrate was concentrated under vacuum, and the residue subjected to reverse phase HPLC purification. Collection and lyophilization of appropriate fractions provided the title product.

$^1$H NMR (400 MHz, CDCl$_3$) δ 7.36 (dd, J=2.2, 6.7 Hz, 1H), 7.28-7.21 (m, 1H), 7.07 (t, J=8.6 Hz, 1H), 6.71 (s, 1H), 5.03 (s, 2H), 4.39 (d, J=5.5 Hz, 2H), 3.67 (d, J=5.5 Hz, 2H), 3.10 (s, 3H), 2.29 (s, 3H).

ES MS M+1=390.

EXAMPLES 33-41

The compounds in the following table were prepared in accordance with the procedure set forth in Example 32 using the appropriate analogous starting materials, except for the compound of Example 34 which was prepared as described in the table.

| Example | Compound | Data |
| --- | --- | --- |
| 33 | 2-(4-Fluorobenzyl)-10-hydroxy-4,8-dimethyl-7,8-di-hydropyrido[3',4':4,5]pyrrolo[1,2-a]pyrazine-1,9(2H,6H)-dione | $^1$H NMR(400MHz, DMSO-d$_6$) □7.30(dd, J=5.5, 8.2Hz, 2H), 7.10(t, J=8.6Hz, 2H), 6.97(s, 1H), 4.99(s, 2H), 4.21(d, J=4.9Hz, 2H), 3.46(d, J=4.9Hz, 2H), 2.89(s, 3H), 2.22(s, 3H). ES MS M + 1 = 356 |
| 34 | 2-(3-Methylbenzyl)-10-hydroxy-4,8-dimethyl-7,8-di-hydropyrido[3',4':4,5]pyrrolo[1,2-a]pyrazine-1,9(2H,6H)-dione<br><br>The 3,4-dimethoxybenzyl group of the compound of Example 32 was cleaved with tosic acid and the resulting pyridinone was alkylated with NaH in DMF at 90° C. with 3-methylbenzylchloride to afford the title compound. | $^1$H NMR(400MHz, DMSO-d$_6$) δ 8.82(br s, 1H), 7.19(m, 2H), 7.07(br s, 1H), 7.04(d, 2H), 4.99(s, 2H), 4.41(t, J=5.6Hz, 2H) 3.65(t, J=5.6Hz, 2H), 2.97(s, 3H), 2.28(s, 3H), 2.26(s, 3H). ES MS M + 1 = 352 |
| 35 | 8-Ethyl-2-(4-fluorobenzyl)-10-hydroxy-4,6-dimethyl-7,8-di-hydropyrido-[3',4':4,5]pyrrolo[1,2-a]pyrazine-1,9(2H,8H)-dione<br><br>The racemic compound was separated into its enantiomers by chromatography on a Chiralcel OJ column using an isocratic elution of 1:1 EtOH/hexanes, and the appropriate fractions were concentrated to afford the crude isomers. Each isomer was subjected to reverse phase chromatography on a C-18 column using a gradient elution of 95—5% H$_2$O (0.1% TFA)/CH$_3$CN (0.1% TFA). Collection and lyophilization of the appropriate fractions afforded the separate enantiomers. | $^1$H NMR(400MHz, CDCl$_3$) δ 8.67(br s, 1H), 7.33(dd, J=5, 9Hz, 2H), 7.00(dt, J=2, 7Hz, 2H), 6.73(d, J=2Hz, 1H), 5.09(d, J=14.7Hz, 1H), 5.07(d, J=14.7Hz, 1H), 4.78-4.80(m, 1H), 3.98(dd, J=4, 13Hz, 1H), 3.68-3.73(m, 1H), 3.46-3.51(m, 1H), 3.24(dd, J=2, 13Hz, 1H), 2.29(s, 3H), 1.40(d, J=11Hz, 3H), 1.22(t, J=7Hz, 3H). ES MS M + 1 = 384 |
| 36 | (6S)-2-(4-Fluorobenzyl)-10-hydroxy-6-isopropyl-4,8-di-methyl-7,8-dihydropyrido-[3',4':4,5]pyrrolo[1,2-a]py-razine-1,9(2H,8H)-dione | $^1$H NMR(400MHz, CDCl$_3$) δ 8.63(br s, 1H), 7.33(dd, J=5, 9Hz, 2H), 7.02(dt, J=2, 7Hz, 2H), 6.72(s, 1H), 5.11(d, J=14.7Hz, 1H), 5.00(d, J=14.7Hz, 1H), 4.28(m, 1H), 3.90(dd, J=4.1, 9.1Hz, 1H), 3.45(dd, J=1.3, 3.1Hz, 1H), 3.09(s, 3H), 2.15(m, 2H), 0.97(d, J=6.5Hz, 3H), 0.74(t, J=7Hz, 3H). ES MS M + 1 = 398 |

-continued

| Example | Compound | Data |
|---|---|---|
| 37 | ((6S)-8-Ethyl-2-(4-fluorobenzyl)-10-hydroxy-6-isopropyl-4-methyl-7,8-dihydropyrido-[3',4':4,5]pyrrolo[1,2-a]pyrazine-1,9(2H,8H)-dione | ES MS M + 1 = 412 |
| 38 | 2-(4-Fluorobenzyl)-10-hydroxy-4-isopropyl-8-methyl-7,8-dihydropyrido-[3',4':4,5]pyrrolo[1,2-a]pyrazine-1,9(2H,6H)-dione | $^1$H NMR(400MHz, CDCl$_3$) δ 7.30(dd, J=5, 9Hz, 2H), 6.99(t, J=8.8Hz, 2H), 6.80(s, 1H), 5.10(s, 2H), 4.35(t, J=5.5Hz, 2H), 3.66(t, J=5.5Hz, 2H), 3.01(s, 3H), 3.1(m, 1H), 1.24(d, J=6.8Hz, 6H). ES MS M + 1 = 384 |
| 39 | 4-Ethyl-2-(4-fluorobenzyl)-10-hydroxy-8-methyl-7,8-dihydropyrido-[3',4':4,5]pyrrolo[1,2-a]pyrazine-1,9(2H,6H)-dione | $^1$H NMR(400MHz, CDCl$_3$) δ 8.66(br s 1H), 7.31(dd, J=5.5, 8.2Hz, 2H), 6.99(t, J=8.6Hz, 2H), 6.74(s, 1H), 5.07(s, 2H), 4.33(t, J=5.7Hz, 2H), 3.66(t, J=5.7Hz, 2H), 3.09(s, 3H), 2.64(q, J=7.3Hz, 2H), 1.24(t, J=7.3Hz, 3H). ES MS M + 1 = 370 |
| 40 | 4-Ethyl-8-(4-fluorobenzyl)-10-hydroxy-2-methyl-7,8-dihydropyrido-[3',4':4,5]pyrrolo[1,2-a]pyrazine-1,9(2H,6H)-dione | $^1$H NMR(400MHz, CDCl$_3$) δ 8.64(br s, 1H), 7.31(dd, J=5.5, 8.2Hz, 2H), 7.03(t, J=8.6Hz, 2H), 6.75(s, 1H), 4.70(s, 2H), 4.26(t, J=5.5Hz, 2H), 3.55(t, J=5.5Hz, 2H), 3.50(s, 3H), 2.63(q, J=7.4Hz, 2H), 1.23(t, J=7.4Hz, 3H). ES MS M + 1 = 370 |
| 41 | 4-Benzyl-8-(4-fluorobenzyl)-10-hydroxy-2-methyl-7,8-dihydropyrido-[3',4':4,5]pyrrolo[1,2-a]pyrazine-1,9(2H,6H)-dione | $^1$H NMR(400MHz, CDCl$_3$) δ 8.63(br s, 1H), 7.35-7.20(m), 7.08(d, J=7.2Hz, 2H), 6.99(t, J=8.6Hz, 2H), 6.78(s, 1H), 4.60(s, 2H), 3.98(s, 2H), 3.88(t, J=5.5Hz, 2H), 3.52(s, 3H), 3.26(t, J=5.5Hz, 2H). ES MS M + 1 = 432 |

EXAMPLE 42

2-(4-Fluorobenzyl)-10-hydroxy-4-isopropyl-8-methyl-3,4,7,8-tetrahydropyrido-[3',4':4,5]pyrrolo[1,2-a]pyrazine-1,9(2H,6H)-dione

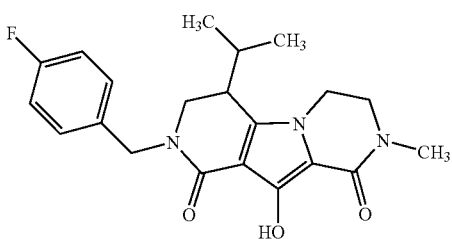

The title compound was isolated as co-product in the preparation of 2-(4-fluorobenzyl)-10-hydroxy-4-isopropyl-8-methyl-7,8-dihydropyrido-[3',4':4,5]pyrrolo[1,2-a]pyrazine-1,9(2H,6H)-dione (Example 38).

$^1$H NMR (400 MHz, CDCl$_3$) δ 7.30 (dd, J=5.5, 8.4 Hz, 2H), 7.00 (t, J=8.6 Hz, 2H), 4.82 (d, J=14.6 Hz, 1H), 4.38 (d, J=14.6 Hz, 1H), 4.35 (t, J=5.5 Hz, 2H), 3.95 (m, 2H), 3.56 (m, 2H), 3.34 (d, J=13.0 Hz, 1H), 3.06 (s, 3H), 3.36 (m, 1H), 1.78 (m, 1H), 0.80 (d, J=6.9 Hz, 3H), 0.67 (d, J=6.9 Hz, 3H).

ES MS M+1=386.

EXAMPLE 43

8-(4-Fluorobenzyl)-10-hydroxy-4-isopropyl-2-methyl-3,4,7,8-tetrahydropyrido-[3',4':4,5]pyrrolo[1,2-a]pyrazine-1,9(2H,6H)-dione

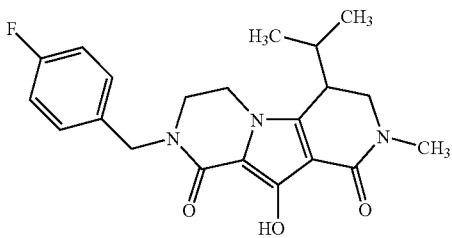

Step 1: N-(3-Methylbut-2-en-1-yl)-8-(benzyloxy)-6-bromo-2-(4-fluorobenzyl)-N-methyl-1-oxo-1,2,3,4-tetrahydropyrrolo-[1,2-a]pyrazine-7-carboxamide To a cold (0° C.) solution of 8-(benzyloxy)-6-bromo-2-(4-fluorobenzyl)-N-methyl-1-oxo-1,2,3,4-tetrahydropyrrolo-[1,2-a]pyrazine-7-carboxamide (0.24 g, 0.50 mmol) in anhydrous DMF (10 mL) under an atmosphere of nitrogen, a solution of lithium bis(trimethylsilyl)amide in THF (1 M, 0.55 mmol) was added. The reaction mixture was stirred at 0° C. for 15 minutes and treated with 4-bromo-2-methyl-2-butene (0.15 mL, 1.5 mmol; passed through activated basic alumina). The reaction mixture was stirred at rt for 40 minutes and concentrated under vacuum. The residue was partitioned between methylene chloride and dilute aqueous HCl. The organic extract was washed with brine, dried over anhydrous magnesium sulfate, filtered, and concentrated under vacuum. The residue was subjected to column chromatography on silica gel eluted with ethyl acetate. Collection and concentration of appropriate fractions provided the titled product. ES MS M+1=486,488 (1:1)

Step 2: 8-(4-Fluorobenzyl)-10-hydroxy-4-isopropyl-2-methyl-3,4,7,8-tetrahydropyrido-[3',4':4,5]pyrrolo[1,2-a]pyrazine-1,9(2H,6H)-dione Using a procedure corresponding to that described in Example 32, Steps 10 and 11, the title compound was obtained by preparative HPLC purification of resultant product mixtures.

$^1$H NMR (400 MHz, CDCl$_3$) δ 7.31 (dd, J=5.3, 8.4 Hz, 2H), 7.03 (t, J=8.7 Hz, 2H), 4.71 (d, J=14.8 Hz, 1H), 4.62 (d, J=14.8 Hz, 1H), 3.89 (t, J=5.7 Hz, 2H), 3.95 (dd, J=5,13 Hz, 1H), 3.49 (m, 2H), 3.39 (d, J=13.2 Hz, 1H), 3.03 (s, 3H), 2.49 (t, J=5.1 Hz, 1H), 1.98 (heptet, J=6.6 Hz, 1H), 0.97 (d, J=6.8 Hz, 3H), 0.92 (d, J=6.8 Hz, 3H).

ES MS M+1=386

EXAMPLE 44

The compound in the following table was obtained using the procedure described in Example 43, using the appropriate analogous starting materials

| Example | Compound | Data |
|---|---|---|
| 44 | 8-(4-Fluorobenzyl)-10-hydroxy-4-propyl-2-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.30(m, 2H), 7.03(t, J=8.6Hz, 2H), 4.79-4.56(m, 2H), 3.95-3.75(m, 3H), 3.56-3.35(m, 2H), 3.05(s, 3H), 249(t, J=5.1Hz, 1H), 2.76(m, 1H), 1.62-1.22(m, 6H), 0.92(m, 3H). ES MS M + 1 = 386 |

EXAMPLE 45

8'-(2,4-Dimethoxybenzyl)-2'-(4-fluorobenzyl)-10'-hydroxy-3',4',7',8'-tetrahydro-1'H-spiro[cyclopentane-1,6'pyrido[3',4':4,5]pyrrolo[1,2-a]pyrazine-1',9'(2'H)-dione

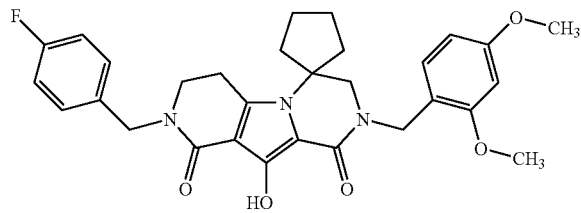

Step 1: 1-[(tert-Butoxycarbonyl)amino]cyclopentanecarboxylic acid

To a solution of 1-amino-1-cyclopentanecarboxylic acid (5.0 g, 38.71 mmol) in dioxane (110 mL) at 0° C. were added aqueous 1N NaOH (77.42 mL. 77.42 mmol) and 1M di-tert-butyldicarbonate in $CH_2Cl_2$. The reaction mixture was allowed to warm to room temperature and stirred overnight. The dioxane was removed in vacuo, and the remaining aqueous solution was cooled to 0° C. and treated to with aqueous 1N HCl solution to pH 2. The mixture was extracted into EtOAc. The resulting aqueous layer was saturated with NaCl and extracted into EtOAc twice more. The organic layers were combined, dried over $MgSO_4$, filtered, and concentrated in vacuo. The resulting oil was azeotroped twice with $CHCl_3$ to afford the product as a white solid.

$^1$H NMR (400 MHz, $CDCl_3$) δ 2.27-2.22 (m, 2H), 1.94 (br s, 2H), 1.80-1.79 (m, 4H), 1.44 (s, 9H).

ES MS M+1=230

Step 2: tert-Butyl 1-{[methoxy(methyl)amino]carbonyl}cyclopentylcarbamate

To a solution of 1-[(tert-butoxycarbonyl)amino)cyclopentanecarboxylic acid (5.89 g, 25.68 mmol) in $CH_2Cl_2$ (25 mL) were added dimethylhydroxylamine hydrochloride (2.51 g, 25.68 mmol) and N-methylmorpholine (2.82 mL, 25.68 mmol), sequentially. The mixture was cooled to 0° C., treated with 1.0M DCC in $CH_2Cl_2$, and stirred under an atmosphere of nitrogen while warming to room temperature overnight. The mixture was filtered, washing with $CH_2Cl_2$, and the resulting filtrate was concentrated in vacuo to afford an oil. The oil was re-suspended in EtOAc, and the mixture was filtered once more. The resulting filtered was subjected to column chromatography eluting with a gradient of 0-100% EtOAc/hexanes. Collection and concentration of the appropriate fractions afforded the product as an opaque white solid.

$^1$H NMR (400 MHz, $CDCl_3$) δ 3.63 (s, 3H), 3.13 (s, 3H), 2.27-2.21 (m, 2H), 1.85-1.80 (m, 2H), 1.66-1.63 (m, 4H), 1.38 (s, 9H).

ES MS M+1=273

Step 3: tert-Butyl 1-formylcyclopentylcarbamate

To a solution of tert-butyl 1-{[methoxy(methyl)amino]carbonyl}-cyclopentylcarbamate (3.34 g, 12.27 mmol) in anhydrous THF (112 mL) at 0° C. under an atmosphere of nitrogen was added LAH (698 mg, 18.40 mmol), portionwise. The reaction was stirred at 0° C. for 30 min, treated with $KHSO_4$ (3.4 g) in water (72 mL), diluted with $Et_2O$, and stirred for 5 min. The layers were separated, and the aqueous was extracted with $Et_2O$ three times more. The combined organic extracts were washed twice each with aqueous 1N HCl solution, saturated aqueous $NaHCO_3$ solution, and brine, dried over $MgSO_4$, and concentrated in vacuo to afford the product as a sticky solid.

$^1$H NMR (400 MHz, $CDCl_3$) δ 9.55 (s, 1H), 2.11-2.07 (m, 2H), 1.77-1.74 (m, 6H), 1.44 (s, 9H).

ES MS M+1=214

Step 4: tert-Butyl 1-{[(2,4-dimethoxybenzyl)amino]methyl}cyclopentylcarbamate

To a solution of tert-butyl 1-formylcyclopentylcarbamate (1.87 g, 8.78 mmol) in anhydrous THF (9 mL) was added 2,4-dimethoxylbenzylamine (1.98 mL, 13.17 mmol). The reaction was stirred for 10 min, treated with sodium triacetoxyborohydride (2.98 g, 14.04 mmol), and stirred for an additional 2 h at room temperature under an atmosphere of nitrogen. Saturated aqueous $NaHCO_3$ solution was added and the mixture stirred until gas evolution ceased. The mixture was diluted with EtOAc, and the separated aqueous layer was saturated with NaCl and extracted into EtOAc once more. The combined organics were dried over $Na_2SO_4$, filtered, and concentrated in vacuo to afford the product.

$^1$H NMR (400 MHz, $CDCl_3$) δ 7.14 (d, J=7.6 Hz, 1H), 6.45-6.43 (m, 2H), 4.30 (br s, 2H), 3.87-80 (m, 6H), 2.80 (s, 2H), 1.96 (br s, 2H), 1.73 (br s, 2H), 1.60-1.57 (m, 4H), 1.41 (s, 9H).

ES MS M+1=365

Step 5: tert-Butyl (1-{[(bromoacetyl)(2,4-dimethoxybenzyl)amino]-methyl}cyclopentyl)carbamate To a solution of tert-butyl 1-{[(2,4-dimethoxybenzyl)amino]methyl}cyclopentyl-carbamate (3.20 g, 8.78 mmol) in anhydrous THF (25 mL) was added $Et_3N$ (1.35 mL, 9.65 mmol). The solution was cooled to 0° C., treated with bromoacetyl bromide (0.84 mL, 9.65 mmol), and stirred for 3 h. The reaction was poured into ice water and extracted three times into $Et_2O$. The combined organics were dried over $Na_2SO_4$, filtered, and concentrated in vacuo. The resulting crude material was subjected to column chromatography eluting with a gradient of 0-100% EtOAc/hexanes. Collection and concentration of the appropriate fractions afforded the product.

$^1$H NMR (400 MHz, $CDCl_3$) δ 6.94 (d, J=7.2 Hz, 1H), 6.46-6.43 (m, 2H), 4.76-4.58 (m, 3H), 3.86-3.74 (m, 10 H), 1.88-1.70 (m, 8H), 1.43 (s, 9H).

ES MS M+1=487

Step 6: tert-Butyl 9-(2,4-dimethoxybenzyl)-8-oxo-6,9-diazaspiro[4.5]decane-6-carboxylate To a solution of tert-butyl (1-{[(bromoacetyl)(2,4-imethoxybenzyl)amino]methyl}cyclopentyl)carbamate (3.84 g, 7.90 mmol) in DMF (79 mL) was added 1.0M sodium hexamethyldisilylazide in THF (7.90 mL, 7.90 mmol) at 0° C. The mixture was stirred at room temperature for 1.5 h, treated with additional 1.0M sodium hexamethyldisilylazide in THF (2.96 mL, 2.96 mmol), and stirred at room temperature for another 3 h. The reaction was quenched with MeOH and concentrated in vacuo. The resulting crude oil was subjected to column chromatography eluting with a gradient of 0-70% EtOAc/hexanes. Collection and concentration of the appropriate fractions afforded the product as a yellow foam.

¹H NMR (400 MHz, CDCl₃) δ 7.20 (d, J=7.6 Hz, 1H), 6.46-6.44 (m, 2H), 4.54 (s, 2H), 4.08 (s, 2H), 3.79 (d, J=2.4 Hz, 6H), 3.14 (s, 2H), 2.15-1.76 (m, 6H), 1.43 (s, 9H), 1.40-1.33 (m, 2H).

ES MS M+1=405

Step 7: 9-(2,4-Dimethoxybenzyl)-6,9-diazaspiro[4.5]decan-8-one

To a solution of tert-butyl 9-2,4-dimethoxybenzyl)-8-oxo-6,9-diazaspiro[4.5]decane-6-carboxylate (1.76 g, 4.36 mmol) in dioxane (34 mL) at 0° C. was added 4.0M HCl in dioxane (10.22 mL, 40.89 mmol). The reaction was stirred at room temperature for 4 days and treated with MP-carbonate resin (6.70 g, load value of 2.62 mmol/g) and Hunig's base (26 μL). The mixture was placed on a rotator for 2 days and filtered, washing with CH₂Cl₂. The resulting filtrate was concentrated in vacuo to afford the product as an orange oil.

¹H NMR (400 MHz, CDCl₃) δ 7.18 (d, J=7.6 Hz, 1H), 6.46-6.44 (m, 2H), 4.55 (s, 2H), 3.80 (s, 6H), 3.70 (s, 1H), 3.57 (s, 2H), 3.11 (s, 2H), 1.73-1.45 (m, 8H).

ES MS M+1=305

Step 8: 8'-(2,4-Dimethoxybenzyl)-2'-(4-fluorobenzyl)-10'-hydroxy-3',4',7',8'-tetrahydro-1'H-spiro[cyclopentane-1,6'pyrido[3',4':4,5]pyrrolo[1,2-a]pyrazine-1',9'(2'H)-dione To a solution of ethyl 1-(4-fluorobenzyl)-4-methoxy-2-oxo-1,2,5,6-tetrahydropyridine-3-carboxylate (75 mg, 0.244 mmol) in 1,2-dichlorobenzene (1.5 mL) was added a solution of 9-(2,4-dimethoxybenzyl)-6,9-diazaspiro[4.5]decan-8-one (297 mg, 0.976 mmol) in 1,2-dichlorobenzene (1.5 mL). The solution was sealed in a glass vessel and heated three times to 250° C. for 20 min in a microwave reactor. The solvent was removed under a stream of nitrogen at 70° C., and the resulting crude residue was subjected to reverse phase chromatography on a C-18 column using a gradient elution of 95-5% H₂O (0.1% TFA)/CH₃CN (0.1% TEA). Collection and concentration of the appropriate fractions afforded the title compound.

¹H NMR (400 MHz, CDCl₃) δ 7.31-7.21 (m, 2H), 7.05-6.97 (m, 3H), 6.48-6.44 (m, 2H), 5.02 (s, 1H), 4.63-4.55 (m, 3H), 3.80 (d, J=1.2 Hz, 6H), 3.79-3.72 (m, 3H), 3.39 (s, 1H), 2.89-2.86 (m, 2H), 1.84-1.49 (m, 8H).

ES MS M+1=534.2383 (Found); 534.2399 (Calculated)

EXAMPLES 46-60

The compounds in the following table were prepared in accordance with the procedure set forth in Example 45 using the appropriate analogous starting materials

| Example | Compound | Data |
|---|---|---|
| 46 | 8-(2,4-Dimethoxybenzyl)-2-(4-fluorobenzyl)-10-hydroxy-6-phenyl-3,4,7,8-tetrahydropyrido-[3',4':4,5]pyrrolo[1,2-a]pyrazine-1,9(2H,6H)-dione | ¹H NMR(500 MHz, CDCl₃) δ 7.28-7.21(m, 7H), 6.98-6.95(m, 1H), 6.91(d, J=8.5Hz, 1H), 6.80(d, J=7.0Hz, 1H), 6.27(m, 2H), 5.09(br s, 1H), 4.68(d, J=14.5Hz, 1H), 4.60(br s, 2H), 4.34(d, J=15.0Hz, 1H), 3.91(dd, J=4.0, 12.5Hz, 1H), 3.76(s, 3H), 3.63(s, 3H), 3.59(dd, J=3.5, 13.0Hz, 1H), 3.37-3.32(m, 1H), 3.28-3.23(m, 1H), 2.52-2.46(m, 1H), 2.30-2.24(m, 1H). APCI HRMS M + 1 = 556.2248(found); 556.2242(calculated) |
| 47 | 8-(2,4-Dimethoxybenzyl)-2-(4-fluorobenzyl)-10-hydroxy-6-(2-hydroxyethyl)-3,4,7,8-tetrahydropyrido-[3',4':4,5]pyrrolo[1,2-a]pyrazine-1,9(2H,6H)-dione | ¹H NMR(400MHz, CDCl₃) δ 7.32-7.23(m, 3H), 7.07-6.99(m, 2H), 6.49-6.46(m, 2H), 5.32(s, 2H), 6.93(d, J=11.2Hz, 1H), 4.68-4.59(m, 2H), 4.34-4.21(m, 2H), 3.82-3.70(m, 8H), 3.47-3.28(m, 4H), 2.89-2.67(m, 2H), 1.89-1.65(m, 2H). ES MS M + 1 = 524.2168(Found); 524.2192(Calculated) |

| Example | Compound | Data |
|---|---|---|
| 48 | 8-(2,4-Dimethoxybenzyl)-2-(4-fluorobenzyl)-10-hydroxy-6-methyl-3,4,7,8-tetrahydropyrido-[3′,4′:4,5]pyrrolo[1,2-a]pyrazine-1,9(2H,6H)-dione | $^1$H NMR(400MHz, CDCl$_3$) δ 7.31-7.26(m, 3H), 7.01-6.97(m, 2H), 6.47-6.45(m, 2H), 4.86(d, J=14.4Hz, 1H), 4.70(d, J=15.2Hz, 1H), 4.57(d, J=14.4Hz, 1H), 4.40(d, J=14.4Hz, 1H), 4.13-4.11(m, 1H), 3.79(s, 6H), 3.74-3.68(m, 1H), 3.49-3.39(m, 2H), 3.26(d, J=12.8Hz, 1H), 2.71(t, J=6.8Hz, 2H), 1.15(d, J=6.8Hz, 3H). ES MS M + 1 = 494.5 |
| 49 | 8-(2,4-Dimethoxybenzyl)-2-(4-fluorobenzyl)-10-hydroxy-6-isobutyl-3,4,7,8-tetrahydropyrido-[3′,4′:4,5]pyrrolo[1,2-a]pyrazine-1,9(2H,6H)-dione | $^1$H NMR(400MHz, CDCl$_3$) δ 7.35-7.24(m, 3H), 7.05-6.98(m, 2H), 6.48-6.45(m, 2H), 5.00(d, J=11.6Hz, 1H), 4.72(d, J=11.6Hz, 1H), 4.55(d, J=11.6Hz, 1H), 4.24(d, J=11.2Hz, 1H), 3.94-3.91(m, 1H), 3.80(s, 6H), 3.68-3.63(m, 1H), 3.48-3.40(m, 2H), 3.33(d, J=10.4Hz, 1H), 2.68(t, J=5.2Hz, 2H), 1.49-1.45(m, 1H), 1.26(m, 1H), 1.14-1.12(m, 2H), 0.80-0.70(m, 6H). ES MS M + 1 = 536 |
| 50 | 6-(Cyclopropylmethyl)-8-(2,4-dimethoxybenzyl)-2-(4-fluorobenzyl)-10-hydroxy-3,4,7,8-tetrahydropyrido-[3′,4′:4,5]pyrrolo[1,2-a]pyrazine-1,9(2H,6H)-dione | $^1$H NMR(400MHz, CDCl$_3$) δ 7.31-7.25(m, 3H), 7.02-6.97(m, 2H), 6.47-6.44(m, 2H), 4.80(d, J=14.4Hz, 1H), 4.65-4.63(m, 2H), 4.46(d, J=14.0Hz, 1H), 3.99-3.98(m, 1H), 3.80-3.79(m, 6H), 3.69-3.65(m, 1H), 3.44-3.40(m, 3H), 2.76-2.71(m, 2H), 1.44-1.37(m, 3H), 0.65-0.32(m, 4H). ES MS M + 1 = 534 |
| 51 | 6-Benzyl-2-(4-fluorobenzyl)-10-hydroxy-8-methyl-3,4,7,8-tetrahydropyrido-[3′,4′:4,5]pyrrolo[1,2-a]pyrazine-1,9(2H,6H)-dione | $^1$H NMR(500 MHz, CDCl$_3$) δ 7.31-7.16(m, 5H), 7.01-6.90(m, 4H), 4.55(m, 2H), 4.12(m, 1H), 3.88(m, 1H), 3.35(m, 1H), 3.19-3.01(m, 4H), 2.98-2.90(m, 1H), 2.29-2.02(m, 5H). APCI HRMS M + 1 = 434.1852(found); 434.1875(calculated |

| Example | Compound | Data |
|---|---|---|
| 52 | 2-(4-fluorobenzyl)-10-hydroxy-8-methyl-6-phenyl-3,4,7,8-tetrahydropyrido-[3',4':4,5]pyrrolo[1,2-a]pyrazine-1,9(2H,6H)-dione | $^1$H NMR(500 MHz, CDCl$_3$) δ 7.36-7.33(m, 3H), 7.28-7.24(m, 2H), 7.01-6.96(m, 4H), 5.18(app t, J=4.5Hz, 1H), 4.63(J$_{AB}$=15.0Hz, 1H), 4.57(J$_{AB}$=15.0Hz, 1H), 4.00(dd, J=4.5, 13.0Hz, 1H), 3.56(dd, J=6.0, 12.5Hz, 1H), 3.37-3.32(m,1H), 3.27-3.22(m, 1H), 2.95(s, 3H), 2.52-2.46(m, 1H), 2.29-2.23(m, 1H), 2.15(br s, 1H). ES HRMS M + 1 = 420.1725(found); 420.1718(calculated) |
| 53 | 2-(4-Fluorobenzyl)-8-(cyclopropylmethyl)-10-hydroxy-6-phenyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.34-7.26(m, 5H), 7.00-6.95(m, 4H), 5.21-5.19(m, 1H), 4.61-4.60(m, 2H), 4.11-4.07(m, 1H), 3.73-3.69(m, 1H), 3.36-3.27(m, 3H), 3.18-3.13(m, 1H), 2.58-2.49(m, 1H), 2.34-2.28(m, 1H), 0.72-0.60(m, 1H),0.34-0.30(m, 2H), 0.12-0.08(m, 2H). ES MS M + 1 = 460.2048(Found); 460.2031(Calculated) |
| 54 | 2-(4-Fluorobenzyl)-8-ethyl-10-hydroxy-6-phenyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.34-7.25(m, 5H), 7.00-6.95(m, 4H), 5.20-5.18(m, 1H), 4.61-4.60(m, 2H), 4.04-4.00(m, 1H), 3.58-3.52(m, 2H), 3.36-3.35(m, 3H), 2.58-2.45(m, 1H), 2.32-2.25(m, 1H), 0.90(t, J=7.4Hz, 3H). ES MSM + 1 = 434.1859(Found); 434.1875(Calculated) |
| 55 | 6-Benzyl-2-(4-Fluorobenzyl)-8-(cyclopropylmethyl)-10-hydroxy-3,4,7,8-tetrahydropyrido-[3',4':4,5]pyrrolo[1,2-a]pyrazine-1,9(2H,6H)-dione | $^1$H NMR(400MHz, CDCl$_3$) δ 7.27-7.16(m, 5H), 7.03-6.97(m, 2H), 6.94-6.90(m, 2H), 4.54(s, 2H), 4.18-4.14(m, 1H), 3.99-3.95(m, 1H), 3.58-3.50(m, 1H), 3.43(d, J=6.8Hz, 2H), 3.17-3.10(m, 2H), 2.97-2.89(m, 2H), 2.22-2.15(m, 1H), 1.19-1.11(m, 1H), 1.05-1.01(m, 1H), 0.59-0.55(m, 2H), 0.34-0.30(m, 2H). ES MS M + 1 = 474.2182(Found); 474.2187(Calculated) |

-continued

| Example | Compound | Data |
|---|---|---|
| 56 | 6-Benzyl-2-(4-fluorobenzyl)-8-ethyl-10-hydroxy-3,4,7,8-tetra-hydropyrido-[3',4':4,5]pyrrolo[1,2-a]pyrazine-1,9(2H,6H)-dione | $^1$H NMR(400MHz, CDCl$_3$) δ 7.26-7.01(m, 5H), 7.00-6.91(m, 2H), 6.90-6.89(m, 2H), 4.54(s, 2H), 4.15-4.13(m, 1H), 3.91-3.87(m, 1H), 3.67-3.55(m, 2H), 3.38-3.35(m, 1H), 3.16-3.06(m, 2H), 2.95-2.88(m, 2H), 2.22-2.14(m, 1H), 1.23(t, J=7.2Hz, 3H), 1.20-1.14(m, 1H). ES MS M + 1 = 448.2017(Found); 448.2031(Calculated) |
| 57 | 8'-Ethyl-2'-(4-fluorobenzyl)-10'-hydroxy-3',4',7',8'-tetra-hydropyrido-1'H-spiro[cyclopropane1,6'-pyrido[3',4':4,5]pyrrolo[1,2-a]pyrazine-1',9'(2'H)-dione | $^1$H NMR(400MHz, CDCl$_3$) δ 7.30-7.28(m, 2H), 7.05-6.97(m, 2H), 4.61(s, 2H), 3.83-3.79(m, 1H), 3.55-3.50(m, 2H), 3.43-3.36(m, 4H), 2.75(t, J=6.8Hz, 2H), 1.37-1.34(m, 1H), 1.18-1.11(m, 4H), 1.09-1.00(m, 1H). ES MS M + 1 = 384.1721(Found); 384.1718(Calculated) |
| 58 | 8'-(Cyclopropylmethyl)-2'-(4-fluorobenzyl)-10'-hydroxy-3',4',7',8'-tetrarahydropyrido-1'H-spiro[cyclopropane1,6'-pyrido[3',4':4,5]pyrrolo[1,2-a]pyrazine-1',9'(2'H)-dione | $^1$H NMR(400MHz, CDCl$_3$) δ 7.31-7.26(m, 2H), 7.02-6.97(m, 2H), 4.62(s, 2H), 3.47(s, 2H), 3.41-3.36(m, 3H), 2.75(t, J=6.8Hz, 2H), 1.65(br s, 1H), 1.36-1.26(m, 3H), 1.05-0.86(m, 2H), 0.55-0.53(m, 2H), 0.27-0.26(m, 2H). ES MS M + 1 = 410.1875(Found); 410.1875(Calculated) |
| 59 | 8'-Cyclopropyl-2'-(4-fluorobenzyl)-10'-hydroxy-3',4',7',8'-tetra-hydropyrido-1'H-spiro[cyclopropane1,6'-pyrido[3',4':4,5]pyrrolo[1,2-a]pyrazine-1',9'(2'H)-dione | $^1$H NMR(400MHz, CDCl$_3$) δ 7.30-7.26(m, 2H), 7.01-6.97(m, 2H), 4.61(s, 2H), 3.93-3.36(m, 4H), 2.74-2.64(m, 3H), 1.82(br s, 1H), 1.34(t, J=6.8Hz, 2H), 0.98-0.86(m, 4H), 0.68-0.64(m, 2H). ES MS M + 1 = 396.1735(Found); 396.1718(Calculated) |

| Example | Compound | Data |
|---|---|---|
| 60 | 2'-(3-Chloro-4-fluorobenzyl)-8'-ethyl-10'-hydroxy-3',4',7',8'-tetra-hydropyrido-1'H-spiro[cyclopropane1,6'-pyrido[3',4':4,5]pyrrolo[1,2-a]pyrazine-1',9'(2H)-dione | $^1$H NMR(400MHz, CDCl$_3$) δ 7.36-7.34(m, 1H), 7.22-7.19(m, 1H), 7.10-7.06(m, 1H), 4.60(s, 2H), 3.56-3.50(m, 2H), 3.43-3.39(m, 2H), 3.36(s, 2H), 2.77(t, J=6.8Hz, 2H), 1.37(t, J=6.8Hz, 2H), 1.17(t, J=7.2Hz, 3H), 1.03(t, J=6.8Hz, 2H). ES MS M + 1 = 418.1324(Found); 418.1328(Calculated) |

EXAMPLE 61

8-Ethyl-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione

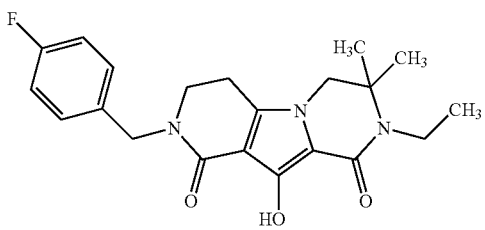

Step 1: Benzyl 2-amino-2-methylpropylcarbamate

To a solution of 2-methylpropane-1,2-diamine (10.00 g, 113.44 mmol) and Hunig's base (23.71 mL, 136.13 mmol) in anhydrous CH$_2$Cl$_2$ (378 mL) at 0° C. under an atmosphere of nitrogen was added dibenzyl dicarbonate (32.48 g, 113.44 mmol). The reaction was stirred at room temperature overnight. The solvent was removed in vacuo, and the resulting residue was suspended in H$_2$O (600 ml) and acidified to pH 2 with aqueous 1N HCl. The mixture was washed twice with CH$_2$Cl$_2$, and the aqueous layer was made strongly basic with aqueous 1N NaOH. The solution was extracted four times with CH$_2$Cl$_2$, and the combined organic layers were dried over Na$_2$SO$_4$, filtered, and concentrated in vacuo to afford the product as a colorless oil.

$^1$H NMR (400 MHz, CDCl$_3$) δ 7.39-7.29 (m, 5H), 5.29-5.23 (br s, 1H), 5.11 (s, 2H), 3.07 (d, J=6.4 Hz, 2H), 1.09 (s, 6H).

ES MS M+1=223

Step 2: Benzyl 2-(ethylamino)-2-methylpropylcarbamate

To a solution of benzyl 2-ethylamino)-2-methylpropylcarbamate (3.50 g, 15.75 mmol) in dichloroethane (56 mL) under an atmosphere of nitrogen was added acetaldehyde (884 µL, 15.75 mmol). The solution was stirred for 10 min and then treated with sodium triacetoxyborohydride (4.67 g, 22.04 mmol) and acetic acid (901 µL, 15.75 mmol). The reaction was stirred at room temperature overnight and quenched with the addition of aqueous 1N NaOH (80 mL). The mixture was extracted twice with 1:1 Et$_2$O/EtOAc. The combined organic layers were washed with brine, dried over Na$_2$SO$_4$, filtered, and concentrated in vacuo to afford the product as a colorless oil.

$^1$H NMR (400 MHz, CDCl$_3$) δ 7.37-7.29 (m, 5H), 5.24 (br s, 1H), 5.10 (s, 2H), 3.09 (d, J=5.6 Hz, 2H), 2.54-2.49 (m, 2H), 1.06 (s, 6H), 1.05-0.96 (m, 3H).

ES MS M+1=251

Step 3: Benzyl 2-[(bromoacetyl)(ethyl)amino]-2-methylpropylcarbamate

The compound was prepared from benzyl 2-(ethylamino)-2-methylpropylcarbamate using a procedure similar to that described in Example 45, Step 5.

$^1$H NMR (400 MHz, CDCl$_3$) δ 7.35-7.30 (m, 5H), 5.15 (br s, 1H), 5.09 (s, 2H), 3.83 (s, 2H), 3.67 (d, J=6.8 Hz, 2H), 3.44-3.38 (m, 2H), 1.39 (s, 6H), 1.25 (m, 3H).

ES MS M+1=397

Step 4: Benzyl 4-ethyl-3,3-dimethyl-5-oxopiperazine-1-carboxylate

The compound was prepared from benzyl 2-[(bromoacetyl)(ethyl)amino]-2-methylpropylcarbamate using a procedure similar to that described in Example 45, Step 6.

$^1$H NMR (400 MHz, CDCl$_3$) δ 7.36-7.31 (m, 5H), 5.16 (s, 2H), 4.15 (s, 2H), 3.50 (s, 2H), 3.39-3.37 (m, 2H), 1.29 (s, 6H), 1.19 (t, J=7.0 Hz, 3H).

ES MS M+1=291

Step 5: 1-Ethyl-6,6-dimethylpiperazin-2-one

The compound was prepared from benzyl 4-ethyl-3,3-dimethyl-5-oxopiperazine-1-carboxylate using a procedure similar to that described in Example 66, Step 6, except that Degussa type 10% palladium on carbon was used as the catalyst, and the additional filtration with toluene was unnecessary.

$^1$H NMR (400 MHz, CDCl$_3$) δ 3.49-3.48 (m, 2H), 3.37-3.31 (m, 2H), 2.85-2.84 (m, 2H), 1.28 (s, 6H), 1.20 (t, J=6.8 Hz, 3H).

ES MS M+1=157

Step 6: 8-Ethyl-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione The title compound was prepared from 1-ethyl-6,6-dimethylpiperazin-2-one using a procedure similar to that described in Example 45, Step 8, except that the reaction was submitted to the microwave reactor conditions once for 60 min. Purification was achieved by subjecting the crude product twice to reverse phase chromatography on a C-18 column using gradient elutions of 95-5% H$_2$O (0.1% TFA)/CH$_3$CN (0.1% TFA) and 65-35% H$_2$O (0.1% TFA)/CH$_3$CN (0.1% TFA). Collection and concentration of the appropriate fractions afforded the title compound.

$^1$H NMR (400 MHz, CDCl$_3$) δ 7.32-7.29 (m, 2H), 7.02-6.98 (m, 2H), 4.65 (s, 2H), 3.67 (s, 2H), 3.54-3.45 (m, 4H), 2.73 (t, J=6.4 Hz, 2H), 1.38 (s, 6H), 1.23 (t, J=6.8 Hz, 3H).

ES MS M+1=386.1871 (Found); 386.1875 (Calculated)

EXAMPLES 62-64

The compounds in the following table were prepared in accordance with the procedure set forth in Example 61 using the appropriate analogous starting materials

| Example | Compound | Data |
|---|---|---|
| 62 | 8-(3,4-Dimethoxybenzyl)-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.33-7.29(m, 3H), 7.03-6.93(m, 2H), 6.86-6.77(m, 2H), 4.69-4.66(m, 4H), 3.86(d, J=3.2Hz, 6H). 3.68(s, 2H), 3.48(t, J=6.8Hz, 2H), 2.74(t, J=6.8Hz, 2H), 1.28(s, 6H), ES MS M + 1 = 508 |
| 63 | 8-(Cyclopropylmethyl)-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.33-7.29(m, 2H), 7.02-6.98(m, 2H), 4.65(s, 2H), 3.70(s, 2H), 3.47(t, J=6.8Hz, 2H), 3.38(d, J=7.2Hz, 2H), 2.74(t, J=6.8Hz, 2H), 1.41(s, 6H), 1.02(m, 1H), 0.55-0.51(m, 2H), 0.41-0.39(m, 2H). ES MS M + 1 = 412.2011(Found); 412.2031(Calculated) |
| 64 | 8-Ethyl-2-(3-chloro-4-fluorobenzyl)-10-hydroxy-7,7-dimethyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.39-7.31(m, 1H), 7.25-7.21(m, 1H), 7.11-7.06(m, 1H), 4.63(s, 2H), 3.69(s, 2H), 3.55-3.46(m, 4H), 2.76(t, J=6.8Hz, 2H), 1.39(s, 6H), 1.23(t, J=7.0Hz, 3H). ES MS M + 1 = 420.1479(Found); 420.1485(Calculated) |

EXAMPLE 65

8'-Ethyl-1-(4-fluorobenzyl)-10'-hydroxy-3',4'-dihydrospiro[cyclopropane1,7'-pyrido[3',4':4,5]pyrrolo[1,2-a]pyrazine-1',9'(2'H,8'H)-dione

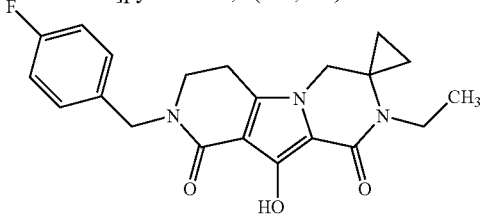

Step 1: Benzyl 1-{[methoxy(methyl)amino]carbonyl}cyclopropylcarbamate

The compound was prepared from 1-{[(benzyloxy)carbonyl]amino}cyclo-propanecarboxylic acid using a procedure similar to that described in Example 45, Step 2.

$^1$H NMR (400 MHz, CDCl$_3$) δ 7.33-7.28 (m, 5H), 5.85 (br s, 1H), 5.11 (br s, 2H), 3.63 (s, 3H), 3.14 (s, 3H), 1.45 (s, 2H), 1.06 (s, 2H).

ES MS M+1=279

Step 2: Benzyl 1-formylcyclopropylcarbamate

The compound was prepared from benzyl 1-{[methoxy(methyl)amino]carbonyl}-yclopropylcarbamate using a procedure similar to that described in Example 45, Step 3.

$^1$H NMR (400 MHz, CDCl$_3$) δ 9.12 (s, 1H), 7.37-7.26 (m, 5H), 5.44 (br s, 1H), 5.13 (s, 2H), 1.52-1.29 (m, 4H).

Step 3: Ethyl N-[(1-{[(benzyloxy)carbonyl]amino}cyclopropyl)methyl]glycinate

To a solution of glycine methyl ester hydrochloride (16.24 g, 116.31 mmol) and Et$_3$N (16.21 mL, 116.31 mmol) in MeOH were added a solution of benzyl 1-formylcyclopropylcarbamate (5.10 g, 23.26 mmol) in MeOH (100 mL) and sodium cyanoborohydride (1.83 g, 29.08 mmol). The reaction was stirred at room temperature overnight, and the solvent was removed in vacuo. The resulting residue was suspended in Et$_2$O and washed with aqueous 5% NaOH solution. The aqueous layer was extracted once with Et$_2$O and once with EtOAc. The combined organic layers were dried over Na$_2$SO$_4$, filtered, and concentrated in vacuo to afford the product.

$^1$H NMR (400 MHz, CDCl$_3$) δ 7.37-7.27 (m, 5H), 5.08 (s, 2H), 4.22-4.09(m, 2H), 3.61-3.40 (m, 2H), 2.71 (s, 2H), 1.29-1.24 (m, 3H), 1.21-0.68 (m, 4H).

ES MS M+1=307

Step 4: Ethyl N-[(1-{[(benzyloxy)carbonyl]amino}cyclopropyl)methyl]-N-(tert-butoxycarbonyl)glycinate To a solution of ethyl N-[(1-{[(benzyloxy)carbonyl]amino}cyclo-propyl)methyl]glycinate (6.95 g, 22.69 mmol) in anhydrous CH$_2$Cl$_2$ 150 mL) were added Et$_3$N (3.48 mL, 24.95 mmol), and dimethylaminopyridine (277 mg, 2.27 mmol). The mixture was treated with di-tert-butyldicarboante (5.45 g, 24.95 mmol) and stirred at room temperature overnight. The reaction was washed once each with aqueous 10% citric acid solution, saturated aqueous NaHCO$_3$, and brine. The organic layer was dried over Na$_2$SO$_4$, filtered, and concentrated in vacuo. The crude product was subjected to column chromatography eluting with a gradient of 0-50% EtOAc/hexanes. Collection and concentration of the appropriate fractions afforded the product.

ES MS M+1=407

Step 5: Ethyl N-({1-[[(benzyloxy)carbonyl](ethyl)amino]cyclopropyl}methyl)-N-(tert-butoxycarbonyl)glycinate To a solution of ethyl N-[(1-{[(benzyloxy)carbonyl]amino}cyclopropyl)methyl]-N-(tert-butoxycarbonyl)glycinate (1.6 g, 3.94 mmol) in DMF (23 mL) at 0° C. under an atmosphere of nitrogen was added NaH (60% dispersion in oil, 19 mg, 7.87 mmol). The mixture was stirred for 40 min until gas evolution ceased. To the reaction was added iodoethane (346 μL, 4.33 mmol), followed stirring at room temperature for 3 h. The reaction was quenched with water, and DMF was removed in vacuo. The resulting aqueous mixture was extracted twice each with EtOAc and CH$_2$Cl$_2$. The combined organics were dried over Na$_2$SO$_4$, filtered, and concentrated in vacuo to afford a pale yellow, sticky solid. The crude product was subjected to column chromatography eluting with a gradient of 0-50% EtOAc/hexanes. Collection and concentration of the appropriate fractions afforded the product as a colorless oil.

ES MS M+1=435

Step 6: Ethyl N-(tert-butoxycarbonyl)-N-{{1-(ethylamino)cyclopropyl]methyl}glycinate The compound was prepared from ethyl N-({1-[[(benzyloxy)carbonyl]-ethyl)amino]cyclopropyl}methyl)-N-(tert-butoxycarbonyl)glycinate using a procedure similar to that described in Example 66, Step 6, except that additional filtration with toluene was unnecessary.

$^1$H NMR (400 MHz, CDCl$_3$) δ 4.34-4.18 (m, 2H), 4.00-3.94 (m, 2H), 3.38-3.36 (m, 2H), 2.75-2.61 (m, 2H), 1.49-1.42 (m, 9H), 1.31-1.24 (m, 3H), 1.11-1.02 (m, 3H), 0.62-0.59 (m, 2H), 0.38-0.37 (m, 2H).

ES MS M+1=301

Step 7: tert-Butyl 4-ethyl-5-oxo-4,7-diaspiro[2.5]octane-7-carboxylate

To a suspension of ethyl N-(tert-butoxycarbonyl)-N-{{1-(ethylamino)cyclopropyl]methyl}glycinate (454 mg, 1.51 mmol) in water (17 mL) was added K$_2$CO$_3$ (1.76 g). The mixture was heated to 100° C. for 30 min. The reaction was extracted with CH$_2$Cl$_2$ three times, and the aqueous layer was saturated with NaCl and extracted into EtOAc once. The combined organic layers were dried over Na$_2$SO$_4$, filtered, and concentrated in vacuo to afford the product as a yellow oil.

$^1$H NMR (400 MHz, CDCl$_3$) δ 4.22-4.18 (m, 2H), 3.38-3.36 (m, 2H), 3.29-3.24 (m, 2H), 1.50-1.43 (m, 9H), 1.32-1.26 (m, 2H), 1.18-1.15 (m, 3H), 1.11-0.90 (m, 2H).

ES MS M+1=255

Step 8: 4-Ethyl-4,7-diazaspiro[2.5]octan-5-one

To a solution of tert-butyl 4-ethyl-5-oxo-4,7-diaspiro[2.5]octane-7-carboxylate (279 mg, 1.10 mmol) in CH$_2$Cl$_2$ under an atmosphere of nitrogen was added TFA (254 μL, 3.29 mmol). The reaction was stirred for 2 h at room temperature, and the solvent was removed in vacuo. The crude product was subjected to reverse phase chromatography on a C-18 column using a gradient elution of 95-5% H$_2$O (0.1% TFA)/CH$_3$CN (0.1% TFA). Collection and concentration of the appropriate fractions afforded a yellow oil which was dissolved in CH$_2$Cl$_2$ and treated with MP-carbonate. The mixture was rotated for 4 h and filtered. The resulting filtrate was concentrated in vacuo to afford the product as a pale yellow oil.

ES MS M+1=155

Step 9: 8'-Ethyl-2'-(4-fluorobenzyl)-10'-hydroxy-3',4'-dihydrospiro[cyclopropane1,7'-pyrido[3',4':4,5]pyrrolo[1,2-a]pyrazine-1',9'(2'H,8'H)-dione The title compound was prepared from 4-ethyl-4,7-diazaspiro[2.5]octan-5-one using a procedure similar to that described in Example 45, Step 8, except that the reaction was submitted to the microwave reactor conditions for 2.8 h. Purification was achieved by reverse phase chromatography on a C-18 column using a gradient elution of 95-5% H$_2$O (0.1% TFA)/CH$_3$CN (0.1% TFA). Collection and concentration of the appropriate fractions afforded the title compound as an orange residue.

$^1$H NMR (400 MHz, CDCl$_3$) δ 7.32-7.27 (m, 2H), 7.02-6.98 (m, 2H), 4.65 (s, 2H), 3.66 (s, 2H), 3.46 (t, J=6.8 Hz, 2H), 3.40-3.34 (m, 2H), 2.69 (t, J=6.8 Hz, 2H), 1.65-1.09 (m, 5H), 0.90-0.86 (m, 2H).

ES MS M+1=384.1702 (Found); 384.1718 (Calculated)

EXAMPLE 66
2-(4-Fluorobenzyl)-10-hydroxy-7,8-dimethyl-3,4,7,8-tetrahydropyrido-[3',4':4,5]pyrrolo[1,2-a]pyrazine-1,9(2H,6H)-dione

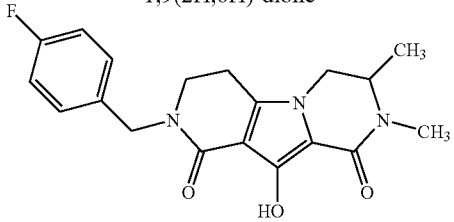

Step 1: N-[(Benzyloxy)carbonyl]-N-(carboxymethyl)glycine

To a solution of N-(carboxymethyl)glycine (13.31 g, 100.00 mmol) in aqueous 2N NaOH (100 mL) was added a solution of benzylchloroformate (18.77 g, 110.00 mmol) in aqueous 2N NaOH (55 mL) at 0° C. The reaction was stirred at room temperature overnight and washed with Et$_2$O. The aqueous layer was acidified to pH 2 with aqueous 1N HCl solution and extracted four times with Et$_2$O. The combined organic layers were dried over MgSO$_4$, filtered, and concentrated in vacuo to afford the product as a clear oil.

$^1$H NMR (400 MHz, CDCl$_3$) δ 10.25 (br s, 1H), 8.71 (br s, 1H), 7.34-7.17 (m, 5H), 5.14 (s, 2H), 4.16 (s, 2H), 4.11 (s, 2H).

ES MS M+1=268

Step 2: [[2-(Methoxymethylamino)-2-oxoethyl][(phenylmethoxy)carbonyl]amino]-acetic acid To a solution of N-[(benzyloxy)carbonyl]-N-(carboxymethyl)glycine (28.45 g, 106.46 mmol) in DMF (163 mL) was added EDC (24.08 g, 125.62 mmol). The solution was cooled to 0° C. and treated with a mixture of N-methoxymethylamine hydrochloride (12.25 g, 125.62 mmol) and Hunig's base (21.88 mL, 125.62 mmol) in DMF (55 mL). The reaction was stirred at room temperature overnight and poured over a mixture of ice and aqueous 10% HCl solution. The mixture was extracted twice with EtOAc. The combined organics were washed twice with aqueous 10% HCl solution and once with brine, dried over Na$_2$SO$_4$, filtered, and concentrated in vacuo to afford a crude oil which was suspended in saturated aqueous NaHCO$_3$ solution. The mixture was washed with EtOAc, adjusted to pH 2 with aqueous 1N HCl, and extracted three times with EtOAc. The final three organic extracts were combined, dried over MgSO$_4$, filtered, and concentrated in vacuo to afford the product as a golden oil.

$^1$H NMR (400 MHz, CDCl$_3$) δ 7.37-7.27 (m, 5H), 5.17 (s, 2H), 4.36 (s, 2H), 4.05 (s, 2H), 3.79 (s, 3H), 3.27 (s, 3H).

ES MS M+1=311

Step 3: N-[(Benzyloxy)carbonyl]-N-(2-oxopropyl)glycine

To a solution of [[2-(methoxymethylamino)-2-oxoethyl][(phenylmethoxy)-arbonyl]amino]acetic acid (6.5 g, 20.95 mmol) in THF (116 mL) at 0° C. was added 1.0M methyl magnesium bromide in THF (69.12 mL, 69.12 mmol). The mixture was stirred at room temperature for 3 h. The reaction was again cooled to 0° C., treated with aqueous saturated NH$_4$Cl solution (56 mL) and water (56 mL), and stirred for 1.5 h. The mixture was partitioned between Et$_2$O and aqueous 1N NaOH, and the aqueous layer was acidified to pH 2 with aqueous 1N HCl and extracted into Et$_2$O twice. The combined organic layers were dried over Na$_2$SO$_4$, filtered, and concentrated in vacuo to afford the product.

$^1$H NMR (400 MHz, CDCl$_3$) δ 7.37-7.27 (m, 5H), 5.17-5.13 (m, 2H), 4.20-4.06 (m, 4H), 2.20 (m, 3H).

ES MS M+1=266

Step 4: N-[(Benzyloxy)carbonyl]-N-[2-(methylamino)propyl]glycine

To a solution of N-[(benzyloxy)carbonyl]-N-(2-oxopropyl)glycine (2.29 g, 8.63 mmol) in CH$_2$Cl$_2$ (44 mL) were added a solution of methylamine hydrochloride (1.52 g, 22.45 mmol) and Et$_3$N (3.13 mL, 22.45 mmol) in CH$_2$Cl$_2$, acetic acid (0.99 mL, 17.27 mmol), and sodium triacetoxyborohydride (5.12 g, 24.17 mmol). The suspension was stirred at room temperature overnight and concentrated in vacuo to afford the product.

ES MS M+1=281

Step 5: Benzyl 3,4-dimethyl-5-oxopiperazine-1-carboxylate

A solution of N-[(benzyloxy)carbonyl]-N-[2-(methylamino)propyl]glycine (2.42 g, 8.63 mmol) in DMF (40 mL) was treated with EDC (1.66 g, 8.63 mmol) and stirred at room temperature overnight. The reaction was diluted with EtOAc and washed once each with aqueous 1N HCl, saturated aqueous NaHCO$_3$, and brine. The combined aqueous layers were extracted once with EtOAc, and the combined organic layers were dried over Na$_2$SO$_4$, filtered, and concentrated in vacuo. The crude material was subjected to column chromatography eluting with a gradient of 50-100% EtOAc/hexanes. Collection and concentration of the appropriate fractions afforded the product.

$^1$H NMR (400 MHz, CDCl$_3$) δ 7.39-7.27 (m, 5H), 5.16 (s, 3H), 4.35-4.30 (m, 1H), 3.99-3.85 (m, 2H), 3.45 (d, J=12.8 Hz, 2H), 2.97 (s, 3H), 1.24 (s, 3H).

ES MS M+1=263

Step 6: 1,6-Dimethylpiperazin-2-one

A solution of benzyl 3,4-dimethyl-5-oxopiperazine-1-carboxylate (780 mg, 2.97 mmol) in EtOH was degassed and purged with nitrogen and treated with 10% palladium on carbon (78 mg). The mixture was degassed and purged with nitrogen again and placed under a balloon atmosphere of hydrogen. The reaction was stirred for 3 h at room temperature and filtered through a pad of Celite, washing with MeOH. The resulting filtrate was concentrated to an oil which was dissolved in toluene. The solution was again filtered through Celite, and the resulting filtrate was concentrated in vacuo to afford the product.

$^1$H NMR (400 MHz, CDCl$_3$) δ 3.49 (m, 2H), 3.45-3.39 (m, 1H), 3.18-3.15 (m, 1H), 2.95 (d, J=1.2 Hz, 3H), 2.81-2.76 (m, 1H), 1.96 (s, 1H), 1.28-1.26 (m, 3H).

Step 7: 2-(4-Fluorobenzyl)-10-hydroxy-7,8-dimethyl-3,4,7,8-tetrahydropyrido-[3',4':4,5]pyrrolo[1,2-a]pyrazine-1,9(2H,6H)-dione The title compound was prepared using a procedure similar to that described in Example 45 Step 8, except that the reaction was heated to 250° C. in the microwave reactor four times for 20 min, once for 1 h, and once for 40 min. The crude product was subjected to reverse phase chromatography on a C-18 column using a gradient elution of 70-55% H$_2$O (0.1% TFA)/CH$_3$CN (0.1% TFA). Collection and concentration of the appropriate fractions afforded the title compound.

$^1$H NMR (400 MHz, CDCl$_3$) δ 7.32-7.29 (m, 2H), 7.02-6.98 (m, 2H), 4.69 (d, J=14.8 Hz, 1H), 4.59 (d, J=14.8 Hz, 1H), 4.05-4.01 (m, 1H), 3.73-3.66 (m, 2H), 3.48-3.45 (m, 2H), 3.03 (s, 3H), 2.74 (t, J=6.8 Hz, 2H), 1.61 (br s, 1H), 1.28 (d, J=6.4 Hz, 3H).

ES MS M+1=358.1560 (Found); 358.1562 (Calculated)

EXAMPLES 67-75

The compounds in the following table were prepared in accordance with the procedure set forth in Example 66 using the appropriate analogous starting materials

| Example | Compound | Data |
|---|---|---|
| 67 | 8-(2,4-Dimethoxybenzyl)-2-(4-fluorobenzyl)-10-hydroxy-7-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 8.15(br s, 1H), 7.32-7.23(m, 3H), 7.01-6.97(m, 2H), 6.46-6.44(m, 2H), 5.10(d, J=14.8Hz, 1H), 4.69(d, J=14.8Hz, 1H), 4.57(d, J=14.8Hz, 1H), 4.13(d, J=14.8Hz, 1H), 3.89-3.79(m, 10H), 3.62(dd, J=1.6, 12.0Hz, 1H), 2.73-2.70(m, 2H), 1.25-1.21(m, 3H). ES MS M + 1 = 494.2064(Found); 494.2086(Calculated) |
| 68 | 8-Ethyl-2-(4-fluorobenzyl)-10-hydroxy-7-methyl-3,4,7,8-tetrahydropyrido-[3',4':4,5]pyrrolo[1,2-a]pyrazine-1,9(2H,6H)-dione<br><br>The mixture was separated by chiral chromatography on a Chiralcel OJ column using an isocratic elution of 1:1 EtOH/hexanes, and appropriate fractions were concentrated to afford the crude isomers. Each isomer was subjected to reverse phase chromatography on a C-18 column using a gradient elution of 95—5% H$_2$O (0.1% TFA)/CH$_3$CN (0.1% TFA). Collection and lyophilization of the appropriate fractions afforded the separate enantiomers. | Racemate: $^1$H NMR(400MHz, CDCl$_3$) δ 7.32-7.26(m, 2H), 7.02-6.98(m, 2H), 4.69(d, J=14.0Hz, 1H), 4.60(d, J=14.0Hz, 1H), 4.07-3.95(m, 2H), 3.82-3.79(m, 1H), 3.71(dd, J=2.6, 12.4Hz, 1H), 3.49-3.44(m, 2H), 3.07-2.99(m, 1H), 2.74(t, J=7.0Hz, 2H), 1.31-1.27(m, 3H), 1.21(t, J=7.0Hz, 3H). ES MS M + 1 = 372.1735(Found); 372.1718(Calculated)<br>Earlier eluting enantiomer: $^1$H NMR(400MHz, CDCl$_3$) δ 7.32-7.26(m, 2H), 7.03-6.99(m, 2H), 4.69(d, J=14.6Hz, 1H), 4.61(d, J=14.6Hz, 1H), 4.08-3.95(m, 2H), 3.82-3.79(m, 1H), 3.71(dd, J=2.2, 12.2Hz, 1H), 3.49-3.43(m, 2H), 3.09-3.00(m, 1H), 2.75(t, J=6.8Hz, 2H), 1.32-1.19(m, 6H). ES MS M + 1 = 372.1736(Found); 372.1718(Calculated)<br>Later eluting enantiomer: $^1$H NMR(400MHz, CDCl$_3$) δ 7.31-7.26(m, 2H), 7.03-6.98(m, 2H), 5.91(br s, 1H), 4.69(d, J=14.8Hz, 1H), 4.60(d, J=14.8Hz, 1H), 4.05-3.96(m, 2H), 3.82-3.73(m, 1H), 3.71(dd, J=2.2, 12.2Hz, 1H), 3.50-3.47(m, 2H), 3.09-3.01(m, 1H), 2.75(t, J=6.8Hz, 2H), 1.32-1.19(m, 6H). ES MS M + 1 = 372.1730(Found); 372.1718(Calculated) |

| Example | Compound | Data |
|---|---|---|
| 69 | 8-Ethyl-2-(3-chloro-4-fluorobenzyl)-10-hydroxy-7-methyl-3,4,7,8-tetra-hydropyrido-[3',4':4,5]pyrrolo[1,2-a]pyrazine-1,9(2H,6H)-dione<br><br>The racemic mixture was separated by chiral chromatography on a ChiralPak AD column using an isocratic elution of MeOH, and the appropriate fractions were concentrated to afford the separated crude isomers, which were subjected to reverse phase chromatography on a C-18 column using a radient elution of 95—5% H₂O (0.1% TFA/CH₃CN (0.1% TFA). Collection and lyophilization of the appropriate fractions gave the earlier and later enantiomers are purple and pink solids respectively. | Earlier eluting enantiomer: $^1$H NMR (400MHz, CDCl₃) δ 7.38-7.36(m, 1H), 7.21(br s, 1H), 7.11-7.07(m, 1H), 4.68(d, J=14.8Hz, 1H), 4.58(d, J=15.2Hz, 1H), 4.09-3.90(m, 2H), 3.82(br s, 1H), 3.74-3.71(m, 1H), 3.50(t, J=6.4Hz, 2H), 3.08-3.02(m, 1H), 2.77(t, J=6.8Hz, 2H), 1.33-1.20(m, 6H). ES MS M + 1 = 406.1326(Found); 406.1328(Calculated)<br>Later eluting enantiomer: $^1$H NMR(400MHz, CDCl₃) δ 7.38-7.36(m, 1H), 7.24-7.21(m, 1H), 7.09(t, J=8.4Hz, 1H), 4.67(d, J=15.2Hz, 1H), 4.57(d, J=15.2Hz, 1H), 4.05-3.96(m, 2H), 3.83-3.80(m, 1H), 3.72(dd, J=2.4, 12.4, 1H), 3.49(t, J=6.4Hz, 2H), 3.06-3.01(m, 1H), 2.77(t, J=6.8Hz, 2H), 1.29(t, J=6.4Hz, 3H), 1.21(t, J=7.2Hz, 3H). ES MS M + 1 = 406.1323(Found); 406.1328(Calculated) |
| 70 | 8-Ethyl-2-(3-chloro-4-fluorobenzyl)-10-hydroxy-7-methyl-3,4,7,8-tetra-hydropyrido-[3',4':4,5]pyrrolo[1,2-a]pyrazine-1,9(2H,6H)-dione | $^1$H NMR(400MHz, CDCl₃) δ 7.38-7.27(m, 1H), 7.24-7.20(m, 1H), 7.12-7.07(m, 1H), 4.68(d, J=15.2Hz, 1H), 4.57(d, J=14.8Hz, 1H), 4.07-3.96(m, 2H), 3.83-3.78(m, 1H), 3.72(dd, J=2.4, 12.4Hz, 1H), 3.54-3.44(m, 2H), 3.08-2.99(m,1H), 2.77(t, J=6.8Hz, 2H), 1.33-1.19(m, 6H). ES MS M + 1 = 406.1324(Found); 406.1328(Calculated) |
| 71 | 8-Cyclopropyl-2-(4-fluorobenzyl)-10-hydroxy-7-methyl-3,4,7,8-tetra-hydropyrido-[3',4':4,5]pyrrolo[1,2-a]pyrazine-1,9(2H,6H)-dione | $^1$H NMR(400MHz, CDCl₃) δ 7.32-7.26(m, 2H), 7.03-6.98(m, 2H), 4.70(d, J=14.4Hz, 1H), 4.60(d, J=14.4Hz, 1H), 3.92(dd, J=4.4, 12.2Hz, 1H), 3.84(t, J=5.6Hz, 1H), 3.71(dd, J=1.4, 12.2Hz, 1H, 3.49-3.46(m, 2H), 2.76-2.66(m, 4H), 1.31(d,J=6.8Hz, 3H), 1.12-1.09(m, 1H), 0.89-0.84(m, 1H), 0.78-0.72(m, 1H), 0.51-0.47(m, 1H). ES MS M + 1 = 384.1709(Found); 384.1718(Calculated) |

| Example | Compound | Data |
|---|---|---|
| 72 | 2-(4-Fluorobenzyl)-8-(cyclopropylmethyl)-10-hydroxy-7-methyl-3,4,7,8-tetrahydropyrido-[3',4':4,5]pyrrolo[1,2-a]pyrazine-1,9(2H,6H)-dione | ¹H NMR(400MHz, CDCl₃) δ 7.32-7.26(m, 2H), 7.03-6.97(m, 2H), 4.70(d, J=14.8Hz, 1H), 4.58(d, J=14.8Hz, 1H), 4.05-3.95(m, 2H), 3.80-3.70(m, 2H), 3.50-3.44(m, 2H), 3.00-2.94(m, 1H), 2.75(t, J=6.8Hz, 2H), 2.01(br s, 1H), 1.29(d, J=6.8Hz, 3H),1.04-0.96(m, 1H), 0.62-0.49(m, 2H), 0.34-0.26(m, 2H). ES MS M + 1 = 398.1878(Found); 398.1875(Calculated) |
| 73 | 2-(3-Chloro-4-fluorobenzyl)-8-(cyclopropylmethyl)-10-hydroxy-7-methyl-3,4,7,8-tetrahydropyrido-[3',4':4,5]pyrrolo[1,2-a]pyrazine-1,9(2H,6H)-dione | ¹H NMR(400MHz, CDCl₃) δ 7.39-7.37(m, 1H), 7.24-7.21(m, 1H), 7.11-7.06(m, 1H), 4.68(d, J=15.2Hz, 1H), 4.57(d, J=15.2Hz, 1H), 4.05-3.96(m, 2H), 3.81-3.71(m, 2H), 3.50-3.47(m, 2H), 3.00-2.94(m, 1H), 2.77(t, J=7.2Hz, 2H), 1.31-1.25(m, 3H), 1.02-0.99(m, 1H), 0.60-0.50(m, 2H), 0.32-0.28(m, 2H). ES MS M + 1 = 432.1473(Found); 432.1485(Calculated) |
| 74 | 2-(3-Chloro-4-fluorobenzyl)-10-hydroxy-7,8-dimethyl-3,4,7,8-tetrahydropyrido-[3',4':4,5]pyrrolo[1,2-a]pyrazine-1,9(2H,6H)-dione | ¹H NMR(400MHz, CDCl₃) δ 7.38-7.28(m, 1H), 7.24-7.20(m, 1H), 7.12-7.06(m, 1H), 4.67(d, J=4.8Hz, 1H), 4.57(d, J=14.8Hz, 1H), 4.06-4.02(m, 1H), 3.76-3.68(m, 2H), 3.04(s, 3H), 2.77(t, J=6.8Hz, 4H), 1.31-1.28(m, 3H). ES MS M + 1 = 392.1162(Found); 392.1172(Calculated) |

| Example | Compound | Data |
|---|---|---|
| 75 | 2-(3-Chloro-4-fluorobenzyl)-8-cyclopropyl-10-hydroxy-7-methyl-3,4,7,8-tetrahydropyrido-[3',4':4,5]pyrrolo[1,2-a]pyrazine-1,9(2H,6H)-dione<br><br>The racemic mixture was separated by chiral chromatography on a Chiralcel OD column using an isocratic elution of 1:1 EtOH/hexanes, and the appropriate fractions were concentrated to afford the separated enantiomers. | Racemate: $^1$H NMR(400MHz, CDCl$_3$) δ 7.38-7.36(m, 1H), 7.24-7.20(m, 1H), 7.10-7.06(m, 1H), 4.68(d, J=15.2Hz, 1H), 4.57(d, J=15.2Hz, 1H), 3.95-3.91(m, 1H), 3.86-3.83(m, 1H), 3.71(dd, J=5.6, 12.0Hz, 1H), 3.50-3.46(m, 2H), 2.77-2.73(m, 2H), 2.71-2.65(m, 1H), 1.31(t, J=3.2Hz, 3H), 1.12-1.08(m, 1H), 0.89-0.83(m, 1H), 0.77-0.72(m, 1H), 0.50-0.47(m, 1H). ES MS M + 1 = 418.1318(Found); 418.1328(Calculated) Earlier eluting enantiomer: $^1$H NMR(400MHz, CDCl$_3$) δ 7.36-7.34(m, 1H), 7.21-7.19(m, 1H), 7.12-7.07(m, 1H), 4.66(d, J=14.8Hz, 1H), 4.55(d, J=14.8Hz, 1H), 3.96-3.92(m, 1H), 3.87-3.84(m, 1H), 3.75(d, J=12.4Hz, 1H), 3.52-3.49(m, 2H), 2.80-2.77(m, 2H), 2.69-2.67(m, 1H),1.32-1.30(m, 3H), 1.07-1.06(m, 1H), 0.85-0.82(m, 1H), 0.77-0.75(m, 1H), 0.53-0.51(m, 1H). ES MS M + 1 = 418.1333(Found); 418.1328(Calculated) |

EXAMPLE 76

2-(4-Fluorobenzyl)-10-hydroxy-4-(methoxycarbonyl)-8-methyl-3,4,7,8-tetrahydropyrido-[3',4':4,5]pyrrolo[1,2-a]pyrazine-1,9(2H,6H)-dione

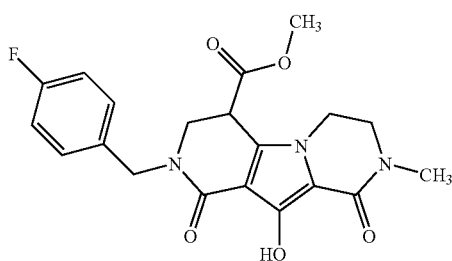

Step 1: Ethyl 8-(benzyloxy)-6-bromo-2-methyl-1-oxo-1,2,3,4-tetrahydro-pyrrolo[1,2-a]-pyrazine-7-carboxylate To a mixture of ethyl 8-(benzyloxy)-2-methyl-1-oxo-1,2,3,4-tetrahydro-pyrrolo[1,2-a]-pyrazine-7-carboxylate (5.0 g, 15.2 mmol; Example 32, step 5) and sodium bicarbonate (19.2 g, 228 mmol) in dichloromethane (150 mL) at 0° C., a solution of bromine in dichloromethane (0.5 M, 32 mL, 16 mmol) was added dropwise. The reaction mixture was stirred at room temperature for 2 h, filtered, and concentrated under vacuum. The residue was subjected to column chromatography on silica gel eluted with a hexane-ethyl acetate gradient to provide the titled product.

$^1$H NMR (400 MHz, CDCl$_3$) δ 7.59 (br d, J=7.1 Hz, 2H), 7.37-7.29 (m, 3H), 5.23 (s, 2H), 4.30 (q, J=7.3 Hz, 2H), 4.14 (t, J=5.9 Hz, 2H), 3.64 (t, J=5.9 Hz, 2H), 3.12 (s, 3H), 1.31 (t, J=7.3 Hz, 3H).

ES MS M+1=407, 409 (1:1)

Step 2: Methyl 10-(benzyloxy)-2-(4-fluorobenzyl)-8-methyl-1,9-dioxo-1,2,3,4,6,7,8,9-octahydropyrido[3',4':4,5]pyrrolo[1,2-a]-pyrazine-4-carboxylate A mixture of ethyl 8-(benzyloxy)-6-bromo-2-methyl-1-oxo-1,2,3,4-tetrahydro-pyrrolo[1,2-a]-pyrazine-7-carboxylate (4.0 g, 9.8 mmol), methyl 2-(tri-n-butylstannyl)acrylate (5.5 g, 14.7 mmol; Zhang, J. Org. Chem. 1990, 1857), bis(tri-t-butylphosphine)palladium (0) (1.2 g, 2.4 mmol), and copper (I) iodide (2.0 g, 10.8 mmol) in dimethylformamide (100 mL) was purged with nitrogen, and heated in a sealed tube in an oil bath at 80° C. overnight. The product mixture was concentrated under vacuum, and the residue subjected to column chromatography on silica gel eluting with ethyl acetate. Collection and concentration of appropriate fractions provided the intermediate unsaturated ester. A solution of this unsaturated ester (0.40 g, 0.97 mmol), 4-fluorobenzylamine (0.73 g, 5.82 mmol), and acetic acid (1.17 g, 19.4 mmol) in absolute ethanol (25 mL) was heated in a sealed tube in an oil bath at 80° C. overnight. The resultant mixture was concentrated under vacuum. The residue was subjected to column chromatography on silica gel eluting with 20% methanol in ethyl acetate. Collection and concentration of appropriate fractions provided the titled compound.

Step 3: 2-(4-Fluorobenzyl)-10-hydroxy-4-(methoxycarbonyl)-8-methyl-3,4,7,8-tetrahydropyrido-[3',4':4,5]pyrrolo[1,2-a]pyrazine-1,9(2H,6H)-dione A mixture of methyl 10-(benzyloxy)-2-(4-fluorobenzyl)-8-methyl-1,9-dioxo-1,2,3,4,6,7,8,9-octahydropyrido[3',4':4,5]pyrrolo[1,2-a]-pyrazine-4-carboxylate (50 mg, 0.10 mmol) and Pearlman's catalyst (5 mg, 20% Pd(OH)$_2$ on carbon) in ethanol (4 mL) was stirred under an atmosphere of hydrogen gas (1 atm) at room temperature for 1 hr. The reaction mixture was filtered through a pad of Celite. The filtrate was concentrated under vacuum, and the residue subjected to reverse phase HPLC purification. Collection and lyophilization of appropriate fractions provided the title product.

$^1$H NMR (400 MHz, CDCl$_3$) δ 8.20 (br s, 1H), 7.30 (dd, J=8.4, 5.5 Hz, 1H), 7.00 (t, J=8.8 Hz, 2H), 4.68 (d, J=14.6 Hz, 1H), 4.59 (d, J=14.6 Hz, 1H), 4.14-3.56 (m), 3.60 (s, 3H), 3.07 (s, 3H).

ES MS M+1=402

EXAMPLE 77

2-(4-Fluorobenzyl)-10-hydroxy-4-(dimethylcarbonyl)-8-methyl-3,4,7,8-tetrahydropyrido-[3',4':4,5]pyrrolo[1,2-a]pyrazine-1,9(2H,6H)-dione

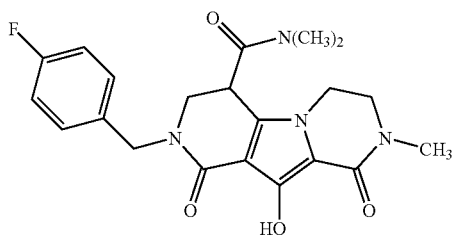

Step 1: 2-(4-Fluorobenzyl)-10-benzyloxy-4-(dimethylcarbonyl)-8-methyl-3,4,7,8-tetrahydropyrido-[3',4':4,5]pyrrolo[1,2-a]pyrazine-1,9(2H,6H)-dione A mixture of methyl 10-(benzyloxy)-2-(4-fluorobenzyl)-8-methyl-1,9-dioxo-1,2,3,4,6,7,8,9-octahydropyrido[3',4':4,5]pyrrolo[1,2-a]-pyrazine-4-carboxylate (0.25 g, 0.51 mmol; Example 76, Step 2) and aq sodium hydroxide (2 mL, 1M) in methanol (15 mL) was stirred at rt for 1 hour. The reaction mixture was concentrated in vacuum, and the residue partitioned between chloroform and aq HCl. The organic extract was dried over anhydrous magnesium sulfate, filtered, and concentrated under vacuum to provide the corresponding carboxylic acid. A mixture of this acid (80 mg, 0.17 mmol), benzotriazol-1-yloxy-tris(dimethylamino)phosphonium hexafluorophophate (BOP, 0.15 g, 0.34 mmol), and a solution of dimethylamine in THF (0.34 mL, 2 M) in anhydrous DMF (5 mL) was stirred at room temperature overnight. The reaction mixture was concentrated in vacuum, and the residue partitioned between dichloromethane and brine. The organic extract was dried over anhydrous sodium sulfate, filtered, and concentrated under vacuum. The residue was subjected to column chromatography on silica gel eluting with 10% methanol in dichloromethane. Collection and concentration of appropriate fractions provided the titled amide.

ES MS M+1=505

Step 2: 2-(4-Fluorobenzyl)-10-hydroxy-4-(dimethylcarbonyl)-8-methyl-3,4,7,8-tetrahydropyrido-[3',4':4,5]pyrrolo[1,2-a]pyrazine-1,9(2H,6H)-dione Following the procedure described in Example 76, step 3 and starting with 2-(4-Fluorobenzyl)-10-benzyloxy-4-(dimethylcarbonyl)-8-methyl-3,4,7,8-tetrahydropyrido-[3',4':4,5]pyrrolo[1,2-a]pyrazine-1,9(2H,6H)-dione, the title product was obtained.

$^1$H NMR (400 MHz, CDCl$_3$) δ 8.28 (br s, 1H), 7.30 (dd, J=8.4, 5.5 Hz, 1H), 6.99 (t, J=8.8 Hz, 2H), 4.93 (d, J=15.0 Hz, 1H), 4.32 (m, 2H), 3.88 (m, 1H), 3.77 (m, 1H), 3.59-3.44 (m), 3.04 (s, 3H), 3.03 (s, 3H), 2.93 (s, 3H).

ES MS M+1=415

EXAMPLES 78-85

The compounds in the following table were prepared in accordance with the procedure set forth in Examples 76 & 77 using the appropriate analogous starting materials

| Example | Compound | Data |
|---------|----------|------|
| 78 | 2-(3-Chloro-4-fluorobenzyl)-10-hydroxy-4-(methoxycarbonyl)-8-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.36(d, J=6.0Hz, 1H), 7.20(br s, 1H), 7.09(t, J=8Hz, 1H), 4.68(d, J=14.6Hz, 1H), 4.59(d, J=14.6Hz, 1H), 4.14-3.56 (m), 3.45(s, 3H), 3.08(s, 3H). ES MS M + 1 = 436 |

-continued

| Example | Compound | Data |
|---|---|---|
| 79 | 2-(3-Chloro-4-fluorobenzyl)-10-hydroxy-4-(dimethylcarbonyl)-8-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.34(d, J=6.2Hz, 1H), 7.18(br s, 1H), 7.09(t, J=8.6Hz, 1H), 4.85(d, J=14.7Hz, 1H), 4.37(d, J=14.7Hz, 1H), 4.29 (m, 1H), 3.89(m, 1H), 3.77(m, 1H), 3.56(m, 2H), 3.06(s, 3H), 3.05 (s, 3H), 2.95(s, 3H). ES MS M + 1 = 449 |
| 80 | 2-(4-Fluorobenzyl)-10-hydroxy-4-(piperidinylcarbonyl)-8-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.26(dd, J=8.4, 5.5Hz, 1H), 6.99 (t, J=8.6Hz, 2H), 4.98(d, J=14.8Hz, 1H), 4.32(t, J=7.7Hz, 1H), 4.24(d, J=14.8Hz, 1H), 3.92-3.78 (m, 2H), 3.56-3.35 (m), 3.03(s, 3H). ES MS M + 1 = 455 |
| 81 | 2-(3-Chloro-4-fluorobenzyl)-10-hydroxy-4-(morpholinylcarbonyl)-8-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.32(d, J=6.8Hz, 1H), 7.16(br s, 1H), 7.09(t, J=8.0Hz, 1H), 5.03(d, J=13.9Hz, 1H), 4.33(br s, 1H), 4.15(d, J=13.9Hz, 1H), 3.87(m, 2H), 3.57(m), 3.05(s, 3H). ES MS M + 1 = 491 |
| 82 | 8-(4-Fluorobenzyl)-10-hydroxy-4-(methoxycarbonyl)-2-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.30(dd, J=8.6, 5.5Hz, 1H), 7.03 (t, J=8.6Hz, 2H), 4.72(d, J=14.7Hz, 1H), 4.62(d, J=14.7Hz, 1H), 4.06-3.53 (m), 3.72(s, 3H), 3.05 (s, 3H). ES MS M + 1 = 402 |

| Example | Compound | Data |
|---|---|---|
| 83 | 8-(4-Fluorobenzyl)-10-hydroxy-4-(morpholinylcarbonyl)-2-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.26(dd, J=8.6, 5.5Hz, 1H), 7.02 (t, J=8.6Hz, 2H), 4.92(d, J=14.6Hz, 1H), 4.58(m, 1H), 4.30 (d, J=14.6Hz, 1H), 3.96-3.39(m), 2.98(s, 3H). ES MS M + 1 = 457 |
| 84 | 8-(4-Fluorobenzyl)-10-hydroxy-4-(dimethylaminocarbonyl)-2-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.26(dd, J=8.6, 5.5Hz, 1H), 7.03 (t, J=8.6Hz, 2H), 4.89(d, J=14.7Hz, 1H), 4.57(m, 1H), 4.34 (d, J=14.7Hz, 1H), 3.79-3.42(m), 3.26(s, 3H), 3.01(s, 3H), 2.98 (s, 3H). ES MS M + 1 = 415 |
| 85 | 8-(4-Fluorobenzyl)-10-hydroxy-4-(piperidinylcarbonyl)-2-methyl-3,4,7,8-tetrahydropyrido-[3',4':4,5]pyrrolo[1,2-a]pyrazine-1,9(2H,6H)-dione | $^1$H NMR(400MHz, CDCl$_3$) δ 7.26(dd, J=8.6, 5.5Hz, 1H), 7.02 (t, J=8.6Hz, 2H), 4.82(d, J=15.9Hz, 1H), 4.45(m, 2H), 3.89-3.41 (m), 3.01(s, 3H). ES MS M + 1 = 455 |

EXAMPLE 86

2-(4-Fluorobenzyl)-10-hydroxy-4-(methoxycarbonyl)-8-methyl-7,8-dihydropyrido-[3',4':4,5]pyrrolo[1,2-a]pyrazine-1,9(2H,6H)-dione

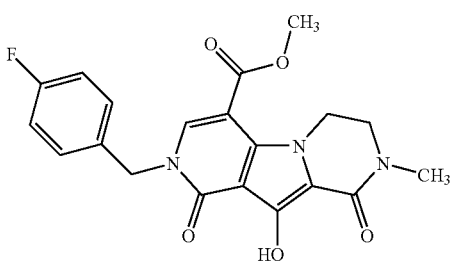

Step 1: Methyl 10-(benzyloxy)-2-(4-fluorobenzyl)-8-methyl-1,9-dioxo-1,2,6,7,8,9-hexahydropyrido[3',4':4,5]pyrrolo[1,2-a]-pyrazine-4-carboxylate A mixture of methyl 10-(benzyloxy)-2-(4-fluorobenzyl)-8-methyl-1,9-dioxo-1,2,3,4,6,7,8,9-octahydropyrido[3',4':4,5]pyrrolo[1,2-a]-pyrazine-4-carboxylate (0.4 g, 0.81 mmol) and manganese(IV) oxide (0.21 g, 2.44 mmol) in toluene (10 mL) was heated in a sealed tube in an oil bath 80° C. overnight. The reaction mixture was cooled to rt, diluted with chloroform (100 mL) and filtered through a pad of Celite. The filtrate was concentrated under vacuum. The filtrate was subjected to column chromatography on silica gel eluting with ethyl acetate. Collection and concentration of appropriate fractions provided the titled compound.

Step 2: 2-(4-Fluorobenzyl)-10-hydroxy-4-(methoxycarbonyl)-8-methyl-7,8-dihydropyrido-[3',4':4,5]pyrrolo[1,2-a]pyrazine-1,9(2H,6H)-dione A solution of methyl 10-(benzyloxy)-2-(4-fluorobenzyl)-8-methyl-1,9-dioxo-1,2,6,7,8,9-hexahydropyrido[3',4':4,5]pyrrolo[1,2-a]-pyrazine-4-carboxylat (30 mg, 0.06 mmol) and hydrogen bromide in acetic acid (0.7 mL, 30% solution) in dichloromethane (10 mL) was stirred at room temperature for 6 hr. The reaction mixture was concentrated under vacuum, and the residue subjected to reverse phase HPLC purification. Collection and lyophilization of appropriate fractions provided the title product.

$^1$H NMR (400 MHz, CDCl$_3$) δ 8.00 (br s, 1H), 7.35 (dd, J=8.4, 5.5 Hz, 2H), 7.02 (t, J=8.8 Hz, 2H), 5.15 (s, 2H), 4.70 (br t, 2H), 3.85 (s, 3H), 3.63 (br t, 2H), 3.10 (s, 3H).

ES MS M+1=400

EXAMPLES 87-98

The compounds in the following table were prepared in accordance with the procedure set forth in Example 86 using the appropriate analogous starting materials.

| Example | Compound | Data |
|---|---|---|
| 87 | 2-(3-Chloro-4-fluorobenzyl)-10-hydroxy-4-(methoxycarbonyl)-8-methyl-7,8-dihydropyrido-[3',4':4,5]pyrrolo[1,2-a]pyrazine-1,9(2H,6H)-dione | $^1$H NMR(400MHz, CDCl$_3$) δ 7.99(br s, 1H), 7.40(d, J=6.1Hz, 1H), 7.26(br s, 1H), 7.11(t, J=8.4Hz, 2H), 5.13(s, 2H), 4.72(br t, 2H), 3.87(s, 3H), 3.64(br t, 2H), 3.11(s, 3H). ES MS M + 1 = 434 |
| 88 | 2-(4-Fluorobenzyl)-10-hydroxy-4-(dimethylaminocarbonyl)-8-methyl-7,8-dihydropyrido-[3',4':4,5]pyrrolo[1,2-a]pyrazine-1,9(2H,6H)-dione | $^1$H NMR(400MHz, CDCl$_3$) δ 7.31(dd, J=8.4, 5.5Hz, 2H), 7.03 (t, J=8.8Hz, 2H), 7.01(s, 1H), 5.12(s, 2H), 4.10(br t, 2H), 3.61(br t, 2H), 3.09 (brs, 9H). ES MS M + 1 = 413 |

| Example | Compound | Data |
|---------|----------|------|
| 89 | 2-(3-Chloro-4-fluorobenzyl)-10-hydroxy-4-(methylaminocarbonyl)-8-methyl-7,8-dihydropyrido-[3',4':4,5]pyrrolo[1,2-a]pyrazine-1,9(2H,6H)-dione | $^1$H NMR(400MHz, DMSO-d$_6$) δ 8.50(br s, 1H), 7.87(br s, 1H), 7.56(br d, J=5.3Hz, 1H), 7.37(m, 2H), 5.07 (s, 2H), 4.22(br t, 2H), 3.62(br t, 2H), 2.96(s, 3H), 2.77(s, 3H). ES MS M + 1 = 433 |
| 90 | 2-(3-Chloro-4-fluorobenzyl)-10-hydroxy-4-(dimethylaminocarbonyl)-8-methyl-7,8-dihydropyrido-[3',4':4,5]pyrrolo[1,2-a]pyrazine-1,9(2H,6H)-dione | $^1$H NMR(400MHz, CDCl$_3$) δ 7.38(br s, 1H), 7.22(br d, J=5.3Hz, 1H), 7.09(m, 2H), 5.09(s, 2H), 4.12(br t, 2H), 3.64(br t, 2H), 3.08(br s, 9H). ES MS M + 1 = 447 |
| 91 | 2-(3-Chloro-4-fluorobenzyl)-10-hydroxy-4-(aminocarbonyl)-8-methyl-7,8-dihydropyrido-[3',4':4,5]pyrrolo[1,2-a]pyrazine-1,9(2H,6H)-dione | $^1$H NMR(400MHz, DMSO-d$_6$) δ 8.05(br s, 1H), 7.64(br d, J=7.1Hz, 1H), 7.22(br s, 1H), 7.45-7.43(m, 2H), 5.13(s, 2H), 4.36 (br t, 2H), 3.68(br t, 2H), 3.02(s, 3H). ES MS M + 1 = 419 |
| 92 | 2-(3-Chloro-4-fluorobenzyl)-10-hydroxy-4-(morpholinylcarbonyl)-8-methyl-7,8-dihydropyrido-[3',4':4,5]pyrrolo[1,2-a]pyrazine-1,9(2H,6H)-dione | $^1$H NMR(400MHz, CDCl$_3$) δ 8.60(s, 1H), 7.38(dd, J=2.2, 6.7, 1H), 7.28-7.26(m, 1H), 7.10(t, J=8.6Hz, 1H), 7.03(s, 1H), 5.09(s, 2H), 4.16(br signal, 2H), 3.63(br signal, 6H), 3.09(s, 3H). ES MS M + 1 = 489 |

-continued

| Example | Compound | Data |
|---|---|---|
| 93 | 2-(3-Chloro-4-fluorobenzyl)-10-hydroxy-4-(N-methylpiperazinylcarbonyl)-8-methyl-7,8-dihydropyrido-[3',4':4,5]pyrrolo[1,2-a]pyrazine-1,9(2H,6H)-dione TFA salt | $^1$H NMR(400MHz, CDCl$_3$) δ 10.26(br s, 1H), 8.88(br s, 1H), 7.80(br s, 1H), 7.55 (br d, J=7.2, 1H), 7.39(t, J=9.0Hz, 1H), 7.32(br s, 1H), 5.76(br s, 2H), 3.88 (br signal, 2H), 2.97(s, 3H), 2.83(s, 3H). ES MS M + 1 = 502 |
| 94 | 2-(3-Chloro-4-fluorobenzyl)-10-hydroxy-4-(N-methyl-N-methoxyaminocarbonyl)-8-methyl-7,8-dihydropyrido-[3',4':4,5]pyrrolo[1,2-a]pyrazine-1,9(2H,6H)-dione | $^1$H NMR(400MHz, CDCl$_3$) δ 7.40(s, 1H), 7.36(dd, J=2.0, 6.9, 1H), 7.25(m, 1H), 7.09 (t, J=8.6Hz, 1H), 5.11(s, 2H), 4.17(t, J=6.4, 2H), 3.61(t, J=6.4, 2H), 3.49(s, 3H). 3.36(s, 3H), 3.09(s, 3H). ES MS M + 1 = 463 |
| 95 | 2-(3-Chloro-4-fluorobenzyl)-10-hydroxy-4-(azetidinylcarbonyl)-8-methyl-7,8-dihydropyrido-[3',4':4,5]pyrrolo[1,2-a]pyrazine-1,9(2H,6H)-dione | $^1$H NMR(400MHz, DMSO-d$_6$) δ 7.88(s, 1H), 7.58(dd, J=2.0, 7.3, 1H), 7.39(t, J=8.6Hz, 1H), 7.34(m, 1H), 5.08(s, 2H), 4.20 (m, 4H), 4.04(m, 2H), 3.63(m, 2H), 2.96(s, 3H), 2.23(p,. J=7.7Hz, 2H). ES MS M + 1 = 459 |
| 96 | 2-(3-Chloro-4-fluorobenzyl)-10-hydroxy-4-(pyrrolidinylcarbonyl)-8-methyl-7,8-dihydropyrido-[3',4':4,5]pyrrolo[1,2-a]pyrazine-1,9(2H,6H)-dione | $^1$H NMR(400MHz, DMSO-d$_6$) δ 7.82(s, 1H), 7.56(dd, J=2.0, 7.2, 1H), 7.39(t, J=8.6Hz, 1H), 7.33(m, 1H), 5.07(s, 2H), 4.03 (t, J=6.2, 2H), 3.61(t, J=6.2, 2H), 3.47(t, J=6.6, 2H), 3.40(t, J=6.4, 2H), 2.95(s, 3H). 1.90-1.82(m, 4H). ES MS M + 1 = 473 |

| Example | Compound | Data |
|---|---|---|
| 97 | 8-(4-Fluorobenzyl)-10-hydroxy-4-(methoxycarbonyl)-2-methyl-7,8-dihydropyrido-[3',4':4,5]pyrrolo[1,2-a]pyrazine-1,9(2H,6H)-dione | $^1$H NMR(400MHz, CDCl$_3$) δ 8.02(s, 1H), 7.31(dd, J=8.4, 5.5Hz, 1H), 7.04(t, J=8.5Hz, 2H), 4.69(s, 2H), 4.64(t, J=5.6Hz, 2H), 3.85(s, 3H), 3.60(s, 3H), 3.52(t, J=5.6Hz, 2H). ES MS M + 1 = 400 |
| 98 | 8-(4-Fluorobenzyl)-10-hydroxy-4-(methylaminocarbonyl)-2-methyl-7,8-dihydropyrido-[3',4':4,5]pyrrolo[1,2-a]pyrazine-1,9(2H,6H)-dione | $^1$H NMR(400MHz, CDCl$_3$) δ 7.,58(br q, J=4.8Hz, 1H), 7.31 (dd, J=8.4, 5.5Hz, 1H), 7.15(s, 1H), 7.04 (t, J=8.5Hz, 2H), 4.64(s, 2H), 4.27(t, J=5.7Hz, 2H), 3.51(t, J=5.7Hz, 2H), 3.39 (s, 3H), 3.02(d, J=4.8Hz, 3H),. ES MS M + 1 = 399 |

EXAMPLE 99

(6S)-2-(3-Chloro-4-fluorobenzyl)-8-ethyl-10-hydroxy-6-methyl-4-(methylaminocarbonyl)-7,8-dihydropyrido-[3',4':4,5]pyrrolo[1,2-a]pyrazine-1,9(2H,8H)-dione

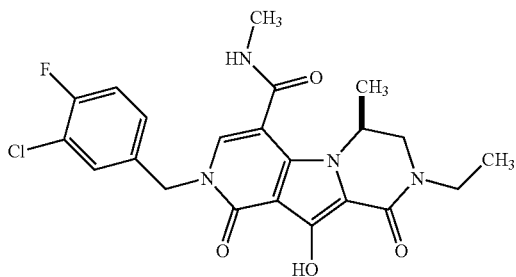

Step 1: Ethyl (4S)-2-ethyl-8-(methoxy)-4-methyl-1-oxo-1,2,3,4-tetrahydro-pyrrolo[1,2-a]-pyrazine-7-carboxylate To a solution of ethyl 4(S)-2-ethyl-8-hydroxy-4-methyl-1-oxo-1,2,3,4-tetrahydro-pyrrolo[1,2-a]-pyrazine-7-carboxylate (6.6 g, 25.8 mmol; prepared in a manner similar to the procedures described in Examples 32 and 45 starting with N-Boc-L-alanine) in DMF (125 mL), potassium carbonate (13.7 g, 99.1 mmol) and iodomethane (1.86 mL, 29.7 mmol) was added. The reaction mixture was stirred at rt over night. The mixture was filtered and the filtrate concentrated under vacuum. The residue was partitioned between dichloromethane and brine. The organic extract was washed with brine, dried over sodium sulfate, filtered, and concentrated under vacuum. The residue was subjected to column chromatography on silica gel eluted with ethyl acetate to give titled material.

$^1$H NMR (400 MHz, CDCl$_3$) δ 7.19 (s, 1H), 4.30 (q, J=7.2 Hz, 2H), 4.24-4.22 (m, 1H), 4.02 (s, 3H), 3.68-3.63 (m, 1H), 3.58-3.50 (m, 2H), 3.49-3.34 (m, 1H), 1.52 (d, J=6.6 Hz, 3H), 1.35 (t, J=7.2 Hz, 3H), 1.19 (t, J=7.1 Hz, 3H).

Step 2: Ethyl (4S)-2-ethyl-8-(methoxy)-6-[methoxy(oxo)acetyl]-4-methyl-1-oxo-1,2,3,4-tetrahydro-pyrrolo[1,2-a]-pyrazine-7-carboxylate To a mixture of ethyl (4S)-2-ethyl-8-(methoxy)-4-methyl-1-oxo-1,2,3,4-tetrahydro-pyrrolo[1,2-a]-pyrazine-7-carboxylate (6.2 g, 22.1 mmol) and sodium bicarbonate (20.0 g, 238.0 mmol) in dichloromethane (500 mL) at 0° C., a solution of bromine in dichloromethane (0.5 M, 24.2 mmol) was added over a period of 60 minutes. The reaction mixture was stirred at room temperature for 2 h, filtered, and concentrated under vacuum. The residue was subjected to column chromatography on silica gel eluted with ethyl acetate. Collection and concentration of appropriate fractions provided the corresponding bromide.

To a cold (−78° C.) solution of the above bromide (2.28 g, 6.35 mmol) in anhydrous THF (250 mL) under an atmosphere of dry nitrogen, a solution of n-BuLi in hexane (3.05 mL, 7.6 mmol, 2.5 M) was added. The resultant mixture was stirred at −60° C. for 50 minutes, and cooled back to −78° C. Dimethyl oxalate (2.40 g, 20.3 mmol; dried from concentration from benzene under vac) was added. The reaction mixture was stirred at −45° C. for 1 hour, cooled back to −78° C., and cannulated into aq sulfuric acid (175 mL, 1M) at 0° C. The mixture was partitioned with ethyl acetate (3 times). The organic extract was washed with brine, dried over anhydrous sodium sulfate, filtered and concentrated under vacuum. The residue was subjected to column chromatography on silica gel eluted with ethyl acetate-hexane gradient. Collection and concentration of appropriate fractions provided the titled compound.

¹H NMR (400 MHz, CDCl₃) δ 5.07 (m, 1H), 4.29 (q, J=7.2 Hz, 2H), 4.00 (s, 3H), 3.99-3.93 (m, 1H), 3.89 (s, 3H), 3.74-3.66 (m, 1H), 3.53-3.48 (m, 1H), 3.23 (dd, J=1.3, 13.2 Hz, 1H), 1.46 (d, J=6.6 Hz, 3H), 1.36 (t, J=7.2 Hz, 3H), 1.22 (t, J=7.1 Hz, 3H).

Step 3: Ethyl (4S)-2-ethyl-8-(methoxy)-6-[1-(methoxycarbonyl)vinyl]-4-methyl-1-oxo-1,2,3,4-tetrahydro-pyrrolo[1,2-a]-pyrazine-7-carboxylate To a cold (0° C.) solution of ethyl (4S)-2-ethyl-8-(methoxy)-6-[methoxy(oxo)-acetyl]-4-methyl-1-oxo-1,2,3,4-tetrahydro-pyrrolo[1,2-a]-pyrazine-7-carboxylate (1.0 g, 2.73 mmol) in anhydrous THF (100 mL), a solution of Tebbe reagent (6.0 mL, 0.5 M) in toluene was added. The reaction mixture was stirred at room temperature for one hour. The product mixture was diluted with ether (100 mL) and treated with aq sodium hydroxide (4 mL, 1M). The mixture was filtered. The organic extract was separated, dried over anhydrous sodium sulfate, filtered, and concentrated under vacuum. The residue was subjected to column chromatography on silica gel eluted with ethyl acetate-hexane gradient. Collection and concentration of appropriate fractions provided the olefination product.

ES MS M+1=365

Step 4: Methyl (6S)-8-ethyl-10-(methoxy)-6-methyl-1,9-dioxo-1,2,6,7,8,9-hexahydropyrido-[3',4':4,5]pyrrolo[1,2-a]-pyrazine-4-carboxylate A solution of ethyl (4S)-2-ethyl-8-(methoxy)-6-[1-(methoxycarbonyl)vinyl]-4-methyl-1-oxo-1,2,3,4-tetrahydro-pyrrolo[1,2-a]-pyrazine-7-carboxylate (0.19 g, 0.54 mmol) in a mixture of toluene (10 mL) and methanol (4 mL) was treated with a saturated solution of ammonia in methanol (10 mL). The mixture was stirred at rt overnight. The product mixture concentrated under vacuum to provide the corresponding cyclization product. Treatment of the above intermediate (0.34 g, 1.01 mmol) and manganese(IV) oxide (0.26 g, 3.04 mmol) in toluene (10 mL) was heated in a sealed tube in an oil bath 80° C. overnight. The reaction mixture was cooled to rt, diluted with chloroform (100 mL) and filtered through a pad of Celite. The filtrate was concentrated under vacuum. The filtrate was subjected to column chromatography on silica gel eluting with ethyl acetate. Collection and concentration of appropriate fractions provided the titled compound.

ES MS M+1=334

Step 5: Methyl (6S)-2-(3-chloro-4-fluorobenzyl)-8-ethyl-10-methoxy-6-methyl-1,9-dioxo-1,2,6,7,8,9-hexahydropyrido[3',4':4,5]pyrrolo[1,2-a]-pyrazine-4-carboxylate To a cold (−25° C.) solution of methyl (6S)-8-ethyl-10-(methoxy)-6-methyl-1,9-dioxo-1,2,6,7,8,9-hexahydropyrido-[3',4':4,5]pyrrolo[1,2-a]-pyrazine-4-carboxylate (0.29 g, 0.87 mmol) in anhydrous DMF (15 mL) under an atmosphere of nitrogen, a solution of lithium bis(trimethylsilyl) amide in THF (1 M, 0.96 mmol) was added. The reaction mixture was stirred at −25° C. for 25 minutes and treated with 3-chloro-4-fluorobenzyl bromide (0.27 g, 1.2 mmol; passed through activated basic alumina). The reaction mixture was stirred at 0° C. for 40 minutes and concentrated under vacuum. The residue was partitioned between ethyl acetate and dilute aqueous HCl. The organic extract was washed with brine, dried over anhydrous sodium sulfate, filtered, and concentrated under vacuum. The residue was subjected to column chromatography on silica gel eluted with ethyl acetate-hexane gradient. Collection and concentration of appropriate fractions provided the titled product.

¹H NMR (400 MHz, CDCl₃) δ 8.00 (s, 1H), 7.40 (dd, J=2.4, 6.8, 1H), 7.28-7.24 (m, 1H), 7.11 (t, J=8.6 Hz, 1H), 5.15 (d, J=15.7 Hz, 1H), 5.08 (d, J=15.7 Hz, 1H), 4.12 (s, 3H), 3.94 (dd, J=3.8, 13.0 Hz, 1H), 3.88 (s, 3H), 3.71 (m, 1H), 3.52 (m, 1H), 3.19 (dd, J=1.8, 13.2, 1H), 1.39 (d, J=6.5 Hz, 3H), 1.22 (t, J=7.2 Hz, 3H).

ES MS M+1=476

Step 6: (6S)-2-(3-Chloro-4-fluorobenzyl)-8-ethyl-10-hydroxy-6-methyl-4-(methylaminocarbonyl)-7,8-dihydropyrido-[3',4':4,5]pyrrolo[1,2-a]pyrazine-1,9(2H,8H)-dione Following the procedures described in Example 77, methyl (6S)-2-(3-chloro-4-fluorobenzyl)-8-ethyl-10-methoxy-6-methyl-1,9-dioxo-1,2,6,7,8,9-hexahydropyrido[3',4':4,5]-pyrrolo[1,2-a]-pyrazine-4-carboxylate was hydrolyzed, coupled with methylamine, and deprotected to provide the title compound.

¹H NMR (400 MHz, CDCl₃) δ 7.34 (br d, J=6.4, 1H), 7.17 (m, 1H), 7.06 (br t, J=8.3 Hz, 1H), 6.82 (br s, 1H), 5.08 (br s, 1H), 4.96 (d, J=14.4 Hz, 1H), 4.81 (d, J=14.4 Hz, 1H), 4.01 (br d, J=10 Hz, 1H), 3.73 (m, 1H), 3.40 (m, 1H), 3.18 (dd, J=12.6, 1H), 3.02 (s, 3H), 1.28 (d, J=6.6 Hz, 3H), 1.21 (t, J=7.1 Hz, 3H).

ES MS M+1=461

EXAMPLE 100

(6S)-2-(3-Chloro-4-fluorobenzyl)-8-ethyl-10-hydroxy-6-methyl-4-(dimethylaminocarbonyl)-7,8-dihydropyrido-[3',4':4,5]pyrrolo[1,2-a]pyrazine-1,9(2H,8H)-dione

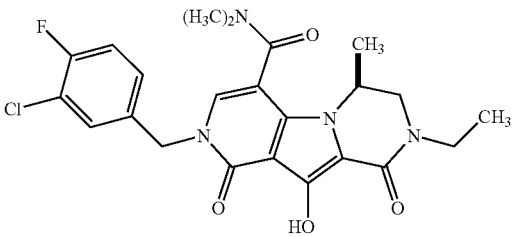

The title compound was prepared in accordance with the procedures set forth in Example 99 using dimethylamine as the coupling agent instead of methylamine.

¹H NMR (400 MHz, CDCl₃) δ 7.39 (dd, J=2.4, 6.8, 1H), 7.25-7.23 (m, 1H), 7.09 (t, J=8.6 Hz, 1H), 5.10 (s, 2H), 4.12 (s, 3H), 3.95 (dd, J=3.8, 13.0 Hz, 1H), 3.68 (m, 1H), 3.49 (m, 1H), 3.19 (dd, J=1.8, 13.2, 1H), 3.13 (s, 3H), 3.03 (s, 3H), 1.26 (d, J=6.6 Hz, 3H), 1.21 (t, J=7.1 Hz, 3H).

ES MS M+1=475

EXAMPLE 101

2-(3-Chloro-4-fluorobenzyl)-10-hydroxy-4-cyano-8-methyl-7,8-dihydropyrido-[3',4':4,5]pyrrolo[1,2-a]pyrazine-1,9(2H,6H)-dione

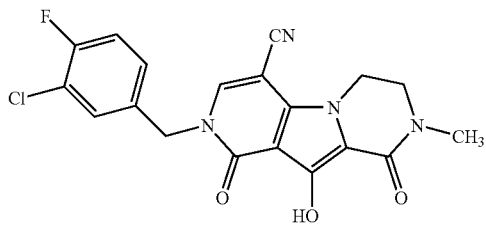

To a solution of 2-(3-chloro-4-fluorobenzyl)-10-benzyloxy-4-(aminocarbonyl)-8-methyl-7,8-dihydropyrido-[3',4':4,5]pyrrolo[1,2-a]pyrazine-1,9(2H,6H)-dione (0.10 g, 0.20 mmol) and triethylamine (87 mg, 0.86 mmol) in anhydrous THF at 0° C., trifluoroacetic anhydride (0.11 g, 0.53 mmol) was added. The reaction mixture was stirred at 0° C. for one hour. The product mixture was diluted with water and diethyl ether. The organic extract was dried over anhydrous sodium sulfate, filtered, and concentrated under vacuum. The residue was subjected to column chromatography on silica gel eluting with 10-20% methanol in dichloromethane. Collection and concentration of appropriate fractions provided the corresponding benzylated nitrile. A solution of above nitrile (22 mg, 0.05 mmol) in dichloromethane (5 mL) was treated with a solution of boron tribromide in dichloromethane (0.13 mL, 1M) and stirred at rt for 2 hours. The product mixture was treated with methanol and concentrated under vacuum. The residue subjected to reverse phase HPLC purification. Collection and lyophilization of appropriate fractions provided the title product.

$^1$H NMR (400 MHz, CDCl$_3$) δ 7.61 (s, 1H), 7.40 (dd, J=2.2, 6.8, 1H), 7.25 (m, 1H, 7.13 (t, J=8.7 Hz, 1H), 5.11 (s, 2H), 4.52 (t, J=5.8, 2H), 3.72 (t, J=5.8, 2H), 3.13 (s, 3H).

ES MS M+1=401

EXAMPLE 102

2-(3-Chloro-4-fluorobenzyl)-10-hydroxy-8-methyl-4-(5-methyl-1,3,4-oxadiazol-2-yl)-7,8-dihydropyrido-[3',4':4,5]pyrrolo[1,2-a]pyrazine-1,9(2H,6H)-dione

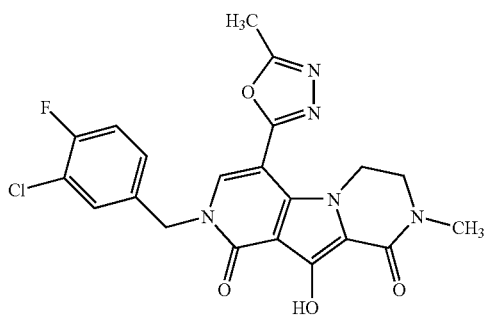

A mixture of 2-(3-chloro-4-fluorobenzyl)-10-methoxy-8-methyl-1,9-dioxo-1,2,6,7,8,9-hexahydropyrido[3',4':4,5]pyrrolo[1,2-a]-pyrazine-4-carboxylic acid (0.22 g, 0.51 mmol), benzotriazol-1-yloxy-tris(dimethylamino)phosphonium hexafluorophophate (BOP, 0.53 g, 1.01 mmol), acetylhydrazine (75 mg, 1.01 mmol), and diisopropylethylamine (0.35 mL, 2.03 mmol) in anhydrous DMF (5 mL) was stirred at room temperature overnight. The reaction mixture was concentrated under vacuum, and the residue partitioned between chloroform and brine. The organic extract was dried over anhydrous sodium sulfate, filtered, and concentrated under vacuum. The residue was triturated with diethyl ether, and the solid filtered to provide the corresponding coupling product. ES MS M+1=490.

A mixture of the above hydrazine amide (87 mg, 0.18 mmol) and Burgess reagent (85 mg, 0.36 mmol; [methoxycarbonylsulfamoyl]triethylammonium hydroxide]) in anhydrous THF was heated in a sealed tube in an oil bath at 70° C. for 36 hours. The reaction mixture was concentrated under vacuum, and the residue partitioned between chloroform and brine. The organic extract was dried over anhydrous sodium sulfate, filtered, and concentrated under vacuum. The residue was subjected to column chromatography on silica gel eluting with a gradient of methanol in ethyl acetate. Collection and concentration of appropriate fractions provided the corresponding oxadiazole. ES MS M+1=472. Treatment of this material with boron tribromide as describe in Example 101 provided the titled compound.

$^1$H NMR (400 MHz, CDCl$_3$) δ 7.73 (s, 1H), 7.42 (dd, J=2.0, 6.9, 1H), 7.31-7.25 (m, 1H), 7.11 (t, J=8.6 Hz, 1H), 5.17 (s, 2H), 4.91 (m, 2H), 3.66 (m, 2H), 3.12 (s, 3H), 2.63 (s, 3H).

ES MS M+1=458

EXAMPLE 103

2-(3-Chloro-4-fluorobenzyl)-10-hydroxy-4-(N-methanesulfonyl-N-methylamino)-8-methyl-7,8-dihydropyrido-[3',4':4,5]pyrrolo[1,2-a]pyrazine-1,9(2H,6H)-dione

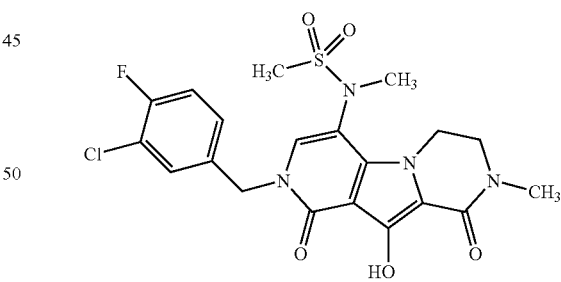

Step 1: 2-(3-Chloro-4-fluorobenzyl)-10-methoxy-4-(N-tert-butoxylcarbonylamino)-8-methyl-7,8-dihydropyrido-[3',4':4,5]pyrrolo[1,2-a]pyrazine-1,9(2H,6H)-dione A solution of 2-(3-chloro-4-fluorobenzyl)-10-methoxy-8-methyl-1,9-dioxo-1,2,6,7,8,9-hexahydropyrido[3',4':4,5]pyrrolo[1,2-a]-pyrazine-4-carboxylic acid (0.74 g, 1.70 mmol), diisopropylethylamine (0.28 g, 2.13 mmol), and diphenylphosphoryl azide (0.57 g, 2.13 mmol) in mixture of 1,2-dichlorobenzene (10 mL) and anhydrous tert-butyl alcohol (10 mL) was heated in a sealed tube in an oil bath 120° C. for one hour. The reaction mixture was concentrated under vacuum. The residue was subjected to column chromatography on silica gel eluting with a methanol in ethyl acetate gradient. Collection and concentration of appropriate fractions provided the titled compound.

$^1$H NMR (400 MHz, CDCl$_3$) δ 7.35 (dd, J=2.2, 6.8, 1H), 7.22-7.18 (m, 1H), 7.06 (t, J=8.6 Hz, 1H), 6.98 (s, 1H), 6.21 (br s, 1H), 4.97 (s, 2H), 4.33 (t, J=5.5 Hz, 2H), 4.03 (s, 3H), 3.58 (t, J=5.5 Hz, 2H), 3.04 (s, 3H), 1.48 (s, 9H).

ES MS M+1=505

Step 2: 2-(3-Chloro-4-fluorobenzyl)-10-methoxy-4-(N-tert-butoxylcarbonyl-N-methanesulfonyl-amino)-8-methyl-7,8-dihydropyrido-[3',4':4,5]pyrrolo[1,2-a]pyrazine-1,9(2H,6H)-dione A cold (0° C.) solution of 2-(3-chloro-4-fluorobenzyl)-10-methoxy-4-(N-tert-butoxylcarbonyl-amino)-8-methyl-7,8-dihydropyrido-[3',4':4,5]pyrrolo[1,2-a]pyrazine-1,9(2H,6H)-dione (0.74 g, 1.70 mmol) in anhydrous DMF (3 mL) was treated with sodium hydride (7 mg, 0.30 mmol). The resultant mixture was stirred at the same temperature for 30 minutes, and treated with methanesulfonyl chloride (34 mg, 0.30 mmol). After stirring at 0° for 1 hour, the product mixture was concentrated under vacuum. The residue was partitioned between chloroform and brine. The organic extract was dried over anhydrous sodium sulfate, filtered, and concentrated under vacuum. The residue was subjected to column chromatography on silica gel eluting with 20% methanol in ethyl acetate. Collection and concentration of appropriate fractions provided the titled compound.

$^1$H NMR (400 MHz, CDCl$_3$) δ 7.29 (dd, J=2.2, 6.8, 1H), 7.18-7.14 (m, 1H), 7.08 (t, J=8.6 Hz, 1H), 7.06 (s, 1H), 5.28 (d, J=15.2 Hz, 1H), 4.90 (d, J=15.2 Hz, 1H), 4.56-4.50 (m, 1H), 4.15-4.06 (m, 1H), 4.13 (s, 3H), 3.72-3.67 (m, 1H), 3.62 (m, 1H), 3.45 (s, 3H), 3.10 (s, 3H), 1.45 (s, 9H).

ES MS M+1=583

Step 3: 2-(3-Chloro-4-fluorobenzyl)-10-methoxy-4-(N-methanesulfonyl-amino)-8-methyl-7,8-dihydropyrido-[3',4':4,5]pyrrolo[1,2-a]pyrazine-1,9(2H,6H)-dione A cold (0° C.) solution of 2-(3-chloro-4-fluorobenzyl)-10-methoxy-4-(N-tert-butoxylcarbonyl-N-methanesulfonyl-amino)-8-methyl-7,8-dihydropyrido-[3',4':4,5]pyrrolo[1,2-a]pyrazine-1,9(2H,6H)-dione (90 mg, 0.15 mmol) and trifluoroacetic acid (2 mL) in anhydrous dichloromethane (3 mL) was stirred for 3 hours. The product mixture was concentrated under vacuum. The residue was subjected to column chromatography on silica gel eluting with 20% methanol in ethyl acetate. Collection and concentration of appropriate fractions provided the titled compound.

$^1$H NMR (400 MHz, CD$_3$OD-CDCl$_3$) δ 7.36 (dd, J=2.2, 6.8, 1H), 7.30 (s, 1H), 7.21-7.18 (, 1H), 7.06 (t, J=8.6 Hz, 1H), 4.90 (s, 2H), 4.58 (t, J=5.5 Hz, 2H), 4.03 (s, 3H), 3.61 (t, J=5.5 Hz, 2H), 3.04 (s, 3H), 2.99 (s, 3H).

ES MS M+1=483

Step 4: 2-(3-Chloro-4-fluorobenzyl)-10-methoxy-4-(N-methyl-N-methanesulfonyl-amino)-8-methyl-7,8-dihydropyrido-[3',4':4,5]pyrrolo[1,2-a]pyrazine-1,9(2H,6H)-dione A cold (0° C.) solution of 2-(3-chloro-4-fluorobenzyl)-10-methoxy-4-(N-tert-butoxylcarbonyl-amino)-8-methyl-7,8-dihydropyrido-[3',4':4,5]pyrrolo[1,2-a]pyrazine-1,9(2H, 6H)-dione (74 mg, 0.15 mmol) in anhydrous DMF (8 mL) was treated with sodium hydride (15 mg, 0.61 mmol). The resultant mixture was stirred at the same temperature for 30 minutes, and treated with iodomethane (87 mg, 0.61 mmol). After stirring at 0° C. for 1 hour, the product mixture was concentrated under vacuum. The residue was partitioned between chloroform and brine. The organic extract was dried over anhydrous sodium sulfate, filtered, and concentrated under vacuum to provide the titled compound.

$^1$H NMR (400 MHz, CDCl$_3$) δ 7.35 (dd, J=2.2, 6.8, 1H), 7.21-7.18 (m, 1H), 7.10 (t, J=8.6 Hz, 1H), 7.07 (s, 1H), 5.09 (d, J=15.1 Hz, 1H), 5.04 (d, J=15.1 Hz, 1H), 4.70-4.64 (m, 1H), 4.38-4.32 (m, 1H), 4.12 (s, 3H), 3.69-3.61 (m, 2H), 3.29 (s, 3H), 3.11 (s, 3H), 2.94 (s, 3H).

ES MS M+1=497

Step 5: 2-(3-Chloro-4-fluorobenzyl)-10-hydroxy-4-(N-methanesulfonyl-N-methylamino)-8-methyl-7,8-dihydropyrido-[3',4':4,5]pyrrolo[1,2-a]pyrazine-1,9(2H,6H)-dione A solution of 2-(3-chloro-4-fluorobenzyl)-10-methoxy-4-(N-methyl-N-methanesulfonyl-amino)-8-methyl-7,8-dihydropyrido-[3',4':4,5]pyrrolo[1,2-a]pyrazine-1,9(2H,6H)-dione (60 mg, 0.12 mmol) and boron tribromide (180 mg, 0.72 mmol) in dichloromethane (30 mL) was stirred at rt for 2 hours. The product mixture was treated with methanol and concentrated under vacuum. The residue subjected to reverse phase HPLC purification. Collection and lyophilization of appropriate fractions provided the title product.

$^1$H NMR (400 MHz, CDCl$_3$) δ 7.36 (dd, J=2.2, 6.8, 1H), 7.20 (br s, 1H), 7.10 (t, J=8.6 Hz, 1H), 7.04 (s, 1H), 5.09 (br s, 2H), 4.66-4.60 (m, 1H), 4.33-4.27 (m, 1H), 3.71-3.44 (m, 2H), 3.27 (s, 3H), 3.10 (s, 3H), 2.94 (s, 3H).

ES MS M+1=483

EXAMPLE 104

2-(3-Chloro-4-fluorobenzyl)-10-hydroxy-4-(N-acetyl-N-methylamino)-8-methyl-7,8-dihydropyrido-[3',4':4,5]pyrrolo[1,2-a]pyrazine-1,9(2H,6H)-dione

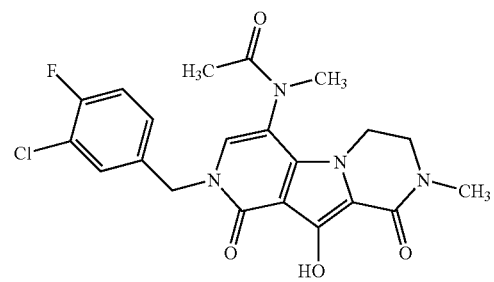

Step 1: 2-(3-Chloro-4-fluorobenzyl)-10-methoxy-4-(N-tert-butoxylcarbonyl-N-methylamino)-8-methyl-7,8-dihydropyrido-[3',4':4,5]pyrrolo[1,2-a]pyrazine-1,9(2H,6H)-dione A cold (0° C.) solution of 2-(3-chloro-4-fluorobenzyl)-10-methoxy-4-(N-tert-butoxylcarbonyl-amino)8-methyl-7,8-dihydropyrido-[3',4':4,5]pyrrolo[1,2-a]pyrazine-1,9(2H,6H)-dione (0.54 g, 1.07 mmol) in anhydrous DMF (6 mL) was treated with sodium hydride (38 mg, 1.60 mmol). The resultant mixture was stirred at the same temperature for 30 minutes, and treated with iodomethane (0.23 g, 1.60 mmol). After stirring at 0° C. for 1 hour, the product mixture was concentrated under vacuum. The residue was partitioned between chloroform and brine. The organic extract was dried over anhydrous sodium sulfate, filtered, and concentrated under vacuum to provide the titled compound.

¹H NMR (400 MHz, CDCl₃) δ 7.29 (dd, J=2.2, 6.8, 1H), 7.18-7.14 (m, 1H), 7.08 (t, J=8.6 Hz, 1H), 7.06 (s, 1H), 5.28 (d, J=15.2 Hz, 1H), 4.90 (d, J=15.2 Hz, 1H), 4.56-4.50 (m, 1H), 4.15-4.06 (m, 1H), 4.13 (s, 3H), 3.72-3.67 (m, 1H), 3.62 (m, 1H), 3.45 (s, 3H), 3.10 (s, 3H), 1.45 (s, 9H).

ES MS M+1=519

Step 2: 2-(3-Chloro-4-fluorobenzyl)-10-methoxy-4-(N-methylamino)-8-methyl-7,8-dihydropyrido-[3',4':4,5]pyrrolo[1,2-a]pyrazine-1,9(2H,6H)-dione A cold (0° C.) solution of 2-(3-chloro-4-fluorobenzyl)-10-methoxy-4-(N-tert-butoxylcarbonyl-N-methylamino)-8-methyl-7,8-dihydropyrido-[3',4':4,5]pyrrolo[1,2-a]pyrazine-1,9 (2H,6H)-dione (0.55 g, 1.06 mmol) in anhydrous dichloromethane (20 mL) was treated with trifluoroacetic acid (8 mL). The resultant mixture was stirred at the same temperature for 3 hours. The product mixture was concentrated under vacuum. The residue was subjected to reverse phase HPLC purification. Collection and lyophilization of appropriate fractions provided the title product as TFA salt.

¹H NMR (400 MHz, CDCl₃) δ 7.32 (dd, J=1.9, 6.8, 1H), 7.20-7.16 (m, 1H), 7.07 (t, J=8.4 Hz, 1H), 6.47 (s, 1H), 5.02 (s, 2H), 4.63 (t, J=5.7 Hz, 2H), 4.03 (s, 3H), 3.61 (t, J=5.7 Hz, 2H), 3.07 (s, 3H), 2.74 (s, 3H).

ES MS M+1=419

Step 3: 2-(3-Chloro-4-fluorobenzyl)-10-hydroxy-4-(N-acetyl-N-methylamino)-8-methyl-7,8-dihydropyrido-[3',4':4,5]pyrrolo[1,2-a]pyrazine-1,9(2H,6H)-dione Acetylation with acetic anhydride, and deprotection with boron tribromide as described in Example 103, step 5.

¹H NMR (400 MHz, CDCl₃) δ 7.39 (dd, J=2.2, 6.8, 1H), 7.26-7.22 (m, 1H), 7.11 (t, J=8.6 Hz, 1H), 5.08 (s, 2H), 4.06 (m, 2H), 3.66 (m, 2H), 3.19 (s, 3H), 3.11 (s, 3H), 1.91 (s, 3H).

ES MS M+1=447.

EXAMPLES 105-106

The compounds in the following table were prepared in accordance with the procedure set forth in Example 104 using the appropriate analogous starting materials.

| Example | Compound | Data |
|---|---|---|
| 105 | 2-(3-Chloro-4-fluorobenzyl)-10-hydroxy-4-(N-ethoxycarbonyl-N-methylamino)-8-methyl-7,8-dihydropyrido-[3',4':4,5]pyrrolo[1,2-a]pyrazine-1,9(2H,6H)-dione | 1H NMR(400MHz, CDCl3) δ 7.35(br d, J=6.3, 1H), 7.24-7.21 (m, 1H), 7.09(t, J=8.6Hz, 1H), 6.99(s, 1H), 5.07(br s, 2H), 4.10(m, 4H), 3.66(m, 2H), 3.20(s, 3H), 3.09 (s, 3H), 1.13(br s, 3H). ES MS M + 1 = 477 |
| 106 | 2-(3-Chloro-4-fluorobenzyl)-10-hydroxy-4-(2-N',N'-dimethylamino-2-oxoacetyl-N-methylamino)-8-methyl-7,8-dihydropyrido-[3',4':4,5]pyrrolo[1,2-a]pyrazine-1,9(2H,6H)-dione | 1H NMR(400MHz, CDCl3) δ 7.32(dd, J=2.4, 6.8, 1H), 7.24-7.20 (m, 1H), 7.12(t, J=8.5Hz, 1H), 6.88(s, 1H), 5.61(d, J=14.8Hz, 1H), 4.52(d, J=14.8Hz, 1H), 4.56-4.52 (m, 1H), 4.07-4.00 (m, 1H), 3.81-3.75 (m, 1H), 3.62-3.44 (m, 1H), 3.26(s, 3H), 3.09(s, 3H), 2.77 (s, 3H), 2.60(s, 3H). ES MS M + 1 = 504 |

EXAMPLE 107

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2-106 can be similarly prepared.

EXAMPLE 108

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1-106 were tested in the integrase assay and all were found to have $IC_{50}$'s less than 1 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 109

Assay for inhibition of HIV replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 1-106 were found to have $IC_{95}$'s of 10 micromolar or less in the present assay.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of Formula I, or a pharmaceutically acceptable salt thereof:

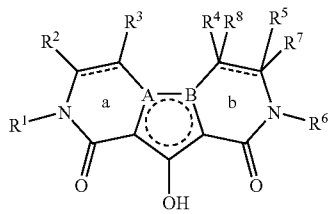

(I)

wherein:
bond "a" in the ring is a single bond or a double bond;
bond "b" in the ring is a single bond or a double bond, with the proviso that when bond "b" is a double bond, $R^7$ and $R^8$ are both absent;
one of A and B is N, and the other of A and B is C;
⋯⋯denotes that the central 5-membered ring is pyrrolyl;
$R^1$ is —$C_{1-6}$ alkyl-$R^J$, wherein $R^J$ is:
(A) aryl which is optionally substituted with from 1 to 5 substituents each of which is independently
(1) —$C_{1-6}$ alkyl, optionally substituted with from 1 to 3 substituents each of which is independently —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^c$, —S(O)$_n R^c$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, or —N($R^a$)C(=O)N($R^a$)$R^b$,
(2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_n R^c$, —C(=O)N($R^a$)$R^b$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, or —N($R^a$)C(=O)N($R^a$)$R^b$,
(3) —$C_{1-6}$ haloalkyl,
(4) —O—$C_{1-6}$ haloalkyl,
(5) —OH,
(6) halo,
(7) —CN,
(8) —$NO_2$,
(9) —N($R^a$)$R^b$,
(10) —C(=O)N($R^a$)$R^b$,
(11) —C(=O)$R^a$,
(12) —$CO_2R^c$,
(13) —$SR^c$,
(14) —S(=O)$R^c$,
(15) —$SO_2R^c$,
(16) —N($R^a$)$SO_2R^c$,
(17) —$SO_2$N($R^a$)$R^b$,
(18) —N($R^a$)C(=O)$R^b$,
(19) —N($R^a$)$CO_2R^c$,
(20) phenyl, or
(21) benzyl; or
(B) a 5- or 6-membered heteroaromatic ring containing from 1 to 4 heteroatoms independently selected from N, O and S; wherein the heteroaromatic ring is
(i) optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl; and
(ii) optionally substituted with 1 or 2 substituents each of which is independently aryl or —$C_{1-6}$ alkyl-aryl;
$R^2$ is:
(1) —H,
(2) —$C_{1-6}$ alkyl,
(3) —$C_{1-6}$ haloalkyl, or
(4) —$C_{1-6}$ alkyl substituted with one of —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^c$, —S(O)$_n R^c$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, —N($R^a$)C(=O)N($R^a$)$R^b$, or —N($R^a$)—$OR^b$;
$R^3$ is:
(1) —H,
(2) —$C_{1-6}$ alkyl optionally substituted with one of —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^c$, —S(O)$_n R^c$, —$SO_2$N($R^a$)$R^b$, —N($R^a$)—C($R^b$)=O, —N($R^a$)$SO_2R^c$, —N($R^a$)$SO_2$N($R^a$)$R^b$, —OC(=O)N($R^a$)$R^b$, —N($R^a$)C(=O)N($R^a$)$R^b$, —O—$C_{1-6}$ alkyl-C(=O)N($R^a$)$R^b$, —S—$C_{1-6}$ alkyl-C(=O)N($R^a$)$R^b$, —N($R^a$)—$C_{1-6}$ alkyl-C(=O)N($R^a$)$R^b$, —N($SO_2R^c$) —$C_{1-6}$ alkyl-C(=O)N($R^a$)$R^b$, or —N($R^a$)—$OR^b$;
(3) —$C_{1-6}$ haloalkyl,
(4) —C(=O)$R^a$,
(5) —$CO_2R^c$,
(6) —C(=O)N($R^a$)$R^b$,
(7) —$SO_2$N($R^a$)$R^b$,
(8) —$C_{2-6}$ alkenyl,
(9) —$C_{2-6}$ alkenyl-C(=O)—N($R^a$)$R^b$,
(10) —$C_{2-5}$ alkynyl,
(11) —$C_{2-5}$ alkynyl-$CH_2$N($R^a$)$R^b$,
(12) —$C_{2-5}$ alkynyl-$CH_2$$OR^a$,
(13) —$C_{2-5}$ alkynyl-$CH_2$S(O)$_n R^c$,
(14) —$R^K$,
(15) —$C_{1-6}$ alkyl substituted with $R^K$,
(16) —$C_{1-6}$ haloalkyl substituted with $R^K$,

(17) —$C_{1-6}$ alkyl-O—$R^K$,
(18) —$C_{1-6}$ alkyl-O—$C_{1-6}$ alkyl-$R^K$,
(19) —$C_{1-6}$ alkyl-S(O)$_n$—$R^K$,
(20) —$C_{1-6}$ alkyl-S(O)$_n$—$C_{1-6}$ alkyl-$R^K$,
(21) —$C_{1-6}$ alkyl-N($R^a$)-$R^K$,
(22) —$C_{1-6}$ alkyl-N($R^a$)-$C_{1-6}$ alkyl-$R^K$,
(23) —$C_{1-6}$ alkyl-N($R^a$)-$C_{1-6}$ alkyl-O$R^K$, with the proviso that the —N($R^a$)- moiety and the —O$R^K$ moiety are not both attached to the same carbon of the —$C_{1-6}$ alkyl-moiety,
(24) —$C_{1-6}$ alkyl-C(=O)—$R^K$,
(25) —$C_{1-6}$ alkyl-C(=O)N($R^a$)—$R^K$,
(26) —$C_{1-6}$ alkyl-N($R^a$)C(=O)—$R^K$,
(27) —$C_{1-6}$ alkyl-C(=O)N($R^a$)—$C_{1-6}$ alkyl-$R^K$,
(28) —$C_{1-6}$ alkyl-N($R^a$)—S(O)$_n$$R^K$,
(29) —$C_{1-6}$ alkyl-N($R^a$)—$C_{1-6}$ alkyl-S(O)$_n$$R^K$,
(30) halogen,
(31) —C(=O)N($R^d$)$R^e$,
(32) —C(=O)N($R^a$)O$R^b$,
(33) —CN,
(34) —N($R^a$)C(=O)$R^b$,
(35) —N($R^a$)CO$_2$$R^c$,
(36) —N($R^a$)SO$_2$$R^c$,
(37) —N($R^a$)C(=O)C(=O)N($R^a$)$R^b$,
(38) —N($R^a$)C(=O)C(=O)N($R^d$)$R^e$,
(39) —N($R^a$)C(=O)N($R^a$)$R^b$,
(40) —N=C($R^a$)N($R^a$)$R^b$,
(41) —N=C[N($R^a$)$R^b$]—N($R^a$)$R^b$,
(42) —S$R^c$,
(43) —S(O)$R^c$,
(44) —SO$_2$$R^c$, or
(45) —SO$_2$N($R^a$)$R^b$;
wherein $R^K$ is
(i) aryl, which is optionally substituted with from 1 to 5 substituents each of which is independently —$C_{1-6}$ alkyl, —$C_{1-6}$ alkyl-OH, —$C_{1-6}$ alkyl-O—$C_{1-6}$ alkyl, —$C_{1-6}$ alkyl-O—$C_{1-6}$ haloalkyl, —$C_{1-6}$ alkyl-N($R^a$)$R^b$, —$C_{1-6}$ alkyl-C(=O)N($R^a$)$R^b$, —$C_{1-6}$ alkyl-C(=O)$R^a$, —$C_{1-6}$ alkyl-CO$_2$$R^c$, —$C_{1-6}$ alkyl-S(O)$_n$$R^c$, —O—$C_{1-6}$ alkyl, —$C_{1-6}$ haloalkyl, —O—$C_{1-6}$ haloalkyl, —OH, halo, —CN, —NO$_2$, —N($R^a$)$R^b$, —C(=O)N($R^a$)$R^b$, —C(=O)$R^a$, —CO$_2$$R^c$, —S(O)$_n$$R^c$, or —SO$_2$N($R^a$)$R^b$;
(ii) a 4- to 7-membered saturated or mono-unsaturated heterocyclic ring containing at least one carbon atom and from 1 to 4 heteroatoms independently selected from N, O and S, wherein the heterocyclic ring is:
(a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
(b) optionally mono-substituted with aryl or HetA; wherein HetA is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl; or
(iii) a 5- or 6-membered heteroaromatic ring containing from 1 to 4 heteroatoms independently selected from N, O and S, wherein the heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl;

$R^4$ is:
(1) —H,
(2) —$C_{1-6}$ alkyl,
(3) —$C_{1-6}$ alkyl substituted with OH, S$R^c$, S(O)$R^c$, SO$_2$$R^c$, or —N($R^a$)SO$_2$$R^c$,
(4) —$C_{1-6}$ alkyl substituted with —$C_{3-8}$ cycloalkyl,
(5) —$C_{1-6}$ alkyl substituted with aryl, wherein the aryl is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl,
(6) —CO$_2$$R^c$,
(7) —C(=O)N($R^a$)$R^b$,
(8) —C(=O)N($R^d$)$R^e$, or
(9) aryl which is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl;

$R^5$ is:
(1) —H,
(2) —$C_{1-6}$ alkyl, or
(3) —$C_{1-6}$ alkyl substituted with —C(=O)N($R^a$)$R^b$ or —C(=O)N($R^d$)$R^e$;

$R^6$ is —H, —$C_{1-6}$ alkyl, $R^L$, or —$C_{1-6}$ alkyl-$R^L$, wherein $R^L$ is:
(A) aryl which is optionally substituted with from 1 to 5 substituents each of which is independently
(1) —$C_{1-6}$ alkyl, optionally substituted with from 1 to 3 substituents each of which is independently —OH, —O—$C_{1-6}$ alkyl, —O—$C_{1-6}$ haloalkyl, —CN, —NO$_2$, —N($R^a$)$R^b$, —C(=O)N($R^a$)$R^b$, —C(=O)$R^a$, —CO$_2$$R^c$, —S(O)$_n$$R^c$, —SO$_2$N($R^a$)$R^b$, —N($R^a$)C(=O)$R^b$, —N($R^a$)CO$_2$$R^c$, —N($R^a$)SO$_2$$R^c$, —N($R^a$)SO$_2$N($R^a$)$R^b$, —OC(=O)N($R^a$)$R^b$, or —N($R^a$)C(=O)N($R^a$)$R^b$,
(2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_n$$R^c$, —C(=O)N($R^a$)$R^b$, —SO$_2$N($R^a$)$R^b$, —N($R^a$)C(=O)$R^b$, —N($R^a$)CO$_2$$R^c$, —N($R^a$)SO$_2$$R^c$, —N($R^a$)SO$_2$N($R^a$)$R^b$, —OC(=O)N($R^a$)$R^b$, or —N($R^a$)C(=O)N($R^a$)$R^b$,
(3) —$C_{1-6}$ haloalkyl,
(4) —O—$C_{1-6}$ haloalkyl,
(5) —OH,
(6) halo,
(7) —CN,
(8) —NO$_2$,
(9) —N($R^a$)$R^b$,
(10) —C(=O)N($R^a$)$R^b$,
(11) —C(=O)$R^a$,
(12) —CO$_2$$R^c$,
(13) —S$R^c$,
(14) —S(=O)$R^c$,
(15) —SO$_2$$R^c$,
(16) —N($R^a$)SO$_2$$R^c$,
(17) —SO$_2$N($R^a$)$R^b$,
(18) —N($R^a$)C(=O)$R^b$,
(19) —N($R^a$)CO$_2$$R^c$,
(20) phenyl, or
(21) benzyl, (B) a 5- or 6-membered heteroaromatic ring containing from 1 to 4 heteroatoms independently selected from N, O and S; wherein the heteroaromatic ring is
   (i) optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl; and
   (ii) optionally substituted with 1 or 2 substituents each of which is independently aryl or —$C_{1-6}$ alkyl-aryl, or
(C) a —$C_{3-8}$ cycloalkyl which is optionally substituted with 1 to 3 substituents each of which is independently a —$C_{1-6}$ alkyl group;

$R^7$ is —H or —$C_{1-6}$ alkyl; or alternatively $R^5$ and $R^7$ together form oxo (=O) or thioxo (=S), or $R^5$ and $R^7$ together with the ring carbon atom to which they are both attached form —$C_{3-8}$ cycloalkyl;

$R^8$ is —H or —$C_{1-6}$ alkyl; or alternatively $R^4$ and $R^8$ together with the ring carbon atom to which they are both attached form —$C_{3-8}$ cycloalkyl;

or alternatively $R^7$ and $R^8$ are absent, and $R^4$ and $R^5$ together with the ring carbon atoms to which each is attached and with bond "b" form:
   (i) a benzene ring or a 6-membered heteroaromatic ring containing 1 or 2 nitrogen atoms, wherein the fused ring is optionally substituted with from 1 to 3 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl, or
   (ii) a $C_{3-6}$ cycloalkane ring;

each $R^a$ and $R^b$ is independently —H or —$C_{1-6}$ alkyl;
each $R^c$ is independently a —$C_{1-6}$ alkyl;
each $R^d$ and $R^e$ together with the N atom to which they are both attached form a 4- to 7-membered saturated heterocyclic ring optionally containing a heteroatom in addition to the nitrogen attached to $R^d$ and $R^e$ selected from N, O, and S, where the S is optionally oxidized to S(O) or $S(O)_2$, and wherein the saturated heterocyclic ring is optionally substituted with 1 or 2 $C_{1-6}$ alkyl groups; and
each n is independently an integer equal to 0, 1 or 2.

2. The compound according to claim 1, or a pharmaceutically acceptable salt thereof, which is a compound of Formula II:

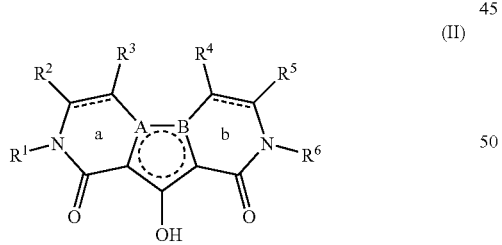

(II)

wherein
bond "a" in the ring is a single bond or a double bond;
bond "b" in the ring is a single bond or a double bond;
$R^3$ is:
(1) —H,
(2) —$C_{1-6}$ alkyl optionally substituted with one of —OH, —O—$C_{1-6}$ alkyl, —O—$C_{1-6}$ haloalkyl, —CN, —$NO_2$, —$N(R^a)R^b$, —C(=O)$N(R^a)R^b$, —C(=O)$R^a$, —$CO_2R^c$, —$S(O)_nR^c$, —$SO_2N(R^a)R^b$, —$N(R^a)$—C($R^b$)=O, —$N(R^a)SO_2R^c$, —$N(R^a)$ $SO_2N(R^a)R^b$, —OC(=O)$N(R^a)R^b$, —$N(R^a)$C(=O)$N(R^a)R^b$, —O—$C_{1-6}$ alkyl-C(=O)$N(R^a)R^b$,
—S—$C_{1-6}$ alkyl-C(=O)$N(R^a)R^b$, —$N(R^a)$—$C_{1-6}$ alkyl-C(=O)$N(R^a)R^b$, —$N(SO_2R^c)$—$C_{1-6}$ alkyl-C(=O)$N(R^a)R^b$, or —$N(R^a)$—$OR^b$;
(3) —$C_{1-6}$ haloalkyl,
(4) —C(=O)$R^a$,
(5) —$CO_2R^c$,
(6) —C(=O)$N(R^a)R^b$,
(7) —$SO_2N(R^a)R^b$,
(8) —$C_{2-6}$ alkenyl,
(9) —$C_{2-6}$ alkenyl-C(=O)—$N(R^a)R^b$,
(10) —$C_{2-5}$ alkynyl,
(11) —$C_{2-5}$ alkynyl-$CH_2N(R^a)R^b$,
(12) —$C_{2-5}$ alkynyl-$CH_2OR^a$,
(13) —$C_{2-5}$ alkynyl-$CH_2S(O)_nR^c$,
(14) —$R^K$,
(15) —$C_{1-6}$ alkyl substituted with $R^K$,
(16) —$C_{1-6}$ haloalkyl substituted with $R^K$,
(17) —$C_{1-6}$ alkyl-O—$R^K$,
(18) —$C_{1-6}$ alkyl-O—$C_{1-6}$ alkyl-$R^K$,
(19) —$C_{1-6}$ alkyl-$S(O)_n$—$R^K$,
(20) —$C_{1-6}$ alkyl-$S(O)_n$—$C_{1-6}$ alkyl-$R^K$,
(21) —$C_{1-6}$ alkyl-$N(R^a)$—$R^K$,
(22) —$C_{1-6}$ alkyl-$N(R^a)$—$C_{1-6}$ alkyl-$R^K$,
(23) —$C_{1-6}$ alkyl-$N(R^a)$—$C_{1-6}$ alkyl-$OR^K$, with the proviso that the —$N(R^a)$— moiety and the —$OR^K$ moiety are not both attached to the same carbon of the —$C_{1-6}$ alkyl-moiety,
(24) —$C_{1-6}$ alkyl-C(=O)—$R^K$,
(25) —$C_{1-6}$ alkyl-C(=O)$N(R^a)$—$R^K$,
(26) —$C_{1-6}$ alkyl-$N(R^a)$C(=O)—$R^K$,
(27) —$C_{1-6}$ alkyl-C(=O)$N(R^a)$—$C_{1-6}$ alkyl-$R^K$,
(28) —$C_{1-6}$ alkyl-$N(R^a)$—$S(O)_nR^K$, or
(29) —$C_{1-6}$ alkyl-$N(R^a)$—$C_{1-6}$ alkyl-$S(O)_nR^K$;
wherein $R^K$ is
(i) aryl, which is optionally substituted with from 1 to 5 substituents each of which is independently —$C_{1-6}$ alkyl, —$C_{1-6}$ alkyl-OH, —$C_{1-6}$ alkyl-O—$C_{1-6}$ alkyl, —$C_{1-6}$ alkyl-O—$C_{1-6}$ haloalkyl, —$C_{1-6}$ alkyl-$N(R^a)R^b$, —$C_{1-6}$ alkyl-C(=O)$N(R^a)R^b$, —$C_{1-6}$ alkyl-C(=O)$R^a$, —$C_{1-6}$ alkyl-$CO_2R^c$, —$C_{1-6}$ alkyl-$S(O)_nR^c$, —O—$C_{1-6}$ alkyl, —$C_{1-6}$ haloalkyl, —O—$C_{1-6}$ haloalkyl, —OH, halo, —CN, —$NO_2$, —$N(R^a)R^b$, —C(=O)$N(R^a)R^b$, —C(=O)$R^a$, —$CO_2R^c$, —$S(O)_nR^c$, or —$SO_2N(R^a)R^b$;
(ii) a 4- to 7-membered saturated or mono-unsaturated heterocyclic ring containing at least one carbon atom and from 1 to 4 heteroatoms independently selected from N, O and S, wherein the heterocyclic ring is:
   (a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
   (b) optionally mono-substituted with aryl or HetA; wherein HetA is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl; or (iii) a 5- or 6-membered heteroaromatic ring containing from 1 to 4 heteroatoms independently selected from N, O and S, wherein the heteroaromatic ring is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl;

$R^4$ is —H or —$C_{1-6}$ alkyl;

$R^5$ is —H or —$C_{1-6}$ alkyl;

$R^6$ is —H, —$C_{1-6}$ alkyl, or —$C_{1-6}$ alkyl-$R^L$, wherein $R^L$ is:
 (A) aryl which is optionally substituted with from 1 to 5 substituents each of which is independently
  (1) —$C_{1-6}$ alkyl, optionally substituted with from 1 to 3 substituents each of which is independently —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^c$, —S(O)$_nR^c$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, or —N($R^a$)C(=O)N($R^a$)$R^b$,
  (2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_nR^c$, —C(=O)N($R^a$)$R^b$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, —OC(=O)N($R^a$)$R^b$, or —N($R^a$)C(=O)N($R^a$)$R^b$,
  (3) —$C_{1-6}$ haloalkyl,
  (4) —O—$C_{1-6}$ haloalkyl,
  (5) —OH,
  (6) halo,
  (7) —CN,
  (8) —$NO_2$,
  (9) —N($R^a$)$R^b$,
  (10) —C(=O)N($R^a$)$R^b$,
  (11) —C(=O)$R^a$,
  (12) —$CO_2R^c$,
  (13) —$SR^c$,
  (14) —S(=O)$R^c$,
  (15) —$SO_2R^c$,
  (16) —N($R^a$)$SO_2R^c$,
  (17) —$SO_2$N($R^a$)$R^b$,
  (18) —N($R^a$)C(=O)$R^b$,
  (19) —N($R^a$)$CO_2R^c$,
  (20) phenyl, or
  (21) benzyl, or
 (B) a 5- or 6-membered heteroaromatic ring containing from 1 to 4 heteroatoms independently selected from N, O and S; wherein the heteroaromatic ring is
  (i) optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl; and
  (ii) optionally substituted with 1 or 2 substituents each of which is independently aryl or —$C_{1-6}$ alkyl-aryl.

3. The compound of Formula I according to claim 1, or a pharmaceutically acceptable salt thereof, wherein:

$R^1$ is —$C_{1-4}$ alkyl-$R^J$, wherein $R^J$ is phenyl which is optionally substituted with from 1 to 3 substituents each of which is independently:
 (1) —$C_{1-4}$ alkyl, optionally mono-substituted with —OH, —O—$C_{1-4}$ alkyl, —O—$C_{1-4}$ haloalkyl, —CN, —N($R^a$)$R^b$, —C(=O)N($R^a$)$R^b$, —C(=O)$R^a$, —$CO_2R^c$, —S(O)$_nR^c$, or —$SO_2$N($R^a$)$R^b$,
 (2) —O—$C_{1-4}$ alkyl,
 (3) —$C_{1-4}$ haloalkyl,
 (4) —O—$C_{1-4}$ haloalkyl,
 (5) —OH,
 (6) halo,
 (7) —CN,
 (8) —$NO_2$,
 (9) —N($R^a$)$R^b$,
 (10) —$SR^c$,
 (11) —S(=O)$R^c$,
 (12) —$SO_2R^c$,
 (13) —N($R^a$)$SO_2R^c$,
 (14) —$SO_2$N($R^a$)$R^b$,
 (15) —N($R^a$)C(=O)$R^b$,
 (16) —N($R^a$)$CO_2R^c$, or
 (17) phenyl;

$R^2$ is:
 (1) —H,
 (2) —$C_{1-4}$ alkyl, or
 (3) —$C_{1-4}$ alkyl substituted with one of —CN, —N($R^a$)$R^b$, —C(=O)N($R^a$)$R^b$, —C(=O)$R^a$, —$CO_2R^c$, —S(O)$_nR^c$, —$SO_2$N($R^a$)$R^b$, —N($R^a$)C(=O)$R^b$, —N($R^a$)$CO_2R^c$, —N($R^a$)$SO_2R^c$, —N($R^a$)$SO_2$N($R^a$)$R^b$, or —N($R^a$)C(=O)N($R^a$)$R^b$;

$R^3$ is:
 (1) —H,
 (2) —$C_{1-4}$ alkyl optionally substituted with one of —OH, —O—$C_{1-4}$ alkyl, —O—$C_{1-4}$ haloalkyl, —CN, —N($R^a$)$R^b$, —C(=O)N($R^a$)$R^b$, —C(=O)$R^a$, —$CO_2R^c$, —S(O)$_nR^c$, —$SO_2$N($R^a$)$R^b$, —N($R^a$)—C($R^b$)=O, —N($R^a$)$SO_2R^c$, —N($R^a$)$SO_2$N($R^a$)$R^b$, or —N($R^a$)—$OR^b$,
 (3) —$CO_2R^c$,
 (4) —C(=O)N($R^a$)$R^b$,
 (5) —$R^K$,
 (6) —$C_{1-4}$ alkyl substituted with $R^K$,
 (7) —$C_{1-4}$ alkyl-O—$R^K$,
 (8) —$C_{1-4}$ alkyl-O—$C_{1-4}$ alkyl-$R^K$,
 (9) halogen,
 (10) —C(=O)N($R^d$)$R^e$,
 (11) —C(=O)N($R^a$)$OR^b$,
 (12) —CN,
 (13) —N($R^a$)C(=O)$R^b$,
 (14) —N($R^a$)$CO_2R^c$,
 (15) —N($R^a$)$SO_2R^c$,
 (16) —N($R^a$)C(=O)C(=O)N($R^a$)$R^b$,
 (17) —N($R^a$)C(=O)C(=O)N($R^d$)$R^e$,
 (18) —N($R^a$)C(=O)N($R^a$)$R^b$,
 (19) —$SR^c$,
 (20) —S(O)$R^c$, or
 (21) —$SO_2R^c$;

wherein $R^K$ is:
 (i) phenyl, which is optionally substituted with from 1 to 3 substituents each of which is independently —$C_{1-4}$ alkyl, —$C_{1-4}$ alkyl-OH, —$C_{1-4}$ alkyl-O—$C_{1-4}$ alkyl, —$C_{1-4}$ alkyl-O—$C_{1-4}$ haloalkyl, —$C_{1-4}$ alkyl-N($R^a$)$R^b$, —$C_{1-4}$ alkyl-C(=O)N($R^a$)$R^b$, —$C_{1-4}$ alkyl-C(=O)$R^a$, —$C_{1-4}$ alkyl-$CO_2R^c$, —$C_{1-4}$ alkyl-S(O)$_nR^c$, —O—$C_{1-4}$ alkyl, —$C_{1-4}$ haloalkyl, —O—$C_{1-4}$ haloalkyl, —OH, halo, —N($R^a$)$R^b$, —C(=O)N($R^a$)$R^b$, —C(=O)$R^a$, —$CO_2R^c$, —S(O)$_nR^c$, or —$SO_2$N($R^a$)$R^b$;
 (ii) a 4- to 7-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is:
  (a) optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo; and
  (b) optionally mono-substituted with phenyl or HetA;
    wherein HetA is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —OH, —$C_{1-4}$ alkyl, —$C_{1-4}$ haloalkyl, —O—$C_{1-4}$ alkyl, or —O—$C_{1-4}$ haloalkyl; or
  (iii) a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —OH, —$C_{1-4}$ alkyl, —$C_{1-4}$ haloalkyl, or —O—$C_{1-4}$ alkyl, —O—$C_{1-4}$ haloalkyl;
$R^4$ is:
  (1) —H,
  (2) —$C_{1-4}$ alkyl,
  (3) —$C_{1-4}$ alkyl substituted with OH, $SR^c$, $S(O)R^c$, $SO_2R^c$, or —$N(R^a)SO_2R^c$,
  (4) —$C_{1-4}$ alkyl substituted with —$C_{3-7}$ cycloalkyl,
  (5) —$C_{1-4}$ alkyl substituted with phenyl, wherein the phenyl is optionally substituted with from 1 to 3 substituents each of which is independently halogen, —OH, —$C_{1-4}$ alkyl, —$C_{1-4}$ haloalkyl, —O—$C_{1-4}$ alkyl, or —O—$C_{1-4}$ haloalkyl,
  (6) —$CO_2R^c$,
  (7) —$C(=O)N(R^a)R^b$,
  (8) —$C(=O)N(R^d)R^e$, or
  (9) phenyl which is optionally substituted with from 1 to 3 substituents each of which is independently halogen, —OH, —$C_{1-4}$ alkyl, —$C_{1-4}$ haloalkyl, —O—$C_{1-4}$ alkyl, or —O—$C_{1-4}$ haloalkyl;
$R^5$ is:
  (1) —H,
  (2) —$C_{1-4}$ alkyl, or
  (3) —$C_{1-4}$ alkyl substituted with —$C(=O)N(R^a)R^b$ or —$C(=O)N(R^d)R^e$;
$R^6$ is —H, —$C_{1-4}$alkyl, $R^L$, or —$C_{1-4}$alkyl-$R^L$, wherein $R^L$ is:
  (A) phenyl which is optionally substituted with from 1 to 3 substituents each of which is independently:
    (1) —$C_{1-4}$ alkyl, optionally mono-substituted with —OH, —O—$C_{1-4}$ alkyl, —O—$C_{1-4}$ haloalkyl, —CN, —$N(R^a)R^b$, —$C(=O)N(R^a)R^b$, —$C(=O)R^a$, —$CO_2R^c$, —$S(O)_nR^c$, or —$SO_2N(R^a)R^b$,
    (2) —O—$C_{1-4}$ alkyl,
    (3) —$C_{1-4}$ haloalkyl,
    (4) —O—$C_{1-4}$ haloalkyl,
    (5) —OH,
    (6) halo,
    (7) —CN,
    (8) —$NO_2$,
    (9) —$N(R^a)R^b$,
    (10) —$SR^c$,
    (11) —$S(=O)R^c$,
    (12) —$SO_2R^c$,
    (13) —$N(R^a)SO_2R^c$,
    (14) —$SO_2N(R^a)R^b$,
    (15) —$N(R^a)C(=O)R^b$,
    (16) —$N(R^a)CO_2R^c$, or
    (17) phenyl,
  (B) a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —OH, —$C_{1-4}$ alkyl, —$C_{1-4}$ haloalkyl, or —O—$C_{1-4}$ alkyl, —O—$C_{1-4}$ haloalkyl, or
  (C) a —$C_{3-7}$ cycloalkyl which is optionally substituted with 1 to 3 substituents each of which is independently a —$C_{1-4}$ alkyl group;
$R^7$ is —H or —$C_{1-4}$ alkyl; or alternatively $R^5$ and $R^7$ together form oxo (=O), or $R^5$ and $R^7$ together with the ring carbon atom to which they are both attached form —$C_{3-7}$ cycloalkyl;
$R^8$ is —H or —$C_{1-4}$ alkyl; or alternatively $R^4$ and $R^8$ together with the ring carbon atom to which they are both attached form —$C_{3-7}$ cycloalkyl;
or alternatively $R^7$ and $R^8$ are absent, and $R^4$ and $R^5$ together with the ring carbon atoms to which each is attached and with bond "b" form:
  (i) a benzene or pyridine ring which is optionally substituted with from 1 to 3 substituents each of which is independently halogen, —OH, —$C_{1-4}$ alkyl, —$C_{1-4}$ haloalkyl, —O—$C_{1-4}$ alkyl, or —O—$C_{1-4}$ haloalkyl, or
  (ii) a $C_{3-6}$ cycloalkane ring;
each $R^a$ and $R^b$ is independently —H or —$C_{1-4}$ alkyl;
each $R^c$ is independently a —$C_{1-4}$ alkyl;
each $R^d$ and $R^e$ together with the N atom to which they are both attached form a 4- to 6-membered saturated heterocyclic ring optionally containing a heteroatom in addition to the nitrogen attached to $R^d$ and $R^e$ selected from N, O, and S, where the S is optionally oxidized to S(O) or $S(O)_2$, and wherein the saturated heterocyclic ring is optionally substituted with a $C_{1-4}$ alkyl group.

4. The compound of Formula I according to claim 1, or a pharmaceutically acceptable salt thereof, wherein:
$R^1$ is —$(CH_2)_{1-3}$-phenyl, wherein the phenyl is optionally substituted with from 1 to 3 substituents each of which is independently methyl, ethyl, methoxy, ethoxy, trifluoromethyl, trifluoromethoxy, fluoro, bromo, chloro, CN, $SCH_3$, $S(O)CH_3$, $SO_2CH_3$, $N(H)SO_2CH_3$, $N(CH_3)SO_2CH_3$, $SO_2N(CH_3)_2$, $SO_2NH_2$, $SO_2NH(CH_3)$, $N(CH_3)C(=O)CH_3$, $N(H)C(=O)CH_3$, $N(CH_3)CO_2CH_3$, or $N(H)CO_2CH_3$;
$R^2$ is —H or —$C_{1-3}$ alkyl;
$R^3$ is:
  (1) —H,
  (2) —$C_{1-3}$ alkyl,
  (3) —$CH_2CH_2OH$,
  (4) —$C(CH_3)_2OH$,
  (5) —$CO_2CH_3$,
  (6) —$C(=O)NH_2$,
  (7) —$C(=O)NH(CH_3)$,
  (8) —$C(=O)N(CH_3)_2$,
  (9) phenyl which is optionally substituted with from 1 to 3 substituents each of which is independently methyl, ethyl, methoxy, ethoxy, trifluoromethyl, trifluoromethoxy, fluoro, bromo, chloro, $SCH_3$, $S(O)CH_3$, $SO_2CH_3$, $SO_2N(CH_3)_2$, $SO_2NH_2$, or $SO_2NH(CH_3)$,
  (10) a 5- or 6-membered heteroaromatic ring selected from the group consisting of oxazolyl, oxadiazolyl, thiazolyl, thiadiazolyl, imidazolyl, pyrrolyl, triazolyl, pyridinyl, pyrimidinyl, pyrazinyl, and pyridazinyl, wherein the heteroaromatic ring is optionally substituted with 1 or 2 substituents each of which is independently methyl or ethyl,
(11) 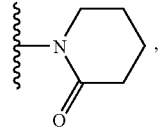
(12) 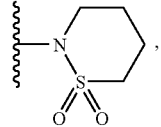
(13) 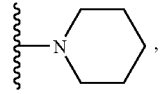
(14) 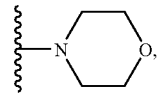
(15) 
(16) 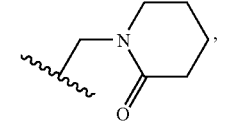
(17) 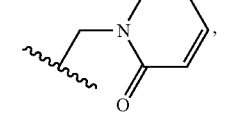
(18) 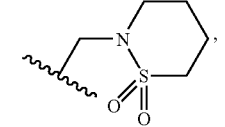
(19) 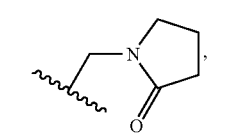
(20) 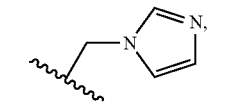
(21) 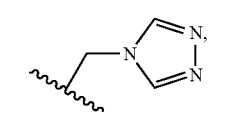
(22) chloro,
(23) bromo,
(24) fluoro,
(25) 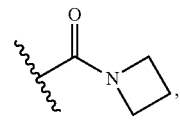
(26) 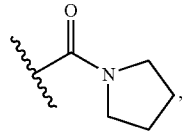
(27) 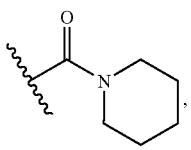
(28) 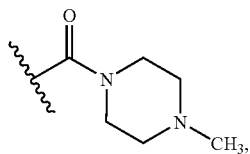
(29) 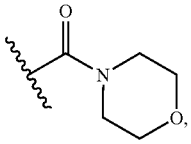
(30) 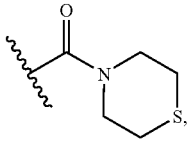
(31) —C(=O)N(CH$_3$)OCH$_3$,
(32) CN,
(33) —N(H)C(=O)CH$_3$,
(34) —N(CH$_3$)C(=O)CH$_3$,
(35) —N(H)CO$_2$CH$_3$,
(36) —N(CH$_3$)CO$_2$CH$_3$,
(37) —N(CH$_3$)CO$_2$CH$_2$CH$_3$,
(38) —N(H)SO$_2$CH$_3$,
(39) —N(CH$_3$)SO$_2$CH$_3$,
(40) —N(H)C(=O)C(=O)N(CH$_3$)$_2$,
(41) —N(CH$_3$)C(=O)C(=O)N(CH$_3$)$_2$,
(42) 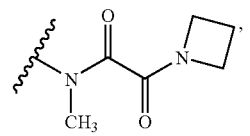
(43) 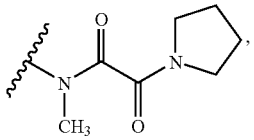

-continued

(44) 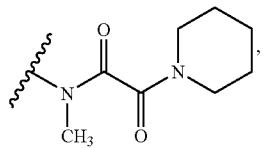

(45) 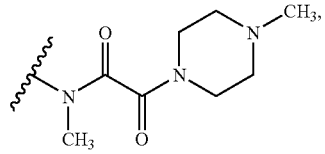

(46) 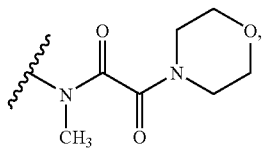

(47) 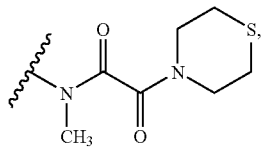

(48) —SCH$_3$,
(49) —S(O)CH$_3$, or
(50) —SO$_2$CH$_3$;

R$^4$ is:
(1) —H,
(2) —C$_{1-3}$ alkyl,
(3) —(CH$_2$)$_{2-3}$OH,
(4) —CH$_2$—SCH$_3$,
(5) —CH$_2$—SO$_2$CH$_3$,
(6) —CH$_2$—N(H)SO$_2$CH$_3$,
(7) —CH$_2$—N(CH$_3$)SO$_2$CH$_3$,
(8) —(CH$_2$)$_{1-3}$—C$_{3-5}$ cycloalkyl,
(9) —(CH$_2$)$_{1-3}$-phenyl, wherein the phenyl is optionally substituted with from 1 to 3 substituents each of which is independently chloro, bromo, fluoro, methyl, ethyl, trifluoromethyl, methoxy, ethoxy, or trifluoromethoxy,
(10) —CO$_2$CH$_3$,
(11) —C(=O)NH$_2$,
(12) —C(=O)NH(CH$_3$),
(13) —C(=O)N(CH$_3$)$_2$,

(14) 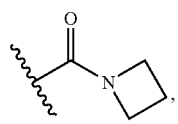

(15) 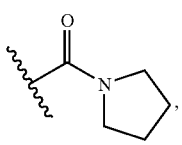

-continued

(16) 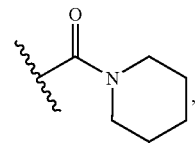

(17) 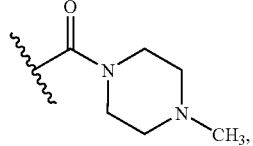

(18) 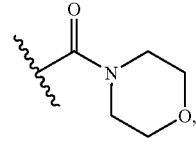

(19) 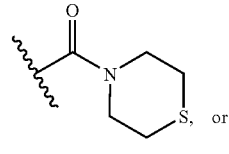, or

(20) phenyl which is optionally substituted with from 1 to 3 substituents each of which is independently chloro, bromo, fluoro, methyl, ethyl, trifluoromethyl, methoxy, ethoxy, or trifluoromethoxy;

R$^5$ is:
(1) —H,
(2) —C$_{1-3}$ alkyl,
(3) —(CH$_2$)$_{1-2}$—C(=O)NH$_2$,
(4) —(CH$_2$)$_{1-2}$—C(=O)NH(CH$_3$),
(5) —(CH$_2$)$_{1-2}$—C(=O)N(CH$_3$)$_2$, (6) 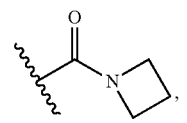

(7) 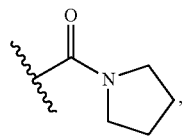

(8) 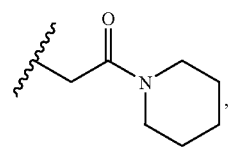

(9) 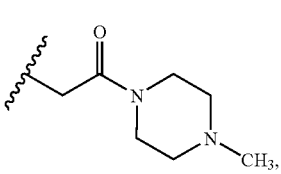

(10)

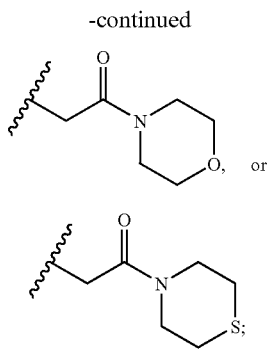

or (11)

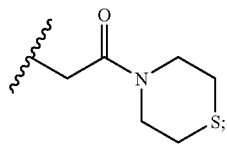

R⁶ is:
  (1) —H,
  (2) —$C_{1-3}$ alkyl,
  (3) phenyl which is optionally substituted with from 1 to 3 substituents each of which is independently methyl, ethyl, methoxy, ethoxy, trifluoromethyl, trifluoromethoxy, fluoro, bromo, chloro, CN, $SCH_3$, $S(O)CH_3$, $SO_2CH_3$, $N(H)SO_2CH_3$, $N(CH_3)SO_2CH_3$, $SO_2N(CH_3)_2$, $SO_2NH_2$, $SO_2NH(CH_3)$, $N(CH_3)C(=O)CH_3$, $N(H)C(=O)CH_3$, $N(CH_3)CO_2CH_3$, or $N(H)CO_2CH_3$,
  (4) a 5- or 6-membered heteroaromatic ring selected from the group consisting of oxazolyl, oxadiazolyl, thiazolyl, thiadiazolyl, imidazolyl, pyrrolyl, triazolyl, pyridinyl, pyrimidinyl, pyrazinyl, and pyridazinyl, wherein the heteroaromatic ring is optionally substituted with 1 or 2 substituents each of which is independently methyl or ethyl,
  (5) —$C_{3-5}$ cycloalkyl,
  (6) —$(CH_2)_{1-3}$-phenyl, wherein the phenyl is optionally substituted with from 1 to 3 substituents each of which is independently methyl, ethyl, methoxy, ethoxy, trifluoromethyl, trifluoromethoxy, fluoro, bromo, chloro, CN, $SCH_3$, $S(O)CH_3$, $SO_2CH_3$, $N(H)SO_2CH_3$, $N(CH_3)SO_2CH_3$, $SO_2N(CH_3)_2$, $SO_2NH_2$, $SO_2NH(CH_3)$, $N(CH_3)C(=O)CH_3$, $N(H)C(=O)CH_3$, $N(CH_3)CO_2CH_3$, or $N(H)CO_2CH_3$,
  (7) —$(CH_2)_{1-3}$-HetC, wherein HetC is a 5- or 6-membered heteroaromatic ring selected from the group consisting of oxazolyl, oxadiazolyl, thiazolyl, thiadiazolyl, imidazolyl, pyrrolyl, triazolyl, pyridinyl, pyrimidinyl, pyrazinyl, and pyridazinyl, wherein the heteroaromatic ring is optionally substituted with 1 or 2 substituents each of which is independently methyl or ethyl, or
  (8) —$(CH_2)_{1-3}$—$C_{3-5}$ cycloalkyl;
$R^7$ is —H or methyl; or alternatively $R^5$ and $R^7$ together form oxo (=O), or $R^5$ and $R^7$ together with the ring carbon atom to which they are both attached form —$C_{3-5}$ cycloalkyl;
$R^8$ is —H or methyl; or alternatively $R^4$ and $R^8$ together with the ring carbon atom to which they are both attached form —$C_{3-5}$ cycloalkyl; and
or alternatively $R^7$ and $R^8$ are absent, and $R^4$ and $R^5$ together with the ring carbon atoms to which each is attached and with bond "b" form:
  (i) a benzene or pyridine ring which is optionally substituted with from 1 to 3 substituents each of which is independently chloro, bromo, fluoro, methyl, ethyl, trifluoromethyl, methoxy, ethoxy, or trifluoromethoxy, or
  (ii) a cycloalkane ring which is cyclopropane, cyclopentane, or cyclohexane.

5. The compound of Formula I according to claim 4, or a pharmaceutically acceptable salt thereof, wherein:
  $R^1$ is —$CH_2$-phenyl, wherein the phenyl is substituted with 1 or 2 substituents each of which is independently methyl, methoxy, fluoro, bromo, or chloro;
  $R^2$ is —H;
  $R^3$ is —H, methyl, ethyl, isopropyl, n-propyl, —$CO_2CH_3$, —$C(=O)NH_2$, —$C(=O)NH(CH_3)$, —$C(=O)N(CH_3)_2$, phenyl, oxadiazolyl (optionally substituted with methyl), chloro, bromo,

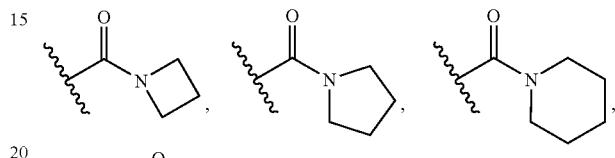

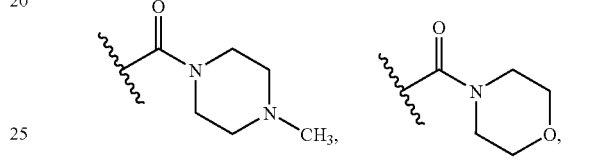

—$C(=O)N(CH_3)OCH_3$, CN, —$N(CH_3)C(=O)CH_3$, —$N(CH_3)CO_2CH_3$, —$N(CH_3)CO_2CH_2CH_3$, —$N(CH_3)SO_2CH_3$, —$N(CH_3)C(=O)C(=O)N(CH_3)_2$, —$SCH_3$, —$S(O)CH_3$, or —$SO_2CH_3$;
  $R^4$ is —H, methyl, ethyl, isopropyl, n-propyl, —$(CH_2)_2OH$, —$CH_2$-cyclopropyl, $CH_2$-phenyl, —$CO_2CH_3$, —$C(=O)NH_2$, —$C(=O)NH(CH_3)$, —$C(=O)N(CH_3)_2$,

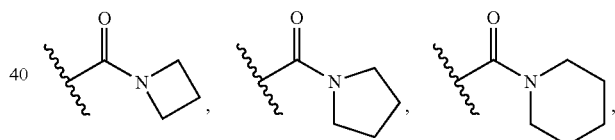

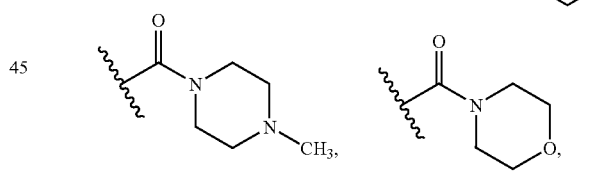

or phenyl;
  $R^5$ is —H, methyl, —$CH_2$—$C(=O)NH(CH_3)$, or —$CH_2$—$C(=O)N(CH_3)_2$;
  $R^6$ is (1) —H, (2) methyl, (3) ethyl, (4) phenyl, (5) pyridinyl, (6) cyclopropyl, (7) —$CH_2$-phenyl or —$CH_2CH_2$-phenyl, wherein the phenyl is optionally substituted with 1 or 2 substituents each of which is independently methyl, ethyl, methoxy, ethoxy, trifluoromethyl, trifluoromethoxy, fluoro, bromo, or chloro, (8) —$CH_2$-pyridinyl, or (9) —$CH_2$-cyclopropyl;
  $R^7$ is —H or methyl; or alternatively $R^5$ and $R^7$ together form oxo (=O), or $R^5$ and $R^7$ together with the ring carbon atom to which they are both attached form cyclopropyl;
  $R^8$ is —H or methyl; or alternatively $R^4$ and $R^8$ together with the ring carbon atom to which they are both attached form cyclopropyl or cyclopentyl; and or alternatively R⁷ and R⁸ are absent, and R⁴ and R⁵ together with the ring carbon atoms to which each is attached and with bond "b" form a benzene ring which is optionally substituted with 1 or 2 substituents each of which is independently chloro, bromo, fluoro, methyl, ethyl, trifluoromethyl, methoxy, ethoxy, or trifluoromethoxy.

6. The compound according to claim 1, or a pharmaceutically acceptable salt thereof, which is a compound of Formula IB:

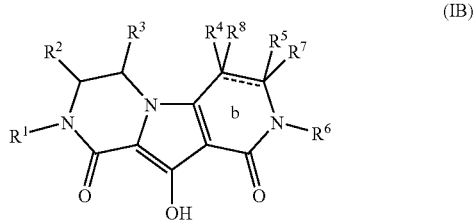

(IB)

wherein bond "b" in the ring is a single bond or a double bond, with the proviso that (i) when "b" is a single bond, R⁷ and R⁸ are both —H, and (ii) when "b" is a double bond, R⁷ and R⁸ are both absent;

R⁴ is:
(1) —H,
(2) —C$_{1-6}$ alkyl,
(3) —C$_{1-6}$ alkyl substituted with OH, SR$^c$, S(O)R$^c$, SO$_2$R$^c$, or —N(R$^a$)SO$_2$R$^c$,
(4) —C$_{1-6}$ alkyl substituted with —C$_{3-8}$ cycloalkyl,
(5) —C$_{1-6}$ alkyl substituted with aryl, wherein the aryl is optionally substituted with from 1 to 3 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl,
(6) —CO$_2$R$^c$,
(7) —C(=O)N(R$^a$)R$^b$,
(8) —C(=O)N(R$^d$)R$^e$, or
(9) aryl which is optionally substituted with from 1 to 3 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl; and R⁵ is:
(1) —H,
(2) —C$_{1-6}$ alkyl, or
(3) —C$_{1-6}$ alkyl substituted with —C(=O)N(R$^a$)R$^b$ or —C(=O)N(R$^d$)R$_e$.

7. The compound according to claim 1, or a pharmaceutically acceptable salt thereof, which is a compound of Formula ID:

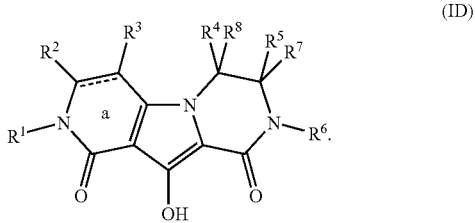

(ID)

8. A compound, or a pharmaceutically acceptable salt thereof, selected from the group consisting of:
8-(3-chloro-4-fluorobenzyl)-10-hydroxy-2-methyl-3,4,7,8-tetrahydropyrido-[3',4':4,5]pyrrolo[1,2-a]pyrazine-1,9(2H,6H)-dione;
2-(4-fluorobenzyl)-10-hydroxy-3,4,7,8-tetrahydropyrido-[3',4':4,5]pyrrolo[1,2-a]pyrazine-1,9(2H,6H)-dione;
8-(4-fluorobenzyl)-10-hydroxy-2,4-dimethyl-7,8-dihydropyrido-[3',4':4,5]pyrrolo[1,2-a]pyrazine-1,9(2H,6H)-dione;
8-(4-fluorobenzyl)-10-hydroxy-6-{2-[methoxy(methyl)amino]ethyl}-2-methyl-3,4,7,8-tetrahydropyrido-[3',4':4,5]pyrrolo[1,2-a]pyrazine-1,9(2H,6H)-dione;
8-(3,4-dichlorobenzyl)-10-hydroxy-2-methyl-3,4,7,8-tetrahydropyrido-[3',4':4,5]pyrrolo-[1,2-a]pyrazine-1,9(2H,6H)-dione;
8-(3-chlorobenzyl)-10-hydroxy-2-methyl-3,4,7,8-tetrahydropyrido-[3',4':4,5]pyrrolo[1,2-a]pyrazine-1,9(2H,6H)-dione;
8-(4-fluorobenzyl)-10-hydroxy-2-methyl-3,4,7,8-tetrahydropyrido-[3',4':4,5]pyrrolo[1,2-a]pyrazine-1,9(2H,6H)-dione;
8-(3,4-difluorobenzyl)-10-hydroxy-2-methyl-3,4,7,8-tetrahydropyrido-[3',4':4,5]pyrrolo-[1,2-a]pyrazine-1,9(2H,6H)-dione;
2,8-bis(4-fluorobenzyl)-10-hydroxy-3,4,7,8-tetrahydropyrido-[3',4':4,5]pyrrolo[1,2-a]pyrazine-1,9(2H,6H)-dione;
2-(3,4-dimethoxybenzyl)-8-(4-fluorobenzyl)-10-hydroxy-3,4,7,8-tetrahydropyrido-[3',4':4,5]pyrrolo[1,2-a]pyrazine-1,9(2H,6H)-dione;
8-(4-fluorobenzyl)-10-hydroxy-3,4,7,8-tetrahydropyrido-[3',4':4,5]pyrrolo[1,2-a]pyrazine-1,9(2H,6H)-dione;
8-(4-fluorobenzyl)-10-hydroxy-2-ethyl-3,4,7,8-tetrahydropyrido-[3',4':4,5]pyrrolo[1,2-a]pyrazine-1,9(2H,6H)-dione;
2-(4-fluorobenzyl)-10-hydroxy-8-methyl-3,4,7,8-tetrahydropyrido-[3',4':4,5]pyrrolo[1,2-a]pyrazine-1,9(2H,6H)-dione;
8-(4-fluorobenzyl)-10-hydroxy-2-methyl-7,8-tetrahydropyrido-[3',4':4,5]pyrrolo[1,2-a]pyrazine-1,9(2H,6H)-dione; and
8-(4-fluorobenzyl)-10-hydroxy-7-(2-dimethylamino-2-oxoethyl)-2-methyl-3,4,7,8-tetrahydropyrido-[3',4':4,5]pyrrolo[1,2-a]pyrazine-1,9(2H,6H)-dione.

9. A compound, or a pharmaceutically acceptable salt thereof, selected from the group consisting of:
2-(4-Fluorobenzyl)-10-hydroxy-7-(2-dimethylamino-2-oxoethyl)-8-methyl-3,4,7,8-tetrahydropyrido-[3',4':4,5]pyrrolo[1,2-a]pyrazine-1,9(2H,6H)-dione;
9-(4-Fluorobenzyl)-7-hydroxy-10,11-dihydropyrido-[3',4':4,5]pyrrolo[1,2-a]quinoxaline-6,8(5H,9H)-dione;
2-Chloro-9-(4-fluorobenzyl)-7-hydroxy-10,11-dihydropyrido-[3',4':4,5]pyrrolo[1,2-a]quinoxaline-6,8(5H,9H)-dione;
9-(4-Fluorobenzyl)-7-hydroxy-5-methyl-10,11-dihydropyrido-[3',4':4,5]pyrrolo[1,2-a]quinoxaline-6,8(5H,9H)-dione;
8-Ethyl-2-(4-fluorobenzyl)-10-hydroxy-6-methyl-3,4,7,8-tetrahydropyrido-[3',4':4,5]pyrrolo[1,2-a]pyrazine-1,9(2H,6H)-dione and enantiomers thereof;
8-Ethyl-2-(3-chloro-4-fluorobenzyl)-10-hydroxy-6-methyl-3,4,7,8-tetrahydropyrido-[3',4':4,5]pyrrolo[1,2-a]pyrazine-1,9(2H,6H)-dione and enantiomers thereof;
2-(4-Fluorobenzyl)-10-hydroxy-8-(2-phenylethyl)-3,4-dihydropyrido-[3',4':4,5]pyrrolo[1,2-a]pyrazine-1,7,9(2H,6H,8H)-trione;

8-(4-Fluorobenzyl)-10-hydroxy-2-(pyridin-4-ylmethyl)-3,4,7,8-tetrahydropyrido-[3',4':4,5]pyrrolo[1,2-a]pyrazine-1,9(2H,6H)-dione;

8-(4-Fluorobenzyl)-10-hydroxy-2-(pyridin-3-ylmethyl)-3,4,7,8-tetrahydropyrido-[3',4':4,5]pyrrolo[1,2-a]pyrazine-1,9(2H,6H)-dione;

8-(4-Fluorobenzyl)-10-hydroxy-2-(pyridin-2-ylmethyl)-3,4,7,8-tetrahydropyrido-[3',4':4,5]pyrrolo[1,2-a]pyrazine-1,9(2H,6H)-dione;

2-(4-Fluorobenzyl)-10-hydroxy-8-(pyridin-3-ylmethyl)-3,4,7,8-tetrahydropyrido-[3',4':4,5]pyrrolo[1,2-a]pyrazine-1,9(2H,6H)-dione;

2-(3-Chloro-4-fluorobenzyl)-10-hydroxy-8-(pyridin-3-ylmethyl)-3,4,7,8-tetrahydropyrido-[3',4':4,5]pyrrolo[1,2-a]pyrazine-1,9(2H,6H)-dione;

2-(Cyclopropylmethyl)-8-(4-fluorobenzyl)-10-hydroxy-3,4,7,8-tetrahydropyrido-[3',4':4,5]pyrrolo[1,2-a]pyrazine-1,9(2H,6H)-dione;

2-(4-Fluorobenzyl)-10-hydroxy-8-pyridin-2-yl-3,4,7,8-tetrahydropyrido-[3',4':4,5]pyrrolo[1,2-a]pyrazine-1,9(2H,6H)-dione;

2-(4-Fluorobenzyl)-10-hydroxy-8-pyridin-3-yl-3,4,7,8-tetrahydropyrido-[3',4':4,5]pyrrolo[1,2-a]pyrazine-1,9(2H,6H)-dione;

2-(4-Fluorobenzyl)-10-hydroxy-8-phenyl-3,4,7,8-tetrahydropyrido-[3',4':4,5]pyrrolo[1,2-a]pyrazine-1,9(2H,6H)-dione;

2-(3-Chloro-4-fluorobenzyl)-10-hydroxy-4,8-dimethyl-7,8-dihydropyrido-[3',4':4,5]pyrrolo[1,2-a]pyrazine-1,9(2H,6H)-dione;

2-(4-Fluorobenzyl)-10-hydroxy-4,8-dimethyl-7,8-dihydropyrido[3',4':4,5]pyrrolo[1,2-a]pyrazine-1,9(2H,6H)-dione;

2-(3-Methylbenzyl)-10-hydroxy-4,8-dimethyl-7,8-dihydropyrido[3',4':4,5]pyrrolo[1,2-a]pyrazine-1,9(2H,6H)-dione;

8-Ethyl-2-(4-fluorobenzyl)-10-hydroxy-4,6-dimethyl-7,8-dihydropyrido-[3',4':4,5]pyrrolo[1,2-a]pyrazine-1,9(2H,8H)-dione and enantiomers thereof;

(6S)-2-(4-Fluorobenzyl)-10-hydroxy-6-isopropyl-4,8-dimethyl-7,8-dihydropyrido-[3',4':4,5]pyrrolo[1,2-a]pyrazine-1,9(2H,8H)-dione;

((6S)-8-Ethyl-2-(4-fluorobenzyl)-10-hydroxy-6-isopropyl-4-methyl-7,8-dihydropyrido-[3',4':4,5]pyrrolo[1,2-a]pyrazine-1,9(2H,8H)-dione;

2-(4-Fluorobenzyl)-10-hydroxy-4-isopropyl-8-methyl-7,8-dihydropyrido-[3',4':4,5]pyrrolo[1,2-a]pyrazine-1,9(2H,6H)-dione;

4-Ethyl-2-(4-fluorobenzyl)-10-hydroxy-8-methyl-7,8-dihydropyrido-[3',4':4,5]pyrrolo[1,2-a]pyrazine-1,9(2H,6H)-dione;

4-Ethyl-8-(4-fluorobenzyl)-10-hydroxy-2-methyl-7,8-dihydropyrido-[3',4':4,5]pyrrolo[1,2-a]pyrazine-1,9(2H,6H)-dione;

4-Benzyl-8-(4-fluorobenzyl)-10-hydroxy-2-methyl-7,8-dihydropyrido-[3',4':4,5]pyrrolo[1,2-a]pyrazine-1,9(2H,6H)-dione;

2-(4-Fluorobenzyl)-10-hydroxy-4-isopropyl-8-methyl-3,4,7,8-tetrahydropyrido-[3',4':4,5]pyrrolo[1,2-a]pyrazine-1,9(2H,6H)-dione;

8-(4-Fluorobenzyl)-10-hydroxy-4-isopropyl-2-methyl-3,4,7,8-tetrahydropyrido-[3',4':4,5]pyrrolo[1,2-a]pyrazine-1,9(2H,6H)-dione;

8-(4-Fluorobenzyl)-10-hydroxy-4-propyl-2-methyl-3,4,7,8-tetrahydropyrido-[3',4':4,5]pyrrolo[1,2-a]pyrazine-1,9(2H,6H)-dione;

8'-(2,4-Dimethoxybenzyl)-2'-(4-fluorobenzyl)-10'-hydroxy-3',4',7',8'-tetrahydro-1'H-spiro[cyclopentane-1,6'pyrido[3',4':4,5]pyrrolo[1,2-a]pyrazine-1',9'(2'H)-dione;

8-(2,4-Dimethoxybenzyl)-2-(4-fluorobenzyl)-10-hydroxy-6-phenyl-3,4,7,8-tetrahydropyrido-[3',4':4,5]pyrrolo[1,2-a]pyrazine-1,9(2H,6H)-dione;

8-(2,4-Dimethoxybenzyl)-2-(4-fluorobenzyl)-10-hydroxy-6-(2-hydroxyethyl)-3,4,7,8-tetrahydropyrido-[3',4':4,5]pyrrolo[1,2-a]pyrazine-1,9(2H,6H)-dione;

8-(2,4-Dimethoxybenzyl)-2-(4-fluorobenzyl)-10-hydroxy-6-methyl-3,4,7,8-tetrahydropyrido-[3',4':4,5]pyrrolo[1,2-a]pyrazine-1,9(2H,6H)-dione;

8-(2,4-Dimethoxybenzyl)-2-(4-fluorobenzyl)-10-hydroxy-6-isobutyl-3,4,7,8-tetrahydropyrido-[3',4':4,5]pyrrolo[1,2-a]pyrazine-1,9(2H,6H)-dione;

6-(Cyclopropylmethyl)-8-(2,4-dimethoxybenzyl)-2-(4-fluorobenzyl)-10-hydroxy-3,4,7,8-tetrahydropyrido-[3',4':4,5]pyrrolo[1,2-a]pyrazine-1,9(2H,6H)-dione;

6-Benzyl-2-(4-fluorobenzyl)-10-hydroxy-8-methyl-3,4,7,8-tetrahydropyrido-[3',4':4,5]pyrrolo[1,2-a]pyrazine-1,9(2H,6H)-dione;

2-(4-fluorobenzyl)-10-hydroxy-8-methyl-6-phenyl-3,4,7,8-tetrahydropyrido-[3',4':4,5]pyrrolo[1,2-a]pyrazine-1,9(2H,6H)-dione;

2-(4-Fluorobenzyl)-8-(cyclopropylmethyl)-10-hydroxy-6-phenyl-3,4,7,8-tetrahydropyrido-[3',4':4,5]pyrrolo[1,2-a]pyrazine-1,9(2H,6H)-dione;

2-(4-Fluorobenzyl)-8-ethyl-10-hydroxy-6-phenyl-3,4,7,8-tetrahydropyrido-[3',4':4,5]pyrrolo[1,2-a]pyrazine-1,9(2H,6H)-dione;

6-Benzyl-2-(4-fluorobenzyl)-8-(cyclopropylmethyl)-10-hydroxy-3,4,7,8-tetrahydropyrido-[3',4':4,5]pyrrolo[1,2-a]pyrazine-1,9(2H,6H)-dione;

6-Benzyl-2-(4-fluorobenzyl)-8-ethyl-10-hydroxy-3,4,7,8-tetrahydropyrido-[3',4':4,5]pyrrolo[1,2-a]pyrazine-1,9(2H,6H)-dione;

8'-Ethyl-2'-(4-fluorobenzyl)-10'-hydroxy-3',4',7',8'-tetrahydropyrido-1'H-spiro[cyclopropane1,6'-pyrido[3',4':4,5]pyrrolo[1,2-a]pyrazine-1',9'(2'H)-dione;

8'-(Cyclopropylmethyl)-2'-(4-fluorobenzyl)-10'-hydroxy-3',4',7',8'-tetrahydropyrido-1'H-spiro[cyclopropane1,6'-pyrido[3',4':4,5]pyrrolo[1,2-a]pyrazine-1',9'(2'H)-dione;

8'-Cyclopropyl-2'-(4-fluorobenzyl)-10'-hydroxy-3',4',7',8'-tetrahydropyrido-1'H-spiro[cyclopropane1,6'-pyrido[3',4':4,5]pyrrolo[1,2-a]pyrazine-1',9'(2'H)-dione;

2'-(3-Chloro-4-fluorobenzyl)-8'-ethyl-10'-hydroxy-3',4',7',8'-tetrahydropyrido-1'H-spiro[cyclopropane1,6'-pyrido[3',4':4,5]pyrrolo[1,2-a]pyrazine-1',9'(2'H)-dione;

8-Ethyl-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione;

8-(3,4-Dimethoxybenzyl)-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione;

8-(Cyclopropylmethyl)-2-(4-fluorobenzyl)-10-hydroxy-7,7-dimethyl-3,4,7,8-tetrahydropyrido-[3',4':4,5]pyrrolo[1,2-a]pyrazine-1,9(2H,6H)-dione;

8-Ethyl-2-(3-chloro-4-fluorobenzyl)-10-hydroxy-7,7-dimethyl-3,4,7,8-tetrahydropyrido-[3',4':4,5]pyrrolo[1,2-a]pyrazine-1,9(2H,6H)-dione;

8'-Ethyl-2'-(4-fluorobenzyl)-10'-hydroxy-3',4'-dihydrospiro[cyclopropane1,7'-pyrido[3',4':4,5]pyrrolo[1,2-a]pyrazine-1',9'(2'H,8'H)-dione;

2-(4-Fluorobenzyl)-10-hydroxy-7,8-dimethyl-3,4,7,8-tetrahydropyrido-[3',4':4,5]pyrrolo[1,2-a]pyrazine-1,9 (2H,6H)-dione;

8-(2,4-Dimethoxybenzyl)-2-(4-fluorobenzyl)-10-hydroxy-7-methyl-3,4,7,8-tetrahydropyrido-[3',4':4,5]pyrrolo[1,2-a]pyrazine-1,9(2H,6H)-dione;

8-Ethyl-2-(4-fluorobenzyl)-10-hydroxy-7-methyl-3,4,7,8-tetrahydropyrido-[3',4':4,5]pyrrolo[1,2-a]pyrazine-1,9(2H,6H)-dione and enantiomers thereof;

8-Ethyl-2-(3-chloro-4-fluorobenzyl)-10-hydroxy-7-methyl-3,4,7,8-tetrahydropyrido-[3',4':4,5]pyrrolo[1,2-a]pyrazine-1,9(2H,6H)-dione and enantiomers thereof;

8-Ethyl-2-(3-Chloro-4-fluorobenzyl)-10-hydroxy-7-methyl-3,4,7,8-tetrahydropyrido-[3',4':4,5]pyrrolo[1,2-a]pyrazine-1,9(2H,6H)-dione;

8-Cyclopropyl-2-(4-fluorobenzyl)-10-hydroxy-7-methyl-3,4,7,8-tetrahydropyrido-[3',4':4,5]pyrrolo[1,2-a]pyrazine-1,9(2H,6H)-dione;

2-(4-Fluorobenzyl)-8-(cyclopropylmethyl)-10-hydroxy-7-methyl-3,4,7,8-tetrahydropyrido-[3',4':4,5]pyrrolo[1,2-a]pyrazine-1,9(2H,6H)-dione;

2-(3-Chloro-4-fluorobenzyl)-8-(cyclopropylmethyl)-10-hydroxy-7-methyl-3,4,7,8-tetrahydropyrido-[3',4':4,5]pyrrolo[1,2-a]pyrazine-1,9(2H,6H)-dione;

2-(3-Chloro-4-fluorobenzyl)-10-hydroxy-7,8-dimethyl-3,4,7,8-tetrahydropyrido-[3',4':4,5]pyrrolo[1,2-a]pyrazine-1,9(2H,6H)-dione;

2-(3-Chloro-4-fluorobenzyl)-8-cyclopropyl-10-hydroxy-7-methyl-3,4,7,8-tetrahydropyrido-[3',4':4,5]pyrrolo[1,2-a]pyrazine-1,9(2H,6H)-dione and enantiomers thereof;

2-(4-Fluorobenzyl)-10-hydroxy-4-(methoxycarbonyl)-8-methyl-3,4,7,8-tetrahydropyrido-[3',4':4,5]pyrrolo[1,2-a]pyrazine-1,9(2H,6H)-dione;

2-(4-Fluorobenzyl)-10-hydroxy-4-(dimethylcarbonyl)-8-methyl-3,4,7,8-tetrahydropyrido-[3',4':4,5]pyrrolo[1,2-a]pyrazine-1,9(2H,6H)-dione;

2-(3-Chloro-4-fluorobenzyl)-10-hydroxy-4-(methoxycarbonyl)-8-methyl-3,4,7,8-tetrahydropyrido-[3',4':4,5]pyrrolo[1,2-a]pyrazine-1,9(2H,6H)-dione;

2-(3-Chloro-4-fluorobenzyl)-10-hydroxy-4-(dimethylcarbonyl)-8-methyl-3,4,7,8-tetrahydropyrido-[3',4':4,5]pyrrolo[1,2-a]pyrazine-1,9(2H,6H)-dione;

2-(4-Fluorobenzyl)-10-hydroxy-4-(piperidinylcarbonyl)-8-methyl-3,4,7,8-tetrahydropyrido-[3',4':4,5]pyrrolo[1,2-a]pyrazine-1,9(2H,6H)-dione;

2-(3-Chloro-4-fluorobenzyl)-10-hydroxy-4-(morpholinylcarbonyl)-8-methyl-3,4,7,8-tetrahydropyrido-[3',4':4,5]pyrrolo[1,2-a]pyrazine-1,9(2H,6H)-dione;

8-(4-Fluorobenzyl)-10-hydroxy-4-(methoxycarbonyl)-2-methyl-3,4,7,8-tetrahydropyrido-[3',4':4,5]pyrrolo[1,2-a]pyrazine-1,9(2H,6H)-dione;

8-(4-Fluorobenzyl)-10-hydroxy-4-(morpholinylcarbonyl)-2-methyl-3,4,7,8-tetrahydropyrido-[3',4':4,5]pyrrolo[1,2-a]pyrazine-1,9(2H,6H)-dione;

8-(4-Fluorobenzyl)-10-hydroxy-4-(dimethylaminocarbonyl)-2-methyl-3,4,7,8-tetrahydropyrido-[3',4':4,5]pyrrolo[1,2-a]pyrazine-1,9(2H,6H)-dione;

8-(4-Fluorobenzyl)-10-hydroxy-4-(piperidinylcarbonyl)-2-methyl-3,4,7,8-tetrahydropyrido-[3',4':4,5]pyrrolo[1,2-a]pyrazine-1,9(2H,6H)-dione;

2-(4-Fluorobenzyl)-10-hydroxy-4-(methoxycarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(methoxycarbonyl)-8-methyl-7,8-dihydropyrido-[3',4':4,5]pyrrolo[1,2-a]pyrazine-1,9(2H,6H)-dione;

2-(4-Fluorobenzyl)-10-hydroxy-4-(dimethylaminocarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(methylaminocarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(dimethylaminocarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(aminocarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(morpholinylcarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(N-methylpiperazinylcarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(N-methyl-N-methoxyaminocarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(azetidinylcarbonyl)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(pyrrolidinylcarbonyl)-8-methyl-7,8-dihydropyrido-[3',4':4,5]pyrrolo[1,2-a]pyrazine-1,9(2H,6H)-dione;

8-(4-Fluorobenzyl)-10-hydroxy-4-(methoxycarbonyl)-2-methyl-7,8-dihydropyrido-[3',4':4,5]pyrrolo[1,2-a]pyrazine-1,9(2H,6H)-dione;

8-(4-Fluorobenzyl)-10-hydroxy-4-(methylaminocarbonyl)-2-methyl-7,8-dihydropyrido-[3',4':4,5]pyrrolo[1,2-a]pyrazine-1,9(2H,6H)-dione;

(6S)-2-(3-Chloro-4-fluorobenzyl)-8-ethyl-10-hydroxy-6-methyl-4-(methylaminocarbonyl)-7,8-dihydropyrido-[3',4':4,5]pyrrolo[1,2-a]pyrazine-1,9(2H,8H)-dione;

(6S)-2-(3-Chloro-4-fluorobenzyl)-8-ethyl-10-hydroxy-6-methyl-4-(dimethylaminocarbonyl)-7,8-dihydropyrido-[3',4':4,5]pyrrolo[1,2-a]pyrazine-1,9(2H,8H)-dione;

2-(3-Chloro-4-fluorobenzyl)-10-hydroxy-4-cyano-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-8-methyl-4-(5-methyl-1,3,4-oxadiazol-2-yl)-7,8-dihydropyrido-[3',4':4,5]pyrrolo[1,2-a]pyrazine-1,9(2H,6H)-dione;

2-(3-Chloro-4-fluorobenzyl)-10-hydroxy-4-(N-methanesulfonyl-N-methylamino)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(N-acetyl-N-methylamino)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(N-ethoxycarbonyl-N-methylamino)-8-methyl-7,8-dihydropyrido-[3',4':4,5]pyrrolo[1,2-a]pyrazine-1,9(2H,6H)-dione;

2-(3-Chloro-4-fluorobenzyl)-10-hydroxy-4-(2-N',N'-dimethylamino-2-oxoacetyl-N-methylamino)-8-methyl-7,8-dihydropyrido-[3',4':4,5]pyrrolo[1,2-a]pyrazine-1,9(2H,6H)-dione;

2-(3-chloro-4-fluorobenzyl)-10-hydroxy-4-bromo-8-methyl-7,8-dihydropyrido-[3',4':4,5]pyrrolo[1,2-a]pyrazine-1,9(2H,6H)-dione;

2-(3-chloro-4-fluorobenzyl)-10-hydroxy-4-methylthio-8-methyl-7,8-dihydropyrido-[3',4':4,5]pyrrolo[1,2-a]pyrazine-1,9(2H,6H)-dione; and 2-(3-chloro-4-fluorobenzyl)-10-hydroxy-4-methylsulfonyl-8-methyl-7,8-dihydropyrido-[3',4':4,5]pyrrolo[1,2-a]pyrazine-1,9(2H,6H)-dione.

10. A pharmaceutical composition comprising a therapeutically effective amount of a compound according to claim 1, or a pharmaceutically acceptable salt thereof, and a pharmaceutically acceptable carrier.

11. A method of inhibiting HIV integrase in a subject in need thereof which comprises administering to the subject a therapeutically effective amount of the compound according to claim 1, or a pharmaceutically acceptable salt thereof.

12. A method for treating infection by HIV or for preventing, treating or delaying the onset of AIDS in a subject in need thereof which comprises administering to the subject a therapeutically effective amount of the compound according to claim 1, or a pharmaceutically acceptable salt thereof.

* * * * *